US011939606B2

(12) United States Patent
Carter et al.

(10) Patent No.: US 11,939,606 B2
(45) Date of Patent: Mar. 26, 2024

(54) CRISPR-ASSOCIATED (CAS) PROTEIN

(71) Applicant: Locanabio, Inc., San Diego, CA (US)

(72) Inventors: Matthew Merrill Carter, San Diego, CA (US); Paul Daniel Donohoue, San Diego, CA (US)

(73) Assignee: Locanabio, Inc., San Diego, CA (US)

(*) Notice: Subject to any disclaimer, the term of this patent is extended or adjusted under 35 U.S.C. 154(b) by 0 days.

(21) Appl. No.: 17/678,369

(22) Filed: Feb. 23, 2022

(65) Prior Publication Data

US 2022/0177864 A1 Jun. 9, 2022

Related U.S. Application Data

(60) Division of application No. 17/097,880, filed on Nov. 13, 2020, now Pat. No. 11,293,011, which is a continuation of application No. 15/937,840, filed on Mar. 27, 2018, now Pat. No. 10,876,101.

(60) Provisional application No. 62/629,641, filed on Feb. 12, 2018, provisional application No. 62/477,494, filed on Mar. 28, 2017.

(51) Int. Cl.

| | |
|---|---|
| ***C12N 9/22*** | (2006.01) |
| ***C12N 15/11*** | (2006.01) |
| ***C12N 15/113*** | (2010.01) |
| ***C12N 15/85*** | (2006.01) |

(52) U.S. Cl.

CPC ................ *C12N 9/22* (2013.01); *C12N 15/11* (2013.01); *C12N 15/111* (2013.01); *C12N 15/1136* (2013.01); *C12N 15/85* (2013.01); *C12N 2310/20* (2017.05); *C12N 2800/22* (2013.01)

(58) Field of Classification Search

None

See application file for complete search history.

(56) References Cited

U.S. PATENT DOCUMENTS

| | | | |
|---|---|---|---|
| 10,876,101 | B2 | 12/2020 | Carter et al. |
| 10,889,808 | B2 | 1/2021 | Carter et al. |
| 11,028,381 | B2 | 6/2021 | Carter et al. |
| 11,293,011 | B2 | 4/2022 | Carter et al. |
| 2014/0068797 | A1 | 3/2014 | Doudna et al. |
| 2019/0002875 | A1 | 1/2019 | Cheng et al. |
| 2019/0002889 | A1 | 1/2019 | Cheng et al. |
| 2019/0062724 | A1 | 2/2019 | Hsu et al. |
| 2021/0079367 | A1 | 3/2021 | Carter et al. |
| 2021/0269785 | A1 | 9/2021 | Carter et al. |

FOREIGN PATENT DOCUMENTS

| | | | |
|---|---|---|---|
| WO | WO-2013098244 | A1 | 7/2013 |
| WO | WO-2014150624 | A1 | 9/2014 |
| WO | WO-2015200555 | A2 | 12/2015 |
| WO | WO-2016123230 | A1 | 8/2016 |
| WO | WO-2016201155 | A1 | 12/2016 |
| WO | WO-2017027423 | A1 | 2/2017 |
| WO | WO-2018035250 | A1 | 2/2018 |
| WO | WO-2018172556 | A1 | 9/2018 |
| WO | WO-2018183403 | A1 | 10/2018 |

OTHER PUBLICATIONS

Abudayyeh et al., "C2c2 is a Single Component Programmable RNA-Guided RNA-targeting CRISPR Effector," Science, vol. 353(6299), aaf5573, p. 1-9, Aug. 2016.

Briner, A.E. et al. (2014). "Guide RNA functional modules direct Cas9 activity and orthogonality," Mol. Cell. 56(2):333-339.

Burstein, D. et al., "New CRISPR-Cas systems from uncultivated microbes," Nature, 542:237-241 (2017), including Methods & Extended Data, 28 pages.

Database Accession No. A0A1C5SD84, Nov. 2, 2016, "Uncharacterized protein," retrieved from uncultured *Ruminococcus* sp., Accession No. 165186 NCBI, 3 pages.

Database Accession No. A0A1C6E6B1, Nov. 2, 2016, "Uncharacterized protein," retrieved from uncultured Ruminococcus, Accession No. 165186 NCBI, 3 pages.

Database Accession No. A0A1C6F3V9, Nov. 2, 2016, "Uncharacterized protein," retrieved from uncultured *Ruminococcus* sp., Accession No. 165186 NCBI, 4 pages.

Database Accession No. A0A1K1WS24, Feb. 15, 2017, "Uncharacterized protein," retrieved from Ruminococcus flavefaciens, Accession No. 1265 NCBI, 3 pages.

Database Accession No. BOMS50, Apr. 8, 2008, "Uncharacterized protein," retrieved from Eubacterium siraeum, Accession No. DSM 15702, 5 pages.

Database Accession No. R6SX09, Jul. 24, 2013, "Uncharacterized protein," retrieved from *Ruminococcus* sp. CAG:57, Accession No. 1262962 NCBI, 4 pages.

Database Accession No. W0U8U3, Mar. 19, 2014, "Uncharacterized protein," retrieved from Ruminococcus bicirculans, Accession No. 1160721 NCBI, 4 pages.

Database Accession No. WP_009985792, Jun. 6, 2013, "Hypothetical protein," retrieved from Ruminococcus flavefaciens, 1 page.

Database Accession No. WP_074833651, Dec. 22, 2016, "Hypothetical protein," retrieved from Ruminococcus albus, 1 page.

East-Seletsky, A. et al., "Two distinct RNase activities of CRISPR-C2c2 enable guide-RNA processing and RNA detection," Nature, 538:270-273 (2016), including Methods & Extended Data, 13 pages.

Fu, Y. et al. (2014). "Improving CRISPR-Cas nuclease specificity using truncated guide RNAs," Nat. Biotechnol. 32:279-284 and additional 2 pp. supplement and 1 p. erratum provided.

(Continued)

*Primary Examiner* — Richard G Hutson

(74) *Attorney, Agent, or Firm* — COOLEY LLP; Ivor R. Elrifi; Andrew R. Henderson

(57) ABSTRACT

A new CRISPR-associated (Cas) protein, termed "CasM," is described, as well as polynucleotides encoding the same and methods of using CasM for site-specific genome engineering. CasM proteins are capable of targeting and cleaving single-stranded RNA.

13 Claims, 5 Drawing Sheets

Specification includes a Sequence Listing.

(56) References Cited

OTHER PUBLICATIONS

GenBank Accession No. HF_545617.1, Feb. 27, 2015, 352 pages.
GenBank Accession No. NZ_DS499551.1, Nov. 25, 2019, 62 pages.
Hein, S. et al., "Adaptation and modification of three CRISPR loci in two closely related cyanobacteria," RNA Biology, 10(5):852-864 (2013).
International Search Report and Written Opinion dated Jun. 28, 2018 for International Application No. PCT/US2018/024677, 14 pages.
Jinek et al., "A Programmable Dual-RNA-Guided DNA Endonuclease in Adaptive Bacterial Immunity", Science Aug. 17, 2012; 337(6096): 816-21. Epub Jun. 28, 2012.
Konermann, S. et al., "Transcriptome Engineering with RNA-Targeting Type VI-D CRISPR Effectors," Cell, Apr. 19, 2018, vol. 173, Issue 3, pp. 665-676, including Methods and Supplemental Figures, 27 total pages, doi: 10.1016.j.cell.2018.02.033.
Little, E. C. et al., "The CaSm (LSm1) oncogene promotes transformation, chemoresistance and metastasis of pancreatic cancer cells," Oncogenesis, 5:e182 (2016), 10 pages; doi:10.1038/oncsis.2015.45.
Makarova, et al., "An updated evolutionary classification of CRISPR-Cas systems". Nat Rev Microbiol. (Nov. 2015); 13(11): 722-736, doi: 10.1038/nrmicro3569 (31 total pages).
Marraffini, L. A. & Sontheimer, E. J., "Crispr interference: RNA-directed adaptive immunity in bacteria and archaea," Nature Reviews Genetics, 11:181-190 (2010).
NCBI Reference Sequence NZ_DS499551.1, Apr. 7, 2017; [Eubacterium] siraeum DSM 15702 Scfld_03_43, whole genome shotgun sequence, 217 pages.
Ngo, J.T., et al., "Computational Complexity, Protein Structure Prediction, and the Levinthal Paradox," The Protein Folding Problem and Tertiary Structure Prediction, Merz et al., (ed.), Birkhauser, Boston, MA, 1994, pp. 491-495.
Protein Expression Handbook, ThermoFisher Scientific, Inc., 2015, 118 pages.
Schumacher, M. A. et al., "Structural basis for cooperative DNA binding by two dimers of the multidrug-binding protein QacR," The EMBO Journal, 21(5):1210-1218 (2002).
Shen, B. et al., "Efficient genome modification by CRISPR-Cas9 nickase with minimal off-target effects," Nature Methods, 11(4):399-402 (2014), including Online Methods, 2 pages.
Shmakov, S. et al. (2015). "Discovery and Functional Characterization of Diverse Class 2 CRISPR-Cas Systems," Mol. Cell. 60:385-397. epub doi 10.1016/j.,olcel.2015.10.008, pp. 1-23 provided.
Shmakov, S et al., "Diversity and evolution of class 2 CRISPR-Cas systems," Nat Rev Microbiol 2017, vol. 15, No. 3, pp. 169-182, doi: 10.1038/nrmicro.2016.184.
Wegmann, U. et al., "Complete genome of a new Firmicutes species belonging to the dominant human colonic microbiota ('Ruminococcus bicirculans') reveals two chromosomes and a selective capacity to utilize plant glucans," Environmental Microbiology, 16(9):2879-2890 (2014).
Yan, W. X. et al., "Cas13d Is a Compact RNA-Targeting Type VI CRISPR Effector Positively Modulated by a WYL-Domain-Containing Accessory Protein," Molecular Cell 70, Apr. 19, 2018, 1-13: e1-e5.
Yang, H et al., "One-Step Generation of Mice Carrying Reporter and Conditional Alleles by CRISPR/Cas-Mediated Genome Engineering," Cell, 154:1370-1379 (2013).

SEQUENCE LISTING

```
<160> NUMBER OF SEQ ID NOS: 165

<210> SEQ ID NO 1
<211> LENGTH: 2862
<212> TYPE: DNA
<213> ORGANISM: Artificial Sequence
<220> FEATURE:
<223> OTHER INFORMATION: Synthetic: CasM DNA sequence from Eubacterium
      siraeum, modified for expression in Escherichia coli

<400> SEQUENCE: 1

atggggaaga agattcatgc gcgcgattta cgcgaacaac gcaaaacgga tcgcactgag      60

aaatttgcgg atcaaaacaa aaagcgcgag gccgagcgcg ctgttcctaa aaaggacgcc     120

gcagtctcgg ttaagagtgt atcgtccgtg tcttcaaaaa aggacaacgt cactaaaagc     180

atggcgaagg ccgctggtgt aaagtctgta tttgccgtag gtaacacggt atacatgaca     240

tcgttcggcc gcggcaacga cgctgtactg gagcaaaaga tcgtggatac atcccatgaa     300

ccacttaaca tcgacgatcc agcatatcaa ttgaacgttg ttacaatgaa cggttattcc     360

gtcaccggcc accgcggaga gaccgtttct gcagtaacgg acaacccttt acgccgtttc     420

aatggccgca aaaaggacga acctgagcaa tcggttccaa ctgacatgct ttgtcttaaa     480

cctacgttag agaagaagtt cttcggcaag gagtttgacg acaacatcca catccagttg     540

atttataaca ttttagatat tgagaagatc ttagcagttt attcaaccaa tgcaatttac     600

gctttgaaca acatgagcgc cgacgaaaac atcgaaaatt cggatttttt catgaaacgt     660

accacagacg aaacctttga cgactttgaa aagaaaaaag aatctactaa ctcacgcgaa     720

aaggcagact tcgacgcgtt tgaaaaattt attggaaact accgtcttgc gtacttcgcg     780

gatgctttct atgtcaataa aaaaaaccct aagggaaagg ctaagaatgt tctgcgtgaa     840

gataaggagc tttactcggt cttaactctt atcggtaaac tgcgccattg gtgcgtacat     900

agcgaggagg gacgtgcaga gttctggctg tataagttag acgagttaaa agacgatttt     960

aaaaatgtat tggacgtcgt gtacaaccgt cccgtggaag aaatcaacaa ccgctttatt    1020
```

```
gagaataaca aagttaatat ccaaattctg ggagcgtgt acaaaaacac agacatcgct   1080

gaacttgtgc gctcgtatta cgaattcttg attaccaaaa aatacaaaaa tatgggcttt   1140

tctattaaga aacttcgtga atcaatgttg gaaggtaaag gttacgcaga caaggaatat   1200

gactccgtcc gtaataagtt gtaccaaatg acagacttca ttctgtatac gggatacatc   1260

aacgaagact cagatcgtgc agacgatctg gtcaataccc tgcgctcttc tctgaaggag   1320

gatgataaga cgactgtata ctgtaaagag gccgactatt tgtggaagaa gtatcgcgaa   1380

tcgatccgtg aggttgcgga tgcactggat ggtgataaca tcaagaagtt gagtaagtcg   1440

aacatcgaga tccaagagga taaacttcgt aagtgcttca ttagttatgc agactccgtt   1500

tcagagttca caaaactgat ctacctgctg acccgcttcc tgagcggaaa ggaaattaat   1560

gacctggtaa ctactcttat caataaattt gataacatcc gctcttttct tgagattatg   1620

gacgagctgg gattagatcg tacgtttacc gccgaatatt cgttctttga aggctcaacg   1680

aaatacttgg cggagcttgt agagttaaat tcttttgtaa aatcttgctc ttttgatatt   1740

aacgccaagc gcacaatgta tcgcgacgcc ttagacattt tggggattga atcggacaag   1800

actgaagagg atattgaaaa gatgattgat aatatccttc agattgatgc gaatggcgac   1860

aagaaactta agaaaaataa tggcctgcgt aacttcattg caagtaacgt tattgacagt   1920

aaccgtttca aatacttagt acgctacggg aaccctaaaa aaatccgcga aacagctaag   1980

tgcaaaccgg ctgttcgctt cgtgttgaac gagatccccg acgcacagat cgagcgctat   2040

tacgaggcat gctgtccaaa gaacacagcc ctttgctcag cgaacaagcg tcgcgagaag   2100

ttagctgaca tgattgccga gattaagttc gagaacttct ctgacgctgg aaattatcaa   2160

aaagctaacg ttacctcgcg cacatcagag gcggaaatca aacgtaaaaa ccaggcgatt   2220

attcgcttgt atttgacggt catgtacatt atgctgaaga acttagtcaa cgtgaacgct   2280

cgttacgtga tcgcatttca ctgtgtggag cgtgatacta agttgtatgc cgaatctgga   2340

ttggaggttg ggaacattga aaagaataaa actaatctta ccatggccgt aatgggagtt   2400

aagcttgaga atggtatcat caagactgag tttgataaat cttttgcgga aaacgcagca   2460

aatcgttacc ttcgtaacgc acgctggtat aaacttatct tagacaattt aaaaaagtca   2520

gaacgcgcgg tagtaaacga atttcgtaac acagtatgtc atttaaacgc catccgcaac   2580

attaacatta acatcaagga gattaaggag gtagaaaatt attttgcctt gtaccactat   2640

ttgatccaaa aacatttgga gaaccgtttc gccgacaaaa aagttgaacg cgatacgggt   2700

gactttattt ccaaattgga agagcataag acgtactgta aggactttgt aaaagcatac   2760

tgtacgccgt ttggatataa tttagtacgt tataagaact tgactattga cggacttttc   2820

gataaaaact accctgggaa ggatgattct gatgaacaga aa                        2862
```

<210> SEQ ID NO 2
<211> LENGTH: 2757
<212> TYPE: DNA
<213> ORGANISM: Artificial Sequence
<220> FEATURE:
<223> OTHER INFORMATION: Synthetic: CasM DNA sequence from Ruminococcus sp., isolate 2789STDY5834971, modified for expression in Escherichia coli

<400> SEQUENCE: 2

```
atggcaaaga aaaataaaat gaagccgcgc gagttacgcg aggcccagaa gaaagctcgt     60

caattaaaag cggccgagat caacaataac gcagccccag caattgcagc aatgccagcg    120

gccgaagtga ttgcgccggc tgcagagaag aagaagagct cagtcaaggc agcagggatg    180
```

```
aagagcatcc ttgttagcga gaacaagatg tacattacat cttttgggaa aggaaactca    240
gcggtattgg aatacgaggt tgataacaac gattacaatc agacgcagtt atcatccaag    300
gacaacagca acatccaact gggtggcgtc aatgaggtca acattacttt ttcaagcaag    360
cacggctttg aaagtggcgt ggaaattaac acttctaatc cgacacaccg ttcaggagaa    420
agttcccctg ttcgtggcga tatgttaggg cttaagtcag aactggaaaa gcgcttcttc    480
ggtaagacct tcgatgataa cattcacatt caacttatct acaacatcct tgatattgaa    540
aagatccttg cagtgtacgt tacgaacatc gtctacgctc tgaataatat gttaggtgtc    600
aaggggtctg aatcccatga tgacttcatt ggttacttgt cgacaaataa tatctacgat    660
gtcttcattg atccagataa tagttccttg agcgacgaca agaaagcaaa cgtacgtaaa    720
agtcttagta aatttaatgc gttgttaaaa actaaacgtc tgggctattt cggattagag    780
gaaccaaaga ccaaagacaa ccgtgtaagc caggcgtata agaagcgtgt gtatcacatg    840
cttgccattg tcgggcaaat tcgtcaatgc gtatttcatg acaaaagcgg tgccaaacgt    900
tttgatcttt attctttcat taacaatatt gatccagagt accgtgacac gcttgattat    960
ttggtagaag agcgcctgaa gtcaattaac aaagacttta ttgaagacaa caaagtaaac   1020
atcagccttt taattgatat gatgaagggt tacgaggcgg acgatatcat tcgcctgtac   1080
tacgacttca ttgtattaaa atctcagaaa aacctggggt tctctattaa gaagttacgt   1140
gagaagatgc tggacgagta tggtttccgt ttcaaagata aacaatacga ttctgttcgt   1200
tccaagatgt ataaattgat ggattttttg ctttttttgta actattaccg caatgatatt   1260
gctgcggggg aatctctggt acgtaaactg cgtttttcga tgacagacga tgaaaaggag   1320
ggcatttatg cggacgaagc cgctaaattg tgggggaaat ttcgtaatga ctttgagaat   1380
atcgcggacc acatgaatgg cgatgttatt aaggagttgg gaaaagctga catggatttc   1440
gacgaaaaga tcttggattc tgagaagaaa aacgcttccg acctgctgta tttttcaaaa   1500
atgatttata tgctgacata tttcttagat gggaaagaga ttaacgactt gctgacgact   1560
ctgatttcaa aatttgacaa tatcaaagag tttttgaaaa ttatgaagtc ttctgcagtc   1620
gatgtagagt gtgaacttac agctgggtac aagctgttca atgacagtca acgtatcacc   1680
aacgaattat ttatcgttaa aaatattgcc tccatgcgta agccagccgc aagtgccaag   1740
ctgacaatgt tccgcgatgc actgacgatt ctgggaattg acgataagat tacggatgac   1800
cgtatttcag gaatcttgaa gcttaaagag aagggcaagg gcattcatgg acttcgtaac   1860
ttcatcacca acaacgtgat cgagagtagc cgttttgttt accttatcaa atatgcgaat   1920
gcacaaaaga tccgcgaagt ggcgaaaaac gagaaggtcg taatgttcgt attaggtgga   1980
attccagata cgcaaattga gcgctattat aagtcatgtg tagagttccc ggatatgaac   2040
agctcattag gagtgaaacg ttcagagctg gcgcgcatga ttaagaatat cagttttgac   2100
gatttcaaga acgtgaaaca acaagcgaaa ggacgcgaaa acgtcgcaaa agagcgcgcc   2160
aaggccgtca ttgggttgta cttaacggta atgtacttac ttgtcaaaaa cctggttaat   2220
gttaacgcgc gctatgtcat cgccatccat tgtctggaac gtgatttcgg tctttataag   2280
gagattattc ctgaactggc gtcaaagaac ctgaaaaacg attaccgcat tttatctcag   2340
actctgtgtg aactgtgtga taagtctccc aatttgttct tgaagaagaa tgagcgcctg   2400
cgtaaatgtg ttgaagtcga catcaataat gcagacagct cgatgactcg taaatatcgc   2460
aactgtatcg ctcacttgac tgtcgtccgt gaattaaaag agtacattgg tgatatttgt   2520
```

```
accgttgact cttatttcag tatttaccat tatgtaatgc aacgctgtat cacaaagcgt   2580

gaaaacgata ccaagcagga ggaaaaaatc aaatacgaag acgatttgct taagaatcac   2640

ggctatacaa aagacttcgt aaaagcattg aactcacctt tcggatacaa catcccgcgt   2700

tttaaaaatc tttcaattga gcaacttttt gatcgtaacg agtatcttac ggaaaaa      2757
```

<210> SEQ ID NO 3
<211> LENGTH: 2754
<212> TYPE: DNA
<213> ORGANISM: Artificial Sequence
<220> FEATURE:
<223> OTHER INFORMATION: Synthetic: CasM DNA sequence from Ruminococcus bicirculans, modified for expression in Escherichia coli

<400> SEQUENCE: 3

```
atggcgaaaa agaataaaat gaaacctcgc gaattgcgcg aggcacaaaa gaaagcgcgt     60

caattgaaag cagcggagat caacaataac gcagttcccg ccatcgctgc tatgccggcc    120

gctgaggccg ctgcccccgc agcggagaaa aagaagtcat cggtcaaagc ggcagggatg    180

aagtcaatct tagtctccga gaacaagatg tacatcacca gttttggaaa aggtaactcg    240

gcggtcttgg agtacgaggt agacaataat gactataaca aaactcagtt atcctcgaag    300

gataatagca atattgagtt gtgtgatgtg gggaaggtta atatcacgtt cagctctcgt    360

cgtggctttg aatcgggagt cgagattaat acgagtaacc caacccaccg ctccggagag    420

tcgtcgtcag tccgtgggga tatgctgggc ttgaaaagcg agttggaaaa acgttttttt    480

ggcaagaatt tcgacgataa tatccatatt caacttattt acaacatctt ggacatcgag    540

aagatccttg ctgtgtatgt tacgaacatt gtttacgccc tgaataatat gcttggcgaa    600

ggggatgaat ctaactacga ctttatgggg tatttgagca cattcaacac atataaagtc    660

tttacgaatc cgaatggttc aacgctgtct gatgacaaga aagagaacat tcgcaaatca    720

ttatcgaaat ttaatgcttt gttgaaaacg aagcgcttag gttatttcgg gttagaggag    780

cctaaaacaa aggacacgcg cgcatcggag gcttacaaga aacgcgtata tcacatgctg    840

gctatcgttg ggcaaatccg tcagtgcgta tttcatgata agagcggggc caagcgtttc    900

gacctttatt catttattaa taacattgat ccagaatatc gtgaaactct ggattacttg    960

gtcgacgaac gctttgacag tattaataaa ggatttatcc aaggtaataa agtaaacatc   1020

agcttactga tcgatatgat gaagggttac gaggcggatg acatcatccg tctttactac   1080

gatttcattg tccttaaatc gcagaaaaac ctgggcttca gtatcaaaaa gttacgcgaa   1140

aagatgttgg atgagtatgg ctttcgtttc aaagataagc aatacgatag cgttcgcagc   1200

aagatgtata aattaatgga tttcttatta ttctgcaatt actaccgcaa cgacattgca   1260

gcgggcgaat ctcttgtccg caagctgcgc tttagtatga ccgatgatga gaaggagggg   1320

atctacgcag atgaggctgc aaaactgtgg ggcaaatttc gtaacgactt tgagaacatc   1380

gccgaccaca tgaacggtga cgtcattaaa gagttgggga aagcagatat ggactttgat   1440

gaaaagatcc ttgattccga aaagaaaaat gcgtcggatc tgttgtattt tagtaaaatg   1500

atttacatgc ttacgtattt tctggacgga aaagaaatca acgacttact tactacatta   1560

atttcgaagt ttgataacat taaggagttt ttaaaaatca tgaaaagcag tgcagttgac   1620

gttgaatgtg aacttacagc aggttataaa ttatttaatg acagccaacg catcacaaat   1680

gaattgttca tcgtgaagaa tatcgcgtct atgcgcaaac ccgctgcttc ggcgaagctg   1740

acaatgtttc gcgacgcttt aacaatcctg ggatcgacg ataagatcac tgatgatcgt   1800
```

```
atttccgaaa tcttaaaatt aaaggagaaa ggaaaaggta tccatggctt acgcaatttt   1860

atcactaata atgtaattga aagtagccgc tttgtgtacc ttatcaagta cgcaaacgca   1920

caaaaaatcc gtgaggtcgc caaaaacgag aaagtcgtta tgtttgtcct gggtgggatt   1980

cccgacacac aaatcgaacg ctactacaaa agttgtgtgg aattcccgga catgaactcg   2040

agtctgggtg ttaagcgtag tgaattggcc cgtatgatca agaatatcag ttttgacgat   2100

ttcaagaatg tgaaacagca ggccaaaggg cgtgagaacg tcgcaaagga acgcgctaaa   2160

gctgtgatcg gtttatatct gaccgtgatg tacttgttgg tgaagaattt ggtgaacgtt   2220

aacgcgcgtt acgttattgc cattcattgc ttagaacgcg actttggact gtataaggag   2280

attattcctg aattagccag caaaaacctg aaaaacgatt atcgtatcct gagccaaacc   2340

ctttgcgaac tttgtgataa aagcccaaac ttgtttttaa aaaaaaatga gcgtttacgc   2400

aaatgcgtgg aggttgatat taataatgct gattcctcga tgacccgcaa ataccgtaac   2460

tgtattgccc atttgacagt agtccgcgag ttgaaggagt acattggaga tatttgcact   2520

gtggacagtt acttcagtat ttaccattat gtaatgcaac gctgcattac aaagcgcgag   2580

aacgacacta agcaggagga aaaaatcaag tacgaggatg atctgctgaa aaatcatggc   2640

tacaccaagg actttgttaa ggccttgaac tctccgttcg ggtataacat tccccgcttc   2700

aaaaatctga gtattgagca gttgtttgat cgtaatgagt atcttacaga gaag         2754
```

<210> SEQ ID NO 4
<211> LENGTH: 2766
<212> TYPE: DNA
<213> ORGANISM: Artificial Sequence
<220> FEATURE:
<223> OTHER INFORMATION: Synthetic: CasM DNA sequence from Ruminococcus sp., isolate 2789STDY5608892, modified for expression in Escherichia coli

<400> SEQUENCE: 4

```
atggccaaaa agaacaaaat gaagccccgc gaacttcgtg aggcccaaaa gaaagctcgc     60

caattaaaag cagccgagat caacaacaac gcagctccgg ccattgcagc aatgcctgct    120

gcagaagtga ttgcgccagt cgccgaaaag aagaaatcca gtgttaaagc tgcaggtatg    180

aagtctattt tggtttcgga gaacaagatg tatatcacaa gcttcgggaa aggtaatagt    240

gctgttcttg agtatgaagt agataacaac gactataata aaacccaact tagttctaag    300

gataactcta atattgaatt gggggacgtt aatgaggtaa atatcacgtt ctcatcgaag    360

catggctttg gttccggggt ggaaatcaat acctctaatc ccactcatcg ttcgggtgaa    420

tcctccccag tccgtggtga tatgttgggg cttaaatcgg agttagagaa acgcttcttt    480

ggtaaaacct ttgatgataa tattcatatt caattgattt ataacatttt ggatatcgag    540

aagattttgg ctgtatacgt tacaaatatc gtgtatgcac ttaataatat gttgggtatt    600

aaagattctg aatcgtatga tgatttcatg ggctatttga gcgcacgcaa tacctatgaa    660

gtcttcactc atcctgataa aagcaactta agtgataagg ttaaagggaa cattaagaag    720

agtttatcaa agttcaatga cttgttaaag accaagcgcc ttgggtactt cggtcttgag    780

gaaccgaaga ccaaagatac ccgcgcttct gaggcgtata agaagcgcgt ctaccacatg    840

cttgcaatcg taggtcaaat ccgtcagtgt gtgtttcacg acaaatcagg agcgaaacgt    900

ttcgatttgt actccttcat taataacatc gacccagagt atcgcgacac tcttgactac    960

ttagttgagg aacgtttgaa gtcaattaat aaggatttca ttgagggaaa taaagtaaac   1020

attagccttc ttatcgacat gatgaaggga tacgaggccg acgatattat tcgcctgtat   1080
```

tatgatttta ttgtgttgaa atcacaaaag aatttggggt ttagcattaa aaaattgcgc 1140
gagaagatgt tggaggagta tgggtttcgc tttaaggata aacagtatga ctcagtccgc 1200
tcaaaaatgt ataagttaat ggacttcctg ctttttgta attattaccg taatgacgtc 1260
gccgccggtg aagccctggt tcgtaaattg cgcttctcaa tgactgacga tgagaaggag 1320
ggaatttatg ctgatgaggc tgcgaagtta tgggggaagt ttcgtaacga cttcgaaaat 1380
atcgccgacc acatgaatgg agatgttatc aaggagcttg gcaaggcgga tatggatttt 1440
gatgaaaaga tccttgacag cgaaaagaag aatgcctccg atttgctgta cttttcgaaa 1500
atgatctaca tgcttaccta tttcctggac ggcaaagaga tcaacgatct tttgaccacc 1560
cttatttcta agttcgataa tatcaaagag tttttgaaaa tcatgaagag ttcggcggtc 1620
gatgttgaat gtgaattaac ggccgggtat aaattattta acgactccca acgtattacg 1680
aatgaattat ttatcgttaa aaacatcgct tctatgcgca aaccagcagc gtccgccaaa 1740
cttacgatgt ttcgtgacgc ccttaccatt ttgggaatcg acgataacat cacagatgat 1800
cgcatttctg agatcttgaa gcttaaggaa aagggcaagg gcatccatgg tttacgtaat 1860
tttatcacaa acaacgtgat cgagtcgagt cgttttgtct atctgatcaa gtatgcaaac 1920
gcgcagaaaa ttcgtgaagt ggcaaaaaat gagaaagtag taatgtttgt tttgggtggt 1980
atccctgaca cccagattga gcgctactac aagtcgtgtg tagaattccc tgacatgaat 2040
agcagcttag aagctaaacg ctctgaactt gcgcgcatga ttaaaaatat ctcgttcgat 2100
gacttcaaga acgttaaaca acaggccaaa ggccgtgaga atgttgctaa agaacgcgcg 2160
aaggctgtaa ttggattata ccttactgta atgtatctgt tagtgaaaaa ccttgtgaac 2220
gtcaacgccc gctacgtcat tgcgatccat tgtttggagc gtgactttgg gttatacaag 2280
gagatcatcc cagaactggc ctcaaaaaac ttaaaaaatg actaccgtat tttgagtcag 2340
accttgtgcg aactgtgcga tgaccgtaac gaatcctcga acttgttctt gaagaagaat 2400
aaacgtttgc gcaaatgtgt cgaggtagat atcaacaatg cagacagctc tatgacgcgt 2460
aagtaccgta actgtattgc tcacttaacc gtagttcgtg aacttaaaga atacattgga 2520
gacattcgta cagttgatag ctacttcagt atttatcact atgtaatgca gcgctgtatc 2580
actaagcgtg ggatgatac gaagcaagaa gagaaaatta agtacgaaga tgacctgttg 2640
aaaaaccacg ggtacactaa ggactttgtc aaagctctga attccccgtt cgggtacaat 2700
atccctcgtt ttaagaatct gagtattgaa cagttatttg accgcaacga ataccttacg 2760
gagaag 2766

<210> SEQ ID NO 5
<211> LENGTH: 2766
<212> TYPE: DNA
<213> ORGANISM: Artificial Sequence
<220> FEATURE:
<223> OTHER INFORMATION: Synthetic: CasM DNA sequence from Ruminococcus sp. CAG:57, modified for expression in Escherichia coli

<400> SEQUENCE: 5
atggctaaaa agaataaaat gaaacctcgc gagttgcgcg aagcccagaa aaaagctcgc 60
cagttaaagg cagcggaaat taataataat gcagcacccg ccatcgcagc gatgcccgca 120
gctgaagtaa tcgcccctgt tgctgaaaag aagaaatcca gcgtgaaagc ggcaggtatg 180
aagtccattt tggtcagcga gaataaaatg tacattacgt cgttcgggaa aggcaactcc 240
gctgtccttg agtatgaagt agacaacaat gactacaaca aaactcaact gtcaagcaaa 300

```
gacaacagta acatcgaact gggagacgtg aatgaggtga atatcacgtt ttcatcaaaa    360
catgggttcg gaagcggtgt ggaaatcaat acaagcaatc cgacccatcg ctcaggggag    420
tcgtcgcctg ttcgtggaga catgttgggt cttaagtccg agcttgagaa gcgtttttttc   480
ggcaagacat tcgatgacaa catccatatt cagttgattt ataatatttt agatatcgaa    540
aagattttag ccgtatatgt gaccaacatt gtttatgcgt taaataacat gttagggatt    600
aaggactcgg aatcgtatga tgatttcatg ggttacttaa gcgctcgtaa tacttatgaa    660
gtcttcactc atcccgataa gagcaatttg agtgataaag tcaagggcaa catcaaaaag    720
tctttgtcga aattcaatga cctgttgaaa actaagcgct tgggttactt cgggttggaa    780
gaaccgaaga ccaaagatac gcgtgccagt gaagcttaca aaaaacgcgt ctatcacatg    840
ctggcaatcg tgggccaaat ccgtcagtgt gtttttcatg acaaaagtgg agctaaacgc    900
tttgatttgt acagcttcat taataacatt gatcctgaat atcgcgacac tttggattat    960
ttagtagaag aacgccttaa atctattaat aaagacttta ttgaagggaa taaggtgaac   1020
atcagcttac tgatcgacat gatgaagggt tacgaggctg acgacattat ccgcttgtat   1080
tatgatttca ttgtattaaa atctcagaaa aacctgggat tcagtattaa gaaattacgc   1140
gagaaaatgc ttgaggagta cggattccgt ttcaaggata aacaatatga ttctgtgcgt   1200
agtaaaatgt acaaacttat ggacttttta ttgttctgta actattaccg taatgacgtt   1260
gccgcaggcg aagccttggt acgtaagtta cgcttcagca tgacagatga cgaaaaggag   1320
ggcatttacg cggatgaagc agcgaagctg tggggtaaat tccgcaacga ttttgaaaat   1380
attgctgacc acatgaatgg tgatgttatc aaagaactgg gaaaagccga tatggatttc   1440
gacgagaaga tcttggacag tgaaaaaaag aatgccagcg atcttttata tttctccaaa   1500
atgatctaca tgcttactta tttccttgac gggaaagaga ttaatgatct gctgaccacg   1560
ctgattagta agttcgacaa cattaaggag tttttaaaga tcatgaaatc gtccgctgtg   1620
gacgtagaat gcgagttgac ggcaggttac aaactgttca acgatagtca acgcatcacc   1680
aatgaacttt tcatcgtcaa aaacattgcc tccatgcgca agcccgcggc tagcgctaaa   1740
ttaacgatgt tccgtgacgc cttgacgatt ttaggcatcg acgacaacat cacggacgat   1800
cgcatttcgg aaatccttaa acttaaggaa aaggggaaag gtatccatgg tctgcgcaat   1860
tttatcacta acaatgtaat tgaatcatca cgcttcgttt acttaatcaa atacgcgaat   1920
gctcaaaaga ttcgtgaagt agccaaggat gaaaaggttg tcatgtttgt cctgggcggg   1980
attccagaca cccaaattga acgttattac aagtcttgtg tggaattccc cgatatgaat   2040
agctccttgg aggccaaacg ctctgagtta gcccgcatga ttaagaacat ttccttcgac   2100
gattttaaaa atgtcaaaca acaggcaaaa ggccgcgaga atgtagccaa ggagcgtgcc   2160
aaggcagtaa tcggattgta tcttactgtc atgtatttgc ttgttaagaa tcttgttaac   2220
gttaacgcgc gctatgtaat cgctattcat tgcttagaac gcgactttgg cctttataag   2280
gagattattc ccgagcttgc atccaaaaat cttaagaacg actaccgtat tttgtcacaa   2340
accttatgcg agttatgcga tgaccgcaac gagtcttcca atctgtttct taaaaaaaac   2400
aaacgtcttc gcaaatgcgt ggaagtggac atcaacaacg ccgacagtag tatgactcgt   2460
aagtatcgta actgtattgc gcacttgact gtagtgcgcg agttgaagga gtatattggg   2520
gatatccgca ccgtggattc atacttcagt atctaccact acgtcatgca acgttgcatc   2580
acgaaacgtg gagacgacac caaacaagag gaaaagatta agtatgaaga cgaccttttg   2640
```

aagaaccacg gctacaccaa agattttgtt aaggctttga atagtccctt cgggtataac 2700
attccccgtt tcaaaaactt gagcattgaa cagctgttcg accgcaatga atacttgaca 2760
gaaaag 2766

<210> SEQ ID NO 6
<211> LENGTH: 2799
<212> TYPE: DNA
<213> ORGANISM: Artificial Sequence
<220> FEATURE:
<223> OTHER INFORMATION: Synthetic: CasM DNA sequence from Ruminococcus flavefaciens FD-1, modified for expression in Escherichia coli

<400> SEQUENCE: 6
atgaaaaaaa aaatgtctct gcgtgaaaag cgtgaggcgg agaagcaagc aaagaaagcc 60
gcgtattccg ctgctagtaa gaatactgac agcaaacccg cagagaagaa ggcggaaaca 120
cccaagcccg cagaaattat ctcggataac tcgcgcaata aaactgctgt taaagccgcc 180
ggcttgaaat caactatcat cagtggggat aaattataca tgacgtcatt tggtaaggga 240
aatgccgccg tgatcgaaca gaagattgat attaatgact actctttttc tgccatgaag 300 gatacccc ta gcttagaggt tgataaggcc gagagcaagg agatctcttt ttcctctcac 360
catcccttcg taaagaatga caaattgacc acttacaacc ccctgtacgg cggcaaggac 420
aatccggaaa agccagtggg acgtgacatg ctggggttga aagacaaatt ggaggaacgt 480
tattttggat gcactttcaa tgataatctg cacatccaga tcatctacaa tatcttagac 540
atcgagaaaa tcctggctgt tcatagcgca aatatcacca ccgcactgga tcacatggta 600
gacgaggatg acgaaaaata cttgaactct gactacattg gttacatgaa caccattaat 660
acgtacgacg tatttatgga cccgtcaaag aactcttctt tgtcgccgaa agatcgcaag 720
aacatcgaca actcccgcgc caagtttgag aagttattgt caacgaagcg tttaggatac 780
tttggttttg actatgatgc gaatggcaag gataagaaga agaacgagga gattaagaag 840
cgtctgtacc atcttaccgc gtttgcgggt cagcttcgtc agtggtcctt tcacagcgct 900
ggcaattatc cacgtacatg gctgtacaaa cttgatagtt tggacaaaga ataccttgat 960
acacttgatc actatttcga taaacgcttc aatgacatta atgacgattt cgttacaaag 1020
aacgcgacga atttatatat tcttaaggaa gtttttccgg aggcgaactt taaagatatc 1080
gcagatcttt attacgactt catcgtaatc aaatcccaca aaaatatggg tttctctatt 1140
aaaaaattgc gtgaaaaaat gttagagtgt gatggtgcgg atcgcatcaa agaacaagat 1200
atggacagcg tacgttcaaa gctgtataaa cttattgact tttgcatttt caaatattac 1260
catgagttcc cggaactgtc tgagaagaat gttgatatct tacgtgctgc cgtctccgac 1320
acgaagaaag ataatcttta tagcgacgag gccgcgcgtc tgtggagtat cttcaaggag 1380
aagttcctgg gtttctgtga caaaattgtc gtatgggtga ctggtgaaca tgaaaaagat 1440
atcacttcgg taatcgataa agacgcgtat cgcaaccgta gcaatgtcag ttatttttcg 1500
aaactgatgt atgcgatgtg ctttttcctt gatggtaagg aaattaacga tttattgaca 1560
accctgatta ataaattcga taatatcgca aatcagatca aaacggcaaa ggaacttggt 1620
attaacacag ccttcgtaaa gaattatgac tttttttaacc actcggagaa gtatgtcgac 1680
gaactgaata ttgtgaaaaa catcgctcgc atgaaaaagc ctagtagcaa cgctaaaaaa 1740
gctatgtacc acgatgcatt gacgatcttg ggattcctg aagatatgga tgagaaagcc 1800
ttagatgagg agctggactt gattctggaa aaaaagaccg atccagtaac cgggaagcct 1860

```
ttgaaaggga aaaacccgct tcgcaacttt atcgctaaca atgtaatcga aaactctcgc   1920

ttcatctatt tgattaagtt ttgcaatccg gaaaacgtac gtaagattgt taataacacc   1980

aaagttacag agtttgtctt gaagcgcatc ccagatgcgc agatcgaacg ctattacaag   2040

tcttgtactg actcggaaat gaaccccca acggaaaaga aaattacgga gttagccggg   2100

aaacttaagg acatgaattt tggaaacttc cgcaacgtgc gtcaaagtgc aaaggagaac   2160

atggaaaagg agcgttttaa agcagtgatt ggtttgtacc ttaccgtagt ctatcgcgtt   2220

gtaaaaaatc tggttgatgt taattcccgc tacatcatgg cgtttcattc gctggagcgc   2280

gacagtcagt tatataatgt ctcggtcgac aacgactacc tggccttaac cgatacgtta   2340

gtaaaagagg gagataattc ccgttcccgt tacttagcgg ggaataaacg cttgcgtgac   2400

tgtgtgaaac aggatattga taatgctaag aaatggttcg tcagtgataa gtacaactct   2460

atcacaaaat accgtaataa cgtagcacat ttaactgcag tacgtaattg cgccgaattt   2520

atcggtgaca ttactaagat cgactcgtat tttgcattat atcactacct tattcagcgt   2580

caactggcta agggtttgga tcacgagcgt tcgggatttg accgcaacta tccgcagtat   2640

gctccacttt ttaagtggca tacttacgtg aaagacgtgg ttaaagcctt aaatgctccc   2700

ttcggataca acatcccacg ctttaagaat ttgtctattg atgctttatt tgatcgcaat   2760

gagatcaaaa agaatgacgg agagaagaag tctgatgat                          2799
```

<210> SEQ ID NO 7
<211> LENGTH: 2832
<212> TYPE: DNA
<213> ORGANISM: Artificial Sequence
<220> FEATURE:
<223> OTHER INFORMATION: Synthetic: CasM DNA sequence from Ruminococcus albus strain KH2T6, modified for expression in Escherichia coli

<400> SEQUENCE: 7

```
atggcaaaga aatccaaggg gatgtcgtta cgtgagaaac gcgaattgga aaaacagaag     60

cgcattcaaa aggctgctgt taactccgtc aacgacactc ctgaaaagac agaagaggct    120

aacgtggtat cagtgaatgt gcgcacttct gccgaaaaca agcactccaa aaagtcagcg    180

gccaaggctt tggggctgaa atctggcttg gtaattggag atgagctgta tctgacatcg    240

ttcggtcgcg gcaacgaagc caagttggaa aagaaaatct caggtgatac ggttgagaaa    300

ttaggtatcg gcgcttttga ggtagctgag cgtgacgagt cgacgctgac gcttgaaagt    360

ggacgcatta aggacaagac ggcgcgtcca aaggacccac gtcacattac ggttgataca    420

caaggtaaat tcaaagagga tatgctgggt attcgcagcg tgttagaaaa aaagattttt    480

gggaagacct ttgacgataa catccatgta caactggcat acaacattct tgatgtcgag    540

aaaattatgg cacagtatgt cagtgatatt gtttatatgc tgcacaacac ggacaagacg    600

gagcgtaatg ataacctgat gggttacatg tcaatccgca acacatacaa gacgttctgt    660

gatacttcaa acttgcctga tgatactaaa caaaaagttg aaaaccaaaa acgtgaattt    720

gataaaatca ttaagagtgg ccgtctgggc tatttcgggg aagcttttat ggtaaatagc    780

ggcaactcta caaaactgcg cccggaaaaa gagatctatc atatttttgc gctgatggcg    840

tcgttacgcc aaagttactt tcatggttat gtcaaagata ccgattacca agggaccact    900

tgggcgtata cactggagga caaactgaag gggccctctc acgagttccg cgagacgatt    960

gacaaaatct ttgacgaggg attttccaaa atctcgaaag atttcggcaa aatgaacaag   1020

gtgaacctgc aaattttgga gcaaatgatc ggggagttgt acgggtccat tgagcgccaa   1080
```

```
aacttaactt gtgactacta cgatttcatc cagttaaaga aacataagta tcttggcttt   1140

agcattaaac gtttacgcga gacgatgctt gagactactc ccgcagagtg ctataaggca   1200

gagtgctaca actctgagcg ccagaaactg tacaagttga tcgacttttt aatctacgac   1260

ctttattaca atcgtaagcc cgcacgtatc gaagagatcg tcgataagct gcgtgaatct   1320

gtgaatgatg aagaaaaaga gtctatttac tcagtagagg ctaagtatgt ctatgaaagc   1380

ctttcaaaag tccttgacaa gagcttgaag aatagtgttt ctggggaaac cattaaagac   1440

cttcagaaac gttatgatga tgaaacagct aaccgtattt gggacatctc gcaacattca   1500

atcagtggca acgtcaattg cttctgtaaa ttaatttaca tcatgactct tatgctggac   1560

ggaaaagaaa tcaatgatct gttgacaacg ctggttaaca aattcgataa cattgccagt   1620

ttcattgatg tcatggatga gttaggatta gagcactcat tcactgataa ctataagatg   1680

ttcgctgatt ctaaagctat ttgtctggat ttgcaattta tcaattcatt tgcccgtatg   1740

tcgaagatcg atgacgaaaa gtcgaaacgt caactttttc gtgacgcgct ggttatttta   1800

gatattggta ataaggacga gacatggatt aataactact tagattccga tatctttaag   1860

ctggacaagg aaggtaataa gttaaaggga gcccgccatg attttcgcaa ctttatcgca   1920

aataacgtga ttaagtcttc acgcttcaaa tatttagtga agtattcgag tgcggatggc   1980

atgattaaat taaagacaaa tgagaagctt attgggttcg ttctggataa gttaccagag   2040

acgcaaatcg accgttacta cgagtcttgc gggttagaca atgccgtcgt ggacaaaaaa   2100

gtccgtattg agaagctgag tgggttaatt cgtgatatga agttcgacga tttttctggc   2160

gtaaaaacta gtaacaaagc tggcgacaat gacaagcagg acaaggccaa atatcaggcc   2220

attatttcgt tataccttat ggtgctttac cagatcgtaa agaacatgat ttacgtcaac   2280

tcacgctacg tcattgcttt ccactgttta gaacgcgatt ttgggatgta tggcaaggat   2340

tttggaaaat attaccaggg gtgccgcaag ctgactgatc acttcatcga agagaaatac   2400

atgaaggaag gaaaattggg atgcaacaaa aaagtaggac gctatcttaa aaataatatt   2460

tcctgctgca cggatggact gattaacaca taccgtaacc aggtggatca tttcgcagtg   2520

gttcgcaaaa ttggtaacta tgcggcctat atcaaatcta tcggaagctg gttcgaactt   2580

taccattatg tgattcaacg tattgtgttt gatgagtatc gtttcgcact taacaacaca   2640

gagtccaact ataaaaactc cattatcaaa caccatacgt actgtaaaga tatggtaaag   2700

gcattgaata cgccctttgg ctacgacctg cctcgctaca agaacttgtc gatcggggac   2760

ttgttcgacc gtaacaatta tttaaacaag acgaaggaat cgattgatgc taattcaagc   2820

attgattcac ag                                                       2832
```

<210> SEQ ID NO 8
<211> LENGTH: 2901
<212> TYPE: DNA
<213> ORGANISM: Artificial Sequence
<220> FEATURE:
<223> OTHER INFORMATION: Synthetic: CasM DNA sequence from Ruminococcus flavefaciens strain XPD3002, modified for expression in Escherichia coli

<400> SEQUENCE: 8

```
atgatcgaga aaaaaaaatc ttttgctaag ggcatgggcg ttaagtccac cttggtttca     60

ggttctaagg tatatatgac cactttcgca gagggatccg acgcacgtct ggagaaaatt    120

gtcgaaggag attcgatccg ttcggtgaat gagggggagg cgttctccgc ggagatggcg    180

gacaaaaatg cgggttataa gattggaaac gctaaatttt cccacccgaa aggatacgca    240
```

```
gtggtagcca ataacccccct ttacacaggg cctgtgcaac aggacatgtt gggattgaag    300
gagactttgg aaaagcgcta ttttggtgag tccgcagatg gaaacgataa tatctgtatc    360
caggtaattc acaatatctt ggatattgaa aagatccttg ctgagtacat taccaacgct    420
gcctacgccg tgaataatat ctccggctta gacaaggaca ttattggctt tgggaagttc    480
agtaccgtct atacgtatga cgaatttaag gacccagaac accatcgtgc cgccttcaat    540
aataatgata agttgatcaa tgcaattaaa gcccagtacg acgaatttga taacttcttg    600
gataatcccc gcttaggcta cttcgggcaa gctttcttca gtaaggaggg gcgtaactac    660
attattaatt acggcaatga gtgttacgat atccttgcat tactttcggg gcttcgccac    720
tgggttgtac acaataatga ggaagagtca cgcattagcc gcacgtggtt gtataacctt    780
gataagaacc ttgacaatga atacatctct accctgaact acttatatga tcgcattacg    840
aatgagttaa ccaattcatt ctcaaagaat agtgcagcca acgtcaacta tatcgcagag    900
acgctgggta tcaacccggc ggaattcgcc gagcagtatt tccgcttttc aatcatgaag    960
gaacaaaaga atctgggttt caatattacc aagttacgtg aagtaatgtt ggatcgtaag   1020
gatatgtctg agattcgcaa aaaccataaa gtgtttgaca gcatccgtac gaaggtctac   1080
actatgatgg acttcgttat ctaccgctat tacatcgaag aggatgccaa agtggcagcg   1140
gcgaacaaat cccttccaga caacgagaaa agtctttctg agaaagacat ctttgtaatc   1200
aacttgcgcg gttcctttaa tgatgaccag aaagatgcgt tgtactatga tgaagctaat   1260
cgtatttggc gtaagttgga aaacatcatg cataacatta aggagtttcg tgggaacaag   1320
acacgtgagt ataaaaaaaa ggatgctcca cgtcttccgc gcattttgcc tgcaggacgc   1380
gatgtcagtg ctttcagcaa attaatgtat gcactgacaa tgtttctgga cgggaaggaa   1440
atcaatgatc ttctgactac acttattaac aagtttgata atattcagtc cttcttaaag   1500
gttatgcctt tgattggtgt aaacgcgaaa tttgtcgaag agtatgcctt tttcaaggat   1560
agcgcgaaaa ttgccgacga actgcgtctt attaagagtt tcgctcgtat gggggagcca   1620
atcgctgacg cccgccgcgc tatgtacatc gatgctattc gcatcttagg tacaaacttg   1680
tcatacgatg aacttaaagc tttagcagac accttttcgc tggatgaaaa cggaaacaag   1740
ttgaaaaagg ggaagcatgg aatgcgcaat tttattatca ataacgtgat ctcaaataag   1800
cgtttccact atcttatccg ttatggagat ccggcacacc tgcatgaaat tgccaagaat   1860
gaggccgtgg tgaaattcgt tttagggcgc attgctgata ttcagaagaa acaggggcag   1920
aatggaaaga atcaaatcga ccgttactat gagacgtgta ttggcaaaga caaggggaaa   1980
tcggtttcgg aaaaagttga cgccttgacg aagatcatca cgggcatgaa ctacgaccag   2040
tttgacaaaa aacgctcggt aattgaagat accggacgtg agaatgcgga acgtgagaaa   2100
tttaaaaaga tcatctcgtt gtatctgacc gtaatttatc atattttaaa aaatatcgta   2160
aacatcaacg cacgctatgt gatcgggttc cactgtgtag aacgcgacgc tcaactttat   2220
aaagaaaagg ggtatgatat taacttgaaa aagttagagg agaagggatt ctcatcagtc   2280
accaagttgt gcgcgggtat tgacgaaacg gcaccggaca agcgcaaaga cgttgaaaag   2340
gagatggccg aacgcgccaa ggaaagtatc gactcattag aaagcgcaaa tcccaagctg   2400
tatgccaatt atatcaagta tagcgatgag aagaaggcgg aggagtttac gcgccagatc   2460
aaccgtgaaa aggccaaaac tgcattgaat gcctacttgc gcaatacgaa atggaatgtg   2520
atcatccgtg aggacctgct gcgtatcgat aacaaaaacat gtactttatt tcgcaataaa   2580
```

gcggtacatc ttgaagtggc gcgttacgtt cacgcgtata tcaatgacat tgcagaggtt 2640
aattcctatt tccagctgta tcactacatt atgcaacgca ttattatgaa cgagcgttac 2700
gagaaaagca gcggcaaagt atccgaatac tttgacgcag ttaacgatga gaagaaatat 2760
aacgaccgct tactgaaatt gctgtgtgta ccttttgggt attgcatccc ccgttttaaa 2820
aacctgagta tcgaagctct gtttgaccgc aacgaggccg ccaaatttga taaggaaaag 2880
aaaaaggttt cgggaaatag t 2901

<210> SEQ ID NO 9
<211> LENGTH: 2388
<212> TYPE: DNA
<213> ORGANISM: Artificial Sequence
<220> FEATURE:
<223> OTHER INFORMATION: Synthetic: CasM DNA sequence from Ruminococcus sp., isolate 2789STDY5834894, modified for expression in Escherichia coli

<400> SEQUENCE: 9
atggaaatca acacttcgaa ccccacccat cgcagcggtg aaagtagcag tgttcgtggg 60
gacatgcttg gactgaagtc agagctggag aaacgctttt ttggaaagac cttcgacgat 120
aacattcata ttcaattgat ctacaatatc ttggacattg aaaaaatcct ggccgtgtac 180
gtcactaata ttgtatatgc actgaacaat atgctgggag tgaagggcag tgagagctac 240
gatgacttca tgggctatct gtcagcgcag aatacatatt acatctttac tcatccagat 300
aagtcaaacc tgagtgacaa agtgaaaggc aacattaaaa agagtctgtc caaatttaat 360
gatctgctga aacaaaacg tttgggttat tttggactgg aggagcccaa aactaaggac 420
aagcgcgtga gcgaagccta caagaaacgt gtttatcata tgctggcaat tgtgggtcag 480
atccgtcaaa gcgtcttcca tgacaagtct aatgaattgg atgagtatct gtactcgttt 540
atcgacatta tcgacagcga atatcgtgac acgctggatt atttggttga tgaacgtttc 600
gatagcatca ataagggctt cgtccagggg aataaggtaa acatctcgtt actgattgac 660
atgatgaagg ggtatgaggc cgatgacatt atccgcttat actatgactt catcgtgttg 720
aaatcccaaa agaaccttgg cttctccatt aaaaaacttc gtgagaagat gcttgatgag 780
tacggtttcc gcttcaagga taaacaatac gattcagtgc gtagcaaaat gtacaagttg 840
atggattttt tattattctg caactattat cgtaacgacg tggtagcggg cgaggctctt 900
gtccgtaaac tgcgcttctc gatgacagat gacgaaaaag aaggcatcta tgccgacgaa 960
gccgagaaat tgtggggcaa gttccgtaat gactttgaga atatcgctga tcatatgaat 1020
ggagacgtta tcaaggaact tggcaaagcc gacatggatt tcgacgagaa gatcctggat 1080
tctgaaaaga agaacgcgtc ggacttgctg tatttttcga agatgatcta tatgcttact 1140
tatttcttgg atggcaaaga aattaacgac ctgttgacca cactgattag caaatttgat 1200
aacattaagg agttccttaa aattatgaag tctagcgcag ttgacgtgga gtgcgagctg 1260
actgcgggat acaaattgtt taacgacagt caacgtatca cgaatgaact tttcattgtg 1320
aagaacattg cgtcgatgcg caagccggct gccagtgcaa agttgaccat gtttcgtgat 1380
gctctgacca tcttaggcat tgatgacaag attaccgatg accgcatttc cgaaattctt 1440
aagttaaaag aaaaagggaa aggaatccat ggtcttcgta actttatcac caacaatgtg 1500
atcgagtcct cgcgttttgt ctacttgatt aaatatgcta acgcacaaaa gattcgcgaa 1560
gtagctaaaa acgaaaaagt tgtgatgttt gttttaggtg gcattcccga tacccagatt 1620
gaacgctact ataaaagctg tgtcgaattc ccggacatga actcatcttt agaggcaaaa 1680
tgttcagagt tagctcgtat gatcaagaat attagtttcg atgacttcaa gaatgtgaaa 1740
cagcaagcaa agggccgcga aaatgtagcc aaagagcgcg ctaaggctgt catcggattg 1800
tatctgacag tcatgtacct tcttgtcaag aatttggtca acgtaaatgc tcgctatgtt 1860
attgctatcc attgtttaga acgcgacttc ggcttatata aagaaattat tccggagttg 1920
gcctcaaaaa acttgaagaa cgattaccgt attttgagtc agaccctgtg cgaactgtgc 1980
gacgaccgcg acgagtcacc taacctgttc ttgaagaaaa acaagcgctt acgtaagtgt 2040
gtggaggtgg acatcaacaa tgcggatagc tccatgaccc gtaaataccg taattgcatt 2100
gcccatctta ccgtggttcg cgaattaaaa gagtatattg gcgatatccg tactgtcgat 2160
tcttatttca gcatctacca ctacgttatg cagcgttgta tcacgaaacg tgaggacgat 2220
accaaacaag aggaaaagat taagtacgaa gacgatctgc tgaaaaacca tgggtatacg 2280
aaggacttcg taaaagcgtt gaactccccc ttcggctata acattcctcg cttcaagaac 2340
ttatctatcg agcaactttt tgaccgtaac gagtatttaa cggagaaa 2388

<210> SEQ ID NO 10
<211> LENGTH: 2862
<212> TYPE: DNA
<213> ORGANISM: Artificial Sequence
<220> FEATURE:
<223> OTHER INFORMATION: Synthetic: CasM DNA sequence from Eubacterium siraeum, modified for expression in human cells

<400> SEQUENCE: 10
atgggcaaaa aaatccacgc ccgggacttg agggagcaga gaaaaactga tcgcacagaa 60
aaattcgccg atcaaaacaa aaaaaaggaa gctgagagag ccgtccctaa gaaagatgca 120
gcggtctcag tgaaaagcgt gagtagcgtt tccagtaaaa aagacaatgt aaccaagagt 180
atggccaagg cagccggcgt aaagtcagtt ttcgcggtgg gtaacactgt ttacatgaca 240
agttttggtc gaggaaacga cgctgtattg gagcagaaga ttgtggatac aagccatgaa 300
cccctgaaca ttgacgatcc agcctatcaa ctgaatgtgg taaccatgaa cggatactca 360
gttacaggcc ataggggtga gactgtttct gccgttaccg acaacccgtt gaggcgcttt 420
aatggacgaa aaaaagacga gcctgagcag tccgtaccaa ccgatatgct ttgcctgaag 480
cccaccctcg agaaaaaatt ttttgggaag gagttcgatg ataatattca catccagctt 540
atatacaaca ttctcgacat agaaaagatt cttgctgtct actcaacaaa tgcgatttac 600
gcactcaata acatgagcgc cgacgagaat atcgaaaata gcgatttttt catgaaaagg 660
actacggacg agacattcga tgactttgaa aagaaaaaag agtccacaaa cagtagggag 720
aaggcggatt ttgacgcctt cgagaaattt atcggtaact acaggcttgc ctattttgcg 780
gacgcgttct atgtgaataa aaaaaatccc aaaggaaaag caaagaatgt gctcagagag 840
gataaagaac tgtactcagt tttgacgctc atcggtaagc tccgccactg gtgtgtacat 900
tctgaagagg ggagagcgga gttctggctc tataaattgg acgagcttaa ggacgacttc 960
aagaacgttc tcgacgtagt gtacaaccga cctgtggaag agataaataa cagatttatc 1020
gaaaacaata aggtaaacat ccaaatattg ggctccgtct acaaaaacac agatattgcc 1080
gaacttgtca gaagctacta cgagtttttg attaccaaga agtataaaaa catgggattt 1140
tcaattaaga agttgagaga aagcatgctc gagggaaaag gttacgcgga taaagagtat 1200
gacagcgtga ggaacaaact ttaccaaatg acggacttca ttctctacac aggttacata 1260
aatgaggaca gcgacagagc agacgatctt gtaaatacgc ttcgctcttc cctgaaggaa 1320

```
gacgacaaga ccactgtgta ctgcaaggag gctgattacc tctggaagaa gtaccgagaa   1380

tccattcggg aagtagccga cgcacttgac ggcgacaata ttaaaaagtt gagtaaaagc   1440

aacattgaga ttcaggaaga taagcttcgc aagtgcttca tctcttatgc ggattctgtc   1500

agtgaattca caaagctgat ctacttgctt actagattct tgagtggtaa ggaaattaat   1560

gaccttgtta caactttgat caataagttc gacaatatta gatcctttct cgaaattatg   1620

gatgagcttg gtctggaccg aactttcact gctgagtact cattctttga aggttcaaca   1680

aaatatctgg ctgaattggt tgagctcaac tcctttgtca agagttgtag ctttgacatc   1740

aatgcaaagc gcacgatgta tcgagatgct ttggatatcc tgggaatcga gtctgacaaa   1800

acggaagagg acatcgaaaa aatgatagac aatatcttgc agattgacgc aaatggggat   1860

aaaaaactca aaaagaataa cggcttgcga aattttattg catctaacgt catagacagc   1920

aaccggttca aatacctcgt gcgctatggc aatccaaaaa agattagaga gaccgcaaag   1980

tgcaaaccag cggtccggtt tgtgctgaac gaaattcccg acgcacagat tgaacggtat   2040

tatgaagcat gctgccctaa aaacacggct ctgtgcagcg cgaataaaag aagggaaaag   2100

ttggcggata tgatcgcgga gattaaattc gagaattttt cagatgcagg caactatcaa   2160

aaagcgaacg ttacctcacg gacctcagag gctgagataa agaggaaaaa ccaggccatc   2220

ataagactgt atcttactgt tatgtacatc atgctgaaaa atctcgtaaa tgtgaacgca   2280

cggtacgtaa tagcgttcca ttgcgtcgag cgggatacga agctgtatgc agagtcaggg   2340

ctggaggtag gaaatatcga aaagaacaag acgaacctta ctatggcagt catgggggta   2400

aaactcgaaa acggtattat caagactgaa ttcgacaagt cattcgctga gaacgccgca   2460

aacaggtatc tgaggaacgc gagatggtac aagctgatat tggataatct gaaaaaaagc   2520

gagcgggcgg ttgtaaacga attcagaaac acagtatgcc atttgaatgc tatacgaaac   2580

attaacatta acattaagga aataaaggaa gtcgagaatt attttgcatt gtaccactat   2640

cttatacaaa aacacctcga aatcgattt gcagacaaga aggttgaaag agataccggg   2700

gattttatct ctaaacttga agagcacaaa acctattgca aagactttgt gaaagcctac   2760

tgcacgccgt tcggctataa cttggtccgc tataaaaact tgaccatcga tggattgttc   2820

gacaaaaact acccggggaa agacgatagt gatgagcaga ag                      2862
```

```
<210> SEQ ID NO 11
<211> LENGTH: 2757
<212> TYPE: DNA
<213> ORGANISM: Artificial Sequence
<220> FEATURE:
<223> OTHER INFORMATION: Synthetic: CasM DNA sequence from Ruminococcus
      sp., isolate 2789STDY5834971, modified for expression in human
      cells

<400> SEQUENCE: 11

atggcaaaaa agaataaaat gaagccgcgg gaacttaggg aagctcagaa aaaggcccga     60

caacttaaag ctgccgagat aaacaacaac gctgcaccgg cgatagccgc catgcctgca    120

gctgaggtga ttgcacctgc tgccgaaaaa aagaaatcaa gcgtgaaagc agccggcatg    180

aaatctatcc tcgtgtccga aaataagatg tatattacgt cttttggaaa agggaatagt    240

gcggttctcg agtacgaagt agataataat gattataatc aaactcaact gtcatccaag    300

gacaatagca atatacaact tggcggggtt aacgaggtta acattacctt ttcaagcaag    360

cacggctttg agtcaggtgt agaaataaat acaagtaacc ccactcatcg ctcaggggaa    420
```

-continued

```
tcatcacctg tacgcgggga catgctcggg cttaagtcag aactggagaa acgcttcttt    480
ggtaaaacat ttgacgacaa tattcatata cagctgatct ataatattct tgatatagag    540
aaaatcttgg ctgtatacgt cacaaacatc gtatacgcac ttaataatat gctcggggtt    600
aaaggcagcg aaagccatga cgacttcatt ggatacctta gcaccaataa catctacgac    660
gtattcatcg acccagacaa tagcagtctg agcgatgaca agaaggctaa cgtgagaaag    720
tcactctcca aatttaatgc cttgcttaaa acaaagagat tggggtactt tggcttgaa     780
gagcctaaga cgaaggataa tcgcgtatca caagcctata agaagcgggt ctatcacatg    840
ctggcgatcg tgggtcaaat tcgccaatgt gttttccacg acaagtctgg cgctaagaga    900
ttcgatcttt acagcttcat caacaacatc gacccccgagt accgggacac cctggactac    960
ctcgtggagg aaagactcaa gtcaatcaat aaggatttta ttgaagataa caaggtaaat   1020
atatccctcc tcatagatat gatgaaaggt tacgaggccg atgatatcat tcgactgtat   1080
tacgatttca ttgtactgaa gagtcaaaaa aatctgggct tctcaatcaa aaaactgcgg   1140
gagaaaatgc tggacgagta tggttttagg ttcaaggata agcaatacga cagtgtccgc   1200
agcaagatgt acaagctcat ggatttttttg ctcttttgta attactaccg aaatgacata   1260
gctgcaggcg agtctttggt gcgaaaattg cgcttttcca tgacagacga tgaaaaggag   1320
ggcatatatg ccgatgaagc tgctaaattg tggggaaaat ttcggaacga tttcgaaaac   1380
atcgccgacc acatgaatgg agatgtcatc aaggagcttg gtaaagctga tatggacttt   1440
gacgaaaaga tattggacag tgaaaaaaaa aacgctagcg atcttcttta tttttccaag   1500
atgatatata tgctgacgta ttttcttgac ggtaaagaaa taaacgacct gctgactaca   1560
ttgatttcaa aatttgacaa catcaaggaa tttctgaaaa taatgaagag ttccgcggta   1620
gatgtagaat gtgagttgac agccggatac aaattgttca atgatagtca gaggatcacc   1680
aatgagttgt tcattgttaa gaatattgcg tctatgagga aaccagcggc aagtgctaag   1740
ttgacgatgt ttcgagacgc gcttacaatt cttgggatcg atgacaaaat cactgacgac   1800
cggatttcag ggatactgaa gctcaaggaa aagggaaaag gcattcatgg gcttaggaac   1860
tttatcacta acaatgtaat tgaatctagc cggttcgtct acttgatcaa gtacgccaat   1920
gcgcaaaaga ttagagaagt tgccaagaat gaaaaggtcg tgatgttcgt attgggggggt   1980
attccagata cacagatcga acgctactac aagtcttgtg ttgagttccc ggacatgaac   2040
tcctctctgg gggtgaagcg ctccgaactg gctcggatga ttaagaacat tagcttcgac   2100
gatttcaaaa acgtcaagca acaagcgaag ggcgcgaaa acgttgccaa ggagagggct    2160
aaagcagtga tcggtcttta tctcacagtg atgtatcttc ttgttaagaa tcttgtcaat   2220
gtcaatgcac ggtatgttat agctatacac tgtctcgaac gagacttcgg tctctacaaa   2280
gaaattattc cagagcttgc aagtaaaaac ctgaaaaatg attatcgcat cttgtcacag   2340
acgttgtgtg agctgtgcga taagtctcca aacctcttcc ttaagaaaaa cgaacgattg   2400
cgaaagtgtg tcgaggtgga tatcaataat gcggactctt ccatgacccg aaaatataga   2460
aactgtattg cgcacttgac cgtagtcaga gaactcaaag agtacatagg ggacatctgt   2520
acggttgact catattttag tatctaccac tatgttatgc aacgctgcat aaccaagagg   2580
gagaatgata cgaagcaaga agaaaagata aagtatgaag atgacctctt gaaaaaccac   2640
ggttatacga aggacttcgt aaaagctctt aactcaccat ttggttacaa tatcccaaga   2700
ttcaagaacc tctcaatcga gcaattgttc gatcgaaatg agtatctgac ggagaaa      2757
```

<210> SEQ ID NO 12
<211> LENGTH: 2754
<212> TYPE: DNA
<213> ORGANISM: Artificial Sequence
<220> FEATURE:
<223> OTHER INFORMATION: Synthetic: CasM DNA sequence from Ruminococcus bicirculans, modified for expression in human cells

<400> SEQUENCE: 12

```
atggcaaaga agaacaaaat gaagccgcgc gagttgcggg aggcccaaaa gaaagctcgc     60
cagctgaagg ccgccgaaat caataacaac gcagtccctg ccatagctgc catgccagca    120
gccgaagccg ccgcaccggc tgcggaaaag aagaagtcct cagtaaaagc tgcgggcatg    180
aaaagtatac ttgtgtcaga gaacaagatg tatatcacca gttttggaaa aggcaactcc    240
gcagtgcttg agtatgaggt agataacaat gattacaaca agacgcagtt gtccagcaaa    300
gataactcaa acattgaact gtgcgacgtt ggcaaggtta atataacttt cagtagtcgc    360
cgcggatttg aatcaggggt ggaaatcaat acttctaacc caactcatcg gtctggggag    420
agctcttcag tacgcgggga tatgttggga cttaaatctg agctcgaaaa gagatttttt    480
ggtaagaact tcgatgataa catccacatc caattgattt ataatatctt ggatatagag    540
aagatactcg cagtatatgt gactaacatc gtctacgcgc ttaacaatat gctcggtgag    600
ggagatgagt ctaactacga ctttatgggc tatctgagca catttaacac ctataaagtg    660
ttcactaatc ccaatggaag tactttgagc gatgacaaga aagaaaacat tcgcaagtca    720
ctctctaagt tcaacgccct cctcaagacc aaacgcttgg ggtattttgg tctggaagaa    780
cccaaaacga aagacactag agcttcagag gcatacaaga aacgagtata ccatatgctc    840
gccattgtcg ggcagatccg ccagtgtgtg tttcatgata agtctggagc aaaacgattc    900
gacctgtata gttttatcaa caatatagac cccgagtata gggaaacttt ggactacctt    960
gtagatgagc ggtttgactc cataaacaag ggctttatac aaggaaataa agtcaatatc   1020
agtctgctca tagatatgat gaaagggtat gaagctgacg acattattcg cctgtactat   1080
gactttatcg ttcttaagtc tcagaaaaat cttggcttca gtataaaaaa gctccgcgag   1140
aagatgctgg atgagtatgg atttagattc aaggataagc agtacgacag tgtaagatct   1200
aaaatgtata aacttatgga ttttctgttg ttctgcaact actaccggaa cgacatcgcc   1260
gcgggtgaga gtttggtgag aaagcttcgg ttctccatga ccgacgacga aaaggaaggg   1320
atatatgcag atgaagcggc taaactctgg ggcaagtttc gaaatgactt cgaaaacatt   1380
gcggatcata tgaacggtga tgtgataaaa gaacttggaa aagccgatat ggactttgat   1440
gaaaagatac tggactcaga aaagaaaaac gccagtgacc tcctttactt cagcaagatg   1500
atctacatgc tcacctactt tctggatggg aaagaaatca atgatttgct tacaaccttg   1560
atctctaagt tcgataatat aaaggaattt ttgaagatca tgaaatctag tgctgtggac   1620
gtagagtgtg aactcacagc aggatataag ctctttaatg atagccaacg aataacaaac   1680
gagcttttca tagtgaaaaa cattgccagc atgcggaagc cggcggcgtc agcaaaattg   1740
accatgttcc gcgatgcact gactattctt gggatcgatg ataaaataac ggatgatcgc   1800
ataagcgaga ttctgaaatt gaaggaaaag ggtaagggta tacacggttt gcggaacttc   1860
attacgaaca acgtcattga atccagtcga tttgtgtatc tgataaagta cgcgaatgcg   1920
cagaaaataa gggaggttgc taaaaatgag aaggtcgtca tgttcgtact tggcggcatt   1980
cccgacacac aaatcgaaag gtattacaaa agttgtgtag agttcccaga tatgaacagt   2040
tccttgggag taaaacggtc tgaactggcg agaatgataa agaatatatc attcgacgac   2100
```

ttcaaaaatg taaagcaaca ggcgaaagga agagagaacg tggctaagga acgggccaaa 2160
gccgttattg gactttacct tacggttatg tacttgttgg ttaaaaacct tgttaatgta 2220
aacgcacgct atgttatagc aatacattgc ctggagagag acttcgggct ctacaaggaa 2280
ataattcccg aactcgcttc aaagaacctt aaaaacgatt accgcattct tagtcaaacg 2340
ctctgcgagc tctgcgacaa atcccctaac ctgttcctca aaaaaaatga gagactcagg 2400
aagtgcgtcg aggttgacat caataatgca gattctagta tgactcgaaa gtatcggaac 2460
tgtatcgcgc acttgacagt tgtgcgcgaa ctgaaagaat acataggcga tatctgtacc 2520
gtagactcat atttctcaat ttaccactat gtgatgcaaa gatgcataac caagagggag 2580
aacgacacga aacaggagga aaagattaag tacgaggatg acttgttgaa aaaccacggt 2640
tatacaaaag attttgtcaa ggcactgaat agtccttttg ggtataatat cccgaggttc 2700
aaaaaccttt caattgaaca actcttcgat aggaacgagt acctgacgga gaag 2754

<210> SEQ ID NO 13
<211> LENGTH: 2766
<212> TYPE: DNA
<213> ORGANISM: Artificial Sequence
<220> FEATURE:
<223> OTHER INFORMATION: Synthetic: CasM DNA sequence from Ruminococcus sp., isolate 2789STDY5608892, modified for expression in human cells

<400> SEQUENCE: 13
atggcaaaaa agaacaagat gaagccccga gagttgcggg aagcgcagaa aaaagcgagg 60
cagcttaagg ccgctgaaat caacaacaat gccgctcccg caatagctgc gatgcctgcc 120
gcggaggtga ttgcaccagt agcggagaag aagaaaagtt ctgtaaaagc tgcaggtatg 180
aaaagcatat tggtaagtga aaacaagatg tatataacta gtttcggcaa aggtaattct 240
gccgtgttgg aatatgaggt tgataataac gattacaata aaacccaact ctcctctaaa 300
gacaattcaa atatagagct cggcgacgta aatgaagtga acattacgtt ctccagcaaa 360
cacggtttcg gctcaggggt ggaaattaat acttctaacc cgacacaccg gagtggtgag 420
tcatctccag tgagaggaga tatgctcgga ttgaaatccg aactcgagaa acggttcttc 480
ggcaagacat tcgacgacaa catccatatc cagttgattt ataacatact cgacatcgag 540
aaaattttgg ccgtgtatgt gacaaacatt gtttatgcat tgaacaacat gctgggtata 600
aaagattcag agagctatga cgactttatg ggtacttgga gtgcacgcaa tacctacgag 660
gtgtttacgc acccagacaa gagtaatttg tctgacaagg tgaagggtaa tattaagaag 720
tccctttcaa aatttaacga cttgctgaaa actaaacgct tggggtactt tggactcgaa 780
gaaccaaaaa ccaaggatac aagggcatca gaagcctaca agaagagggt gtaccatatg 840
ctggctatag taggtcagat tcggcagtgc gtattccacg acaagtcagg tgcaaagaga 900
tttgatcttt actcattcat aaacaacatt gatccggaat accgggatac gctggactat 960
ctggtagaag agcgattgaa gtcaatcaat aaagatttta ttgaaggaaa caaagtgaat 1020
attagcctgc tgatcgacat gatgaaaggg tatgaagctg atgacatcat acggctctac 1080
tacgacttca tagtactcaa gagtcagaag aacctgggtt tttccatcaa aaaactgcga 1140
gaaaagatgt tggaagaata cggctttcgc ttcaaagaca aacagtatga ttccgtccga 1200
agcaaaatgt ataagcttat ggatttcctg ctcttctgca attattacag aaatgacgta 1260
gccgcgggag aagccctggt acgaaagttg agattctcta tgacggatga cgagaaggaa 1320

```
ggcatctatg ctgacgaggc agcgaagctg tggggaaaat tccgcaacga cttcgaaaac   1380
atagcggatc atatgaatgg ggacgttata aaagaactcg gaaaagcgga tatggacttt   1440
gatgagaaga tcctggattc tgagaaaaaa aacgctagtg atcttctcta tttctctaag   1500
atgatttaca tgctcacgta tttttggat ggcaaagaaa ttaatgatct cctcactacc    1560
ctcatttcta agttcgacaa tattaaggaa ttccttaaga tcatgaagag ttcagcggtc   1620
gacgtagaat gtgagcttac tgccggatac aaattgttta acgatagcca gcgaatcacg   1680
aatgagctgt tcattgtcaa gaatatcgcc agtatgagga agcccgctgc gtctgcaaaa   1740
ttgactatgt tccgcgatgc tcttaccatt ctgggcattg acgacaatat aactgacgac   1800
cgcatcagtg agatcctgaa gctcaaggag aaggggaagg ggatccacgg attgcggaat   1860
ttcatcacaa ataacgtaat tgagagttcc cggttcgtgt atcttattaa atatgccaat   1920
gctcaaaaga taagagaagt agcaaaaaac gagaaggtgg tcatgtttgt actgggcgga   1980
atacccgaca cccaaatcga acggtattat aaatcttgtg tagaattccc agacatgaac   2040
agttcactcg aagcgaagag atcagaactc gcgcggatga ttaaaaacat ttccttcgac   2100
gacttcaaaa acgtcaaaca gcaggcgaaa ggtagggaga atgttgcgaa agaaagagct   2160
aaagcggtaa ttggtctgta tctgaccgtc atgtacctgt tggtgaaaaa tcttgtcaac   2220
gtaaatgcgc gatacgtcat cgcgatccat tgtcttgagc gagacttcgg gctctataag   2280
gagattatcc ctgagttggc cagtaaaaat cttaaaaacg actacagaat ccttagccag   2340
acgctttgtg agctttgtga cgacaggaac gagtcttcca atctgtttct caagaaaaat   2400
aagaggctca gaaaatgtgt agaggttgat atcaataacg ctgatagctc tatgactcga   2460
aagtatcgga attgtattgc acaccttacg gtagttaggg agctgaaaga atatatcggc   2520
gatatacgaa cagtagacag ctatttcagt atataccatt atgtcatgca acgctgcatt   2580
accaagaggg gggacgatac caagcaggag gagaaaatca aatacgaaga tgacttgctc   2640
aagaatcacg gttatactaa ggattttgtt aaagcgctca atagtccttt tggctacaac   2700
atcccccgat tcaagaacct gagtattgaa caacttttcg atagaaacga gtaccttact   2760
gagaaa                                                              2766
```

<210> SEQ ID NO 14
<211> LENGTH: 2766
<212> TYPE: DNA
<213> ORGANISM: Artificial Sequence
<220> FEATURE:
<223> OTHER INFORMATION: Synthetic: CasM DNA sequence from Ruminococcus sp. CAG:57, modified for expression in human cells

<400> SEQUENCE: 14

```
atggccaaaa aaaataagat gaaaccacgc gaattgcggg aagctcagaa aaaggctaga     60
cagttgaagg ccgcggagat aaacaacaat gcagcacctg ctatcgccgc catgccagct    120
gccgaggtga ttgcccccgt agcggaaaag aagaaatcct ccgtaaaagc ggcggggatg    180
aagagcatcc ttgtgagcga gaacaaaatg tacattacaa gctttggtaa agggaactca    240
gctgtgttgg agtacgaagt cgacaataac gactacaaca agacccagct gtcctctaaa    300
gacaatagca acatagaact gggcgacgta aacgaggtaa atataacgtt ctcttctaag    360
catggctttg gcagtggtgt ggagataaat acttccaacc ccactcatcg aagcggggaa    420
agtagcccgg ttaggggaga catgctcggc ttgaaatcag agctggagaa gagatttttt    480
gggaaaacat tcgacgataa tatacacatc cagctgatat ataacattct ggatatagaa    540
```

```
aaaatacttg cagtgtacgt tacgaacatt gtctatgctt tgaacaatat gctcggaatt    600
aaggattccg agtcctacga tgatttcatg ggttacctga gcgcccgaaa cacgtacgag    660
gtgttcactc atccggacaa atccaatctc agtgataaag tgaagggcaa cataaagaaa    720
tccctttcta aatttaacga tctcctcaag acgaaaagac tcgggtactt tgggctggag    780
gaacctaaaa cgaaagacac tagagccagc gaggcttata aaaaaagagt ctaccacatg    840
ctcgctatag ttggacaaat taggcaatgt gtgtttcatg acaaaagtgg tgcaaaacgg    900
ttcgatctgt actcatttat caacaacatt gatccagagt accgagacac tctcgactat    960
ttggttgagg aacgattgaa atctataaac aaggatttca ttgaggggaa caaggtaaat   1020
ataagccttc tcattgatat gatgaagggg tacgaagccg acgatataat ccgcctctac   1080
tatgatttta ttgtgctgaa aagtcagaag aatctggggt ttagtattaa aaagcttagg   1140
gagaagatgc tggaagaata tggttttcgg tttaaagata aacaatatga ctccgtgagg   1200
agtaaaatgt acaaacttat ggatttcctc ctgttctgta actattatcg gaatgatgtt   1260
gcagcaggcg aagcactcgt ccgcaaactt agattcagta tgacagatga tgagaaggaa   1320
ggaatatacg ctgacgaagc ggcgaaactg tgggggaaat ttcgcaacga ctttgagaac   1380
atagctgacc atatgaatgg cgacgttatc aaagagctcg gtaaggcgga catggacttc   1440
gacgagaaaa ttctcgacag tgagaaaaag aacgccagtg atctgctgta ttttagcaaa   1500
atgatataca tgctcacata ctttctcgat ggtaaagaga tcaacgactt gttgaccacg   1560
cttattagca aatttgataa catcaaagag ttcttgaaaa taatgaagtc cagtgccgtg   1620
gatgtggagt gcgagctcac ggcaggttat aaacttttta acgatagtca acggatcact   1680
aatgagctgt tcattgtcaa gaatattgca agcatgcgca agcccgcggc aagtgcaaag   1740
cttacgatgt ttcgggacgc cctcacgata ttgggtatag atgacaatat aactgatgat   1800
agaatcagtg agatacttaa gctcaaggaa aaggggaaag ggatacacgg tctgcgcaac   1860
ttcataacga ataacgtgat tgagagctcc cgatttgtct atctgataaa gtacgccaat   1920
gcccaaaaga taagggaagt agctaaagat gaaaaagtgg tcatgttcgt ccttggcggg   1980
attcccgaca cgcagattga gaggtactac aagtcttgtg tggagtttcc ggatatgaac   2040
agctccctcg aggctaagcg cagtgagctg gctagaatga ttaagaatat ttcctttgat   2100
gattttaaaa atgtaaagca acaagctaag ggacgggaga acgtcgccaa agaacgggcg   2160
aaagcagtga ttgggcttta tctcacggtc atgtatctgc ttgttaagaa cttggtcaac   2220
gtcaatgcaa gatatgttat agcgatccac tgccttgaac gagatttcgg gttgtacaaa   2280
gaaatcatcc cggagttggc atctaaaaac cttaagaatg actatcgaat actgtcacaa   2340
accttgtgcg aactctgcga tgaccgaaac gaatcatcta acctcttcct taaaaaaaac   2400
aagagactca gaaagtgtgt ggaggtggat atcaataatg ccgattccag tatgactaga   2460
aaataccgca actgcatcgc acacctgact gtggtcagag aacttaagga gtacattgga   2520
gatattagaa cggtcgactc atattttagc atctatcatt atgtcatgca gaggtgtatc   2580
accaagagag gagatgatac aaagcaggaa gagaagataa agtacgagga cgatcttctt   2640
aagaaccatg gctacactaa ggacttcgta aaagcgttga actccccgtt cgggtataac   2700
atacctaggt ttaagaatct ttcaattgag caattgtttg accgcaatga gtaccttaca   2760
gagaag                                                               2766
```

<210> SEQ ID NO 15
<211> LENGTH: 2799

<212> TYPE: DNA
<213> ORGANISM: Artificial Sequence
<220> FEATURE:
<223> OTHER INFORMATION: Synthetic: CasM DNA sequence from Ruminococcus flavefaciens FD-1, modified for expression in human cells

<400> SEQUENCE: 15

```
atgaaaaaga aaatgtcctt gcgagaaaaa agggaagctg aaaaacaagc aaagaaggcc     60
gcgtactcag cagcttccaa gaataccgac tccaaaccag cggaaaagaa ggcagaaacc    120
ccgaagccgg cagagataat aagtgacaac agtcggaata aaacggctgt gaaagctgcg    180
ggccttaaat ctaccattat atctggagat aagctgtaca tgacatcatt tggtaagggg    240
aacgctgcgg ttattgaaca gaagatcgac atcaatgact atagcttctc tgctatgaaa    300
gatacaccat ccctggaagt ggacaaggct gaaagcaagg aaatttcatt tagcagccac    360
cacccgttcg tgaaaaatga taaactgacc acctacaacc cattgtatgg tgggaaagat    420
aatccggaaa aaccagtagg aagagacatg ctgggactga aggacaagct tgaagaacgg    480
tatttcggat gcaccttcaa tgataacttg catattcaga ttatatataa catactcgat    540
atcgaaaaga tacttgcagt gcactccgca aacatcacga ccgcgctgga tcacatggtg    600
gacgaagatg atgagaaata tcttaacagt gattacatcg ggtacatgaa cacaattaac    660
acatacgacg tatttatgga cccttctaaa aattccagcc tctcacctaa ggaccgcaag    720
aatatcgaca acagtcgagc caagtttgaa aaactgttga gcacgaaaag gcttggatat    780
ttcggattcg attatgacgc caatggtaag gacaaaaaaa agaatgaaga gataaaaaaa    840
cggctgtatc atttgactgc attcgctggc caactgagac agtggtcctt ccattctgct    900
gggaactacc ctcgcacgtg gctctacaaa ttggacagct tggacaagga ataccttgac    960
acgctggacc attactttga taaacggttc aatgatatta acgatgattt tgttaccaaa   1020
aacgccacta acttgtatat actcaaggaa gtatttccgg aggcaaattt caaagacata   1080
gccgaccttt actacgactt tattgttatc aagagccaca agaacatggg gttttccatt   1140
aaaaaactcc gcgagaagat gctcgaatgc gatggtgctg accgcatcaa ggagcaggat   1200
atggactcag taaggagtaa gctttacaaa ctgatcgact tttgtatttt taagtattac   1260
cacgaatttc ctgagttgtc agagaagaac gtcgacatac ttcgagcagc ggtttctgat   1320
acgaaaaagg ataaccttta ttcagacgag gctgctcggc tgtggagcat attcaaagaa   1380
aagttcctcg gcttttgtga caaaattgtg gtttgggtca ccggagagca cgaaaaggac   1440
atcacgtcag tgattgataa agacgcatat cgaaatcgca gtaacgtttc ttacttctcc   1500
aagcttatgt acgcaatgtg tttctttctt gatggtaagg agataaacga cctcctcacg   1560
acccttatca ataagttcga caatatagca aatcagatta agacggccaa agaactcgga   1620
ataaacactg catttgtaaa gaactacgac ttcttcaatc atagcgagaa atacgtagac   1680
gagctgaata tcgtgaaaaa tatcgctcgg atgaaaaaac ccagttcaaa cgcaaaaaag   1740
gcaatgtatc atgacgcatt gacgatattg ggaatcccag aggacatgga tgagaaggct   1800
ctcgacgaag aattggacct cattttggag aaaaagactg atccggtgac tggcaaacca   1860
ctgaaaggca aaaaccctct gcgaaatttc atagccaaca acgtaatcga aaacagtaga   1920
ttcatatacc ttattaagtt ctgcaacccc gagaatgtcc gcaagatagt caacaacaca   1980
aaggtcacgg aattcgttct gaagcgcatt cctgatgccc aaatcgagcg gtactacaag   2040
agttgtactg atagtgagat gaaccccccc acggaaaaaa agattacgga gctcgctggt   2100
aagctgaaag atatgaattt tgggaacttc aggaacgtaa ggcaatctgc aaaggaaaac   2160
```

```
atggaaaagg agcgcttcaa agcagtgatt ggcctgtatc tcaccgttgt gtaccgagtc   2220

gtcaagaatc ttgtagatgt gaacagtcga tacatcatgg cttttcacag tctggaacgg   2280

gatagtcagc tgtacaacgt ctccgtggat aacgattacc tcgcacttac ggacactctt   2340

gtcaaggaag gcgacaattc ccggtcacga tatctggccg gaaataaacg ccttcgagat   2400

tgtgtaaagc aggatattga taacgcaaag aagtggtttg tgagcgacaa gtacaatagc   2460

ataactaaat accgaaacaa tgtagctcac cttaccgctg taaggaattg cgcggaattt   2520

atcggtgata ttactaagat tgattcctat ttcgcactgt atcattatct gatacagagg   2580

caacttgcca agggcctgga ccatgaacgg agtggctttg atcgaaacta tccccaatac   2640

gcaccattgt ttaaatggca tacttacgtt aaggacgttg tgaaggctct taatgctcct   2700

ttcggttaca atatacctag attcaaaaat ctgagcatcg atgcactgtt cgaccgcaat   2760

gagattaaaa agaacgacgg agagaaaaag tccgacgat                          2799
```

<210> SEQ ID NO 16
<211> LENGTH: 2832
<212> TYPE: DNA
<213> ORGANISM: Artificial Sequence
<220> FEATURE:
<223> OTHER INFORMATION: Synthetic: CasM DNA sequence from Ruminococcus albus strain KH2T6, modified for expression in human cells

<400> SEQUENCE: 16

```
atggctaaaa aatcaaaagg aatgagcctc cgcgaaaagc gggaactcga gaagcaaaag     60

aggattcaaa aggccgcggt taattcagtg aacgatacac ccgaaaaaac ggaggaagct    120

aatgtcgtca gcgtcaacgt tcgaacctca gctgagaata agcactccaa aaaatctgcg    180

gccaaagctc tgggccttaa gagtggtctg gttataggag acgaacttta cttgacgagc    240

ttcggtcgcg gtaatgaagc gaagttggag aaaaagatta gcggcgacac ggtcgagaag    300

ctggggatcg gcgccttcga ggttgctgaa agggacgaat ctactctcac gctcgagagc    360

ggtcgcatca aagacaagac agccagacca aaagatccac ggcatattac tgttgataca    420

caaggaaaat tcaaagaaga tatgttgggt atccggagcg tactcgagaa aaaaatattt    480

ggcaaaactt ttgatgataa catccacgta caactggcgt ataacattct tgacgttgaa    540

aaaatcatgg ctcagtacgt ctcagacata gtatacatgt tgcacaacac ggataagacc    600

gagcgcaatg ataacctgat gggatatatg tccattcgaa acacatataa gacattttgc    660

gacactagca atctgcctga cgacacaaag caaaaagttg aaaaccaaaa gagagagttc    720

gataagataa tcaagtccgg ccgactcgga tattttggag aagcatttat ggtaaattca    780

ggcaatagta cgaagctccg acctgagaaa gaaatctacc atattttcgc gcttatggca    840

tccctgcgcc aaagctactt tcatggttac gtcaaggata cagattacca gggtaccacg    900

tgggcgtata cgcttgaaga caaactcaag ggtccatctc atgagtttcg agaaacgatc    960

gataagattt ttgacgaggg gttttcaaaa atcagtaaag atttcggaaa gatgaacaag   1020

gttaatctcc agattttgga acaaatgata ggcgagctgt atggctccat cgagcgccaa   1080

aaccttacgt gtgactatta tgattttata cagcttaaaa aacacaaata tctgggtttc   1140

tccataaaac gcctcaggga aacgatgctt gagacaacac ctgcggaatg ttataaggca   1200

gaatgttata actctgagag gcaaaaactg tacaagctga tcgacttcct gatctacgat   1260

ctctactaca atcgcaagcc agcacgaatt gaagagatag tcgataagct gcgggagagc   1320

gtgaacgacg aggagaagga gtccatatac tcagttgagg caaagtatgt ctatgagtcc   1380
```

```
ttgtcaaaag tgctcgacaa gagtctcaaa aactctgtga gcggtgagac gatcaaagac   1440

cttcagaaac ggtatgacga tgagacggcc aaccggatct gggacatctc ccagcattcc   1500

atatccggta acgtgaactg tttctgtaag cttatctaca tcatgacact gatgctcgac   1560

ggcaaggaaa tcaatgatct cctgactaca cttgttaaca agttcgataa cattgcttct   1620

ttcatagacg ttatggatga gcttgggctg gagcacagtt ttaccgataa ctataagatg   1680

tttgcagatt ccaaggccat atgcttggat ctgcaattta taaattcctt cgctagaatg   1740

tctaagattg atgacgaaaa atctaaacga cagcttttca gggatgcgct cgtaattctt   1800

gacatcggaa ataaagatga gacctggata aacaactact tggattccga catattcaag   1860

ttggataagg aaggaaacaa actcaagggt gcccggcatg actttaggaa ctttattgcg   1920

aacaacgtca tcaagtcctc ccggtttaag tatctcgtta agtactctag cgctgacggg   1980

atgataaagc tgaaaacgaa cgagaaactc atcggattcg tcctggacaa gctgcctgag   2040

acgcagatag atcgatatta tgaatcatgc ggccttgaca atgcggtcgt cgacaagaaa   2100

gtgcgaatag agaagttgag cggacttatc agggacatga agtttgatga cttctccggc   2160

gtgaagactt ctaacaaggc cggagacaat gataaacaag ataaggcgaa gtaccaggct   2220

attattagtt tgtatctgat ggtactgtac cagatagtaa aaaacatgat ttacgtcaat   2280

tcccgctatg tcattgcttt ccactgcctt gaacgcgact ttgggatgta tggcaaagat   2340

tttggaaagt actaccaggg ctgtcggaag ttgaccgacc acttcataga agaaaagtac   2400

atgaaggaag gaaagttggg gtgcaacaaa aaggtcgggc ggtacctgaa aaacaatatt   2460

tcctgctgta cggacggatt gataaatact taccgaaatc aggtggacca ttttgcggta   2520

gtccgaaaga taggaaacta cgcagcctac attaagtcaa taggctcttg gtttgaactg   2580

taccactacg taattcagag gattgtcttc gacgaataca gattcgctct taacaacacc   2640

gagtcaaatt ataagaattc catcatcaaa catcacacgt attgtaagga tatggtgaag   2700

gcgctgaaca cgccgtttgg ttatgatttg ccacggtaca aaaatctctc cattggggat   2760

cttttcgacc gcaataacta tctcaacaaa actaaggaaa gcatcgacgc taatagttca   2820

atagattctc aa                                                       2832
```

```
<210> SEQ ID NO 17
<211> LENGTH: 2901
<212> TYPE: DNA
<213> ORGANISM: Artificial Sequence
<220> FEATURE:
<223> OTHER INFORMATION: Synthetic: CasM DNA sequence from Ruminococcus
      flavefaciens strain XPD3002, modified for expression in human
      cells

<400> SEQUENCE: 17

atgatagaga aaaaaaaaag ctttgcgaaa gggatgggcg taaaaagtac actggtatca     60

ggctctaagg tctacatgac aacgttcgca gaaggaagcg atgcacgcct cgaaaagatt    120

gttgagggag atagcattag gtccgtcaat gaaggagaag cctttagtgc agaaatggca    180

gacaagaacg ctggatacaa gattggaaac gcaaaatttt cccatccaaa gggatacgca    240

gttgtagcta acaatcccct ctataccggg cccgtccagc aagacatgct tggcctcaaa    300

gagacgcttg agaagaggta ttttggagag agtgctgatg gtaatgacaa tatctgtatc    360

caagttattc ataacatcct cgacatagag aaaatccttg cagaatatat caccaacgcc    420

gcatatgcag tgaataatat atccggtctg gataaagaca taatcggatt cggcaagttt    480
```

```
agtacagtat atacctatga cgagttcaaa gacccggagc atcatcgagc cgctttcaat    540
aacaacgaca aacttatcaa tgccattaag gctcaatatg acgagttcga taattttttg    600
gacaatccca gacttgggta tttcggccag gccttctttt ctaaggaagg caggaattac    660
atcattaatt acggaaacga atgttacgat atcctcgctt tgctctctgg cctgcgccac    720
tgggttgtac acaacaacga ggaggaatct cgaatttcac gaacttggct gtacaatttg    780
gataaaaact tggataatga atacatcagt actctgaact atctctacga taggatcacc    840
aacgaactta cgaattcatt ttcaaaaaat tccgccgcaa acgttaatta catcgctgag    900
acgttgggca taaatccggc cgagttcgcc gagcaatatt ttaggttcag tatcatgaag    960
gagcaaaaga atttggggtt caacatcacg aaactccgag aagtcatgct cgaccgaaaa   1020
gatatgtccg aaattcggaa gaaccataag gtattcgaca gcatccgcac aaaagtgtac   1080
acaatgatgg atttcgttat atacaggtat tatatagagg aagatgcaaa agttgccgcc   1140
gcaaacaaaa gtcttccaga taatgaaaag agcttgagtg aaaaagatat ttttgttata   1200
aaccttcgcg gttccttcaa tgatgaccaa aaggatgctc tgtactacga cgaggcaaac   1260
cgaatctggc gaaaactgga aaacatcatg cataatataa aggaatttcg cgggaacaaa   1320
acgagggagt ataagaagaa ggatgctcct cgcctcccca ggatactccc tgcgggcaga   1380
gacgtctccg catttagcaa actgatgtat gctctcacta tgtttttgga tgggaaggag   1440
ataaacgatc ttctgactac gttgattaac aaatttgaca acattcagag ttttctcaag   1500
gtcatgccac ttatcggcgt aaatgcaaag tttgttgagg aatacgcctt ctttaaagac   1560
tccgctaaaa tagcggacga gctccgcctg attaaatcct tcgcccgaat gggtgaaccg   1620
atagcggatg cccggcgagc tatgtacatc gatgctatca ggatccttgg aactaacttg   1680
agctacgacg aacttaaggc tctggcggac actttcagtt tggacgagaa tgggaacaag   1740
ctgaaaaagg gaaagcacgg gatgagaaac ttcataataa ataatgtcat ttccaacaag   1800
aggttccatt atttgattcg gtatggtgat cctgcgcacc ttcatgaaat tgcgaagaat   1860
gaagctgtgg ttaaatttgt tcttggcaga attgccgaca tccaaaaaaa acaggggcaa   1920
aatggtaaga accaaattga tagatactac gaaacttgca taggtaaaga caaaggtaaa   1980
agtgtctctg aaaaggtgga tgccctgacg aaaatcatca caggtatgaa ctatgaccaa   2040
ttcgacaaaa agagaagtgt aattgaggat actggtcggg aaaacgctga aagagagaag   2100
tttaagaaga ttattagtct ctatcttacc gttatttatc acattctcaa aaacatagtc   2160
aacatcaatg ccagatatgt catcggattc cactgcgttg aacgagatgc tcagttgtac   2220
aaggagaaag gctacgacat caacctcaaa aaactggagg aaaaggggtt tagttccgtt   2280
acaaagttgt gcgccggaat tgacgagacg gccccagata aacgaaagga cgttgagaaa   2340
gaaatggcgg aacgagcgaa agagtccatc gactctcttg agtcagctaa tcctaaattg   2400
tatgcaaact atattaaata ctctgatgag aagaaagcgg aggaattcac acgacagatc   2460
aatcgggaga aagcaaaaac ggcactgaat gcatacttga ggaacacgaa gtggaacgtg   2520
attatcagag aggacctgtt gaggatcgac aataaaacgt gtaccctgtt tagaaataaa   2580
gccgttcatc tcgaggtggc ccggtacgtg cacgcctata ttaatgacat tgcggaagtt   2640
aattcttatt ttcaactgta ccattacatc atgcagagaa ttatcatgaa tgaacgatac   2700
gaaaagagca gcggcaaagt gtctgagtat tttgatgccg tcaatgatga gaaaaaatac   2760
aatgacaggc tgttgaagct gctgtgcgta ccatttggtt attgtattcc tcggtttaaa   2820
aatcttagta ttgaggctct tttgatcgg aatgaagccg caaagtttga taaggagaag   2880
```

aaaaaggtat ccggtaacag c 2901

<210> SEQ ID NO 18
<211> LENGTH: 2388
<212> TYPE: DNA
<213> ORGANISM: Artificial Sequence
<220> FEATURE:
<223> OTHER INFORMATION: Synthetic: CasM DNA sequence from Ruminococcus sp., isolate 2789STDY5834894, modified for expression in human cells

<400> SEQUENCE: 18
atggaaatta atactagtaa tcccactcat aggtccggtg aatcttctag cgtacgagga 60
gacatgcttg gtctcaaatc agagctcgag aagagatttt tcgggaaaac atttgatgat 120
aatatccaca ttcaacttat atataatatc cttgatatcg agaagatcct tgcagtctat 180
gtgactaata ttgtctacgc acttaacaat atgctcggtg taaaaggctc agagtcctat 240
gacgacttta tgggctatct ttcagcacag aatacgtact acatatttac acatcccgac 300
aagagcaact tgagcgataa agtgaagggc aatattaaga aatctcttag taaattcaat 360
gaccttctga agacgaagcg acttggctat tttgggctgg aggagcccaa aaccaaagat 420
aagcgagtgt ctgaagctta taaaaaacga gtgtatcaca tgctggctat agtgggtcaa 480
attcgccagt cagtctttca cgacaagtcc aacgaattgg atgagtactt gtattccttt 540
atagacatca tcgatagcga gtatcgagac acattggact acctggttga tgaacgattt 600
gattccatta acaaaggatt cgttcagggg aataaggtaa acatctcctt gcttatcgac 660
atgatgaagg gctacgaggc tgatgatata ataagattgt actatgactt tattgtcctc 720
aagtctcaaa agaatctggg tttcagtata aaaaaattgc gggagaagat gctcgacgag 780
tatggattta ggtttaagga caagcagtat gatagcgttc gctctaagat gtataaactt 840
atggactttc ttctgttctg taactactat cggaacgacg tagtcgcagg ggaggcactg 900
gttaggaaac tgaggtttag catgaccgac gacgagaaag aaggtattta tgcggacgaa 960
gcggagaagc tttggggaaa gtttaggaat gactttgaga acatcgccga tcacatgaac 1020
ggtgatgtga taaaggagct cgggaaggcg gatatggact ttgacgagaa aatactggat 1080
tctgaaaaga agaatgcaag tgacctcctt tacttcagca aaatgatcta catgttgacg 1140
tattttttgg atggtaaaga gatcaacgat ctgcttacaa cgcttatttc taaatttgat 1200
aacataaagg agtttttgaa gatcatgaaa tcctccgccg tggatgtaga gtgtgagctg 1260
accgcgggct ataaactgtt taacgattct caacggataa cgaacgagct cttcatagtg 1320
aagaacatcg cttccatgcg caagccggcg gcttcagcca aattgactat gttccgcgat 1380
gcgctgacaa tactcgggat tgacgataaa attacggacg accgaatatc agaaattctt 1440
aaattgaagg aaaagggcaa gggcatccat ggcctgcgga acttcatcac gaacaacgtt 1500
atcgagtcta gtcggtttgt ttatcttata aaatacgcga atgcgcagaa aattcgggag 1560
gtcgcaaaaa atgaaaaggt ggtaatgttt gtgctcgggg ggattcctga cacacagatt 1620
gagcggtact ataaaagttg cgttgagttc cctgacatga attcttcact cgaagccaag 1680
tgcagtgagc tggcacggat gatcaagaat atctccttcg atgattttaa gaacgtaaaa 1740
caacaagcta aaggacgcga aaatgtggcg aaagagaggg ccaaggcagt catcggtctc 1800
taccttacag ttatgtacct ccttgtgaaa aaccttgtaa acgtcaatgc tcggtatgta 1860
atagcaatcc actgtttgga gagagatttc ggcctctata aggagatcat cccggagctc 1920

```
gcttcaaaaa acttgaaaaa tgattatcgc attctttctc aaactctttg tgaactttgt   1980

gatgacaggg acgagagtcc taacctgttc ttgaagaaga acaaaagact gcggaaatgt   2040

gtggaggtcg atataaacaa tgcggattct agcatgaccc ggaaataccg gaattgcatt   2100

gcacacctta cagtggtacg cgagctcaag gaatacatcg gtgatatacg caccgtcgac   2160

tcctactttt ctatctacca ctatgttatg caacggtgta tcaccaaaag ggaggatgat   2220

actaagcaag aagaaaaaat caagtatgaa gatgacctgc ttaagaacca tggatacacg   2280

aaagattttg tgaaagccct taatagtcca ttcgggtaca atattccgcg attcaaaaac   2340

ctttccatcg aacaactctt cgatcgaaat gagtacctta ccgagaaa                2388
```

<210> SEQ ID NO 19
<211> LENGTH: 2862
<212> TYPE: DNA
<213> ORGANISM: Artificial Sequence
<220> FEATURE:
<223> OTHER INFORMATION: Synthetic: CasM DNA sequence from Eubacterium siraeum, modified for expression in Zea mays cells

<400> SEQUENCE: 19

```
atgggtaaaa agatacatgc acgggacttg cgcgagcaga ggaagacgga ccggaccgaa     60

aaattcgcag accaaaacaa aaaaagagag gctgaacggg cagtccccaa gaaagatgca    120

gccgtgtcag tcaaatcggt ctcaagcgtc tcatccaaaa aggacaatgt taccaaatct    180

atggcgaaag ccgccggagt caagtctgtt ttcgctgttg gcaatacggt ctacatgaca    240

tccttcgggc gcgggaatga tgcggttctt gaacagaaaa ttgttgatac ttcacacgaa    300

ccactcaaca ttgatgaccc agcttatcaa ctcaatgtgg ttacgatgaa tgggtattca    360

gtgaccgggc ataggggaga aacggtctcg gcagtcacag acaatccctt gagaagattc    420

aacggcagaa aaaaggacga gccggaacaa tcagtgccga ctgacatgtt gtgtctcaaa    480

ccaaccctgg aaaagaaatt ttttggcaaa gagttcgacg acaatatcca cattcagttg    540

atatataaca tcctggatat tgagaaaatt ttggccgtct actcgaccaa cgccatatac    600

gctctcaaca acatgtcagc agatgagaac attgagaact cagacttttt tatgaaacgc    660

accacggatg agaccttcga tgacttcgag aaaaagaaag agtccacgaa cagcagagag    720

aaagctgatt tcgatgcgtt cgaaaagttc atcggcaact acaggctggc gtatttcgca    780

gatgcatttt atgtcaacaa gaaaaatccc aagggtaagg ccaaaaaatgt cctccgcgaa    840

gacaaggaac tctactcagt gctcacattg atcggaaagt tgcggcattg gtgcgttcat    900

tccgaggagg gtcgggcaga gttctggctt tataaactgg acgaattgaa ggacgatttt    960

aagaacgtgc ttgatgtcgt ctacaataga ccagtcgaag aaattaataa ccgctttatt   1020

gaaaacaata aggtcaacat acaaatcttg ggatcggtct ataaaaacac cgacatcgca   1080

gagctggtca gaagctacta cgagtttctg ataactaaaa agtacaagaa catgggcttc   1140

tcaataaaaa aactgcgcga atcaatgctt gaaggtaagg gatatgcgga taaagaatac   1200

gattctgtta gaaacaagct ctaccagatg actgacttca ttctctatac cggttatata   1260

aacgaagata gcgacagggc tgatgacctg gtcaacacac tgcggagctc cctgaaagag   1320

gacgataaga ccacagtgta ctgtaaggag gccgattacc tgtggaagaa ataccgcgag   1380

tctattaggg aggtcgcgga cgccctggac ggtgacaata ttaaaaaact ctctaaaagc   1440

aatatcgaga tacaagaaga caaactgcgc aagtgtttta tatcttatgc ggattcagtc   1500

tcggagttca cgaaactgat atatctcctg acacgctttc tgagcgggaa ggagattaat   1560
```

```
gacttggtga caactttgat taacaagttc gacaacataa ggagctttct tgaaatcatg   1620
gatgagctgg gcctcgatag aacgttcacc gcggagtact cgttcttcga gggttcaaca   1680
aaatatcttg cggaactcgt tgaattgaat tcgttcgtga aaagctgttc ttttgatata   1740
aatgccaaaa gaacaatgta ccgggacgcg cttgatatcc tgggcataga atcggataaa   1800
accgaggaag atatcgaaaa gatgatagac aatatcctgc aaatcgacgc aaatggtgac   1860
aagaagctta aaaagaataa cggcttgcgc aattttatcg cttcgaatgt catcgattcg   1920
aacaggttca aatatctggt tcggtacggt aacccgaaga agattagaga aacagctaag   1980
tgtaagccag cggtcagatt tgtcttgaac gaaataccgg atgcgcagat cgaaagatat   2040
tacgaagcct gctgccctaa gaacaccgca ttgtgtagcg cgaataagcg gcgggagaaa   2100
ctcgctgata tgatagcgga gattaaattc gaaaatttct cggacgcggg caactaccaa   2160
aaagctaacg ttacttcccg cacttcggag gcggagatta aacggaagaa tcaagcgata   2220
attagacttt atctgaccgt catgtacatt atgcttaaga atctcgtcaa cgttaatgct   2280
agatatgtca tcgcctttca ctgcgtggaa cgcgatacta aactgtatgc cgaatcgggt   2340
cttgaagtcg ggaacataga aaaaaataag accaacctta ctatggccgt gatgggtgtc   2400
aaactggaga acggcattat caaaactgaa tttgataaaa gcttcgccga aaacgcagcg   2460
aatcgctatc tgcggaacgc aagatggtat aagcttatac tcgataatct taagaagtcg   2520
gaaagggccg tggtcaacga gttccggaat accgtttgcc acttgaacgc gatccggaat   2580
attaacatca atatcaaaga aattaaagaa gtcgaaaact actttgcgct ctatcattac   2640
ttgatacaga agcatctcga gaatcgcttc gccgataaaa aggtggagag ggacacaggt   2700
gactttattt ccaagctcga agagcataaa acctattgca aggattttgt taaagcatat   2760
tgtacgccat tcggttataa tcttgttagg tacaagaatc tgacaatcga cggcttgttc   2820
gataaaaatt atccgggcaa ggacgatagc gatgagcaga ag                      2862
```

```
<210> SEQ ID NO 20
<211> LENGTH: 2757
<212> TYPE: DNA
<213> ORGANISM: Artificial Sequence
<220> FEATURE:
<223> OTHER INFORMATION: Synthetic: CasM DNA sequence from Ruminococcus
      sp., isolate 2789STDY5834971, modified for expression in Zea mays
      cells

<400> SEQUENCE: 20
```

```
atggccaaga agaataaaat gaagccacgc gagctgaggg aggctcaaaa aaaagcccgg     60
cagcttaagg ctgcggagat caataataat gctgcccccg ctatcgcagc aatgcccgcc    120
gcagaggtca ttgcgccggc cgccgaaaag aaaaaaagct cagtgaaggc tgcaggaatg    180
aagtcaattt tggttagcga gaataagatg tatattacct cgtttggcaa gggaaacagc    240
gccgtgctgg aatacgaagt tgataacaat gactataacc agacacagct ttcatcgaag    300
gataattcca acatccaatt ggggggcgtg aacgaagtta atataacgtt ttcttcaaaa    360
catggtttcg aatctggagt cgaaataaat acgtctaatc cgactcatag gtccggtgag    420
tccagccctg tccgggggga catgctcggt ctcaagtccg aactcgaaaa acggtttttc    480
ggtaagactt tcgatgataa tattcatatt cagcttatat acaatatctt ggatatagag    540
aaaattctgg cggtgtatgt cacaaatata gtgtatgctc tgaataatat gctcggtgtg    600
aaaggttcgg agagccatga tgatttcatc ggatatcttt ctacaaataa catctacgat    660
gtgtttatag acccggataa ctcttctctg agcgatgaca aaaaagccaa tgtgagaaag    720
```

```
agcctttcga agtttaacgc cctgctcaaa acaaaacgct tgggctattt tggattggaa    780
gaaccgaaga caaaagacaa tcgggtttcg caggcctaca aaaagcgcgt gtatcacatg    840
cttgcaatcg tcgggcaaat caggcaatgt gtctttcacg acaaaagcgg ggcaaaacgc    900
ttcgacctgt actcttttat taataacata gatccggaat atagggatac acttgattac    960
ctggtcgaag aacgccttaa atccataaac aaagacttta tagaagacaa taaagtgaat   1020
atttctttgc tgatcgacat gatgaagggc tacgaagcgg acgacataat aaggttgtat   1080
tatgacttta tcgttcttaa gtcccagaaa aatctggggt tttcaattaa aaagcttagg   1140
gaaaaaatgt tggatgagta tggtttccgg ttcaaagata agcaatacga ttcagtcaga   1200
tccaaaatgt acaagctcat ggactttctt ctgttctgta attactaccg caatgacata   1260
gcagctggtg aaagcctcgt gaggaagttg agattttcca tgaccgacga tgagaaagag   1320
ggtatttatg cagatgaggc agccaagctc tggggaaagt ttagaaatga cttcgagaat   1380
atcgccgacc atatgaacgg ggatgtcatc aaagagctgg gaaaggcgga tatggacttc   1440
gacgagaaaa tactggattc tgaaaaaaaa aatgcgagcg acctccttta cttctccaag   1500
atgatctata tgcttactta tttcctcgat ggaaaggaga taaacgacct gctgactaca   1560
cttatatcga aattcgacaa tatcaaagaa ttcctcaaaa taatgaagtc ttcagcggtt   1620
gatgtggagt gcgaattgac cgctggttac aagctgttta acgattcgca gcggatcacc   1680
aatgaattgt ttattgtcaa aaatatcgcc tctatgagaa aacctgctgc atctgcgaag   1740
ctcaccatgt tcagggatgc actcaccata ttgggcattg acgataagat caccgatgac   1800
aggatttctg gtatattgaa gcttaaggaa aagggtaagg gaatacatgg tctcagaaac   1860
tttatcacta acaacgtcat cgaatcctcg cgctttgtct acctgataaa atatgctaac   1920
gctcagaaga tccgggaggt tgcgaagaat gaaaaagtcg tcatgttcgt tttggggggg   1980
attcccgata cgcaaattga gaggtattat aagtcgtgtg tcgaatttcc tgacatgaac   2040
tcatcacttg gcgtcaaacg ctccgaattg gcacggatga tcaaaaacat ttcattcgac   2100
gacttcaaaa acgtcaaaca gcaagctaag ggccgcgaga acgttgcaaa ggaaagggca   2160
aaggcagtca taggacttta ccttactgtt atgtacctgc tcgttaagaa cctggtcaat   2220
gtcaacgcgc ggtatgtcat tgccattcat tgcttggaac gggacttcgg actttacaaa   2280
gagattatcc ctgaactggc gtcgaagaac ttgaaaaacg actaccggat tctgagccag   2340
acgctctgtg aactttgcga caagagccct aaccttttc ttaaaaaaaa cgagcggctt   2400
aggaaatgtg tggaggtgga tattaacaac gctgatagct cgatgactcg gaagtaccgg   2460
aattgtattg cgcacctgac agtcgttcgg gaactgaagg aatacatagg tgatatatgc   2520
acggttgact catacttttc catatatcat tacgttatgc aaagatgcat aacgaaaaga   2580
gagaacgata ctaaacagga ggaaaagata aagtatgaag atgacttgct taaaaatcac   2640
ggctacacta aagactttgt taaagcactc aatagccctt ttggctacaa catacctaga   2700
ttcaaaaatc tgtcaattga gcagcttttt gacagaaacg aatatctgac agaaaag      2757
```

<210> SEQ ID NO 21
<211> LENGTH: 2754
<212> TYPE: DNA
<213> ORGANISM: Artificial Sequence
<220> FEATURE:
<223> OTHER INFORMATION: Synthetic: CasM DNA sequence from Ruminococcus bicirculans, modified for expression in Zea mays cells

<400> SEQUENCE: 21

```
atggcaaaaa agaataagat gaagccgcgg gagcttcgcg aggcccagaa aaaggcgcgg     60
cagcttaaag cggctgaaat taataataat gctgtcccag cgatagccgc aatgcctgcg    120
gctgaagcgg cggctcccgc ggccgagaag aaaaaatcat ctgttaaagc cgccgggatg    180
aaaagcatcc tcgtgtcgga gaataagatg tacattacgt cgttcggtaa ggggaattcg    240
gcggtccttg aatacgaagt tgataacaat gattataaca aaactcagct ttccagcaaa    300
gacaattcga atattgagct ctgtgacgtc gggaaagtga atataacgtt ttcttcccgg    360
aggggtttcg agagcggtgt ggaaatcaat acaagcaatc caactcatcg gtcgggcgag    420
tcctcctctg tgcggggcga catgttgggg cttaagtcgg aacttgaaaa gcggtttttt    480
ggaaaaaatt tcgacgacaa tatacacatc caacttatct acaacatact ggacatagag    540
aagattttgg cagtgtatgt gaccaatata gtctacgccc tcaacaacat gctgggtgag    600
ggcgacgaat caaattacga ctttatgggt tatctgtcaa cttttaacac atataaggtc    660
tttacaaacc cgaatgggtc tacattgtcc gacgataaga aagaaaatat aaggaagtcc    720
ctttctaaat tcaacgcgct ccttaaaaca aagagattgg gctacttcgg ccttgaagag    780
cccaagacaa aggacactcg ggcctcagaa gcttataaga agagagtcta ccacatgctc    840
gccatagtgg gccaaattag gcagtgcgtc ttccacgaca agtctggtgc aaagagattt    900
gatctgtact cattcattaa taatatcgat ccagagtacc gcgagacatt ggattatctt    960
gtcgacgaaa ggttcgattc tatcaataag ggttttatcc aaggtaataa agtcaacatc   1020
tccctcctga ttgacatgat gaaaggctat gaagccgatg acatcattag gctgtactac   1080
gactttatag ttctcaaatc acagaaaaac ctggggttct ctattaagaa gcttagagag   1140
aaaatgttgg acgaatacgg tttccgcttc aaagataagc aatacgactc agtgaggtct   1200
aaaatgtaca aactcatgga ttttcttctg ttctgtaact actatcggaa tgatatcgca   1260
gccggtgaat ctctcgtcag aaaactcagg ttttcgatga cggacgacga gaaagaaggg   1320
atatacgcgg acgaagccgc taagttgtgg ggaaaatttc gcaacgattt tgaaaatata   1380
gctgatcaca tgaatgggga cgttataaaa gagcttggaa aagccgacat ggattttgac   1440
gagaagatat tggactctga gaagaagaat gcgtcagact tgctttattt ttcaaaaatg   1500
atatatatgc tcacgtactt cttggacggg aaggagataa acgatctgtt gacgacgctg   1560
attagcaaat tcgacaatat caaagagttc ctgaaaataa tgaagagctc agctgtcgat   1620
gtcgagtgtg aactgacggc tggctacaaa ttgtttaacg attcgcaacg cattacgaat   1680
gagctgttta tagtgaaaaa cattgcatct atgcgcaaac cagctgccag cgctaagctt   1740
acaatgtttc gggacgctct gacgattttg ggcatcgacg ataaaattac tgacgatagg   1800
atcagcgaga tactgaaatt gaaagagaaa gggaaaggga ttcacggcct cagaaacttt   1860
attactaata atgtcatcga atcgtcaagg tttgtgtact tgattaaata tgcaaatgca   1920
caaaagattc gggaagtcgc taaaaatgaa aaggttgtta tgtttgtcct cgggggggata   1980
cccgataccc aaattgagcg gtattacaag agctgcgtgg agtttccaga catgaactcg   2040
tctctggggg tgaaacggtc cgaactcgct cgcatgatta aaaacatatc cttcgacgac   2100
tttaagaacg tgaagcaaca agctaagggg cgcgagaacg tcgcgaaaga aagggccaaa   2160
gcggttatcg gtctgtacct tacggtcatg tacttgttgg tgaaaaacct tgtgaatgtg   2220
aacgctcggt acgtgatcgc gatccactgt ctggagcgcg attttgggct gtataaagag   2280
atcatcccgg agctggcttc caaaaacctg aaaaatgact accgcatact gtcccagaca   2340
```

```
ctttgcgagt tgtgcgacaa gagcccgaat ctgtttctga aaaaaaacga gcgcctgcgg   2400

aagtgcgttg aggttgatat aaacaacgcc gactcctcaa tgacgagaaa gtacagaaat   2460

tgcatagctc atttgaccgt cgtcagggag ctcaaagaat acatagggga catttgcact   2520

gtggactcgt atttttccat ctaccactac gtgatgcaaa ggtgtatcac taagcgggaa   2580

aacgatacca aacaagagga gaagatcaag tacgaggatg accttttgaa aaatcacggt   2640

tatacgaagg acttcgtgaa ggcattgaac tctccgttcg gttataatat ccctaggttc   2700

aagaatttgt ccatagaaca gctcttcgat cgcaatgagt atcttacaga aaaa         2754
```

```
<210> SEQ ID NO 22
<211> LENGTH: 2766
<212> TYPE: DNA
<213> ORGANISM: Artificial Sequence
<220> FEATURE:
<223> OTHER INFORMATION: Synthetic: CasM DNA sequence from Ruminococcus
      sp., isolate 2789STDY5608892, modified for expression in Zea mays
      cells

<400> SEQUENCE: 22
```

```
atggcaaaga agaacaaaat gaagccacgc gaactgagag aagctcaaaa gaaggcgaga     60

cagcttaaag ctgcggagat caataataac gcagctccgg ccattgccgc aatgcccgcc    120

gctgaagtga tagctccagt tgcggagaag aagaaatctt cagttaaagc agctggaatg    180

aaatccattc tcgtctcgga gaataaaatg tatattacgt ccttcggaaa aggaaattcc    240

gcggttctcg agtatgaggt ggacaacaac gactacaaca agactcaact gtcgagcaaa    300

gacaactcaa atattgaact cggggacgtt aacgaagtca atataacatt ttcctcaaag    360

catggattcg gcagcggtgt cgaaattaat acttcaaatc cgacacatag gtctggagaa    420

tcgtcgcctg tcaggggcga tatgcttggt ttgaagtccg aactggagaa gcggttcttt    480

gggaagactt ttgacgataa cattcatata caactgatct acaacatact ggatatcgag    540

aaaatcctcg cagtgtatgt cactaatatt gtttacgcct tgaacaacat gctgggcatt    600

aaagactctg aatcatatga tgacttcatg gggtatctca gcgccaggaa cacatatgaa    660

gtgtttacgc acccggacaa gtctaatctg tctgataagg tcaagggtaa tattaagaag    720

tcactcagca agttcaacga cttgcttaag acgaagcgcc tcggctactt tgggcttgag    780

gaaccaaaaa cgaaggacac cagagcctct gaggcttata agaaaagagt gtatcatatg    840

ctcgcgatag tcggtcaaat tagacagtgt gttttccacg ataaatctgg agcaaagagg    900

ttcgaccttt actcatttat aaacaatatc gaccctgaat atagagacac gctggattac    960

cttgtggagg agcggctgaa gtcgattaat aaggacttta tagaaggcaa taaagtcaat   1020

atctctctcc tcatagacat gatgaaaggt tatgaagccg acgacataat aaggctttat   1080

tacgatttta tcgttcttaa gtcacagaaa aatttgggtt tttcgatcaa aaaacttcgg   1140

gaaaagatgt tggaagaata cgggttcaga ttcaaagaca agcagtacga tagcgtgagg   1200

tcaaaaatgt acaagctgat ggacttcctg ctgttttgca attactacag aaatgatgtc   1260

gccgccgggg aggcgttggt tcgcaagctt cgcttttcaa tgacagatga tgaaaaagag   1320

gggatttatg cggatgaggc cgccaagctc tggggcaaat ttaggaatga ttttgaaaac   1380

attgctgatc atatgaatgg cgatgtgatt aaggaactgg gcaaagcaga catggatttt   1440

gatgaaaaga tcctcgactc agaaaagaag aatgccagcg atttgttgta tttctcaaag   1500

atgatctaca tgctgacgta ttttttggac ggtaaagaga taaacgatct gctcacgacg   1560

ttgatttcta aattcgacaa tattaaggag tttcttaaga ttatgaagtc ttcggcagtt   1620
```

```
gacgttgaat gcgaactgac tgctggctac aaactcttca acgactcaca acgcatcacc   1680

aatgaacttt ttatcgttaa aaatatagcc agcatgcgga agccggcagc ttctgccaag   1740

ctcaccatgt ttcgcgatgc tttgaccatc ttgggcattg atgacaatat tacagatgat   1800

cggatatctg agatactcaa acttaaggag aaaggcaagg gcatacatgg ccttcggaat   1860

ttcattacta ataacgtgat agaaagcagc cgctttgttt acctcattaa atacgcaaat   1920

gcccaaaaaa taagggaagt tgctaaaaac gaaaaagtgg tgatgttcgt gcttggagga   1980

atacctgaca cacaaatcga gcgctattac aagtcgtgtg tcgaattccc cgatatgaat   2040

tcttccttgg aggctaaacg gtcagagctc gccagaatga tcaagaacat ttcctttgat   2100

gacttcaaaa atgtgaaaca gcaagctaag ggtcgcgaaa acgtcgctaa agagagggcc   2160

aaggctgtta tcggcctcta tcttacggtg atgtatttgt tggtgaagaa cctcgttaat   2220

gtcaacgcca ggtatgttat agcaatacat tgcctcgaac gggattttgg tctttacaaa   2280

gagattatcc cagaattggc gtccaagaac ctcaagaacg actatcgcat attgtctcag   2340

acgctttgtg aattgtgcga tgaccgcaat gagtcttcca acttgttctt gaaaaagaat   2400

aagcggttgc gcaagtgcgt tgaagtggac ataaataacg ccgactcttc aatgactcgc   2460

aagtacagaa attgtatagc gcacctcact gtcgtgcggg aattgaaaga atacatcgga   2520

gacataagga ccgtcgatag ctattttagc atttaccact atgtcatgca aaggtgtata   2580

actaaacgcg gtgatgatac caaacaggaa gaaaagatca aatacgaaga cgatctgctc   2640

aagaatcatg gctacaccaa agatttcgtt aaagcattga atagcccttt cgggtataat   2700

attcccagat ttaaaaacct cagcattgaa caactgttcg accgcaacga atacctcacg   2760

gaaaag                                                              2766
```

<210> SEQ ID NO 23
<211> LENGTH: 2766
<212> TYPE: DNA
<213> ORGANISM: Artificial Sequence
<220> FEATURE:
<223> OTHER INFORMATION: Synthetic: CasM DNA sequence from Ruminococcus sp. CAG:57, modified for expression in Zea mays cells

<400> SEQUENCE: 23

```
atggcgaaga agaacaaaat gaaaccacgc gaactcagag aggcacaaaa gaaagcccgg     60

cagttgaagg ccgccgagat aaacaacaac gcggcaccgg caattgcggc aatgccagct    120

gcggaggtca tcgctcccgt cgccgagaag aagaagagct cggtcaaggc agccgggatg    180

aaatctattc tggtgtcaga gaataagatg tacattacgt ctttcggcaa gggaaatagc    240

gcagtcttgg agtatgaagt tgacaacaac gactataaca aaacacaact ttctagcaaa    300

gacaactcga atatagaatt gggagatgtc aatgaggtca acataacctt tagctccaag    360

catggctttg gctcgggtgt ggaaattaac acgtccaatc ctacccatcg gtcgggcgag    420

tcgtcgccag ttaggggga catgctgggt ctcaagagcg agttggagaa aagatttttc    480

ggtaagacct tcgatgataa cattcatatc caacttatct ataacatctt ggacatagaa    540

aaaatacttg cagtgtacgt cactaatatc gtttatgcct tgaataatat gttgggaatt    600

aaggactctg aatcctatga cgattttatg ggctatctga gcgctcggaa tacctacgaa    660

gtgtttactc atccagataa aagcaacctt agcgataagg tcaagggcaa cataaaaaag    720

tccctgtcaa agtttaacga tcttctcaaa accaaacggc tgggctactt tggactcgag    780

gagcctaaga cgaaagacac gcgggcatct gaggcataca agaaaagggt ttatcatatg    840
```

```
ctggcaatag tcggtcaaat caggcagtgc gtctttcacg acaagagcgg agcgaagcgg    900

tttgaccttt attctttcat caataacatc gatccggaat accgcgacac attggattac    960

ctggtcgagg aaaggttgaa gtccataaac aaggacttca tcgagggaaa caaggttaac   1020

atttcacttc tgattgacat gatgaaaggc tacgaggctg acgatatcat aagactttat   1080

tatgacttta tcgtgctgaa atcgcagaaa aatttgggat tttctatcaa aaagctcaga   1140

gagaagatgc ttgaggagta tggatttaga tttaaggaca agcagtacga ttctgtgcgc   1200

tctaaaatgt acaagctcat ggattttctc ctcttttgca attactacag gaacgatgtt   1260

gccgcaggcg aggctcttgt ccggaagctc cgcttctcca tgacggacga cgaaaaggaa   1320

ggcatatacg cggatgaggc agcgaaattg tggggtaagt tcaggaatga ttttgaaaat   1380

atagctgatc acatgaacgg tgacgtcatc aaggagctgg ggaaagccga tatggatttt   1440

gatgagaaaa tcctggattc ggaaaagaaa aatgcgagcg acttgctcta ctttagcaaa   1500

atgatttata tgttgaccta tttcctcgat ggcaaagaga tcaacgattt gcttacgact   1560

ctgataagca aattcgataa tataaaagag tttttgaaaa taatgaagtc ctcagcggtt   1620

gatgttgaat gcgaactgac agccggctat aagcttttca atgattcaca gaggattacc   1680

aacgaacttt ttatagtgaa aaacatcgcc tcaatgagga aacccgccgc gagcgcgaag   1740

ttgacaatgt ttagggacgc tctgacgatt ttgggaatcg acgataatat cactgacgac   1800

aggatttcgg agatcctcaa attgaaagag aagggcaaag ggatccacgg gttgagaaat   1860

tttataacca ataacgttat agaatcatcg aggtttgtgt atctgatcaa atacgcgaat   1920

gctcaaaaga tcagggaagt ggcaaaggac gagaaggttg tcatgttcgt cctgggtggg   1980

atccctgaca cccagataga aagatactat aagtcctgcg tggaattccc tgatatgaat   2040

tcttccctcg aggctaaaag atctgagttg gcacggatga tcaagaatat ttcgtttgac   2100

gatttcaaaa acgtgaagca acaagctaaa gggcgggaaa acgttgccaa ggaacgggct   2160

aaagctgtca ttggccttta cctcactgtg atgtatttgc tcgttaagaa tctcgtgaac   2220

gttaacgcaa gatacgtgat cgctatccac tgcttggagc gcgatttcgg actgtacaag   2280

gagattatac cagagcttgc ttccaagaat cttaagaatg actatcgcat attgtcccaa   2340

actctttgcg agttgtgcga cgatcggaac gagtcttcca atctgttcct taagaaaaat   2400

aaaaggctgc ggaaatgcgt cgaagtcgac attaacaatg cggattcttc tatgacgaga   2460

aagtaccgca actgcatcgc ccatctcacg gttgtcaggg agctcaagga atacatagga   2520

gacattagaa cggtggactc atatttttca atataccatt atgttatgca aaggtgtatt   2580

acaaaacggg ggatgacac aaaacaagag gaaaagatta aatatgaaga cgatttgctt   2640

aagaaccatg gttacacgaa agatttcgtt aaagcgctta attcgccatt tggttataat   2700

attccgagat tcaaaaattt gagcatagag cagcttttcg atagaaatga atacttgacc   2760

gagaag                                                              2766
```

```
<210> SEQ ID NO 24
<211> LENGTH: 2799
<212> TYPE: DNA
<213> ORGANISM: Artificial Sequence
<220> FEATURE:
<223> OTHER INFORMATION: Synthetic: CasM DNA sequence from Ruminococcus
      flavefaciens FD-1, modified for expression in Zea mays cells

<400> SEQUENCE: 24

atgaaaaaaa agatgagctt gcgggaaaaa agagaggcag aaaagcaggc caagaaagct     60
```

```
gcatacagcg ctgcgtctaa gaacactgat tccaaaccag cggagaaaaa agcggagact    120
ccaaaacctg ccgaaattat atctgataac tcacgcaata agacggcggt caaggcagcg    180
ggactcaagt cgacgatcat atcaggcgat aaattgtata tgaccagctt tggcaagggc    240
aatgcagctg tgatagaaca aaagatagac atcaatgact attcttttag cgcaatgaag    300
gacaccccaa gccttgaagt cgacaaggca gaatctaagg aaatatcctt ttcgtcccat    360
catccctttg tgaagaacga caagttgacg acatataatc ctctttacgg tgggaaggat    420
aacccagaga agccggttgg gcgcgatatg ttggggttga aagataaact tgaggaacgg    480
tactttggtt gtacattcaa tgacaacctc cacattcaga tcatttacaa tattttggat    540
attgagaaga tcctcgctgt tcattccgca aatattacga cagctcttga tcatatggtg    600
gatgaggacg atgagaaata ccttaactct gactatatcg gctacatgaa cacgatcaac    660
acctacgacg tcttcatgga tccctctaag aattcctctt tgtcgccaaa agacaggaaa    720
aacatcgaca attcgagggc gaagtttgag aagctcctct ctacaaaaag gttggggtac    780
tttgggttcg actatgacgc gaacgggaaa gacaaaaaga agaatgagga aattaaaaag    840
cggctttacc acttgacggc atttgcaggc cagctgaggc agtggtcctt ccactcagca    900
ggaaactatc ccagaacctg gttgtataaa ttggactccc tggataaaga gtatctggac    960
acgctcgacc actatttcga taagaggttt aatgatataa atgacgattt tgtcactaaa   1020
aacgcaacga acctgtatat actgaaggag gttttccctg aggctaactt taaagatatt   1080
gcggacttgt attatgactt tattgtcatc aagtcacaca agaacatggg attctcgatc   1140
aagaaacttc gggaaaaaat gctcgagtgc gatggagctg accgcatcaa agaacaggat   1200
atggattctg tccgctccaa gctctacaag ctcattgatt tttgcatatt caagtattac   1260
catgagttcc cagagctcag cgagaagaac gtcgacatcc tgagggctgc cgtgagcgat   1320
actaagaagg acaatctcta ctcagatgaa gctgctcggt tgtggtcaat tttcaaggaa   1380
aaatttctcg gattttgtga caaaattgtt gtctgggtga ccggagagca tgagaaagat   1440
atcacgtctg tcattgataa agacgcctac aggaacagaa gcaatgtctc gtatttttca   1500
aagctcatgt acgcaatgtg tttttttctt gatgggaagg agataaacga ccttctgact   1560
accttgatta acaagtttga caatatcgcc aaccagatta agacagcaaa ggaattgggg   1620
atcaacacgg cgttcgttaa aaactatgac ttcttcaacc attctgagaa atatgtcgac   1680
gaattgaaca tagtgaaaaa tatcgctcgg atgaaaaaac cctcttcaaa cgcgaaaaaa   1740
gctatgtacc atgacgccct tactattctt ggcattcctg aagatatgga cgaaaaggct   1800
ttggatgaag aactcgacct tatactcgaa aaaaagaccg atcccgtcac aggtaaaccg   1860
ctgaagggta agaatccttt gcgcaatttt atagctaaca acgttataga gaactctcgg   1920
ttcatctacc ttataaaatt ctgtaatccg gaaaacgtga gaaaaattgt gaataacact   1980
aaggtgacag agttcgtgct gaaacgcata ccagatgccc aaattgagag gtattacaaa   2040
tcttgtacgg atagcgagat gaaccctccg actgaaaaaa aaattaccga gttggctggt   2100
aaacttaaag acatgaactt cggcaacttc cggaatgtcc ggcagtctgc aaaagagaat   2160
atggagaaag agaggtttaa agccgtcatt ggactgtacc ttaccgttgt gtacagggtg   2220
gttaagaatc tcgtcgacgt gaactcaaga tacattatgg cattccattc actcgagaga   2280
gactcccaat tgtataacgt ctcagtcgac aacgattatc tggcactgac cgatacactg   2340
gtcaaagagg gtgacaactc acgctcacgg tacttggccg ggaataaaag attgcgggat   2400
```

tgtgtcaaac aggatattga taacgcaaaa aagtggtttg ttagcgataa atataattcc 2460
ataaccaagt ataggaacaa tgtggcgcac ctgaccgccg ttcggaactg tgccgaattt 2520
ataggcgaca taacgaagat tgactcctac ttcgccctct accactacct tatccagcgg 2580
caactcgcca aggtctcgga tcatgagagg tcaggttttg accgcaatta tccacagtac 2640
gcaccactgt tcaagtggca tacttatgtg aaagatgttg tgaaagcgct gaatgcacct 2700
ttcggttata atattccaag gttcaagaat ctttccattg acgcactctt cgaccggaat 2760
gagatcaaga agaatgatgg agaaaagaaa tctgacgac 2799

<210> SEQ ID NO 25
<211> LENGTH: 2832
<212> TYPE: DNA
<213> ORGANISM: Artificial Sequence
<220> FEATURE:
<223> OTHER INFORMATION: Synthetic: CasM DNA sequence from Ruminococcus albus strain KH2T6, modified for expression in Zea mays cells

<400> SEQUENCE: 25
atggccaaaa aatctaaagg catgtccctg agggaaaaac gcgagctgga gaagcaaaag 60
cggatccaga aagctgcagt gaactctgtc aacgacactc ccgaaaagac cgaggaagca 120
aacgttgttt ctgtcaatgt gagaacgtct gcggaaaaca agcacagcaa gaagagcgct 180
gctaaagctc ttggacttaa atcggggttg gttattgggg acgaattgta cctcacatca 240
tttggcagag gaaatgaggc gaaactcgaa aagaaaataa gcggggatac cgtggaaaaa 300
ttgggcattg gtgctttcga agtggcggaa agggatgagt ctacactcac acttgaatct 360
gggcgcatta aagataaaac tgccagaccg aaagatccca gacatattac agtggacaca 420
caagggaagt ttaaggaaga tatgctcgga atacgctctg tgcttgagaa aaagatattt 480
ggtaagacct tcgatgacaa catccatgtc caacttgcgt acaatatcct cgatgtcgag 540
aagatcatgg cacagtacgt ctctgacatt gtttacatgc tccacaacac cgataagacg 600
gaacgcaatg acaacctgat ggggtatatg tccatcagga atacttacaa aaccttttgt 660
gatacttcca accttccgga cgatacaaaa caaaaggtcg agaatcaaaa acgggaattc 720
gacaagataa ttaagtctgg gcgcttggga tactttggcg aggcatttat ggtcaactcc 780
ggcaactcta caaaattgcg gcctgagaaa gaaatctatc atattttcgc tctcatggcc 840
tcacttaggc agtcctactt ccacgggtat gtgaaggaca cggactacca aggaacaacg 900
tgggcgtaca cattggagga caagttgaag ggcccgtcac acgagttcag agaaacaatt 960
gataagatat ttgatgaagg attctctaag atatcaaaag acttcgggaa aatgaacaaa 1020
gttaatctgc aaattctgga gcagatgata ggcgagctgt acggttctat tgagcgccag 1080
aatctcacat gtgattacta cgacttcatc caattgaaga aacataagta cttggggttc 1140
tctataaagc ggttgagaga aacgatgttg gaaacgacac cggcggaatg ttacaaggca 1200
gaatgctaca atagcgagcg gcagaagctt tacaaactta tagattttct gatctatgat 1260
ttgtactata accgcaagcc ggcgcggatc gaggaaattg tcgataagct tagggagtct 1320
gtgaacgatg aggagaaaga atcgatttat agcgtcgaag ctaagtatgt ctatgagtcc 1380
ctctccaaag tgctggataa gtccctcaag aactccgttt ccggggagac catcaaagat 1440
ctccagaaaa ggtatgatga cgaaactgct aatagaatat gggacatctc gcaacactcg 1500
atttctggga acgtcaactg tttctgcaaa ttgatctaca taatgaccct catgctggac 1560
gggaaagaaa ttaacgacct ccttacaacg ctcgtgaaca aattcgataa tattgcttca 1620

-continued

```
ttcattgatg ttatggacga attgggtttg gaacactcat ttactgataa ttataaaatg   1680

tttgcagatt caaaggctat ctgccttgat cttcaattta ttaattcgtt tgcacggatg   1740

agcaaaatcg acgatgaaaa atctaagcgc caattgttta gggacgctct ggttatcctc   1800

gacataggca ataaggacga gacctggata aataactact tggactccga tattttcaaa   1860

ttggataaag agggaaataa gttgaagggc gcaaggcatg actttcggaa ctttattgct   1920

aacaacgtga ttaagtcgtc acggtttaaa taccttgtta aatactcgtc agcagatggt   1980

atgataaaac tgaaaactaa cgaaaagctt ataggctttg tcctggacaa gctccctgag   2040

acacagatag atagatacta cgaatcgtgt ggacttgata atgctgttgt cgacaaaaaa   2100

gtcaggatcg agaagctgtc agggcttata cgcgacatga aatttgatga tttctccggt   2160

gtcaaaacat caaataaggc gggcgataac gataagcaag acaaagcaaa gtatcaggca   2220

attatcagct tgtaccttat ggttctgtac caaattgtga aaaacatgat ctatgtcaat   2280

tcacggtacg tgatcgcgtt ccattgcctt gagagggatt tcggcatgta cggaaaagac   2340

ttcgggaaat attaccaggg atgtagaaaa ttgactgacc atttcataga agagaaatat   2400

atgaaggaag ggaaacttgg ttgcaataag aaggtgggaa ggtatctcaa aaataatatt   2460

tcatgctgta cggatggtct gatcaatacc tataggaacc aagtggacca tttcgctgtt   2520

gttcggaaga tagggaatta tgcagcatat atcaaatcta tcggctcatg gtttgaactg   2580

tatcactacg tcattcagag gatcgtgttt gatgagtaca gatttgcact gaataatacg   2640

gagagcaact acaagaattc aatcattaag caccatactt attgcaaaga catggtgaag   2700

gctctcaata cgccttttgg gtatgacctc cccagatata agaatctctc catcggggat   2760

cttttcgata gaaacaatta tcttaataag acgaaggaat cgatagatgc taattccagc   2820

attgactcac ag                                                       2832
```

<210> SEQ ID NO 26
<211> LENGTH: 2901
<212> TYPE: DNA
<213> ORGANISM: Artificial Sequence
<220> FEATURE:
<223> OTHER INFORMATION: Synthetic: CasM DNA sequence from Ruminococcus flavefaciens strain XPD3002, modified for expression in Zea mays cells

<400> SEQUENCE: 26

```
atgatcgaga agaaaaagtc tttcgcaaaa ggaatgggag tcaagtctac attggtttct     60

ggttcgaagg tttatatgac gacgttcgcc gagggctctg acgcgcgctt ggagaagata    120

gtggaggggg attcaatacg gtctgtgaac gaaggcgaag ctttttcggc cgagatggcg    180

gacaagaatg cagggtataa aattgggaat gcaaagtttt cgcaccccaa aggttacgca    240

gtcgttgcga ataacccgct ctatactggt ccagtccagc aagatatgct cgggctgaaa    300

gagaccctcg agaaacgcta ttttggggag agcgcggatg ggaatgacaa tatatgtatc    360

caagttatac ataatattct ggatatcgaa aagatccttg ctgaatacat taccaacgct    420

gcttatgcgg tcaacaatat ttcgggactt gataaagata taatcggctt cggtaaattc    480

agcactgtct atacatacga tgagttcaag gatccagagc atcatagagc ggcgttcaat    540

aataacgaca aactgattaa cgcaattaaa gcgcaatatg acgagttcga caattttctc    600

gacaacccac ggcttggcta ctttggccag gcatttttct cgaaggaggg taggaactac    660

ataatcaatt atggcaatga atgctatgac atacttgctc tgctttcagg tctcagacat    720

tgggtcgttc acaataacga agaagaatct cggatctctc ggacttggct ctataacctt    780
```

```
gacaagaacc ttgataacga gtacatctct acgctgaact acctttacga cagaatcact    840
aacgagctca ccaattcatt ctccaaaaat tctgccgcaa acgtcaacta catcgcggaa    900
acccttggga tcaacccagc agagtttgct gaacagtatt ttcgcttctc aatcatgaaa    960
gaacagaaaa atctgggctt caatataacg aaactgcgcg aggtcatgtt ggatagaaaa   1020
gatatgtccg aaatcaggaa aaaccataaa gtcttcgact caataaggac caaagtgtat   1080
accatgatgg attttgtcat ctaccgctat tacatagagg aggatgcaaa agtcgctgcc   1140
gctaacaaga gccttccaga taatgaaaag tctctgtcgg aaaaggatat atttgtgatt   1200
aatctccggg gaagctttaa cgacgatcaa aaggatgccc tgtactacga tgaggcaaac   1260
agaatttgga ggaagctgga aaacattatg cataacatta aggagttccg cgggaataaa   1320
acgagggaat ataagaagaa agatgctccg aggttgcctc ggattcttcc tgctggtagg   1380
gatgtttcgg cattctcgaa gctgatgtac gcactcacca tgttccttga cggtaaagag   1440
atcaacgatc tcttgacaac gcttattaat aagtttgata atatacagtc tttccttaag   1500
gttatgcccc ttattggagt taatgctaaa ttcgtggaag agtatgcttt cttcaaggac   1560
agcgcgaaaa ttgctgacga actgcgcctt atcaagtcct tcgcgcggat gggagagcct   1620
atagctgacg ctcgcagggc aatgtatatc gacgccatcc gcatccttgg caccaatctg   1680
agctatgatg agcttaaagc cctcgccgac accttcagcc tggacgaaaa cggcaacaaa   1740
ctcaagaagg gcaagcacgg catgcgcaat ttcattatca ataacgtgat ctcgaataag   1800
agatttcact atctgatacg gtatggcgac ccggcccacc tccatgagat tgcgaaaaac   1860
gaagctgttg tgaaatttgt gcttggtaga attgcggaca tacaaaaaaa acaaggccaa   1920
aatggcaaaa atcaaattga cagatattac gaaacatgca ttggaaagga taagggaaag   1980
tctgtgagcg agaaggttga tgcgttgacc aaaataatca caggaatgaa ttacgatcag   2040
ttcgataaaa agaggtcagt gatagaagac acggggcggg aaaacgctga acgcgaaaaa   2100
tttaagaaaa taatttcgct ctatcttacg gtcatttatc acatcttgaa gaatatagtc   2160
aatatcaacg ctagatacgt gattggtttc cattgtgtgg aaagagacgc tcaactgtac   2220
aaggaaaagg gttatgatat aaacctcaag aagctggagg aaaagggttt tagctcggtg   2280
actaaattgt gcgctggaat cgatgaaacc gcgccagata aaaggaagga tgttgagaag   2340
gagatggccg agagagcgaa ggaatctatc gacagcctgg aaagcgcgaa tcccaaactt   2400
tatgccaact acatcaagta ctctgacgag aaaaaagcgg aagagtttac tagacaaatc   2460
aatcgggaga aagctaagac cgccctcaat gcttacttgc gcaataccaa atggaacgtt   2520
atcattcgcg aagacctctt gcgcatagat aataaaacat gtacattgtt tagaaataaa   2580
gcagtgcacc tcgaggtcgc cagatacgtt cacgcatata taaatgacat cgctgaggtg   2640
aactcgtact ttcagctgta ccattacatt atgcaaagga tcataatgaa cgaaaggtac   2700
gagaaatcgt caggtaaagt ttccgaatat tttgacgcag tcaatgatga aaagaagtac   2760
aacgaccggc ttttgaagtt gctttgtgtg cctttcgggt actgtatccc tcggttcaaa   2820
aacctgtcca tagaggcatt gtttgacagg aacgaggcag caaagttcga caaggaaaag   2880
aaaaaggtgt cgggtaactc g                                             2901
```

<210> SEQ ID NO 27
<211> LENGTH: 2388
<212> TYPE: DNA
<213> ORGANISM: Artificial Sequence
<220> FEATURE:

<223> OTHER INFORMATION: Synthetic: CasM DNA sequence from Ruminococcus sp., isolate 2789STDY5834894, modified for expression in Zea mays cells

<400> SEQUENCE: 27

```
atggaaatta atacgtccaa tccgacacac agatcaggcg aatcttcctc agttagaggt     60
gatatgttgg gacttaaatc cgaattggaa aagaggtttt ttggcaagac attcgatgat    120
aacattcaca tacaacttat atataacatc cttgatatag aaaagatact tgctgtgtat    180
gtgacaaaca tagtttatgc actgaacaac atgcttggcg tgaagggatc agaaagctac    240
gatgatttca tggggtacct ctccgctcag aacacctatt acatattcac gcacccagat    300
aaatctaacc tgtcggataa agttaagggg aatattaaga agtcgctttc taaatttaac    360
gaccttctta agacaaaaag actgggctac tttgggcttg aggagccaaa gacgaaagac    420
aaacgggtta gcgaggcata taaaaagagg gtttatcata tgcttgccat agtgggccag    480
atacgccagt ccgtctttca tgataaatct aacgagttgg acgagtatct ttactctttc    540
atcgacatca tcgactccga atatagagac acgctcgact atcttgtcga cgaacggttt    600
gattcgataa ataagggttt tgtccaaggc aacaaagtca atatatcact cctcatagat    660
atgatgaaag gatacgaagc agacgatata atcagacttt attacgactt tattgttctt    720
aagagccaga aaaatcttgg attctcaata aagaaactga gggagaaaat gttggacgag    780
tatgggtttc ggtttaaaga taaacaatat gactcggtca ggtccaagat gtacaagctt    840
atggactttc ttttgttctg taattactat aggaatgacg ttgttgccgg ggaggccttg    900
gttagaaaat tgagattcag catgaccgat gacgaaaaag aaggcatcta tgcggatgag    960
gcagagaagt tgtgggggaa atttaggaat gactttgaaa acatagccga tcatatgaat   1020
ggcgatgtca taaaggagtt ggggaaagct gacatggatt ttgacgaaaa aatcctggat   1080
agcgaaaaaa agaatgcttc cgatctgttg tatttctcta agatgatcta tatgctcact   1140
tactttctgg acggtaaaga gatcaacgac cttcttacta cccttatttc aaagttcgat   1200
aacattaagg aatttctgaa aataatgaaa tcctcggctg tcgacgttga atgcgaactt   1260
actgcagggt acaagctgtt taacgactcg caaaggatta ctaatgaact gttcattgtc   1320
aagaacatag cgtccatgag aaagcctgca gcaagcgcaa agctgacgat gttccgcgat   1380
gctctcacca ttctgggaat tgatgacaag attaccgatg accgcatttc ggagatcctt   1440
aagcttaagg aaaaggggaa ggggattcac ggactgagaa attttatcac caataacgtg   1500
atcgaatcgt ctaggtttgt ctatttgata aagtatgcca atgcgcaaaa aattcgcgaa   1560
gtcgccaaga atgagaaggt cgttatgttc gtgctcggag gaattcccga tacacagatt   1620
gaacggtact ataaatcctg tgtggaattc ccggatatga actcatccct cgaggccaaa   1680
tgctctgagc ttgcgaggat gatcaagaat atctcctttg atgattttaa aaacgtgaag   1740
cagcaggcga agggccggga gaatgtggcg aaggagcggg ctaaagctgt gatagggctt   1800
tatcttactg ttatgtacct tctcgtgaaa aacctggtga atgtgaacgc caggtacgtt   1860
atagcgatcc attgtcttga gcgcgacttc ggtttgtata aggagataat tccagagctg   1920
gcatcgaaga acctgaaaaa cgattacaga attctgtcac aaactctctg tgaactctgc   1980
gatgaccgcg atgagtcacc gaatctcttc ctcaaaaaaa acaagaggct gaggaaatgt   2040
gtggaagttg acatcaataa cgcggattcg agcatgacac gcaagtaccg gaattgtatt   2100
gctcatctca cagtcgtccg cgagctcaaa gagtatatag gtgatatccg gaccgttgat   2160
tcttattttt ctatctatca ttacgttatg cagcggtgca ttacaaaaag ggaagatgat   2220
```

```
accaaacaag aagaaaaaat aaagtatgag gatgacttgt tgaaaaatca tggatatact   2280

aaagactttg tcaaggctct caactcaccg ttcggttaca acatacccag atttaaaaac   2340

ttgtcaattg aacagttgtt tgaccggaac gaatacctga cagaaaaa                2388


<210> SEQ ID NO 28
<211> LENGTH: 2865
<212> TYPE: DNA
<213> ORGANISM: Eubacterium siraeum
<220> FEATURE:
<221> NAME/KEY: misc_feature
<222> LOCATION: (1)..(2865)
<223> OTHER INFORMATION: native CasM DNA sequence from Eubacterium
      siraeum

<400> SEQUENCE: 28

atgggtaaga aaatacacgc acgagatctc agagaacaaa gaaagaccga tagaacggaa     60

aaatttgcag atcagaacaa aaaacgtgaa gcagagaggg cagttccgaa aaaagacgca    120

gccgtttctg taaaatcagt ttcttctgtt tcatcaaaaa aagacaatgt aacaaaatct    180

atggctaaag ccgcaggcgt gaagtcggtt tttgctgtag gaaatactgt ttatatgact    240

tcattcggca gaggaaacga tgctgtactt gagcagaaaa tagtcgatac atcgcacgaa    300

ccgctgaata ttgacgatcc tgcatatcag ttgaacgttg tcacaatgaa cggttattcg    360

gttaccggtc acagaggtga aacggtatct gccgtaacgg ataatccgct gcgccgtttt    420

aacggaagaa agaaagatga accggaacag tctgtgccta cggatatgct gtgcctgaaa    480

ccgactcttg aaaagaaatt cttcggcaaa gaattcgatg ataatataca tatccagctt    540

atttacaata ttcttgacat tgaaaaaata ctggcggttt attcgaccaa cgctatttac    600

gcattgaata atatgagtgc tgacgaaaat atcgaaaaca gcgatttctt catgaaacgt    660

accaccgatg aaacctttga cgattttgaa aagaaaaagg agagtacaaa cagtcgagag    720

aaagccgatt ttgacgcatt tgaaaaattc atcggcaatt acaggctggc ttattttgcc    780

gatgcatttt atgtaaataa aaagaatccc aaaggtaaag caaaaaatgt tctgcgtgag    840

gataaagaac tttactccgt gctcactctg atcggtaaac tgcgtcattg gtgtgttcac    900

agtgaggagg gcagagcaga attctggctg tataagctcg atgaacttaa agatgatttc    960

aaaaatgtac tcgacgttgt ttataaccgt cctgttgaag aaataaacaa ccgctttata   1020

gaaaacaata aggtaaacat acagatactg ggctcggtat acaagaacac cgatattgcc   1080

gaacttgtaa ggtcatatta cgaatttctt atcacaaaga agtataaaaa tatgggcttt   1140

tcaataaaga agctccgtga gagtatgctc gaaggtaaag gttacgccga taaagaatat   1200

gattctgtaa ggaataagct gtatcagatg acggatttca tcttatacac aggatatatc   1260

aacgaagaca gcgatagagc cgacgatctt gtgaacactt tgagaagttc gctcaaagag   1320

gatgataaga caaccgtata ttgcaaggaa gcggattatc tgtggaaaaa ataccgtgaa   1380

tccataagag aggttgccga tgcgcttgat ggcgataaca ttaaaaagct gagcaaatcg   1440

aatattgaaa ttcaggaaga caagctgaga aaatgtttta tcagctatgc cgacagcgta   1500

tcggaattta ccaagcttat ttatctgctg acaagatttt taagcggtaa ggagatcaac   1560

gatcttgtca caacgctgat aaacaagttt gacaatatca gaagcttcct tgaaataatg   1620

gacgagcttg ggcttgacag gaccttcacc gccgagtaca gcttctttga aggcagtaca   1680

aagtatcttg ccgagcttgt cgagcttaac agctttgtga aatcgtgttc gtttgatata   1740

aacgcaaaaa gaacaatgta tcgcgatgcg ctggatattc tcggcattga atcggataag   1800
```

```
accgaagaag atattgagaa gatgatcgat aatatccttc agatcgacgc aaacggtgat   1860
aaaaagctca agaaaaacaa cggtctgaga aatttcattg caagtaacgt tatagattca   1920
aaccgattca agtaccttgt gcggtacgga aatccaaaga agattcgtga aacggcaaaa   1980
tgcaagcccg ctgtaaggtt tgtgctgaat gagatcccgg acgcacagat cgaaagatat   2040
tatgaggctt gttgcccaaa aaatacagct ttatgctctg caaataagag acgtgagaaa   2100
ctggctgata tgatagctga aataaagttt gagaattttt cggatgccgg caattatcag   2160
aaagcaaatg tcacatcaag aacgtctgaa gctgaaatca agcggaagaa tcaggctata   2220
atccgtcttt atcttaccgt tatgtacatt atgctgaaga accttgtaaa tgtgaacgcc   2280
agatacgtta tcgctttcca ttgcgttgaa agggatacga agctgtatgc ggaaagcggt   2340
ctggaagtcg gtaatataga aaaaaacaag acaaatctta ctatggctgt aatgggagtc   2400
aagctcgaaa acggaatcat aaaaacggaa tttgacaaga gctttgcaga aaatgccgca   2460
aacagatatc tcaggaatgc acgctggtac aagctgatac tggataattt aaagaagtcg   2520
gaaagagcgg ttgtcaatga gttcagaaat actgtctgcc atctgaatgc gataaggaat   2580
atcaatatca atatcaagga aataaaagag gtcgagaact actttgctct gtaccactac   2640
ctcattcaga aacatctcga aaatcgtttt gccgataaaa aagtagaaag agacaccggc   2700
gattttataa gcaagctcga agaacacaag acttactgca aggactttgt aaaagcatat   2760
tgtacgcctt tcggatataa ccttgtgaga tataaaaacc ttacgataga cgggctgttt   2820
gataagaatt accccggaaa agacgattct gatgaacaga aataa                   2865
```

<210> SEQ ID NO 29
<211> LENGTH: 2760
<212> TYPE: DNA
<213> ORGANISM: Ruminococcus sp.
<220> FEATURE:
<221> NAME/KEY: misc_feature
<222> LOCATION: (1)..(2760)
<223> OTHER INFORMATION: native CasM DNA sequence from Ruminococcus sp., isolate 2789STDY5834971

<400> SEQUENCE: 29

```
atggcaaaaa agaataaaat gaagcctaga gagctgcgtg aggctcagaa aaaagccaga     60
cagctcaaag cggctgagat aaataataac gctgctcctg caatcgctgc catgcctgct    120
gcagaggtca ttgcacctgc ggcagagaag aaaaaatcct ccgtaaaggc ggcaggaatg    180
aagtctattc ttgtcagcga aaataaaatg tacataacct ctttcggcaa gggcaattct    240
gctgtgcttg aatatgaggt ggataataat gactacaacc aaactcagct ttcttcaaag    300
gacaacagca atatccagct tggtggtgta aacgaagtaa acatcacttt ttcaagcaag    360
catggctttg agagcggagt ggaaataaac acttcaaacc ctactcacag aagcggtgaa    420
agctcgcctg taagagggga tatgctgggg cttaaatcgg agcttgaaaa gcgctttttc    480
ggcaaaactt ttgatgataa tatacatatc cagcttattt acaacattct ggatatcgaa    540
aagatacttg cggtgtatgt aacgaatatc gtttatgcgc tgaacaatat gctcggtgta    600
aagggttcag aaagtcatga cgattttatt gggtatcttt ccacaaataa tatttatgat    660
gtttttattg accctgataa cagcagttta tctgatgata agaaagcgaa tgtcagaaaa    720
agccttagca agttcaatgc cctgctgaaa actaagcgcc ttggctattt cggtcttgaa    780
gagccaaaga cgaaagataa tagagtttcg caagcttaca aaaagcgtgt ttatcatatg    840
cttgcaattg tgggtcagat aagacagtgt gtttttcatg ataaatcggg tgcaaaaaga    900
```

tttgaccttt acagttttat taacaatatt gatcccgaat acagagacac tcttgactat 960
cttgttgagg aacgcttaaa gtccataaac aaggacttta tcgaggacaa caaggtcaat 1020
atcagcttgc ttattgatat gatgaaaggc tatgaggctg atgatatcat acgcctttat 1080
tacgatttca ttgtgcttaa atctcagaaa aatctcggtt tttctatcaa aaagcttcgt 1140
gagaaaatgc tggacgaata cggcttcaga tttaaggaca agcaatatga ctctgtgcgc 1200
tcaaagatgt acaagcttat ggattttctg cttttctgca actactacag aaatgacatt 1260
gccgcaggcg aatctcttgt gcgcaaactg cgtttttcaa tgaccgatga tgaaaaagag 1320
gggatatatg ctgatgaagc ggcaaagctt tggggcaaat tcaggaatga ttttgaaaat 1380
atcgccgacc acatgaacgg tgacgttatc aaggagcttg gcaaggctga catggatttt 1440
gatgagaaaa ttcttgacag cgaaaagaag aatgcgtctg acctttttgta tttctccaaa 1500 atgatatata tgctcacata ttttcttgac ggcaaggaga taaacgacct tcttacaacg 1560
cttatcagca agtttgataa catcaaggag tttttgaaga taatgaaaag ctctgctgtt 1620
gatgttgagt gtgaacttac ggcgggctac aagctgttca atgacagcca gaggataacc 1680
aacgagcttt ttatcgtaaa gaacattgct tccatgagaa agcctgcggc ttcggcgaag 1740
cttacgatgt tccgtgacgc actgactata ctcggtatag acgacaagat cacggacgat 1800
aggataagcg ggattctaaa acttaaagaa aaaggcaagg gcatacatgg cctgagaaat 1860
ttcataacaa acaatgttat cgagtcctct cggtttgtat accttatcaa gtatgcgaac 1920
gctcagaaga taagagaagt ggctaagaat gagaaagttg tcatgtttgt tcttgggggt 1980
atccctgaca cgcagataga gcgttattac aagagttgtg tggaatttcc tgacatgaac 2040
agttctttgg gagtaaagcg cagtgagctt gcgagaatga taaagaacat cagctttgat 2100
gatttcaaaa atgtgaaaca gcaggcaaag ggcagagaaa acgtggctaa ggagagggca 2160
aaggctgtta tcgggcttta tcttacggtc atgtatctgc tggtgaaaaa tcttgtgaat 2220
gtcaatgcaa ggtatgttat tgcgatacac tgccttgaac gtgattttgg gctgtataag 2280
gagataattc ctgagttggc ttcaaagaac ttgaaaaatg actacaggat actttcacag 2340
acgctttgtg aactttgtga taagtcgccg aatttgttct tgaaaaagaa cgagcggctg 2400
cgcaagtgcg ttgaagttga tatcaataat gcagacagca gcatgacaag aaaataccgc 2460
aactgtattg ctcatcttac tgtagttcgt gaactgaaag aatacatagg agatatttgt 2520
acagtggatt cttacttctc catttatcat tatgttatgc agcgctgtat cacgaaaagg 2580
gaaaatgaca caaagcaaga agagaaaata aagtatgagg acgatctttt aaaaaatcac 2640
ggctatacga aagactttgt aaaggctctc aactcgccgt ttggatacaa cattccgagg 2700
tttaaaaatc tttcaattga gcagttgttt gacagaaatg aatatcttac tgaaaagtag 2760

<210> SEQ ID NO 30
<211> LENGTH: 2757
<212> TYPE: DNA
<213> ORGANISM: Ruminococcus bicirculans
<220> FEATURE:
<221> NAME/KEY: misc_feature
<222> LOCATION: (1)..(2757)
<223> OTHER INFORMATION: native CasM DNA sequence from Ruminococcus bicirculans

<400> SEQUENCE: 30
atggcaaaaa agaataaaat gaagcctaga gagctgcgtg aggctcagaa aaaagccaga 60
cagctcaaag cggctgagat aaataataac gctgttcctg caatcgctgc catgcctgct 120

```
gcagaggctg ctgcacctgc ggcagagaag aaaaaatcct ccgtaaaggc ggcaggaatg    180
aagtctattc ttgtcagtga aaataaaatg tacataacct ctttcggcaa gggcaattct    240
gcggtgcttg aatatgaggt ggataataat gactacaaca aaactcagct ttcctcaaag    300
gacaacagta atatcgagct ctgtgatgta ggcaaagtaa acatcacttt ttcgagcaga    360
cgtggctttg agagcggtgt ggagataaac acttcaaacc ctactcacag aagcggtgaa    420
agctcgtctg taagagggga tatgctgggg cttaaatcgg agcttgaaaa gcgctttttc    480
ggcaagaatt ttgatgataa tatacatatc cagcttattt acaacattct ggatatcgaa    540
aagatacttg cagtgtatgt gacgaatatc gtttatgcac tgaacaatat gcttggggaa    600
ggcgatgaga gcaattacga tttcatgggg tatctttcca catttaacac ttataaagtt    660
tttactaatc ctaatggcag cactttatcc gacgataaga aagagaatat cagaaaaagt    720
cttagcaaat tcaatgccct gctgaaaact aagcgtcttg gctatttcgg ccttgaagag    780
ccaaagacaa aggatacaag agcttcggaa gcatacaaaa agcgtgttta tcatatgctt    840
gcaattgtgg ggcagataag acagtgtgtt tttcatgata aatcgggtgc aaaaagattt    900
gacctttaca gttttattaa caatattgat cccgaataca gagaaaccct tgactatctt    960
gtagatgaga gatttgattc tataaataag ggctttatcc agggcaacaa ggtcaatatc   1020
agcttgctta ttgatatgat gaaaggctat gaggctgatg atatcatacg cctttattac   1080
gatttcattg tgcttaaatc tcagaaaaat ctcggttttt ctatcaaaaa gcttcgtgag   1140
aaaatgctgg acgaatacgg cttcagattt aaggacaagc aatatgactc tgtgcgctca   1200
aagatgtaca agcttatgga ttttctgctt ttctgcaact actacagaaa tgacattgcc   1260
gcaggcgaat ctcttgtgcg caaactgcgt tttcaatga ccgatgatga aaaagagggg    1320
atatatgctg atgaagcggc aaagctttgg ggcaaattca ggaatgattt tgaaaatatc   1380
gccgaccaca tgaacggtga cgttatcaag gagcttggca aggctgacat ggattttgat   1440
gagaaaattc ttgacagcga aaagaagaat gcgtctgacc ttttgtattt ctccaaaatg   1500
atatatatgc tcacatattt tcttgacggc aaggagataa acgaccttct tacaacgctt   1560
atcagcaagt ttgataacat caaggagttt ttgaagataa tgaaaagctc tgctgttgat   1620
gttgagtgtg aacttacggc gggctacaag ctgttcaatg acagccagag gataaccaac   1680
gagcttttta tcgtaaagaa cattgcttcc atgagaaagc ctgcggcttc ggcgaagctt   1740
acgatgttcc gtgacgcact gactatactc ggtatagacg acaagatcac ggacgatagg   1800
ataagcgaga ttctaaaact taaagaaaaa ggcaagggca tacatggcct gagaaatttc   1860
ataacaaaca atgttatcga gtcctctcgg tttgtatacc ttatcaagta tgcgaacgct   1920
cagaagataa gagaagtggc taagaatgag aaagttgtca tgtttgttct tgggggtatc   1980
cctgacacgc agatagagcg ttattacaag agttgtgtgg aatttcctga catgaacagt   2040
tctttgggag taaagcgcag tgagcttgcg agaatgataa agaacatcag ctttgatgat   2100
ttcaaaaatg tgaaacagca ggcaaagggc agagaaaacg tggctaagga gagggcaaag   2160
gctgttatcg ggctttatct tacggtcatg tatctgctgg tgaaaaatct tgtgaatgtc   2220
aatgcaaggt atgttattgc gatacactgc cttgaacgtg attttgggct gtataaggag   2280
ataattcctg agttggcttc aaagaacttg aaaaatgact acaggatact ttcacagacg   2340
ctttgtgaac tttgtgataa gtcgccgaat ttgttcttga aaaagaacga gcggctgcgc   2400
aagtgcgttg aagttgatat caataatgca gacagcagca tgacaagaaa ataccgcaac   2460
```

```
tgtattgctc atcttactgt agttcgtgaa ctgaaagaat acataggaga tatttgtaca   2520

gtggattctt acttctccat ttatcattat gttatgcagc gctgtatcac gaaaagggaa   2580

aatgacacaa agcaagaaga gaaaataaag tatgaggacg atcttttaaa aaatcacggc   2640

tatacgaaag actttgtaaa ggctctcaac tcgccgtttg gatacaacat tccgaggttt   2700

aaaaatcttt caattgagca gttgtttgac agaaatgaat atcttactga aaagtag      2757
```

```
<210> SEQ ID NO 31
<211> LENGTH: 2769
<212> TYPE: DNA
<213> ORGANISM: Ruminococcus sp.
<220> FEATURE:
<221> NAME/KEY: misc_feature
<222> LOCATION: (1)..(2769)
<223> OTHER INFORMATION: native CasM DNA sequence from Ruminococcus sp.,
      isolate 2789STDY5608892

<400> SEQUENCE: 31

atggcaaaaa agaataaaat gaagcctaga gagctgcgtg aggctcagaa aaaagccaga     60

cagctcaaag cggctgagat aaataataac gctgctcctg cgatcgctgc catgcctgct    120

gcagaggtca ttgcacctgt ggcagagaag aaaaaatcct ccgtaaaggc ggcaggaatg    180

aagtctattc ttgtcagcga aaataaaatg tacataacct ctttcggcaa gggcaattct    240

gctgtgcttg aatatgaggt ggacaataat gactacaaca aaactcagct ttcttcaaag    300

gacaacagca atatcgagct tggtgatgta aacgaggtaa acatcacttt ttcaagcaag    360

catggctttg ggagcggagt ggagataaat acttcaaacc ctactcacag aagcggtgaa    420

agctcgcctg taagagggga tatgctgggg cttaaatcgg agcttgaaaa gcgctttttc    480

ggcaaaactt ttgatgataa tatacatatc cagcttattt acaacattct ggatatcgaa    540

aagatacttg cggtgtatgt aacgaatatc gtttatgcgc tgaacaatat gcttggtata    600

aaggattctg aaagttatga tgattttatg ggtatctttt ctgcaagaaa tacttatgaa    660

gtttttactc accctgacaa aagcaatctt tccgataagg taaagggtaa tatcaagaaa    720

agccttagca agtttaatga cttgctgaaa actaagcgcc ttggctattt cggccttgaa    780

gagccaaaga caaaagacac aagagcttcg gaagcataca aaaagcgtgt ttatcatatg    840

cttgcaattg tggggcagat aagacagtgt gtttttcatg ataaatcggg tgcaaaaaga    900

tttgaccttt acagttttat taacaatatt gatcccgaat acagagatac tcttgactat    960

cttgttgagg agcgtttaaa gtccataaac aaggacttta tcgagggtaa caaggtcaat   1020

atcagcctgc ttattgatat gatgaaaggc tatgaggctg atgatatcat acgcctttat   1080

tacgatttca ttgtgcttaa atctcagaaa aatctcggct tttctatcaa aaagcttcgt   1140

gagaaaatgc tggaggaata cggtttcaga tttaaggaca agcaatatga ctctgtgcgc   1200

tcaaagatgt acaagcttat ggatttcctg cttttctgca actactacag aaatgacgtt   1260

gccgcaggcg aagctcttgt gcgtaaactg cgtttttcaa tgaccgatga tgaaaaagag   1320

gggatatatg ctgatgaagc ggcaaagctt tggggcaaat tcaggaatga ttttgaaaat   1380

atcgccgacc acatgaacgg tgacgttatc aaggagcttg gcaaggctga catggatttt   1440

gatgagaaaa ttcttgacag tgaaaagaag aatgcgtctg accttttgta tttctccaaa   1500

atgatatata tgctcacata ttttcttgac ggcaaggaga taaacgatct tcttacaacg   1560

cttatcagca agtttgataa catcaaggag tttttgaaga taatgaaaag ctctgctgtt   1620

gatgttgagt gtgagcttac ggcgggctac aagctgttca atgacagcca gaggataacc   1680
```

aacgagcttt ttatcgtaaa gaacattgct tccatgagaa agcctgcggc ttcagcgaag 1740
cttacgatgt tccgtgacgc actgactata ctcggtatag acgacaatat cacggacgat 1800
aggataagcg agattctaaa acttaaagaa aaaggcaagg gcatacatgg tctgagaaat 1860
tttataacaa acaatgttat cgagtcctct cggtttgtat accttatcaa gtatgcgaac 1920
gctcagaaga taagagaagt ggctaagaat gagaaagttg tcatgtttgt tcttgggggt 1980
atccctgaca cgcagataga gcgttattac aagagttgtg tggagtttcc tgacatgaat 2040
agttctttgg aagcaaagcg cagtgagctt gcgagaatga taaagaacat cagctttgat 2100
gatttcaaaa atgtgaaaca gcaggcaaag ggcagagaaa acgtggctaa ggagagggca 2160
aaggctgtta tcgggcttta tcttacggtc atgtatctgc tggtgaaaaa tcttgtgaat 2220
gtcaatgcaa ggtatgttat tgcgatacac tgccttgaac gtgattttgg gctgtataag 2280
gagataattc ctgagttggc ttcaaagaac ttgaaaaatg actacaggat actttcacag 2340
acgctttgtg aactttgtga tgatcgtaat gagtcgtcga atttgttctt gaaaaagaac 2400
aagcggctgc gcaagtgcgt tgaagttgat atcaataatg cagacagcag catgacaaga 2460
aaataccgca actgtattgc tcatcttact gtagttcgtg aactgaaaga atacatagga 2520
gatattcgta cagtggattc ttacttctcc atttatcatt atgttatgca gcgttgtatc 2580
acgaaaaggg gagatgacac aaagcaagaa gagaaaataa agtatgagga cgatctttta 2640
aaaaatcacg gctatacgaa agactttgta aaggctctca actcgccgtt tggatacaac 2700
attccgaggt ttaaaaatct ttcaattgag cagttgtttg acagaaatga atatcttact 2760
gaaaagtag 2769

<210> SEQ ID NO 32
<211> LENGTH: 2769
<212> TYPE: DNA
<213> ORGANISM: Ruminococcus sp.
<220> FEATURE:
<221> NAME/KEY: misc_feature
<222> LOCATION: (1)..(2769)
<223> OTHER INFORMATION: native CasM DNA sequence from Ruminococcus sp. CAG:57

<400> SEQUENCE: 32
atggcaaaaa agaataaaat gaagcctaga gagctgcgtg aggctcagaa aaaagccaga 60
cagctcaaag cggctgagat aaataataac gctgctcctg cgatcgctgc catgcctgct 120
gcagaggtca ttgcacctgt ggcagagaag aaaaaatcct ccgtaaaggc ggcaggaatg 180
aagtctattc ttgtcagcga aaataaaatg tacataacct ctttcggcaa gggcaattct 240
gctgtgcttg aatatgaggt ggacaataat gactacaaca aaactcagct ttcttcaaag 300
gacaacagca atatcgagct tggtgatgta aacgaggtaa acatcacttt ttcaagcaag 360
catggctttg ggagcggagt ggagataaat acttcaaacc ctactcacag aagcggtgaa 420
agctcgcctg taagagggga tatgctgggg cttaaatcgg agcttgaaaa gcgctttttc 480
ggcaaaactt ttgatgataa tatacatatc cagcttattt acaacattct ggatatcgaa 540
aagatacttg cggtgtatgt aacgaatatc gtttatgcgc tgaacaatat gcttggtata 600
aaggattctg aaagttatga tgattttatg gggtatcttt ctgcaagaaa tacttatgaa 660
gtttttactc accctgacaa aagcaatctt tccgataagg taaagggtaa tatcaagaaa 720
agccttagca agtttaatga cttgctgaaa actaagcgcc ttggctattt cggccttgaa 780
gagccaaaga caaaagacac aagagcttcg gaagcataca aaaagcgtgt ttatcatatg 840

-continued

```
cttgcaattg tggggcagat aagacagtgt gtttttcatg ataaatcggg tgcaaaaaga    900
tttgaccttt acagttttat taacaatatt gatcccgaat acagagatac tcttgactat    960
cttgttgagg agcgtttaaa gtccataaac aaggacttta tcgagggtaa caaggtcaat   1020
atcagcctgc ttattgatat gatgaaaggc tatgaggctg atgatatcat acgcctttat   1080
tacgatttca ttgtgcttaa atctcagaaa aatctcggct tttctatcaa aaagcttcgt   1140
gagaaaatgc tggaggaata cggtttcaga tttaaggaca agcaatatga ctctgtgcgc   1200
tcaaagatgt acaagcttat ggatttcctg cttttctgca actactacag aaatgacgtt   1260
gccgcaggcg aagctcttgt gcgtaaactg cgtttttcaa tgaccgatga tgaaaaagag   1320
gggatatatg ctgatgaagc ggcaaagctt tggggcaaat tcaggaatga ttttgaaaat   1380
atcgccgacc acatgaacgg tgacgttatc aaggagcttg gcaaggctga catggatttt   1440
gatgagaaaa ttcttgacag tgaaaagaag aatgcgtctg accttttgta tttctccaaa   1500
atgatatata tgctcacata ttttcttgac ggcaaggaga taaacgatct tcttacaacg   1560
cttatcagca agtttgataa catcaaggag tttttgaaga taatgaaaag ctctgctgtt   1620
gatgttgagt gtgagcttac ggcgggctac aagctgttca atgacagcca gaggataacc   1680
aacgagcttt ttatcgtaaa gaacattgct tccatgagaa agcctgcggc ttcagcgaag   1740
cttacgatgt tccgtgacgc actgactata ctcggtatag acgacaatat cacggacgat   1800
aggataagcg agattctaaa acttaaagaa aaaggcaagg gcatacatgg tctgagaaat   1860
tttataacaa acaatgttat cgagtcctct cggtttgtat accttatcaa gtatgcgaac   1920
gctcagaaga taagagaagt ggctaaggat gagaaagttg tcatgtttgt tcttgggggt   1980
atccctgaca cgcagataga gcgttattac aagagttgtg tggagtttcc tgacatgaat   2040
agttctttgg aagcaaagcg cagtgagctt gcgagaatga taaagaacat cagctttgat   2100
gatttcaaaa atgtgaaaca gcaggcaaag ggcagagaaa acgtggctaa ggagagggca   2160
aaggctgtta tcgggcttta tcttacggtc atgtatctgc tggtgaaaaa tcttgtgaat   2220
gtcaatgcaa ggtatgttat tgcgatacac tgccttgaac gtgattttgg gctgtataag   2280
gagataattc ctgagttggc ttcaaagaac ttgaaaaatg actacaggat actttcacag   2340
acgctttgtg aactttgtga tgatcgtaat gagtcgtcga atttgttctt gaaaaagaac   2400
aagcggctgc gcaagtgcgt tgaagttgat atcaataatg cagacagcag catgacaaga   2460
aaataccgca actgtattgc tcatcttact gtagttcgtg aactgaaaga atacatagga   2520
gatattcgta cagtggattc ttacttctcc atttatcatt atgttatgca gcgttgtatc   2580
acgaaaaggg gagatgacac aaagcaagaa gagaaaataa agtatgagga cgatctttta   2640
aaaaatcacg gctatacgaa agactttgta aaggctctca actcgccgtt tggatacaac   2700
attccgaggt ttaaaaatct ttcaattgag cagttgtttg acagaaatga atatcttact   2760
gaaaagtag                                                           2769
```

<210> SEQ ID NO 33
<211> LENGTH: 2802
<212> TYPE: DNA
<213> ORGANISM: Ruminococcus flavefaciens
<220> FEATURE:
<221> NAME/KEY: misc_feature
<222> LOCATION: (1)..(2802)
<223> OTHER INFORMATION: native CasM DNA sequence from Ruminococcus flavefaciens FD-1

<400> SEQUENCE: 33

```
atgaaaaaga aaatgtctct ccgtgaaaag cgtgaagccg agaaacaggc taaaaaagct     60
gcatattcag cagcttcaaa aaatacagat tctaagcctg cggaaaagaa agcagaaact    120
ccaaagcctg cggagattat ttccgataat tccagaaata agaccgctgt aaaggcggct    180
ggtctgaaat caacaattat cagcggcgat aagctgtata tgacatcttt cggcaagggt    240
aacgctgctg ttattgagca gaaaatagat atcaatgatt attctttttc agctatgaaa    300
gatactccgt cgcttgaagt tgataaagca gaatcaaaag agatctcttt ttcaagtcac    360
catccttttg taaagaatga taagctgaca acatataacc ctttatacgg cggcaaggat    420
aaccccgaaa agcctgtcgg cagggatatg ctcggcttaa aagataagct tgaagaacgc    480
tatttcggat gtacattcaa tgataatctt cacatccaga ttatctataa catacttgac    540
atcgagaaga ttttagctgt tcattctgca aatatcacaa ctgcgcttga ccacatggtt    600
gatgaagacg atgaaaaata tcttaacagc gattatatcg gctacatgaa taccataaat    660
acatatgacg tgtttatgga tccttcaaag aattcttcat taagccctaa agatagaaag    720
aatattgaca acagccgtgc aaaatttgag aaactgcttt caactaagcg ccttggctat    780
tttggatttg actatgatgc aaacggtaag gacaagaaaa agaacgagga aataaaaaag    840
cgtttatatc atctcacagc ttttgcaggt cagctccgtc agtggagttt tcatagtgct    900
ggcaattatc cgagaacatg gctttacaag ctcgattcac tggataagga atatcttgat    960
actcttgacc attacttcga taaacgtttt aacgatataa acgatgattt cgtaactaag   1020
aatgctacca atctctatat tctgaaagaa gtatttcccg aagcaaactt caaggatatt   1080
gccgatcttt attacgattt catagttata aagtcgcaca aaaatatggg attctccata   1140
aaaaagctga gggagaagat gcttgaatgt gatggtgcag acaggataaa agaacaggat   1200
atggactctg ttcgctcaaa gctgtataag ctcatagact tttgcatttt caagtattat   1260
cacgaatttc ctgaacttag tgaaaagaat gtggatatac tcagagcggc tgtatccgat   1320
acaaaaaaag ataaccttta ttctgatgag gctgcacgtt tatggagcat atttaaagaa   1380
aaattcctcg gcttctgtga taagatagtt gtatgggtaa caggagagca tgagaaagat   1440
atcacatccg ttattgataa ggatgcttac aggaacagga gcaatgtttc atatttctca   1500
aagctgatgt atgcaatgtg ctttttcctt gacggaaaag agataaatga ccttctcact   1560
actcttatca acaaattcga taatatcgct aaccagataa aaacagccaa agaacttggc   1620
attaatactg cttttgtaaa gaattacgat ttcttcaatc acagcgagaa atatgtcgat   1680
gaactgaaca tcgtcaagaa tattgcaaga atgaagaagc cttcaagtaa tgccaaaaaa   1740
gctatgtatc atgatgcgct tactattctc ggaatacctg aggatatgga tgaaaaagct   1800
cttgatgagg aactggattt aattcttgaa aaaaagacag acccagtaac tggcaagcca   1860
ctgaaaggta agaatccttt acgtaatttt atcgcaaaca atgtgataga gaattcaaga   1920
ttcatatatc ttatcaagtt ctgcaatcct gagaatgtac gtaaaatcgt gaataataca   1980
aaggtcactg agtttgtgtt aaagcgtatt cccgatgctc agatcgaacg ctattataag   2040
tcgtgtacag attctgaaat gaatccgcct actgaaaaga agatcaccga acttgctggt   2100
aagttaaagg atatgaactt tggcaacttc cgaaatgtga gacagtctgc taaagagaat   2160
atggagaagg agcgcttcaa agctgttata gggctttatc tcacggtagt atatcgtgtt   2220
gtcaagaatc ttgttgatgt aaactcacga tatatcatgg cttttcattc gcttgaacgt   2280
gattcacaac tgtataacgt atctgttgat aatgattatc ttgcacttac cgatactctt   2340
gttaaggagg gagataattc cagaagcaga tatcttgcag gcaacaagcg tctgagagat   2400
```

```
tgtgtgaagc aggatatcga taatgcaaaa aagtggtttg ttagtgataa gtacaatagc   2460

ataaccaagt acaggaataa cgttgcccat cttaccgctg tacgtaactg cgctgaattc   2520

atcggagata taacgaagat agactcctat tttgcattgt atcattatct cattcagaga   2580

cagcttgcga aaggtcttga ccatgagcga agtggctttg acagaaacta tccacagtat   2640

gcaccgctgt ttaagtggca tacgtatgta aaggatgttg tcaaggctct gaatgctcca   2700

tttggctaca atatccctcg tttcaagaat ctcagcatag atgcactttt tgaccgcaac   2760

gaaataaaga agaatgacgg cgagaaaaaa tccgatgatt ga                       2802
```

<210> SEQ ID NO 34
<211> LENGTH: 2835
<212> TYPE: DNA
<213> ORGANISM: Ruminococcus albus
<220> FEATURE:
<221> NAME/KEY: misc_feature
<222> LOCATION: (1)..(2835)
<223> OTHER INFORMATION: native CasM DNA sequence from Ruminococcus albus strain KH2T6

<400> SEQUENCE: 34

```
atggcaaaaa aatcgaaagg tatgagcctt agagaaaaac gtgaacttga aaagcagaaa     60

aggatacaaa aggcagctgt gaattcagtt aatgatacac ctgaaaaaac agaagaagca    120

aatgtcgtat ctgtaaatgt caggacatcg gctgagaata agcatagtaa aaaatctgct    180

gccaaagctt tgggactgaa atccgggctg gttatcggtg atgagctgta ccttacttca    240

ttcggcagag gtaacgaagc aaagcttgaa aagaagatat ccggtgacac tgtcgaaaaa    300

cttggcattg gtgcttttga agtcgccgaa cgtgacgaat caacgcttac cctcgaaagt    360

ggcaggataa aggacaagac cgccagaccc aaagacccca gacatataac cgtcgataca    420

caaggtaaat tcaaggaaga tatgcttggg atacgcagtg tactggagaa aaagatattt    480

ggcaaaacat ttgatgataa tatccatgtt cagcttgcgt acaatatcct ggatgtcgaa    540

aagataatgg cacagtatgt cagcgatatc gtatatatgc tgcataatac tgataaaaca    600

gaaagaaacg ataatcttat ggggtatatg agcatcagga atacctataa gacattttgt    660

gatacgtcaa atcttcccga tgatacaaaa caaaaagttg aaaatcagaa gagagagttt    720

gacaagatca taaaaagcgg cagacttggg tatttcggcg aagcttttat ggtaaacagc    780

ggcaatagta ccaagcttag acccgagaaa gagatatatc atatctttgc gcttatggcg    840

agcctgaggc agagttactt tcacggatat gtaaaagata ccgattatca gggaaccaca    900

tgggcatata ctcttgagga caagctgaaa ggtccgagcc atgagttcag ggaaaccatt    960

gataagatat ttgatgaggg attcagcaag atcagcaagg actttggcaa gatgaacaag   1020

gtcaaccttc agatacttga acagatgatt ggtgaactgt atggcagtat agaacgacaa   1080

aacctcactt gcgattacta tgacttcatt caactgaaaa agcataagta tcttggattt   1140

tctataaagc gtcttagaga gaccatgctt gaaacaacac cggctgaatg ttataaagct   1200

gaatgctata acagcgagcg tcaaaagctg tataagctga tagatttcct gatatatgat   1260

ctttactata accgtaagcc tgcacgcatc gaagaaatcg tggacaagct gagggaatct   1320

gtgaacgacg aagagaaaga atccatatat tcagttgagg cgaagtatgt ctatgaatca   1380

cttagcaaag ttctggataa atcgctgaaa aacagtgtgt ctggtgaaac gataaaggat   1440

ctccaaaaga gatatgatga cgaaacagca aacaggatct gggatatctc acagcacagt   1500

ataagtggaa atgtcaactg tttctgcaag ctaatttata ttatgaccct gatgcttgac   1560
```

```
ggcaaggaga taaatgatct gctgacaacg ctggtaaaca agttcgataa catagcatca   1620

tttatagatg ttatggacga acttggcttg gagcatagtt ttacagataa ctataaaatg   1680

tttgccgaca gcaaggctat atgccttgat ctgcagttca taaacagttt tgcacgtatg   1740

tcaaagatcg atgatgagaa gtcaaaaaga cagcttttcc gtgatgcgct tgtcatactg   1800

gatatcggta ataaagatga gacttggata aataattatc tggattctga tattttcaaa   1860

ctggacaaag aaggtaacaa gttaaagggc gcaaggcatg atttcaggaa ctttatagcc   1920

aataatgtta taaagtcatc acgtttcaaa tacctagtaa aatacagcag tgccgatggt   1980

atgataaagc tgaaaacgaa tgaaaagctg ataggctttg ttctggataa gcttccagaa   2040

acgcagatag accgctacta tgaatcatgc ggacttgaca atgcggtagt agataagaaa   2100

gtcaggatag aaaagctatc ggggcttatc agagatatga agttcgatga tttcagcggt   2160

gtcaaaacct caaacaaagc aggagataat gacaaacagg ataaggcgaa atatcaggcg   2220

ataataagcc tgtacctcat ggtgctgtat cagatagtca agaacatgat atatgtcaac   2280

tcacgttatg ttatcgcttt ccattgtctt gaacgtgact ttggtatgta tggaaaagat   2340

tttggaaagt attatcaagg ctgccgaaaa cttacagatc attttattga agaaaagtac   2400

atgaaagagg gtaaacttgg ctgcaataaa aaagtcggca gatatctgaa aaataatatt   2460

tcctgctgca ctgatggact gataaatacc taccgtaatc aggttgatca ctttgcagtg   2520

gtaaggaaga taggcaacta tgcggcatat atcaagagta tcggttcgtg gtttgaactt   2580

tatcactatg taatacagag gatagttttt gacgaataca gatttgcact taacaacact   2640

gaaagcaact ataagaacag catcatcaag caccatacct actgtaagga tatggtcaag   2700

gcactgaaca cacctttcgg ttatgacctg ccgagataca agaatctttc tatcggtgat   2760

ctgtttgatc gcaataatta tctgaataaa acaaaagagt caatagatgc aaatagctct   2820

attgacagtc agtga                                                    2835
```

<210> SEQ ID NO 35
<211> LENGTH: 2904
<212> TYPE: DNA
<213> ORGANISM: Ruminococcus flavefaciens
<220> FEATURE:
<221> NAME/KEY: misc_feature
<222> LOCATION: (1)..(2904)
<223> OTHER INFORMATION: native CasM DNA sequence from Ruminococcus flavefaciens strain XPD3002

<400> SEQUENCE: 35

```
atgatcgaaa agaagaagtc atttgcaaag ggcatgggag taaaatcaac acttgtatcc     60

ggttcaaagg tatacatgac gacgttcgca gaaggaagcg atgccagact tgaaaagatc    120

gttgaaggcg attctatcag atctgtcaac gaaggagaag cgttctcagc tgaaatggct    180

gataagaatg caggctacaa gatcggtaac gcaaagttca gccacccaaa gggctatgct    240

gtagttgcaa acaacccctt atacaccgga ccggtacagc aggatatgct cggtctgaag    300

gaaacgcttg aaaagagata ttttggagag tctgccgacg gaaatgataa tatctgtatt    360

caggtcatcc ataatatcct cgatatcgaa aagatcctcg ctgaatatat aaccaatgct    420

gcttatgcgg taaacaatat ttccggtctt gataaggata tcatcggttt tggtaagttc    480

agtacggtct atacttatga tgagttcaag gatcctgaac atcacagagc agctttcaac    540

aataacgata agttaattaa tgccatcaag gcacagtatg atgaatttga caatttcctt    600

gataatcctc gtctcggcta ctttggacag gctttttca gtaaggaagg cagaaattac    660
```

-continued

```
attatcaatt acggcaacga gtgttatgat attcttgctt tactcagcgg attgcgtcac    720
tgggtagtac ataataatga ggaagaatca aggatttccc gtacatggct ttataatctc    780
gacaagaatc ttgacaacga atatatctct actctcaatt atctgtatga tagaattaca    840
aacgaattaa caaattcctt ctcaaagaat agtgcagcca acgtaaacta tatcgctgaa    900
acccttggta ttaatcctgc tgaatttgca gagcagtatt tcagattcag tatcatgaag    960
gaacagaaga atctcggttt caatattact aagctgagag aagtaatgct tgacagaaag   1020
gatatgtctg agatccgtaa aaatcataag gtctttgatt caatccgtac taaggtctat   1080
actatgatgg atttcgttat ctacagatat tacattgaag aggatgcaaa ggttgctgct   1140
gccaacaagt ctctgccgga taacgaaaaa agcctcagtg aaaaggatat ctttgttata   1200
aatctcagag gaagctttaa cgatgatcag aaggatgccc tttattatga tgaggccaat   1260
cgtatttgga gaaagctcga aaacattatg cacaatatca aggaattcag aggcaataag   1320
acacgtgaat acaagaagaa ggatgctcca agactcccca gaattcttcc tgccggaagg   1380
gatgtttccg cgttctcaaa gttgatgtac gctcttacca tgttccttga tggtaaggag   1440
atcaatgatc ttctcaccac gctcatcaat aagttcgata acatccagag tttcctcaag   1500
gtaatgcctc ttatcggagt gaatgcaaag tttgttgagg aatatgcctt cttcaaggac   1560
agcgcaaaga ttgctgacga actcaggctg attaagagct ttgccagaat gggagaacct   1620
atcgcagatg caagacgtgc tatgtatatc gatgctatca ggattctcgg aacaaacctc   1680
agctatgatg agcttaaggc ccttgccgat actttttcgc ttgatgaaaa cggcaacaag   1740
cttaagaagg gcaagcacgg catgagaaac ttcatcatta ataatgtaat cagtaacaag   1800
cgcttccatt atctcattcg ttacggtgat cctgcacatc tccatgagat cgccaagaat   1860
gaagctgttg taaagttcgt cctcggcagg atagctgata tccagaagaa gcagggacag   1920
aacggaaaga atcagatcga caggtactat gagacctgta tcggcaagga caagggcaag   1980
tctgtctccg aaaaggttga tgccctcaca aagattatca ccggtatgaa ctacgatcag   2040
ttcgataaga agagaagcgt tattgaggat actggaagag aaaacgctga gagagaaaag   2100
ttcaagaaga tcatcagcct ctatcttact gtcatttatc acatccttaa gaatattgtt   2160
aatatcaatg cgcgttacgt tatcggcttc cattgcgttg agcgtgatgc acagctctat   2220
aaggaaaagg gctatgatat caacctcaag aagctcgaag aaaaggggtt ttcatcagtc   2280
acaaagctgt gtgcaggtat tgatgagact gctcctgaca agcgtaagga tgttgaaaag   2340
gaaatggctg agcgtgcaaa ggaatctatc gatagccttg aatctgcaaa tcctaagctt   2400
tacgcaaact atatcaagta ttctgacgag aagaaggctg aggaatttac tagacagatc   2460
aaccgtgaga aggcaaagac cgctctgaat gcatatctca gaaatactaa gtggaatgtg   2520
ataatcaggg aagatcttct tagaatcgat aataagacat gtacgctctt tagaaataag   2580
gccgttcatc ttgaagttgc aagatatgtt catgcatata tcaacgatat tgccgaagta   2640
aacagctatt tccagcttta tcattacatc atgcagagaa tcatcatgaa cgaaagatat   2700
gaaaagtctt ctggaaaggt aagcgaatac ttcgatgctg tgaacgatga aaagaagtac   2760
aacgacaggc ttctgaagct gttgtgcgtt ccatttggtt actgcatccc gagattcaag   2820
aatctctcca ttgaagcttt gttcgacagg aacgaagcag ctaagtttga caaggaaaag   2880
aagaaagtat caggtaattc atag                                          2904
```

<210> SEQ ID NO 36

<211> LENGTH: 2391
<212> TYPE: DNA
<213> ORGANISM: Ruminococcus sp.
<220> FEATURE:
<221> NAME/KEY: misc_feature
<222> LOCATION: (1)..(2391)
<223> OTHER INFORMATION: native CasM DNA sequence from Ruminococcus sp., isolate 2789STDY5834894

<400> SEQUENCE: 36

```
gtggagataa acacttcaaa ccctactcac agaagcggtg aaagctcgtc tgtaagaggg     60

gatatgctgg ggcttaaatc ggagcttgaa aagcgctttt tcggcaagac ttttgatgat    120

aatatacata tccagcttat ttacaacatt ctggatatcg aaaagatact tgcagtgtat    180

gtgacgaata tcgtttatgc actgaacaat atgcttggtg taaagggttc tgaaagttat    240

gatgatttta tggggtatct ttctgcccaa aatacttatt atatttttac tcaccctgac    300

aaaagtaatc tttccgataa ggtaaagggt aatatcaaga aaagccttag caagtttaat    360

gacctgctga aaactaagcg tcttggctat tttggtcttg aagagcctaa gacgaaagat    420

aaaagagttt cggaggcata caaaaagcgt gtttatcata tgcttgcaat tgtggggcag    480

ataaggcaga gtgttttcca tgataagtca aatgagcttg atgagtacct ttacagcttt    540

attgacatta ttgattccga atacagagac actcttgact atcttgtaga tgagagattt    600

gattctataa ataagggctt tgtccagggc aacaaggtca atatcagctt gcttattgat    660

atgatgaaag gctatgaggc tgatgatatc atacgccttt attatgattt cattgtgctt    720

aaatctcaga aaaatctcgg tttttctatc aaaaagcttc gtgagaaaat gctggacgaa    780

tacggcttca gatttaagga caagcaatat gactctgtgc gctcaaagat gtacaagctt    840

atggattttc tgcttttctg caactattac agaaatgacg ttgtcgcagg cgaagctctt    900

gtgcgcaaac tgcgtttttc aatgaccgat gatgaaaaag aggggatata tgctgatgaa    960

gcggaaaagc tttggggcaa attcaggaat gatttgaaa atatcgccga ccacatgaac    1020

ggtgacgtta tcaaggagct tggcaaggct gacatggatt ttgatgagaa aattcttgac   1080

agcgaaaaga agaatgcgtc tgaccttttg tatttctcca aaatgatata tatgctcaca   1140

tattttcttg acggcaagga gataaacgat cttcttacaa cgcttatcag caagtttgat   1200

aacatcaagg agtttttgaa gataatgaaa agctctgctg ttgatgttga gtgtgagctt   1260

acggcgggct acaagctgtt caatgacagc cagaggataa ccaacgagct tttatcgta    1320

aagaacattg cttccatgag aaagcctgcg gcttcggcga agcttacgat gttccgtgac   1380

gcactgacta tactcggtat agacgacaag atcacggacg ataggataag cgagatttta   1440

aaacttaaag aaaaaggcaa gggcatacat ggtctgagaa attttataac aaacaatgtt   1500

atcgagtcct ctcggtttgt ataccttatc aagtatgcga acgctcagaa gataagagaa   1560

gtggctaaga atgagaaagt tgtcatgttt gttcttgggg gtatccctga cacgcagata   1620

gagcgttatt acaagagttg tgtggaattt cctgacatga acagttcttt ggaagcaaag   1680

tgcagtgagc ttgcgagaat gataaagaac atcagctttg atgatttcaa aaatgtgaaa   1740

cagcaggcaa agggcagaga aaacgtggct aaggagaggg caaaggctgt tatcgggctt   1800

tatcttacgg tcatgtatct gctggtgaaa aatcttgtga atgtcaatgc aaggtatgtt   1860

attgcgatac actgccttga acgtgatttt gggctgtata aggagataat tcctgagttg   1920

gcttcaaaga acttgaaaaa tgactacagg atactttcac agacgctttg tgaactttgt   1980

gatgatcgtg atgagtcgcc gaatttgttc ttgaaaaaga acaagcggct gcgcaagtgc   2040
```

```
gttgaagttg atatcaataa tgcagacagc agcatgacaa gaaaataccg caactgtatt   2100

gctcatctta ctgtagttcg tgaactgaaa gaatacatag gagatattcg tacagtggat   2160

tcttacttct ccatttatca ttatgttatg cagcgctgta tcacgaaaag ggaagatgac   2220

acaaagcaag aagagaaaat aaagtatgag gacgatcttt taaaaaatca cggctatacg   2280

aaagactttg taaaggctct caactcgccg tttggataca acattccgag gtttaaaaat   2340

ctttcaattg agcagttgtt tgacagaaat gaatatctta ctgaaaagta g            2391


<210> SEQ ID NO 37
<211> LENGTH: 954
<212> TYPE: PRT
<213> ORGANISM: Eubacterium siraeum
<220> FEATURE:
<221> NAME/KEY: misc_feature
<222> LOCATION: (1)..(954)
<223> OTHER INFORMATION: native CasM protein sequence from Eubacterium
      siraeum

<400> SEQUENCE: 37

Met Gly Lys Lys Ile His Ala Arg Asp Leu Arg Glu Gln Arg Lys Thr
1               5                   10                  15

Asp Arg Thr Glu Lys Phe Ala Asp Gln Asn Lys Lys Arg Glu Ala Glu
            20                  25                  30

Arg Ala Val Pro Lys Lys Asp Ala Ala Val Ser Val Lys Ser Val Ser
        35                  40                  45

Ser Val Ser Ser Lys Lys Asp Asn Val Thr Lys Ser Met Ala Lys Ala
    50                  55                  60

Ala Gly Val Lys Ser Val Phe Ala Val Gly Asn Thr Val Tyr Met Thr
65                  70                  75                  80

Ser Phe Gly Arg Gly Asn Asp Ala Val Leu Glu Gln Lys Ile Val Asp
                85                  90                  95

Thr Ser His Glu Pro Leu Asn Ile Asp Asp Pro Ala Tyr Gln Leu Asn
            100                 105                 110

Val Val Thr Met Asn Gly Tyr Ser Val Thr Gly His Arg Gly Glu Thr
        115                 120                 125

Val Ser Ala Val Thr Asp Asn Pro Leu Arg Arg Phe Asn Gly Arg Lys
    130                 135                 140

Lys Asp Glu Pro Glu Gln Ser Val Pro Thr Asp Met Leu Cys Leu Lys
145                 150                 155                 160

Pro Thr Leu Glu Lys Lys Phe Phe Gly Lys Glu Phe Asp Asp Asn Ile
                165                 170                 175

His Ile Gln Leu Ile Tyr Asn Ile Leu Asp Ile Glu Lys Ile Leu Ala
            180                 185                 190

Val Tyr Ser Thr Asn Ala Ile Tyr Ala Leu Asn Asn Met Ser Ala Asp
        195                 200                 205

Glu Asn Ile Glu Asn Ser Asp Phe Phe Met Lys Arg Thr Thr Asp Glu
    210                 215                 220

Thr Phe Asp Asp Phe Glu Lys Lys Lys Glu Ser Thr Asn Ser Arg Glu
225                 230                 235                 240

Lys Ala Asp Phe Asp Ala Phe Glu Lys Phe Ile Gly Asn Tyr Arg Leu
                245                 250                 255

Ala Tyr Phe Ala Asp Ala Phe Tyr Val Asn Lys Lys Asn Pro Lys Gly
            260                 265                 270

Lys Ala Lys Asn Val Leu Arg Glu Asp Lys Glu Leu Tyr Ser Val Leu
        275                 280                 285
```

```
Thr Leu Ile Gly Lys Leu Arg His Trp Cys Val His Ser Glu Glu Gly
    290                 295                 300

Arg Ala Glu Phe Trp Leu Tyr Lys Leu Asp Glu Leu Lys Asp Asp Phe
305                 310                 315                 320

Lys Asn Val Leu Asp Val Val Tyr Asn Arg Pro Val Glu Glu Ile Asn
                325                 330                 335

Asn Arg Phe Ile Glu Asn Asn Lys Val Asn Ile Gln Ile Leu Gly Ser
            340                 345                 350

Val Tyr Lys Asn Thr Asp Ile Ala Glu Leu Val Arg Ser Tyr Tyr Glu
        355                 360                 365

Phe Leu Ile Thr Lys Lys Tyr Lys Asn Met Gly Phe Ser Ile Lys Lys
    370                 375                 380

Leu Arg Glu Ser Met Leu Glu Gly Lys Gly Tyr Ala Asp Lys Glu Tyr
385                 390                 395                 400

Asp Ser Val Arg Asn Lys Leu Tyr Gln Met Thr Asp Phe Ile Leu Tyr
                405                 410                 415

Thr Gly Tyr Ile Asn Glu Asp Ser Asp Arg Ala Asp Asp Leu Val Asn
            420                 425                 430

Thr Leu Arg Ser Ser Leu Lys Glu Asp Asp Lys Thr Thr Val Tyr Cys
        435                 440                 445

Lys Glu Ala Asp Tyr Leu Trp Lys Lys Tyr Arg Glu Ser Ile Arg Glu
    450                 455                 460

Val Ala Asp Ala Leu Asp Gly Asp Asn Ile Lys Lys Leu Ser Lys Ser
465                 470                 475                 480

Asn Ile Glu Ile Gln Glu Asp Lys Leu Arg Lys Cys Phe Ile Ser Tyr
                485                 490                 495

Ala Asp Ser Val Ser Glu Phe Thr Lys Leu Ile Tyr Leu Leu Thr Arg
            500                 505                 510

Phe Leu Ser Gly Lys Glu Ile Asn Asp Leu Val Thr Thr Leu Ile Asn
        515                 520                 525

Lys Phe Asp Asn Ile Arg Ser Phe Leu Glu Ile Met Asp Glu Leu Gly
    530                 535                 540

Leu Asp Arg Thr Phe Thr Ala Glu Tyr Ser Phe Phe Glu Gly Ser Thr
545                 550                 555                 560

Lys Tyr Leu Ala Glu Leu Val Glu Leu Asn Ser Phe Val Lys Ser Cys
                565                 570                 575

Ser Phe Asp Ile Asn Ala Lys Arg Thr Met Tyr Arg Asp Ala Leu Asp
            580                 585                 590

Ile Leu Gly Ile Glu Ser Asp Lys Thr Glu Glu Asp Ile Glu Lys Met
        595                 600                 605

Ile Asp Asn Ile Leu Gln Ile Asp Ala Asn Gly Asp Lys Lys Leu Lys
    610                 615                 620

Lys Asn Asn Gly Leu Arg Asn Phe Ile Ala Ser Asn Val Ile Asp Ser
625                 630                 635                 640

Asn Arg Phe Lys Tyr Leu Val Arg Tyr Gly Asn Pro Lys Lys Ile Arg
                645                 650                 655

Glu Thr Ala Lys Cys Lys Pro Ala Val Arg Phe Val Leu Asn Glu Ile
            660                 665                 670

Pro Asp Ala Gln Ile Glu Arg Tyr Tyr Glu Ala Cys Cys Pro Lys Asn
        675                 680                 685

Thr Ala Leu Cys Ser Ala Asn Lys Arg Arg Glu Lys Leu Ala Asp Met
    690                 695                 700

Ile Ala Glu Ile Lys Phe Glu Asn Phe Ser Asp Ala Gly Asn Tyr Gln
```

```
705                 710                 715                 720

Lys Ala Asn Val Thr Ser Arg Thr Ser Glu Ala Glu Ile Lys Arg Lys
                725                 730                 735

Asn Gln Ala Ile Ile Arg Leu Tyr Leu Thr Val Met Tyr Ile Met Leu
            740                 745                 750

Lys Asn Leu Val Asn Val Asn Ala Arg Tyr Val Ile Ala Phe His Cys
        755                 760                 765

Val Glu Arg Asp Thr Lys Leu Tyr Ala Glu Ser Gly Leu Glu Val Gly
    770                 775                 780

Asn Ile Glu Lys Asn Lys Thr Asn Leu Thr Met Ala Val Met Gly Val
785                 790                 795                 800

Lys Leu Glu Asn Gly Ile Ile Lys Thr Glu Phe Asp Lys Ser Phe Ala
                805                 810                 815

Glu Asn Ala Ala Asn Arg Tyr Leu Arg Asn Ala Arg Trp Tyr Lys Leu
            820                 825                 830

Ile Leu Asp Asn Leu Lys Lys Ser Glu Arg Ala Val Val Asn Glu Phe
        835                 840                 845

Arg Asn Thr Val Cys His Leu Asn Ala Ile Arg Asn Ile Asn Ile Asn
    850                 855                 860

Ile Lys Glu Ile Lys Glu Val Glu Asn Tyr Phe Ala Leu Tyr His Tyr
865                 870                 875                 880

Leu Ile Gln Lys His Leu Glu Asn Arg Phe Ala Asp Lys Lys Val Glu
                885                 890                 895

Arg Asp Thr Gly Asp Phe Ile Ser Lys Leu Glu Glu His Lys Thr Tyr
            900                 905                 910

Cys Lys Asp Phe Val Lys Ala Tyr Cys Thr Pro Phe Gly Tyr Asn Leu
        915                 920                 925

Val Arg Tyr Lys Asn Leu Thr Ile Asp Gly Leu Phe Asp Lys Asn Tyr
    930                 935                 940

Pro Gly Lys Asp Asp Ser Asp Glu Gln Lys
945                 950
```

<210> SEQ ID NO 38
<211> LENGTH: 919
<212> TYPE: PRT
<213> ORGANISM: Ruminococcus sp.
<220> FEATURE:
<221> NAME/KEY: misc_feature
<222> LOCATION: (1)..(919)
<223> OTHER INFORMATION: native CasM protein sequence from Ruminococcus sp., isolate 2789STDY5834971

<400> SEQUENCE: 38

```
Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Ala
            20                  25                  30

Pro Ala Ile Ala Ala Met Pro Ala Ala Glu Val Ile Ala Pro Ala Ala
        35                  40                  45

Glu Lys Lys Lys Ser Ser Val Lys Ala Ala Gly Met Lys Ser Ile Leu
    50                  55                  60

Val Ser Glu Asn Lys Met Tyr Ile Thr Ser Phe Gly Lys Gly Asn Ser
65                  70                  75                  80

Ala Val Leu Glu Tyr Glu Val Asp Asn Asn Asp Tyr Asn Gln Thr Gln
                85                  90                  95

Leu Ser Ser Lys Asp Asn Ser Asn Ile Gln Leu Gly Gly Val Asn Glu
```

```
            100                 105                 110

Val Asn Ile Thr Phe Ser Ser Lys His Gly Phe Glu Ser Gly Val Glu
        115                 120                 125

Ile Asn Thr Ser Asn Pro Thr His Arg Ser Gly Glu Ser Ser Pro Val
    130                 135                 140

Arg Gly Asp Met Leu Gly Leu Lys Ser Glu Leu Glu Lys Arg Phe Phe
145                 150                 155                 160

Gly Lys Thr Phe Asp Asp Asn Ile His Ile Gln Leu Ile Tyr Asn Ile
                165                 170                 175

Leu Asp Ile Glu Lys Ile Leu Ala Val Tyr Val Thr Asn Ile Val Tyr
            180                 185                 190

Ala Leu Asn Asn Met Leu Gly Val Lys Gly Ser Glu Ser His Asp Asp
        195                 200                 205

Phe Ile Gly Tyr Leu Ser Thr Asn Asn Ile Tyr Asp Val Phe Ile Asp
    210                 215                 220

Pro Asp Asn Ser Ser Leu Ser Asp Asp Lys Lys Ala Asn Val Arg Lys
225                 230                 235                 240

Ser Leu Ser Lys Phe Asn Ala Leu Leu Lys Thr Lys Arg Leu Gly Tyr
                245                 250                 255

Phe Gly Leu Glu Glu Pro Lys Thr Lys Asp Asn Arg Val Ser Gln Ala
            260                 265                 270

Tyr Lys Lys Arg Val Tyr His Met Leu Ala Ile Val Gly Gln Ile Arg
        275                 280                 285

Gln Cys Val Phe His Asp Lys Ser Gly Ala Lys Arg Phe Asp Leu Tyr
    290                 295                 300

Ser Phe Ile Asn Asn Ile Asp Pro Glu Tyr Arg Asp Thr Leu Asp Tyr
305                 310                 315                 320

Leu Val Glu Glu Arg Leu Lys Ser Ile Asn Lys Asp Phe Ile Glu Asp
                325                 330                 335

Asn Lys Val Asn Ile Ser Leu Leu Ile Asp Met Met Lys Gly Tyr Glu
            340                 345                 350

Ala Asp Asp Ile Ile Arg Leu Tyr Tyr Asp Phe Ile Val Leu Lys Ser
        355                 360                 365

Gln Lys Asn Leu Gly Phe Ser Ile Lys Lys Leu Arg Glu Lys Met Leu
    370                 375                 380

Asp Glu Tyr Gly Phe Arg Phe Lys Asp Lys Gln Tyr Asp Ser Val Arg
385                 390                 395                 400

Ser Lys Met Tyr Lys Leu Met Asp Phe Leu Leu Phe Cys Asn Tyr Tyr
                405                 410                 415

Arg Asn Asp Ile Ala Ala Gly Glu Ser Leu Val Arg Lys Leu Arg Phe
            420                 425                 430

Ser Met Thr Asp Asp Glu Lys Glu Gly Ile Tyr Ala Asp Glu Ala Ala
        435                 440                 445

Lys Leu Trp Gly Lys Phe Arg Asn Asp Phe Glu Asn Ile Ala Asp His
    450                 455                 460

Met Asn Gly Asp Val Ile Lys Glu Leu Gly Lys Ala Asp Met Asp Phe
465                 470                 475                 480

Asp Glu Lys Ile Leu Asp Ser Glu Lys Lys Asn Ala Ser Asp Leu Leu
                485                 490                 495

Tyr Phe Ser Lys Met Ile Tyr Met Leu Thr Tyr Phe Leu Asp Gly Lys
            500                 505                 510

Glu Ile Asn Asp Leu Leu Thr Thr Leu Ile Ser Lys Phe Asp Asn Ile
        515                 520                 525
```

```
Lys Glu Phe Leu Lys Ile Met Lys Ser Ser Ala Val Asp Val Glu Cys
    530                 535                 540

Glu Leu Thr Ala Gly Tyr Lys Leu Phe Asn Asp Ser Gln Arg Ile Thr
545                 550                 555                 560

Asn Glu Leu Phe Ile Val Lys Asn Ile Ala Ser Met Arg Lys Pro Ala
                565                 570                 575

Ala Ser Ala Lys Leu Thr Met Phe Arg Asp Ala Leu Thr Ile Leu Gly
            580                 585                 590

Ile Asp Asp Lys Ile Thr Asp Asp Arg Ile Ser Gly Ile Leu Lys Leu
        595                 600                 605

Lys Glu Lys Gly Lys Gly Ile His Gly Leu Arg Asn Phe Ile Thr Asn
    610                 615                 620

Asn Val Ile Glu Ser Ser Arg Phe Val Tyr Leu Ile Lys Tyr Ala Asn
625                 630                 635                 640

Ala Gln Lys Ile Arg Glu Val Ala Lys Asn Glu Lys Val Val Met Phe
                645                 650                 655

Val Leu Gly Gly Ile Pro Asp Thr Gln Ile Glu Arg Tyr Tyr Lys Ser
            660                 665                 670

Cys Val Glu Phe Pro Asp Met Asn Ser Ser Leu Gly Val Lys Arg Ser
        675                 680                 685

Glu Leu Ala Arg Met Ile Lys Asn Ile Ser Phe Asp Asp Phe Lys Asn
    690                 695                 700

Val Lys Gln Gln Ala Lys Gly Arg Glu Asn Val Ala Lys Glu Arg Ala
705                 710                 715                 720

Lys Ala Val Ile Gly Leu Tyr Leu Thr Val Met Tyr Leu Leu Val Lys
                725                 730                 735

Asn Leu Val Asn Val Asn Ala Arg Tyr Val Ile Ala Ile His Cys Leu
            740                 745                 750

Glu Arg Asp Phe Gly Leu Tyr Lys Glu Ile Ile Pro Glu Leu Ala Ser
        755                 760                 765

Lys Asn Leu Lys Asn Asp Tyr Arg Ile Leu Ser Gln Thr Leu Cys Glu
    770                 775                 780

Leu Cys Asp Lys Ser Pro Asn Leu Phe Leu Lys Lys Asn Glu Arg Leu
785                 790                 795                 800

Arg Lys Cys Val Glu Val Asp Ile Asn Asn Ala Asp Ser Ser Met Thr
                805                 810                 815

Arg Lys Tyr Arg Asn Cys Ile Ala His Leu Thr Val Val Arg Glu Leu
            820                 825                 830

Lys Glu Tyr Ile Gly Asp Ile Cys Thr Val Asp Ser Tyr Phe Ser Ile
        835                 840                 845

Tyr His Tyr Val Met Gln Arg Cys Ile Thr Lys Arg Glu Asn Asp Thr
    850                 855                 860

Lys Gln Glu Glu Lys Ile Lys Tyr Glu Asp Asp Leu Leu Lys Asn His
865                 870                 875                 880

Gly Tyr Thr Lys Asp Phe Val Lys Ala Leu Asn Ser Pro Phe Gly Tyr
                885                 890                 895

Asn Ile Pro Arg Phe Lys Asn Leu Ser Ile Glu Gln Leu Phe Asp Arg
            900                 905                 910

Asn Glu Tyr Leu Thr Glu Lys
        915
```

<210> SEQ ID NO 39
<211> LENGTH: 918

```
<212> TYPE: PRT
<213> ORGANISM: Ruminococcus bicirculans
<220> FEATURE:
<221> NAME/KEY: misc_feature
<222> LOCATION: (1)..(918)
<223> OTHER INFORMATION: native CasM protein sequence from Ruminococcus
      bicirculans

<400> SEQUENCE: 39

Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Val
            20                  25                  30

Pro Ala Ile Ala Ala Met Pro Ala Ala Glu Ala Ala Ala Pro Ala Ala
        35                  40                  45

Glu Lys Lys Lys Ser Ser Val Lys Ala Ala Gly Met Lys Ser Ile Leu
    50                  55                  60

Val Ser Glu Asn Lys Met Tyr Ile Thr Ser Phe Gly Lys Gly Asn Ser
65                  70                  75                  80

Ala Val Leu Glu Tyr Glu Val Asp Asn Asn Asp Tyr Asn Lys Thr Gln
                85                  90                  95

Leu Ser Ser Lys Asp Asn Ser Asn Ile Glu Leu Cys Asp Val Gly Lys
            100                 105                 110

Val Asn Ile Thr Phe Ser Ser Arg Arg Gly Phe Glu Ser Gly Val Glu
        115                 120                 125

Ile Asn Thr Ser Asn Pro Thr His Arg Ser Gly Glu Ser Ser Ser Val
    130                 135                 140

Arg Gly Asp Met Leu Gly Leu Lys Ser Glu Leu Glu Lys Arg Phe Phe
145                 150                 155                 160

Gly Lys Asn Phe Asp Asp Asn Ile His Ile Gln Leu Ile Tyr Asn Ile
                165                 170                 175

Leu Asp Ile Glu Lys Ile Leu Ala Val Tyr Val Thr Asn Ile Val Tyr
            180                 185                 190

Ala Leu Asn Asn Met Leu Gly Glu Gly Asp Glu Ser Asn Tyr Asp Phe
        195                 200                 205

Met Gly Tyr Leu Ser Thr Phe Asn Thr Tyr Lys Val Phe Thr Asn Pro
    210                 215                 220

Asn Gly Ser Thr Leu Ser Asp Asp Lys Lys Glu Asn Ile Arg Lys Ser
225                 230                 235                 240

Leu Ser Lys Phe Asn Ala Leu Leu Lys Thr Lys Arg Leu Gly Tyr Phe
                245                 250                 255

Gly Leu Glu Glu Pro Lys Thr Lys Asp Thr Arg Ala Ser Glu Ala Tyr
            260                 265                 270

Lys Lys Arg Val Tyr His Met Leu Ala Ile Val Gly Gln Ile Arg Gln
        275                 280                 285

Cys Val Phe His Asp Lys Ser Gly Ala Lys Arg Phe Asp Leu Tyr Ser
    290                 295                 300

Phe Ile Asn Asn Ile Asp Pro Glu Tyr Arg Glu Thr Leu Asp Tyr Leu
305                 310                 315                 320

Val Asp Glu Arg Phe Asp Ser Ile Asn Lys Gly Phe Ile Gln Gly Asn
                325                 330                 335

Lys Val Asn Ile Ser Leu Leu Ile Asp Met Met Lys Gly Tyr Glu Ala
            340                 345                 350

Asp Asp Ile Ile Arg Leu Tyr Tyr Asp Phe Ile Val Leu Lys Ser Gln
        355                 360                 365
```

```
Lys Asn Leu Gly Phe Ser Ile Lys Lys Leu Arg Glu Lys Met Leu Asp
    370                 375                 380

Glu Tyr Gly Phe Arg Phe Lys Asp Lys Gln Tyr Asp Ser Val Arg Ser
385                 390                 395                 400

Lys Met Tyr Lys Leu Met Asp Phe Leu Leu Phe Cys Asn Tyr Tyr Arg
                405                 410                 415

Asn Asp Ile Ala Ala Gly Glu Ser Leu Val Arg Lys Leu Arg Phe Ser
            420                 425                 430

Met Thr Asp Asp Glu Lys Glu Gly Ile Tyr Ala Asp Glu Ala Ala Lys
        435                 440                 445

Leu Trp Gly Lys Phe Arg Asn Asp Phe Glu Asn Ile Ala Asp His Met
    450                 455                 460

Asn Gly Asp Val Ile Lys Glu Leu Gly Lys Ala Asp Met Asp Phe Asp
465                 470                 475                 480

Glu Lys Ile Leu Asp Ser Glu Lys Lys Asn Ala Ser Asp Leu Leu Tyr
                485                 490                 495

Phe Ser Lys Met Ile Tyr Met Leu Thr Tyr Phe Leu Asp Gly Lys Glu
            500                 505                 510

Ile Asn Asp Leu Leu Thr Thr Leu Ile Ser Lys Phe Asp Asn Ile Lys
        515                 520                 525

Glu Phe Leu Lys Ile Met Lys Ser Ser Ala Val Asp Val Glu Cys Glu
    530                 535                 540

Leu Thr Ala Gly Tyr Lys Leu Phe Asn Asp Ser Gln Arg Ile Thr Asn
545                 550                 555                 560

Glu Leu Phe Ile Val Lys Asn Ile Ala Ser Met Arg Lys Pro Ala Ala
                565                 570                 575

Ser Ala Lys Leu Thr Met Phe Arg Asp Ala Leu Thr Ile Leu Gly Ile
            580                 585                 590

Asp Asp Lys Ile Thr Asp Asp Arg Ile Ser Glu Ile Leu Lys Leu Lys
        595                 600                 605

Glu Lys Gly Lys Gly Ile His Gly Leu Arg Asn Phe Ile Thr Asn Asn
    610                 615                 620

Val Ile Glu Ser Ser Arg Phe Val Tyr Leu Ile Lys Tyr Ala Asn Ala
625                 630                 635                 640

Gln Lys Ile Arg Glu Val Ala Lys Asn Glu Lys Val Val Met Phe Val
                645                 650                 655

Leu Gly Gly Ile Pro Asp Thr Gln Ile Glu Arg Tyr Tyr Lys Ser Cys
            660                 665                 670

Val Glu Phe Pro Asp Met Asn Ser Ser Leu Gly Val Lys Arg Ser Glu
        675                 680                 685

Leu Ala Arg Met Ile Lys Asn Ile Ser Phe Asp Asp Phe Lys Asn Val
    690                 695                 700

Lys Gln Gln Ala Lys Gly Arg Glu Asn Val Ala Lys Glu Arg Ala Lys
705                 710                 715                 720

Ala Val Ile Gly Leu Tyr Leu Thr Val Met Tyr Leu Leu Val Lys Asn
                725                 730                 735

Leu Val Asn Val Asn Ala Arg Tyr Val Ile Ala Ile His Cys Leu Glu
            740                 745                 750

Arg Asp Phe Gly Leu Tyr Lys Glu Ile Ile Pro Glu Leu Ala Ser Lys
        755                 760                 765

Asn Leu Lys Asn Asp Tyr Arg Ile Leu Ser Gln Thr Leu Cys Glu Leu
    770                 775                 780

Cys Asp Lys Ser Pro Asn Leu Phe Leu Lys Lys Asn Glu Arg Leu Arg
```

```
785                 790                 795                 800

Lys Cys Val Glu Val Asp Ile Asn Asn Ala Asp Ser Ser Met Thr Arg
                805                 810                 815

Lys Tyr Arg Asn Cys Ile Ala His Leu Thr Val Val Arg Glu Leu Lys
            820                 825                 830

Glu Tyr Ile Gly Asp Ile Cys Thr Val Asp Ser Tyr Phe Ser Ile Tyr
        835                 840                 845

His Tyr Val Met Gln Arg Cys Ile Thr Lys Arg Glu Asn Asp Thr Lys
    850                 855                 860

Gln Glu Glu Lys Ile Lys Tyr Glu Asp Asp Leu Leu Lys Asn His Gly
865                 870                 875                 880

Tyr Thr Lys Asp Phe Val Lys Ala Leu Asn Ser Pro Phe Gly Tyr Asn
                885                 890                 895

Ile Pro Arg Phe Lys Asn Leu Ser Ile Glu Gln Leu Phe Asp Arg Asn
            900                 905                 910

Glu Tyr Leu Thr Glu Lys
        915


<210> SEQ ID NO 40
<211> LENGTH: 922
<212> TYPE: PRT
<213> ORGANISM: Ruminococcus sp.
<220> FEATURE:
<221> NAME/KEY: misc_feature
<222> LOCATION: (1)..(922)
<223> OTHER INFORMATION: native CasM protein sequence from Ruminococcus
      sp., isolate 2789STDY5608892

<400> SEQUENCE: 40

Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Ala
            20                  25                  30

Pro Ala Ile Ala Ala Met Pro Ala Ala Glu Val Ile Ala Pro Val Ala
        35                  40                  45

Glu Lys Lys Lys Ser Ser Val Lys Ala Ala Gly Met Lys Ser Ile Leu
    50                  55                  60

Val Ser Glu Asn Lys Met Tyr Ile Thr Ser Phe Gly Lys Gly Asn Ser
65                  70                  75                  80

Ala Val Leu Glu Tyr Glu Val Asp Asn Asn Asp Tyr Asn Lys Thr Gln
                85                  90                  95

Leu Ser Ser Lys Asp Asn Ser Asn Ile Glu Leu Gly Asp Val Asn Glu
            100                 105                 110

Val Asn Ile Thr Phe Ser Ser Lys His Gly Phe Gly Ser Gly Val Glu
        115                 120                 125

Ile Asn Thr Ser Asn Pro Thr His Arg Ser Gly Glu Ser Ser Pro Val
    130                 135                 140

Arg Gly Asp Met Leu Gly Leu Lys Ser Glu Leu Glu Lys Arg Phe Phe
145                 150                 155                 160

Gly Lys Thr Phe Asp Asp Asn Ile His Ile Gln Leu Ile Tyr Asn Ile
                165                 170                 175

Leu Asp Ile Glu Lys Ile Leu Ala Val Tyr Val Thr Asn Ile Val Tyr
            180                 185                 190

Ala Leu Asn Asn Met Leu Gly Ile Lys Asp Ser Glu Ser Tyr Asp Asp
        195                 200                 205

Phe Met Gly Tyr Leu Ser Ala Arg Asn Thr Tyr Glu Val Phe Thr His
```

```
    210                 215                 220

Pro Asp Lys Ser Asn Leu Ser Asp Lys Val Lys Gly Asn Ile Lys Lys
225                 230                 235                 240

Ser Leu Ser Lys Phe Asn Asp Leu Leu Lys Thr Lys Arg Leu Gly Tyr
                245                 250                 255

Phe Gly Leu Glu Glu Pro Lys Thr Lys Asp Thr Arg Ala Ser Glu Ala
            260                 265                 270

Tyr Lys Lys Arg Val Tyr His Met Leu Ala Ile Val Gly Gln Ile Arg
        275                 280                 285

Gln Cys Val Phe His Asp Lys Ser Gly Ala Lys Arg Phe Asp Leu Tyr
    290                 295                 300

Ser Phe Ile Asn Asn Ile Asp Pro Glu Tyr Arg Asp Thr Leu Asp Tyr
305                 310                 315                 320

Leu Val Glu Glu Arg Leu Lys Ser Ile Asn Lys Asp Phe Ile Glu Gly
                325                 330                 335

Asn Lys Val Asn Ile Ser Leu Leu Ile Asp Met Met Lys Gly Tyr Glu
            340                 345                 350

Ala Asp Asp Ile Ile Arg Leu Tyr Tyr Asp Phe Ile Val Leu Lys Ser
        355                 360                 365

Gln Lys Asn Leu Gly Phe Ser Ile Lys Lys Leu Arg Glu Lys Met Leu
    370                 375                 380

Glu Glu Tyr Gly Phe Arg Phe Lys Asp Lys Gln Tyr Asp Ser Val Arg
385                 390                 395                 400

Ser Lys Met Tyr Lys Leu Met Asp Phe Leu Leu Phe Cys Asn Tyr Tyr
                405                 410                 415

Arg Asn Asp Val Ala Ala Gly Glu Ala Leu Val Arg Lys Leu Arg Phe
            420                 425                 430

Ser Met Thr Asp Asp Glu Lys Glu Gly Ile Tyr Ala Asp Glu Ala Ala
        435                 440                 445

Lys Leu Trp Gly Lys Phe Arg Asn Asp Phe Glu Asn Ile Ala Asp His
    450                 455                 460

Met Asn Gly Asp Val Ile Lys Glu Leu Gly Lys Ala Asp Met Asp Phe
465                 470                 475                 480

Asp Glu Lys Ile Leu Asp Ser Glu Lys Lys Asn Ala Ser Asp Leu Leu
                485                 490                 495

Tyr Phe Ser Lys Met Ile Tyr Met Leu Thr Tyr Phe Leu Asp Gly Lys
            500                 505                 510

Glu Ile Asn Asp Leu Leu Thr Thr Leu Ile Ser Lys Phe Asp Asn Ile
        515                 520                 525

Lys Glu Phe Leu Lys Ile Met Lys Ser Ser Ala Val Asp Val Glu Cys
    530                 535                 540

Glu Leu Thr Ala Gly Tyr Lys Leu Phe Asn Asp Ser Gln Arg Ile Thr
545                 550                 555                 560

Asn Glu Leu Phe Ile Val Lys Asn Ile Ala Ser Met Arg Lys Pro Ala
                565                 570                 575

Ala Ser Ala Lys Leu Thr Met Phe Arg Asp Ala Leu Thr Ile Leu Gly
            580                 585                 590

Ile Asp Asp Asn Ile Thr Asp Asp Arg Ile Ser Glu Ile Leu Lys Leu
        595                 600                 605

Lys Glu Lys Gly Lys Gly Ile His Gly Leu Arg Asn Phe Ile Thr Asn
    610                 615                 620

Asn Val Ile Glu Ser Ser Arg Phe Val Tyr Leu Ile Lys Tyr Ala Asn
625                 630                 635                 640
```

```
Ala Gln Lys Ile Arg Glu Val Ala Lys Asn Glu Lys Val Val Met Phe
                645                 650                 655

Val Leu Gly Gly Ile Pro Asp Thr Gln Ile Glu Arg Tyr Tyr Lys Ser
            660                 665                 670

Cys Val Glu Phe Pro Asp Met Asn Ser Ser Leu Glu Ala Lys Arg Ser
        675                 680                 685

Glu Leu Ala Arg Met Ile Lys Asn Ile Ser Phe Asp Asp Phe Lys Asn
    690                 695                 700

Val Lys Gln Gln Ala Lys Gly Arg Glu Asn Val Ala Lys Glu Arg Ala
705                 710                 715                 720

Lys Ala Val Ile Gly Leu Tyr Leu Thr Val Met Tyr Leu Leu Val Lys
                725                 730                 735

Asn Leu Val Asn Val Asn Ala Arg Tyr Val Ile Ala Ile His Cys Leu
            740                 745                 750

Glu Arg Asp Phe Gly Leu Tyr Lys Glu Ile Ile Pro Glu Leu Ala Ser
        755                 760                 765

Lys Asn Leu Lys Asn Asp Tyr Arg Ile Leu Ser Gln Thr Leu Cys Glu
    770                 775                 780

Leu Cys Asp Asp Arg Asn Glu Ser Ser Asn Leu Phe Leu Lys Lys Asn
785                 790                 795                 800

Lys Arg Leu Arg Lys Cys Val Glu Val Asp Ile Asn Asn Ala Asp Ser
                805                 810                 815

Ser Met Thr Arg Lys Tyr Arg Asn Cys Ile Ala His Leu Thr Val Val
            820                 825                 830

Arg Glu Leu Lys Glu Tyr Ile Gly Asp Ile Arg Thr Val Asp Ser Tyr
        835                 840                 845

Phe Ser Ile Tyr His Tyr Val Met Gln Arg Cys Ile Thr Lys Arg Gly
    850                 855                 860

Asp Asp Thr Lys Gln Glu Glu Lys Ile Lys Tyr Glu Asp Asp Leu Leu
865                 870                 875                 880

Lys Asn His Gly Tyr Thr Lys Asp Phe Val Lys Ala Leu Asn Ser Pro
                885                 890                 895

Phe Gly Tyr Asn Ile Pro Arg Phe Lys Asn Leu Ser Ile Glu Gln Leu
            900                 905                 910

Phe Asp Arg Asn Glu Tyr Leu Thr Glu Lys
        915                 920


<210> SEQ ID NO 41
<211> LENGTH: 922
<212> TYPE: PRT
<213> ORGANISM: Ruminococcus sp.
<220> FEATURE:
<221> NAME/KEY: misc_feature
<222> LOCATION: (1)..(922)
<223> OTHER INFORMATION: native CasM protein sequence from Ruminococcus
      sp. CAG:57

<400> SEQUENCE: 41

Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Ala
            20                  25                  30

Pro Ala Ile Ala Ala Met Pro Ala Ala Glu Val Ile Ala Pro Val Ala
        35                  40                  45

Glu Lys Lys Lys Ser Ser Val Lys Ala Ala Gly Met Lys Ser Ile Leu
    50                  55                  60
```

```
Val Ser Glu Asn Lys Met Tyr Ile Thr Ser Phe Gly Lys Gly Asn Ser
65                  70                  75                  80

Ala Val Leu Glu Tyr Glu Val Asp Asn Asn Asp Tyr Asn Lys Thr Gln
                85                  90                  95

Leu Ser Ser Lys Asp Asn Ser Asn Ile Glu Leu Gly Asp Val Asn Glu
            100                 105                 110

Val Asn Ile Thr Phe Ser Ser Lys His Gly Phe Gly Ser Gly Val Glu
        115                 120                 125

Ile Asn Thr Ser Asn Pro Thr His Arg Ser Gly Glu Ser Ser Pro Val
    130                 135                 140

Arg Gly Asp Met Leu Gly Leu Lys Ser Glu Leu Glu Lys Arg Phe Phe
145                 150                 155                 160

Gly Lys Thr Phe Asp Asp Asn Ile His Ile Gln Leu Ile Tyr Asn Ile
                165                 170                 175

Leu Asp Ile Glu Lys Ile Leu Ala Val Tyr Val Thr Asn Ile Val Tyr
            180                 185                 190

Ala Leu Asn Asn Met Leu Gly Ile Lys Asp Ser Glu Ser Tyr Asp Asp
        195                 200                 205

Phe Met Gly Tyr Leu Ser Ala Arg Asn Thr Tyr Glu Val Phe Thr His
    210                 215                 220

Pro Asp Lys Ser Asn Leu Ser Asp Lys Val Lys Gly Asn Ile Lys Lys
225                 230                 235                 240

Ser Leu Ser Lys Phe Asn Asp Leu Leu Lys Thr Lys Arg Leu Gly Tyr
                245                 250                 255

Phe Gly Leu Glu Glu Pro Lys Thr Lys Asp Thr Arg Ala Ser Glu Ala
            260                 265                 270

Tyr Lys Lys Arg Val Tyr His Met Leu Ala Ile Val Gly Gln Ile Arg
        275                 280                 285

Gln Cys Val Phe His Asp Lys Ser Gly Ala Lys Arg Phe Asp Leu Tyr
    290                 295                 300

Ser Phe Ile Asn Asn Ile Asp Pro Glu Tyr Arg Asp Thr Leu Asp Tyr
305                 310                 315                 320

Leu Val Glu Glu Arg Leu Lys Ser Ile Asn Lys Asp Phe Ile Glu Gly
                325                 330                 335

Asn Lys Val Asn Ile Ser Leu Leu Ile Asp Met Met Lys Gly Tyr Glu
            340                 345                 350

Ala Asp Asp Ile Ile Arg Leu Tyr Tyr Asp Phe Ile Val Leu Lys Ser
        355                 360                 365

Gln Lys Asn Leu Gly Phe Ser Ile Lys Lys Leu Arg Glu Lys Met Leu
    370                 375                 380

Glu Glu Tyr Gly Phe Arg Phe Lys Asp Lys Gln Tyr Asp Ser Val Arg
385                 390                 395                 400

Ser Lys Met Tyr Lys Leu Met Asp Phe Leu Leu Phe Cys Asn Tyr Tyr
                405                 410                 415

Arg Asn Asp Val Ala Ala Gly Glu Ala Leu Val Arg Lys Leu Arg Phe
            420                 425                 430

Ser Met Thr Asp Asp Glu Lys Glu Gly Ile Tyr Ala Asp Glu Ala Ala
        435                 440                 445

Lys Leu Trp Gly Lys Phe Arg Asn Asp Phe Glu Asn Ile Ala Asp His
    450                 455                 460

Met Asn Gly Asp Val Ile Lys Glu Leu Gly Lys Ala Asp Met Asp Phe
465                 470                 475                 480
```

```
Asp Glu Lys Ile Leu Asp Ser Glu Lys Lys Asn Ala Ser Asp Leu Leu
                485                 490                 495

Tyr Phe Ser Lys Met Ile Tyr Met Leu Thr Tyr Phe Leu Asp Gly Lys
            500                 505                 510

Glu Ile Asn Asp Leu Leu Thr Thr Leu Ile Ser Lys Phe Asp Asn Ile
        515                 520                 525

Lys Glu Phe Leu Lys Ile Met Lys Ser Ser Ala Val Asp Val Glu Cys
    530                 535                 540

Glu Leu Thr Ala Gly Tyr Lys Leu Phe Asn Asp Ser Gln Arg Ile Thr
545                 550                 555                 560

Asn Glu Leu Phe Ile Val Lys Asn Ile Ala Ser Met Arg Lys Pro Ala
                565                 570                 575

Ala Ser Ala Lys Leu Thr Met Phe Arg Asp Ala Leu Thr Ile Leu Gly
            580                 585                 590

Ile Asp Asp Asn Ile Thr Asp Asp Arg Ile Ser Glu Ile Leu Lys Leu
        595                 600                 605

Lys Glu Lys Gly Lys Gly Ile His Gly Leu Arg Asn Phe Ile Thr Asn
    610                 615                 620

Asn Val Ile Glu Ser Ser Arg Phe Val Tyr Leu Ile Lys Tyr Ala Asn
625                 630                 635                 640

Ala Gln Lys Ile Arg Glu Val Ala Lys Asp Glu Lys Val Val Met Phe
                645                 650                 655

Val Leu Gly Gly Ile Pro Asp Thr Gln Ile Glu Arg Tyr Tyr Lys Ser
            660                 665                 670

Cys Val Glu Phe Pro Asp Met Asn Ser Ser Leu Glu Ala Lys Arg Ser
        675                 680                 685

Glu Leu Ala Arg Met Ile Lys Asn Ile Ser Phe Asp Asp Phe Lys Asn
    690                 695                 700

Val Lys Gln Gln Ala Lys Gly Arg Glu Asn Val Ala Lys Glu Arg Ala
705                 710                 715                 720

Lys Ala Val Ile Gly Leu Tyr Leu Thr Val Met Tyr Leu Leu Val Lys
                725                 730                 735

Asn Leu Val Asn Val Asn Ala Arg Tyr Val Ile Ala Ile His Cys Leu
            740                 745                 750

Glu Arg Asp Phe Gly Leu Tyr Lys Glu Ile Ile Pro Glu Leu Ala Ser
        755                 760                 765

Lys Asn Leu Lys Asn Asp Tyr Arg Ile Leu Ser Gln Thr Leu Cys Glu
    770                 775                 780

Leu Cys Asp Asp Arg Asn Glu Ser Ser Asn Leu Phe Leu Lys Lys Asn
785                 790                 795                 800

Lys Arg Leu Arg Lys Cys Val Glu Val Asp Ile Asn Asn Ala Asp Ser
                805                 810                 815

Ser Met Thr Arg Lys Tyr Arg Asn Cys Ile Ala His Leu Thr Val Val
            820                 825                 830

Arg Glu Leu Lys Glu Tyr Ile Gly Asp Ile Arg Thr Val Asp Ser Tyr
        835                 840                 845

Phe Ser Ile Tyr His Tyr Val Met Gln Arg Cys Ile Thr Lys Arg Gly
    850                 855                 860

Asp Asp Thr Lys Gln Glu Glu Lys Ile Lys Tyr Glu Asp Asp Leu Leu
865                 870                 875                 880

Lys Asn His Gly Tyr Thr Lys Asp Phe Val Lys Ala Leu Asn Ser Pro
                885                 890                 895

Phe Gly Tyr Asn Ile Pro Arg Phe Lys Asn Leu Ser Ile Glu Gln Leu
```

```
            900                 905                 910

Phe Asp Arg Asn Glu Tyr Leu Thr Glu Lys
        915                 920


<210> SEQ ID NO 42
<211> LENGTH: 933
<212> TYPE: PRT
<213> ORGANISM: Ruminococcus flavefaciens
<220> FEATURE:
<221> NAME/KEY: misc_feature
<222> LOCATION: (1)..(933)
<223> OTHER INFORMATION: native CasM protein sequence from Ruminococcus
      flavefaciens FD-1

<400> SEQUENCE: 42

Met Lys Lys Lys Met Ser Leu Arg Glu Lys Arg Glu Ala Glu Lys Gln
1               5                   10                  15

Ala Lys Lys Ala Ala Tyr Ser Ala Ala Ser Lys Asn Thr Asp Ser Lys
            20                  25                  30

Pro Ala Glu Lys Lys Ala Glu Thr Pro Lys Pro Ala Glu Ile Ile Ser
        35                  40                  45

Asp Asn Ser Arg Asn Lys Thr Ala Val Lys Ala Ala Gly Leu Lys Ser
    50                  55                  60

Thr Ile Ile Ser Gly Asp Lys Leu Tyr Met Thr Ser Phe Gly Lys Gly
65                  70                  75                  80

Asn Ala Ala Val Ile Glu Gln Lys Ile Asp Ile Asn Asp Tyr Ser Phe
                85                  90                  95

Ser Ala Met Lys Asp Thr Pro Ser Leu Glu Val Asp Lys Ala Glu Ser
            100                 105                 110

Lys Glu Ile Ser Phe Ser Ser His His Pro Phe Val Lys Asn Asp Lys
        115                 120                 125

Leu Thr Thr Tyr Asn Pro Leu Tyr Gly Gly Lys Asp Asn Pro Glu Lys
    130                 135                 140

Pro Val Gly Arg Asp Met Leu Gly Leu Lys Asp Lys Leu Glu Glu Arg
145                 150                 155                 160

Tyr Phe Gly Cys Thr Phe Asn Asp Asn Leu His Ile Gln Ile Ile Tyr
                165                 170                 175

Asn Ile Leu Asp Ile Glu Lys Ile Leu Ala Val His Ser Ala Asn Ile
            180                 185                 190

Thr Thr Ala Leu Asp His Met Val Asp Glu Asp Asp Glu Lys Tyr Leu
        195                 200                 205

Asn Ser Asp Tyr Ile Gly Tyr Met Asn Thr Ile Asn Thr Tyr Asp Val
    210                 215                 220

Phe Met Asp Pro Ser Lys Asn Ser Ser Leu Ser Pro Lys Asp Arg Lys
225                 230                 235                 240

Asn Ile Asp Asn Ser Arg Ala Lys Phe Glu Lys Leu Leu Ser Thr Lys
                245                 250                 255

Arg Leu Gly Tyr Phe Gly Phe Asp Tyr Asp Ala Asn Gly Lys Asp Lys
            260                 265                 270

Lys Lys Asn Glu Glu Ile Lys Lys Arg Leu Tyr His Leu Thr Ala Phe
        275                 280                 285

Ala Gly Gln Leu Arg Gln Trp Ser Phe His Ser Ala Gly Asn Tyr Pro
    290                 295                 300

Arg Thr Trp Leu Tyr Lys Leu Asp Ser Leu Asp Lys Glu Tyr Leu Asp
305                 310                 315                 320

Thr Leu Asp His Tyr Phe Asp Lys Arg Phe Asn Asp Ile Asn Asp Asp
```

```
                325                 330                 335

Phe Val Thr Lys Asn Ala Thr Asn Leu Tyr Ile Leu Lys Glu Val Phe
            340                 345                 350

Pro Glu Ala Asn Phe Lys Asp Ile Ala Asp Leu Tyr Tyr Asp Phe Ile
        355                 360                 365

Val Ile Lys Ser His Lys Asn Met Gly Phe Ser Ile Lys Lys Leu Arg
    370                 375                 380

Glu Lys Met Leu Glu Cys Asp Gly Ala Asp Arg Ile Lys Glu Gln Asp
385                 390                 395                 400

Met Asp Ser Val Arg Ser Lys Leu Tyr Lys Leu Ile Asp Phe Cys Ile
                405                 410                 415

Phe Lys Tyr Tyr His Glu Phe Pro Glu Leu Ser Glu Lys Asn Val Asp
            420                 425                 430

Ile Leu Arg Ala Ala Val Ser Asp Thr Lys Lys Asp Asn Leu Tyr Ser
        435                 440                 445

Asp Glu Ala Ala Arg Leu Trp Ser Ile Phe Lys Glu Lys Phe Leu Gly
    450                 455                 460

Phe Cys Asp Lys Ile Val Val Trp Val Thr Gly Glu His Glu Lys Asp
465                 470                 475                 480

Ile Thr Ser Val Ile Asp Lys Asp Ala Tyr Arg Asn Arg Ser Asn Val
                485                 490                 495

Ser Tyr Phe Ser Lys Leu Met Tyr Ala Met Cys Phe Phe Leu Asp Gly
            500                 505                 510

Lys Glu Ile Asn Asp Leu Leu Thr Thr Leu Ile Asn Lys Phe Asp Asn
        515                 520                 525

Ile Ala Asn Gln Ile Lys Thr Ala Lys Glu Leu Gly Ile Asn Thr Ala
    530                 535                 540

Phe Val Lys Asn Tyr Asp Phe Phe Asn His Ser Glu Lys Tyr Val Asp
545                 550                 555                 560

Glu Leu Asn Ile Val Lys Asn Ile Ala Arg Met Lys Lys Pro Ser Ser
                565                 570                 575

Asn Ala Lys Lys Ala Met Tyr His Asp Ala Leu Thr Ile Leu Gly Ile
            580                 585                 590

Pro Glu Asp Met Asp Glu Lys Ala Leu Asp Glu Glu Leu Asp Leu Ile
        595                 600                 605

Leu Glu Lys Lys Thr Asp Pro Val Thr Gly Lys Pro Leu Lys Gly Lys
    610                 615                 620

Asn Pro Leu Arg Asn Phe Ile Ala Asn Asn Val Ile Glu Asn Ser Arg
625                 630                 635                 640

Phe Ile Tyr Leu Ile Lys Phe Cys Asn Pro Glu Asn Val Arg Lys Ile
                645                 650                 655

Val Asn Asn Thr Lys Val Thr Glu Phe Val Leu Lys Arg Ile Pro Asp
            660                 665                 670

Ala Gln Ile Glu Arg Tyr Tyr Lys Ser Cys Thr Asp Ser Glu Met Asn
        675                 680                 685

Pro Pro Thr Glu Lys Lys Ile Thr Glu Leu Ala Gly Lys Leu Lys Asp
    690                 695                 700

Met Asn Phe Gly Asn Phe Arg Asn Val Arg Gln Ser Ala Lys Glu Asn
705                 710                 715                 720

Met Glu Lys Glu Arg Phe Lys Ala Val Ile Gly Leu Tyr Leu Thr Val
                725                 730                 735

Val Tyr Arg Val Val Lys Asn Leu Val Asp Val Asn Ser Arg Tyr Ile
            740                 745                 750
```

```
Met Ala Phe His Ser Leu Glu Arg Asp Ser Gln Leu Tyr Asn Val Ser
        755                 760                 765

Val Asp Asn Asp Tyr Leu Ala Leu Thr Asp Thr Leu Val Lys Glu Gly
    770                 775                 780

Asp Asn Ser Arg Ser Arg Tyr Leu Ala Gly Asn Lys Arg Leu Arg Asp
785                 790                 795                 800

Cys Val Lys Gln Asp Ile Asp Asn Ala Lys Lys Trp Phe Val Ser Asp
                805                 810                 815

Lys Tyr Asn Ser Ile Thr Lys Tyr Arg Asn Asn Val Ala His Leu Thr
            820                 825                 830

Ala Val Arg Asn Cys Ala Glu Phe Ile Gly Asp Ile Thr Lys Ile Asp
        835                 840                 845

Ser Tyr Phe Ala Leu Tyr His Tyr Leu Ile Gln Arg Gln Leu Ala Lys
    850                 855                 860

Gly Leu Asp His Glu Arg Ser Gly Phe Asp Arg Asn Tyr Pro Gln Tyr
865                 870                 875                 880

Ala Pro Leu Phe Lys Trp His Thr Tyr Val Lys Asp Val Val Lys Ala
                885                 890                 895

Leu Asn Ala Pro Phe Gly Tyr Asn Ile Pro Arg Phe Lys Asn Leu Ser
            900                 905                 910

Ile Asp Ala Leu Phe Asp Arg Asn Glu Ile Lys Lys Asn Asp Gly Glu
        915                 920                 925

Lys Lys Ser Asp Asp
    930


<210> SEQ ID NO 43
<211> LENGTH: 944
<212> TYPE: PRT
<213> ORGANISM: Ruminococcus albus
<220> FEATURE:
<221> NAME/KEY: misc_feature
<222> LOCATION: (1)..(944)
<223> OTHER INFORMATION: native CasM protein sequence from Ruminococcus
      albus strain KH2T6

<400> SEQUENCE: 43

Met Ala Lys Lys Ser Lys Gly Met Ser Leu Arg Glu Lys Arg Glu Leu
1               5                   10                  15

Glu Lys Gln Lys Arg Ile Gln Lys Ala Ala Val Asn Ser Val Asn Asp
            20                  25                  30

Thr Pro Glu Lys Thr Glu Glu Ala Asn Val Val Ser Val Asn Val Arg
        35                  40                  45

Thr Ser Ala Glu Asn Lys His Ser Lys Lys Ser Ala Ala Lys Ala Leu
    50                  55                  60

Gly Leu Lys Ser Gly Leu Val Ile Gly Asp Glu Leu Tyr Leu Thr Ser
65                  70                  75                  80

Phe Gly Arg Gly Asn Glu Ala Lys Leu Glu Lys Lys Ile Ser Gly Asp
                85                  90                  95

Thr Val Glu Lys Leu Gly Ile Gly Ala Phe Glu Val Ala Glu Arg Asp
            100                 105                 110

Glu Ser Thr Leu Thr Leu Glu Ser Gly Arg Ile Lys Asp Lys Thr Ala
        115                 120                 125

Arg Pro Lys Asp Pro Arg His Ile Thr Val Asp Thr Gln Gly Lys Phe
    130                 135                 140

Lys Glu Asp Met Leu Gly Ile Arg Ser Val Leu Glu Lys Lys Ile Phe
145                 150                 155                 160
```

```
Gly Lys Thr Phe Asp Asp Asn Ile His Val Gln Leu Ala Tyr Asn Ile
                165                 170                 175

Leu Asp Val Glu Lys Ile Met Ala Gln Tyr Val Ser Asp Ile Val Tyr
            180                 185                 190

Met Leu His Asn Thr Asp Lys Thr Glu Arg Asn Asp Asn Leu Met Gly
        195                 200                 205

Tyr Met Ser Ile Arg Asn Thr Tyr Lys Thr Phe Cys Asp Thr Ser Asn
    210                 215                 220

Leu Pro Asp Asp Thr Lys Gln Lys Val Glu Asn Gln Lys Arg Glu Phe
225                 230                 235                 240

Asp Lys Ile Ile Lys Ser Gly Arg Leu Gly Tyr Phe Gly Glu Ala Phe
                245                 250                 255

Met Val Asn Ser Gly Asn Ser Thr Lys Leu Arg Pro Glu Lys Glu Ile
            260                 265                 270

Tyr His Ile Phe Ala Leu Met Ala Ser Leu Arg Gln Ser Tyr Phe His
        275                 280                 285

Gly Tyr Val Lys Asp Thr Asp Tyr Gln Gly Thr Thr Trp Ala Tyr Thr
    290                 295                 300

Leu Glu Asp Lys Leu Lys Gly Pro Ser His Glu Phe Arg Glu Thr Ile
305                 310                 315                 320

Asp Lys Ile Phe Asp Glu Gly Phe Ser Lys Ile Ser Lys Asp Phe Gly
                325                 330                 335

Lys Met Asn Lys Val Asn Leu Gln Ile Leu Glu Gln Met Ile Gly Glu
            340                 345                 350

Leu Tyr Gly Ser Ile Glu Arg Gln Asn Leu Thr Cys Asp Tyr Tyr Asp
        355                 360                 365

Phe Ile Gln Leu Lys Lys His Lys Tyr Leu Gly Phe Ser Ile Lys Arg
    370                 375                 380

Leu Arg Glu Thr Met Leu Glu Thr Thr Pro Ala Glu Cys Tyr Lys Ala
385                 390                 395                 400

Glu Cys Tyr Asn Ser Glu Arg Gln Lys Leu Tyr Lys Leu Ile Asp Phe
                405                 410                 415

Leu Ile Tyr Asp Leu Tyr Tyr Asn Arg Lys Pro Ala Arg Ile Glu Glu
            420                 425                 430

Ile Val Asp Lys Leu Arg Glu Ser Val Asn Asp Glu Glu Lys Glu Ser
        435                 440                 445

Ile Tyr Ser Val Glu Ala Lys Tyr Val Tyr Glu Ser Leu Ser Lys Val
    450                 455                 460

Leu Asp Lys Ser Leu Lys Asn Ser Val Ser Gly Glu Thr Ile Lys Asp
465                 470                 475                 480

Leu Gln Lys Arg Tyr Asp Asp Glu Thr Ala Asn Arg Ile Trp Asp Ile
                485                 490                 495

Ser Gln His Ser Ile Ser Gly Asn Val Asn Cys Phe Cys Lys Leu Ile
            500                 505                 510

Tyr Ile Met Thr Leu Met Leu Asp Gly Lys Glu Ile Asn Asp Leu Leu
        515                 520                 525

Thr Thr Leu Val Asn Lys Phe Asp Asn Ile Ala Ser Phe Ile Asp Val
    530                 535                 540

Met Asp Glu Leu Gly Leu Glu His Ser Phe Thr Asp Asn Tyr Lys Met
545                 550                 555                 560

Phe Ala Asp Ser Lys Ala Ile Cys Leu Asp Leu Gln Phe Ile Asn Ser
                565                 570                 575
```

```
Phe Ala Arg Met Ser Lys Ile Asp Asp Glu Lys Ser Lys Arg Gln Leu
            580                 585                 590

Phe Arg Asp Ala Leu Val Ile Leu Asp Ile Gly Asn Lys Asp Glu Thr
        595                 600                 605

Trp Ile Asn Asn Tyr Leu Asp Ser Asp Ile Phe Lys Leu Asp Lys Glu
    610                 615                 620

Gly Asn Lys Leu Lys Gly Ala Arg His Asp Phe Arg Asn Phe Ile Ala
625                 630                 635                 640

Asn Asn Val Ile Lys Ser Ser Arg Phe Lys Tyr Leu Val Lys Tyr Ser
                645                 650                 655

Ser Ala Asp Gly Met Ile Lys Leu Lys Thr Asn Glu Lys Leu Ile Gly
            660                 665                 670

Phe Val Leu Asp Lys Leu Pro Glu Thr Gln Ile Asp Arg Tyr Tyr Glu
        675                 680                 685

Ser Cys Gly Leu Asp Asn Ala Val Val Asp Lys Lys Val Arg Ile Glu
    690                 695                 700

Lys Leu Ser Gly Leu Ile Arg Asp Met Lys Phe Asp Asp Phe Ser Gly
705                 710                 715                 720

Val Lys Thr Ser Asn Lys Ala Gly Asp Asn Asp Lys Gln Asp Lys Ala
                725                 730                 735

Lys Tyr Gln Ala Ile Ile Ser Leu Tyr Leu Met Val Leu Tyr Gln Ile
            740                 745                 750

Val Lys Asn Met Ile Tyr Val Asn Ser Arg Tyr Val Ile Ala Phe His
        755                 760                 765

Cys Leu Glu Arg Asp Phe Gly Met Tyr Gly Lys Asp Phe Gly Lys Tyr
    770                 775                 780

Tyr Gln Gly Cys Arg Lys Leu Thr Asp His Phe Ile Glu Glu Lys Tyr
785                 790                 795                 800

Met Lys Glu Gly Lys Leu Gly Cys Asn Lys Lys Val Gly Arg Tyr Leu
                805                 810                 815

Lys Asn Asn Ile Ser Cys Cys Thr Asp Gly Leu Ile Asn Thr Tyr Arg
            820                 825                 830

Asn Gln Val Asp His Phe Ala Val Val Arg Lys Ile Gly Asn Tyr Ala
        835                 840                 845

Ala Tyr Ile Lys Ser Ile Gly Ser Trp Phe Glu Leu Tyr His Tyr Val
    850                 855                 860

Ile Gln Arg Ile Val Phe Asp Glu Tyr Arg Phe Ala Leu Asn Asn Thr
865                 870                 875                 880

Glu Ser Asn Tyr Lys Asn Ser Ile Ile Lys His His Thr Tyr Cys Lys
                885                 890                 895

Asp Met Val Lys Ala Leu Asn Thr Pro Phe Gly Tyr Asp Leu Pro Arg
            900                 905                 910

Tyr Lys Asn Leu Ser Ile Gly Asp Leu Phe Asp Arg Asn Asn Tyr Leu
        915                 920                 925

Asn Lys Thr Lys Glu Ser Ile Asp Ala Asn Ser Ser Ile Asp Ser Gln
    930                 935                 940
```

<210> SEQ ID NO 44
<211> LENGTH: 967
<212> TYPE: PRT
<213> ORGANISM: Ruminococcus flavefaciens
<220> FEATURE:
<221> NAME/KEY: misc_feature
<222> LOCATION: (1)..(967)
<223> OTHER INFORMATION: native CasM protein sequence from Ruminococcus flavefaciens strain XPD3002

<400> SEQUENCE: 44

```
Met Ile Glu Lys Lys Lys Ser Phe Ala Lys Gly Met Gly Val Lys Ser
1               5                   10                  15

Thr Leu Val Ser Gly Ser Lys Val Tyr Met Thr Thr Phe Ala Glu Gly
            20                  25                  30

Ser Asp Ala Arg Leu Glu Lys Ile Val Glu Gly Asp Ser Ile Arg Ser
        35                  40                  45

Val Asn Glu Gly Glu Ala Phe Ser Ala Glu Met Ala Asp Lys Asn Ala
    50                  55                  60

Gly Tyr Lys Ile Gly Asn Ala Lys Phe Ser His Pro Lys Gly Tyr Ala
65                  70                  75                  80

Val Val Ala Asn Asn Pro Leu Tyr Thr Gly Pro Val Gln Gln Asp Met
                85                  90                  95

Leu Gly Leu Lys Glu Thr Leu Glu Lys Arg Tyr Phe Gly Glu Ser Ala
            100                 105                 110

Asp Gly Asn Asp Asn Ile Cys Ile Gln Val Ile His Asn Ile Leu Asp
        115                 120                 125

Ile Glu Lys Ile Leu Ala Glu Tyr Ile Thr Asn Ala Ala Tyr Ala Val
    130                 135                 140

Asn Asn Ile Ser Gly Leu Asp Lys Asp Ile Ile Gly Phe Gly Lys Phe
145                 150                 155                 160

Ser Thr Val Tyr Thr Tyr Asp Glu Phe Lys Asp Pro Glu His His Arg
                165                 170                 175

Ala Ala Phe Asn Asn Asn Asp Lys Leu Ile Asn Ala Ile Lys Ala Gln
            180                 185                 190

Tyr Asp Glu Phe Asp Asn Phe Leu Asp Asn Pro Arg Leu Gly Tyr Phe
        195                 200                 205

Gly Gln Ala Phe Phe Ser Lys Glu Gly Arg Asn Tyr Ile Ile Asn Tyr
    210                 215                 220

Gly Asn Glu Cys Tyr Asp Ile Leu Ala Leu Leu Ser Gly Leu Arg His
225                 230                 235                 240

Trp Val Val His Asn Asn Glu Glu Glu Ser Arg Ile Ser Arg Thr Trp
                245                 250                 255

Leu Tyr Asn Leu Asp Lys Asn Leu Asp Asn Glu Tyr Ile Ser Thr Leu
            260                 265                 270

Asn Tyr Leu Tyr Asp Arg Ile Thr Asn Glu Leu Thr Asn Ser Phe Ser
        275                 280                 285

Lys Asn Ser Ala Ala Asn Val Asn Tyr Ile Ala Glu Thr Leu Gly Ile
    290                 295                 300

Asn Pro Ala Glu Phe Ala Glu Gln Tyr Phe Arg Phe Ser Ile Met Lys
305                 310                 315                 320

Glu Gln Lys Asn Leu Gly Phe Asn Ile Thr Lys Leu Arg Glu Val Met
                325                 330                 335

Leu Asp Arg Lys Asp Met Ser Glu Ile Arg Lys Asn His Lys Val Phe
            340                 345                 350

Asp Ser Ile Arg Thr Lys Val Tyr Thr Met Met Asp Phe Val Ile Tyr
        355                 360                 365

Arg Tyr Tyr Ile Glu Glu Asp Ala Lys Val Ala Ala Ala Asn Lys Ser
    370                 375                 380

Leu Pro Asp Asn Glu Lys Ser Leu Ser Glu Lys Asp Ile Phe Val Ile
385                 390                 395                 400

Asn Leu Arg Gly Ser Phe Asn Asp Asp Gln Lys Asp Ala Leu Tyr Tyr
```

```
                405                 410                 415

Asp Glu Ala Asn Arg Ile Trp Arg Lys Leu Glu Asn Ile Met His Asn
            420                 425                 430

Ile Lys Glu Phe Arg Gly Asn Lys Thr Arg Glu Tyr Lys Lys Lys Asp
        435                 440                 445

Ala Pro Arg Leu Pro Arg Ile Leu Pro Ala Gly Arg Asp Val Ser Ala
    450                 455                 460

Phe Ser Lys Leu Met Tyr Ala Leu Thr Met Phe Leu Asp Gly Lys Glu
465                 470                 475                 480

Ile Asn Asp Leu Leu Thr Thr Leu Ile Asn Lys Phe Asp Asn Ile Gln
                485                 490                 495

Ser Phe Leu Lys Val Met Pro Leu Ile Gly Val Asn Ala Lys Phe Val
            500                 505                 510

Glu Glu Tyr Ala Phe Phe Lys Asp Ser Ala Lys Ile Ala Asp Glu Leu
        515                 520                 525

Arg Leu Ile Lys Ser Phe Ala Arg Met Gly Glu Pro Ile Ala Asp Ala
    530                 535                 540

Arg Arg Ala Met Tyr Ile Asp Ala Ile Arg Ile Leu Gly Thr Asn Leu
545                 550                 555                 560

Ser Tyr Asp Glu Leu Lys Ala Leu Ala Asp Thr Phe Ser Leu Asp Glu
                565                 570                 575

Asn Gly Asn Lys Leu Lys Lys Gly Lys His Gly Met Arg Asn Phe Ile
            580                 585                 590

Ile Asn Asn Val Ile Ser Asn Lys Arg Phe His Tyr Leu Ile Arg Tyr
        595                 600                 605

Gly Asp Pro Ala His Leu His Glu Ile Ala Lys Asn Glu Ala Val Val
    610                 615                 620

Lys Phe Val Leu Gly Arg Ile Ala Asp Ile Gln Lys Lys Gln Gly Gln
625                 630                 635                 640

Asn Gly Lys Asn Gln Ile Asp Arg Tyr Tyr Glu Thr Cys Ile Gly Lys
                645                 650                 655

Asp Lys Gly Lys Ser Val Ser Glu Lys Val Asp Ala Leu Thr Lys Ile
            660                 665                 670

Ile Thr Gly Met Asn Tyr Asp Gln Phe Asp Lys Lys Arg Ser Val Ile
        675                 680                 685

Glu Asp Thr Gly Arg Glu Asn Ala Glu Arg Glu Lys Phe Lys Lys Ile
    690                 695                 700

Ile Ser Leu Tyr Leu Thr Val Ile Tyr His Ile Leu Lys Asn Ile Val
705                 710                 715                 720

Asn Ile Asn Ala Arg Tyr Val Ile Gly Phe His Cys Val Glu Arg Asp
                725                 730                 735

Ala Gln Leu Tyr Lys Glu Lys Gly Tyr Asp Ile Asn Leu Lys Lys Leu
            740                 745                 750

Glu Glu Lys Gly Phe Ser Ser Val Thr Lys Leu Cys Ala Gly Ile Asp
        755                 760                 765

Glu Thr Ala Pro Asp Lys Arg Lys Asp Val Glu Lys Glu Met Ala Glu
    770                 775                 780

Arg Ala Lys Glu Ser Ile Asp Ser Leu Glu Ser Ala Asn Pro Lys Leu
785                 790                 795                 800

Tyr Ala Asn Tyr Ile Lys Tyr Ser Asp Glu Lys Lys Ala Glu Glu Phe
                805                 810                 815

Thr Arg Gln Ile Asn Arg Glu Lys Ala Lys Thr Ala Leu Asn Ala Tyr
            820                 825                 830
```

Leu Arg Asn Thr Lys Trp Asn Val Ile Ile Arg Glu Asp Leu Leu Arg
835 840 845

Ile Asp Asn Lys Thr Cys Thr Leu Phe Arg Asn Lys Ala Val His Leu
850 855 860

Glu Val Ala Arg Tyr Val His Ala Tyr Ile Asn Asp Ile Ala Glu Val
865 870 875 880

Asn Ser Tyr Phe Gln Leu Tyr His Tyr Ile Met Gln Arg Ile Ile Met
885 890 895

Asn Glu Arg Tyr Glu Lys Ser Ser Gly Lys Val Ser Glu Tyr Phe Asp
900 905 910

Ala Val Asn Asp Glu Lys Lys Tyr Asn Asp Arg Leu Leu Lys Leu Leu
915 920 925

Cys Val Pro Phe Gly Tyr Cys Ile Pro Arg Phe Lys Asn Leu Ser Ile
930 935 940

Glu Ala Leu Phe Asp Arg Asn Glu Ala Ala Lys Phe Asp Lys Glu Lys
945 950 955 960

Lys Lys Val Ser Gly Asn Ser
965

<210> SEQ ID NO 45
<211> LENGTH: 796
<212> TYPE: PRT
<213> ORGANISM: Ruminococcus sp.
<220> FEATURE:
<221> NAME/KEY: misc_feature
<222> LOCATION: (1)..(796)
<223> OTHER INFORMATION: native CasM protein sequence from Ruminococcus sp., isolate 2789STDY5834894

<400> SEQUENCE: 45

Met Glu Ile Asn Thr Ser Asn Pro Thr His Arg Ser Gly Glu Ser Ser
1 5 10 15

Ser Val Arg Gly Asp Met Leu Gly Leu Lys Ser Glu Leu Glu Lys Arg
20 25 30

Phe Phe Gly Lys Thr Phe Asp Asp Asn Ile His Ile Gln Leu Ile Tyr
35 40 45

Asn Ile Leu Asp Ile Glu Lys Ile Leu Ala Val Tyr Val Thr Asn Ile
50 55 60

Val Tyr Ala Leu Asn Asn Met Leu Gly Val Lys Gly Ser Glu Ser Tyr
65 70 75 80

Asp Asp Phe Met Gly Tyr Leu Ser Ala Gln Asn Thr Tyr Tyr Ile Phe
85 90 95

Thr His Pro Asp Lys Ser Asn Leu Ser Asp Lys Val Lys Gly Asn Ile
100 105 110

Lys Lys Ser Leu Ser Lys Phe Asn Asp Leu Leu Lys Thr Lys Arg Leu
115 120 125

Gly Tyr Phe Gly Leu Glu Glu Pro Lys Thr Lys Asp Lys Arg Val Ser
130 135 140

Glu Ala Tyr Lys Lys Arg Val Tyr His Met Leu Ala Ile Val Gly Gln
145 150 155 160

Ile Arg Gln Ser Val Phe His Asp Lys Ser Asn Glu Leu Asp Glu Tyr
165 170 175

Leu Tyr Ser Phe Ile Asp Ile Ile Asp Ser Glu Tyr Arg Asp Thr Leu
180 185 190

Asp Tyr Leu Val Asp Glu Arg Phe Asp Ser Ile Asn Lys Gly Phe Val
195 200 205

```
Gln Gly Asn Lys Val Asn Ile Ser Leu Leu Ile Asp Met Met Lys Gly
    210                 215                 220

Tyr Glu Ala Asp Asp Ile Ile Arg Leu Tyr Tyr Asp Phe Ile Val Leu
225                 230                 235                 240

Lys Ser Gln Lys Asn Leu Gly Phe Ser Ile Lys Lys Leu Arg Glu Lys
                245                 250                 255

Met Leu Asp Glu Tyr Gly Phe Arg Phe Lys Asp Lys Gln Tyr Asp Ser
            260                 265                 270

Val Arg Ser Lys Met Tyr Lys Leu Met Asp Phe Leu Leu Phe Cys Asn
        275                 280                 285

Tyr Tyr Arg Asn Asp Val Val Ala Gly Glu Ala Leu Val Arg Lys Leu
    290                 295                 300

Arg Phe Ser Met Thr Asp Asp Glu Lys Glu Gly Ile Tyr Ala Asp Glu
305                 310                 315                 320

Ala Glu Lys Leu Trp Gly Lys Phe Arg Asn Asp Phe Glu Asn Ile Ala
                325                 330                 335

Asp His Met Asn Gly Asp Val Ile Lys Glu Leu Gly Lys Ala Asp Met
            340                 345                 350

Asp Phe Asp Glu Lys Ile Leu Asp Ser Glu Lys Lys Asn Ala Ser Asp
        355                 360                 365

Leu Leu Tyr Phe Ser Lys Met Ile Tyr Met Leu Thr Tyr Phe Leu Asp
    370                 375                 380

Gly Lys Glu Ile Asn Asp Leu Leu Thr Thr Leu Ile Ser Lys Phe Asp
385                 390                 395                 400

Asn Ile Lys Glu Phe Leu Lys Ile Met Lys Ser Ser Ala Val Asp Val
                405                 410                 415

Glu Cys Glu Leu Thr Ala Gly Tyr Lys Leu Phe Asn Asp Ser Gln Arg
            420                 425                 430

Ile Thr Asn Glu Leu Phe Ile Val Lys Asn Ile Ala Ser Met Arg Lys
        435                 440                 445

Pro Ala Ala Ser Ala Lys Leu Thr Met Phe Arg Asp Ala Leu Thr Ile
    450                 455                 460

Leu Gly Ile Asp Asp Lys Ile Thr Asp Asp Arg Ile Ser Glu Ile Leu
465                 470                 475                 480

Lys Leu Lys Glu Lys Gly Lys Gly Ile His Gly Leu Arg Asn Phe Ile
                485                 490                 495

Thr Asn Asn Val Ile Glu Ser Ser Arg Phe Val Tyr Leu Ile Lys Tyr
            500                 505                 510

Ala Asn Ala Gln Lys Ile Arg Glu Val Ala Lys Asn Glu Lys Val Val
        515                 520                 525

Met Phe Val Leu Gly Gly Ile Pro Asp Thr Gln Ile Glu Arg Tyr Tyr
    530                 535                 540

Lys Ser Cys Val Glu Phe Pro Asp Met Asn Ser Ser Leu Glu Ala Lys
545                 550                 555                 560

Cys Ser Glu Leu Ala Arg Met Ile Lys Asn Ile Ser Phe Asp Asp Phe
                565                 570                 575

Lys Asn Val Lys Gln Gln Ala Lys Gly Arg Glu Asn Val Ala Lys Glu
            580                 585                 590

Arg Ala Lys Ala Val Ile Gly Leu Tyr Leu Thr Val Met Tyr Leu Leu
        595                 600                 605

Val Lys Asn Leu Val Asn Val Asn Ala Arg Tyr Val Ile Ala Ile His
    610                 615                 620
```

```
Cys Leu Glu Arg Asp Phe Gly Leu Tyr Lys Glu Ile Ile Pro Glu Leu
625                 630                 635                 640

Ala Ser Lys Asn Leu Lys Asn Asp Tyr Arg Ile Leu Ser Gln Thr Leu
                645                 650                 655

Cys Glu Leu Cys Asp Asp Arg Asp Glu Ser Pro Asn Leu Phe Leu Lys
            660                 665                 670

Lys Asn Lys Arg Leu Arg Lys Cys Val Glu Val Asp Ile Asn Asn Ala
        675                 680                 685

Asp Ser Ser Met Thr Arg Lys Tyr Arg Asn Cys Ile Ala His Leu Thr
    690                 695                 700

Val Val Arg Glu Leu Lys Glu Tyr Ile Gly Asp Ile Arg Thr Val Asp
705                 710                 715                 720

Ser Tyr Phe Ser Ile Tyr His Tyr Val Met Gln Arg Cys Ile Thr Lys
                725                 730                 735

Arg Glu Asp Asp Thr Lys Gln Glu Glu Lys Ile Lys Tyr Glu Asp Asp
            740                 745                 750

Leu Leu Lys Asn His Gly Tyr Thr Lys Asp Phe Val Lys Ala Leu Asn
        755                 760                 765

Ser Pro Phe Gly Tyr Asn Ile Pro Arg Phe Lys Asn Leu Ser Ile Glu
    770                 775                 780

Gln Leu Phe Asp Arg Asn Glu Tyr Leu Thr Glu Lys
785                 790                 795
```

<210> SEQ ID NO 46
<211> LENGTH: 96
<212> TYPE: RNA
<213> ORGANISM: Artificial Sequence
<220> FEATURE:
<223> OTHER INFORMATION: Synthetic: CRISPR Arrays Component

<400> SEQUENCE: 46

```
ugauacugcu uugaugucag cauugcauau cuacuauacu ggugcgaauu ugcacuaguc     60

uaaaaucuau aaccauaagu ucuucugcgu ucauau                               96
```

<210> SEQ ID NO 47
<211> LENGTH: 66
<212> TYPE: RNA
<213> ORGANISM: Artificial Sequence
<220> FEATURE:
<223> OTHER INFORMATION: Synthetic: CRISPR Arrays Component

<400> SEQUENCE: 47

```
ugauacugcu uugaugucag cauugcauau cuacuauacu ggugcgaauu ugcacuaguc     60

uaaaau                                                                66
```

<210> SEQ ID NO 48
<211> LENGTH: 66
<212> TYPE: RNA
<213> ORGANISM: Artificial Sequence
<220> FEATURE:
<223> OTHER INFORMATION: Synthetic: CRISPR Arrays Component

<400> SEQUENCE: 48

```
cuacuauacu ggugcgaauu ugcacuaguc uaaaauugau acugcuuuga ugucagcauu     60

gcauau                                                                66
```

<210> SEQ ID NO 49
<211> LENGTH: 45
<212> TYPE: DNA

<213> ORGANISM: Artificial Sequence
<220> FEATURE:
<223> OTHER INFORMATION: Synthetic: Forward primer

<400> SEQUENCE: 49
cgaaattaat acgactcact ataggtttcg attatgcggc cgtgt 45

<210> SEQ ID NO 50
<211> LENGTH: 22
<212> TYPE: DNA
<213> ORGANISM: Artificial Sequence
<220> FEATURE:
<223> OTHER INFORMATION: Synthetic: Reverse primer

<400> SEQUENCE: 50
aggagatata ccatgggcag ca 22

<210> SEQ ID NO 51
<211> LENGTH: 36
<212> TYPE: RNA
<213> ORGANISM: Artificial Sequence
<220> FEATURE:
<223> OTHER INFORMATION: Synthetic: CasM repeat sequence

<400> SEQUENCE: 51
cuacuauacu ggugcgaauu ugcacuaguc uaaaau 36

<210> SEQ ID NO 52
<211> LENGTH: 824
<212> TYPE: PRT
<213> ORGANISM: Eubacterium siraeum
<220> FEATURE:
<221> NAME/KEY: misc_feature
<222> LOCATION: (1)..(824)
<223> OTHER INFORMATION: WYL Eubacterium siraeum

<400> SEQUENCE: 52

Met Lys Lys Thr Glu Lys Phe Asp Asp Val Gln Ser Gly Tyr Glu Tyr
1 5 10 15

Lys Tyr Phe Leu Glu Ser Ile Asp Lys Tyr Arg Ala Ala Val Gln Asn
20 25 30

Ile Tyr Thr Tyr Gly Cys Phe Asn Gln Lys Gln Leu Ser Glu Gln Cys
35 40 45

Asn Cys Ser Asp Gln Thr Ile Lys Lys Ala Phe Asn Phe Tyr Asn Leu
50 55 60

Cys Leu Ala Asn Tyr Ile Lys Lys Lys Lys Gly Thr Leu Ser Lys Lys
65 70 75 80

Ala Lys Gly Arg Pro Thr Glu Ala Lys Tyr Leu Glu Tyr Asp Arg Phe
85 90 95

Thr Leu Asn Glu Asn Tyr Leu Tyr Asn Ile Tyr Leu Trp Ala Arg Ile
100 105 110

Thr Lys Lys Gln Met Trp Ala Phe Ser Tyr Phe Arg Arg His Thr Ser
115 120 125

Leu Leu Ile Asn Ala Ser Arg Thr Glu Ile Lys Asn Gln Leu Ser Asp
130 135 140

Phe Phe Leu Tyr Phe Ser Glu Tyr Met Asp Arg Ser Lys Lys Ala Glu
145 150 155 160

Asn Ser Gln Asp Leu Gly Tyr Ile Ile Asp Met Thr Ala Pro Thr Glu
165 170 175

Lys Asn Met Leu Ile Ser Ser Met Cys Asp Ala Leu Ala Val Phe Gly
180 185 190

```
Arg Lys Ala Pro Tyr Ser Val Pro Ala Tyr Ser Ile Ser His Lys Leu
        195                 200                 205

Lys Lys Leu Cys Gly Asn Asp Ser Lys Ser Leu Trp Ser Phe Met Tyr
    210                 215                 220

Asp Asn Tyr Asp Arg Ile Leu Tyr Asp Glu Ala Val Tyr Thr Ile Arg
225                 230                 235                 240

Gln Ala Ile Arg Asp Arg Lys Leu Ile Gly Tyr Gln Thr Val Gly Thr
                245                 250                 255

Glu Lys Gln Lys Ser Val Asn Tyr Val Val Pro Leu Lys Ile Met Tyr
            260                 265                 270

Glu Tyr Asn Leu Gly Arg Cys Tyr Leu Leu Tyr Ser Pro Leu Asn Ser
        275                 280                 285

Asp Ser Ile Ile Lys Ser Ile Arg Leu Asp Lys Leu Tyr Lys Val Ala
    290                 295                 300

Ala Tyr Glu Pro Asp Ser Ile Ile Asn Tyr Glu Lys Leu Tyr Asp Val
305                 310                 315                 320

Leu Ala Val Ala Glu Asn Glu Ile Trp Leu Ser Gly Asp Tyr Thr Lys
                325                 330                 335

Lys Asp Cys Leu Ser Arg Ile Val Leu Lys Asn Val Lys Pro Gln Ala
            340                 345                 350

Phe Ser Leu Ile Glu Lys Tyr Gly Val Cys Tyr Thr Glu Asp Arg Glu
        355                 360                 365

Ala Lys Thr Val Thr Phe Asn Ile Arg Lys Ala Asp Asp Ile Lys Pro
    370                 375                 380

Phe Ile Arg Thr Leu Gly Gly Asp Ala Val Ile Ser Glu Glu Asp Asn
385                 390                 395                 400

Pro Gly Leu Phe Arg Glu Phe Ala Tyr Asp Ala Arg Ile Gly Arg Gln
                405                 410                 415

Met Tyr Tyr Asp Asp Ser Phe Ala Asp Cys Pro Ala Glu Lys Asp Ser
            420                 425                 430

Gln Pro Ala Lys Asp Ser Lys Thr Ala Ser Gly Asn Asp Asn Ile Lys
        435                 440                 445

Lys Tyr Ala Ser Tyr Pro Thr Leu Arg Leu Phe Asn Lys Tyr Gly Ser
    450                 455                 460

Phe Met Asn Ile Leu Ala Glu Glu Leu Ala Glu His Ile Phe Ser Glu
465                 470                 475                 480

Ile Ile Arg Met Pro Val Glu Lys Arg Ala Gly Gln Ile Glu Tyr Ser
                485                 490                 495

Ser Asn Arg Leu Glu Arg Val Leu Asn Ser Tyr Phe Lys Ile Tyr Gly
            500                 505                 510

Phe Asp Glu Leu Arg Thr Glu Ala Ser Asn Ile Thr Glu Trp Phe Thr
        515                 520                 525

Lys Ala Thr Glu Glu Leu Ser Asp Ser Asp Tyr Ser Ser Trp Phe Ser
    530                 535                 540

Val Asn Gly Gly Lys Phe Glu Ala Val Ala Asp Leu Asn Glu Tyr Glu
545                 550                 555                 560

His Lys Gln Leu Leu Thr Asn Ile Glu Tyr Glu Tyr Leu Arg Leu Met
                565                 570                 575

Leu Gly Asp Pro Asp Ala Arg Ala Ile Ile Gly Asn Glu Tyr Cys Glu
            580                 585                 590

Lys Leu Ser Glu Tyr Val Gly Ser Ala Asp Thr Thr Leu Asp Glu Phe
        595                 600                 605
```

```
Phe Thr Val Arg Tyr Ala Asn Arg Asn Glu Lys Thr Ile Glu Asn Lys
    610                 615                 620

His Ser Val Leu Arg Thr Ile Met Arg Ala Met Asn Asn Glu Lys Lys
625                 630                 635                 640

Ala Asp Ile Glu Tyr Lys Gly Lys His Tyr Ile Cys Ser Ala Tyr Arg
                645                 650                 655

Phe Thr Tyr Ser Leu Arg Glu Arg Lys His Arg Leu Met Val Phe Asp
            660                 665                 670

Gly Asn Tyr Ile Met Gln Ile Asn Leu Cys Asp Ile Lys Asp Ala Gln
        675                 680                 685

Met Thr Lys Glu Pro Ser Leu Ser Asp Glu Glu Met Asn Lys Leu Leu
    690                 695                 700

Thr Glu Arg Lys Lys Tyr Ile Glu Ile Ala Ile Pro Gln Asn Ala Asp
705                 710                 715                 720

Ala Gln Gln Arg Asn Val Phe Glu Arg Ala Leu Arg Leu Phe Gly Gly
                725                 730                 735

Phe Glu Arg Tyr Ser Trp Asn Asp Ala Lys Asn Gly Glu Tyr Val Ile
            740                 745                 750

Ala Val Ala Tyr Tyr Glu Pro Asp Ile Ser Val Ser Ser Ser Ala Asp
        755                 760                 765

Arg Arg Ile Tyr Arg Arg Asp Thr Val Ala Ala Asp Ile Met Ser Leu
    770                 775                 780

Gly Arg Tyr Ala Arg Val Met Lys Gln Pro Gly Phe Glu Leu Asp Gly
785                 790                 795                 800

Val Arg Tyr Asp Ser Ser Leu Tyr Asp Tyr Ile Ser Lys Asn Tyr Ser
                805                 810                 815

Gly Thr Ala Ala Arg Tyr Glu Lys
            820


<210> SEQ ID NO 53
<211> LENGTH: 389
<212> TYPE: PRT
<213> ORGANISM: Ruminococcus sp.
<220> FEATURE:
<221> NAME/KEY: misc_feature
<222> LOCATION: (1)..(389)
<223> OTHER INFORMATION: WYL Ruminococcus sp.isolate 2789STDY5834971

<400> SEQUENCE: 53

Met Leu Ile Leu Pro Ser Thr Phe Leu Pro Lys Arg Asp Lys Asn Val
1               5                   10                  15

Pro Tyr Ile Ala Glu Val Gln Ser Ile Pro Leu Ser Pro Ser Ala Tyr
            20                  25                  30

Ser Val Ile Ile Lys Asp Lys Ser Ile Phe Glu Thr Ser Leu Ser Pro
        35                  40                  45

Asn Gly Ser Val Ser Met Ser Ser Phe Leu Thr Ser Ile Phe Asp Ser
    50                  55                  60

Ala Tyr Ile Ala Ser Leu Lys Tyr Lys Ser Glu Lys Tyr Asn Gly Ile
65                  70                  75                  80

Pro Leu Leu Asn Ala Phe Val Lys Trp Gln Ile Glu Glu Ile Asn Asp
                85                  90                  95

Gly Leu Asp Asp Lys Ser Lys Glu Ile Ile Lys Ser Tyr Leu Ile Ser
            100                 105                 110

Lys Leu Ser Ala Lys Tyr Glu Lys Thr Lys Thr Glu Asn Ala Val Arg
        115                 120                 125

Val Arg Leu Ser Ile Cys Arg Asp Leu Tyr Asp Thr Leu Ser Ser Asp
```

```
    130                 135                 140

Asp Leu Tyr Tyr Glu Asn Lys Val Tyr Ser Ser Thr Leu Arg Arg Phe
145                 150                 155                 160

Leu Lys Ala Val Tyr Glu Asp Tyr Ala Leu Leu Ser Asp Cys Glu Arg
                165                 170                 175

Glu Arg Leu Ile Phe Ala Asp Asn Ile Ile Lys Ile Asn Glu Val Ile
            180                 185                 190

Lys Gln Asn Gly Ser Arg Tyr Tyr Ser Phe Ile Tyr Ala Tyr Ser Asn
        195                 200                 205

Met Tyr Ser Arg Glu Lys Arg Arg Ile Arg Leu Ile Pro Tyr Arg Ile
    210                 215                 220

Val Ser Asp Glu Tyr Lys Met Tyr Asn Tyr Leu Val Cys Leu Ser Asp
225                 230                 235                 240

Glu Lys Ser Ala Gly Lys Glu Phe Lys Ala Asp Ser Tyr Arg Ile Ser
                245                 250                 255

Arg Leu Ser Gly Leu Ser Ile Ala Glu Lys Leu Ser Gln Lys Glu Tyr
            260                 265                 270

Ser Ser Val Thr Glu Tyr Glu Arg Leu Lys Glu Gly His Val Lys Ser
        275                 280                 285

Val Lys His Leu Leu Ser Asp Pro Arg Phe Gly Ser Asp Glu Ser Asp
    290                 295                 300

Ile Ser Lys Val Tyr Leu Thr Glu Lys Gly Val Glu Met Phe Gly Lys
305                 310                 315                 320

Ile Leu Tyr Gln Arg Pro Ile Leu Lys Gly Asn Glu Lys Pro Lys Pro
                325                 330                 335

Asn Ala Val Asn Glu Phe Ile Ser Pro Pro Ile Gln Val Lys Tyr Tyr
            340                 345                 350

Phe Asn Lys Phe Gly Lys Asp Gly Val Ile Leu Ser Pro Ser Asp Ser
        355                 360                 365

Phe Glu Glu Met Arg Thr Leu Tyr Val Glu Gly Ala Glu Ala Tyr Asn
    370                 375                 380

Arg Glu Val Glu Met
385


<210> SEQ ID NO 54
<211> LENGTH: 392
<212> TYPE: PRT
<213> ORGANISM: Ruminococcus bicirculans
<220> FEATURE:
<221> NAME/KEY: misc_feature
<222> LOCATION: (1)..(392)
<223> OTHER INFORMATION: WYL Ruminococcus bicirculans

<400> SEQUENCE: 54

Met Ser Met Thr Pro Ser Thr Phe Leu Pro Lys Arg Glu Asp Gly Val
1               5                   10                  15

Pro Tyr Ile Ala Glu Val Gln Ser Ile Pro Leu Ser Pro Ser Ala Tyr
            20                  25                  30

Ser Val Ile Ile Lys Asp Lys Ser Ile Phe Glu Thr Ser Leu Ser Pro
        35                  40                  45

Asn Gly Ser Val Ser Met Ser Ser Phe Leu Thr Ser Ile Phe Asp Ser
    50                  55                  60

Ala Tyr Ile Ala Ser Leu Lys Tyr Lys Ser Asp Asp Asn Tyr Lys Tyr
65                  70                  75                  80

Ile Gly Ile Pro Leu Leu Asn Ala Phe Val Lys Trp Gln Ile Glu Glu
                85                  90                  95
```

```
Ile Asp Asp Ser Leu Asp Asp Lys Ser Lys Glu Ile Ile Lys Ser Tyr
            100                 105                 110

Leu Ile Ser Lys Leu Ser Ala Lys Tyr Glu Lys Thr Lys Thr Glu Asn
        115                 120                 125

Ala Val Arg Val Arg Leu Ser Ile Cys Arg Asp Leu Tyr Asp Thr Leu
    130                 135                 140

Ser Ser Asp Asp Leu Tyr Tyr Glu Asn Lys Val Tyr Ser Ser Thr Leu
145                 150                 155                 160

Arg Arg Phe Leu Lys Ala Val Tyr Glu Asp Tyr Ala Leu Leu Ser Asp
                165                 170                 175

Cys Glu Arg Glu Arg Leu Ile Phe Ala Asp Asn Ile Ile Lys Ile Asn
            180                 185                 190

Glu Val Ile Lys Gln Asn Gly Ser Arg Tyr Tyr Ser Phe Ile Tyr Ala
        195                 200                 205

Tyr Ser Asn Met Tyr Ser Arg Glu Lys Arg Arg Ile Arg Leu Ile Pro
    210                 215                 220

Tyr Arg Ile Val Ser Asp Glu Tyr Lys Met Tyr Asn Tyr Leu Val Cys
225                 230                 235                 240

Leu Ser Asp Glu Lys Ser Ala Gly Lys Glu Phe Lys Ala Asp Ser Tyr
                245                 250                 255

Arg Ile Ser Arg Leu Ser Gly Leu Ser Ile Ala Glu Lys Leu Ser Gln
            260                 265                 270

Lys Glu Tyr Ser Ser Val Thr Glu Tyr Glu Arg Leu Lys Glu Gly His
        275                 280                 285

Val Lys Ser Val Lys His Leu Leu Ser Asp Pro Arg Phe Gly Ser Asp
    290                 295                 300

Glu Ser Asp Ile Ser Lys Val Tyr Leu Thr Glu Lys Gly Val Glu Met
305                 310                 315                 320

Phe Gly Lys Ile Leu Tyr Gln Arg Pro Ile Leu Lys Gly Asn Glu Lys
                325                 330                 335

Pro Lys Pro Asn Ala Val Asn Glu Phe Ile Ser Pro Pro Ile Gln Val
            340                 345                 350

Lys Tyr Tyr Phe Asn Lys Phe Gly Lys Asp Gly Val Ile Leu Ser Pro
        355                 360                 365

Ser Asp Ser Phe Glu Glu Met Arg Thr Leu Tyr Val Glu Gly Ala Glu
    370                 375                 380

Ala Tyr Asn Arg Glu Val Glu Met
385                 390
```

<210> SEQ ID NO 55
<211> LENGTH: 392
<212> TYPE: PRT
<213> ORGANISM: Ruminococcus sp.
<220> FEATURE:
<221> NAME/KEY: misc_feature
<222> LOCATION: (1)..(392)
<223> OTHER INFORMATION: WYL Ruminococcus sp. isolate 2789STDY5608892

<400> SEQUENCE: 55

```
Met Leu Ile Pro Pro Ser Thr Phe Leu Pro Lys Arg Asp Lys Asn Val
1               5                   10                  15

Pro Tyr Ile Ala Glu Val Gln Ser Ile Pro Leu Ser Pro Ser Ala Tyr
            20                  25                  30

Ser Val Ile Ile Lys Asp Lys Ser Ile Phe Glu Thr Ser Leu Ser Pro
        35                  40                  45
```

```
Asn Gly Ser Val Ser Met Ser Ser Phe Leu Thr Ser Ile Phe Asp Ser
    50                  55                  60

Ala Tyr Ile Ala Ser Leu Lys Tyr Lys Ser Asp Asp Asn Tyr Lys Tyr
65                  70                  75                  80

Ile Gly Ile Pro Leu Leu Asn Ala Phe Val Glu Trp Gln Ile Glu Glu
                85                  90                  95

Ile Asp Asp Ser Leu Asp Asp Lys Ser Lys Glu Ile Ile Lys Ser Tyr
            100                 105                 110

Leu Ile Ser Lys Leu Ser Ala Lys Tyr Glu Lys Thr Lys Thr Glu Asn
        115                 120                 125

Ala Val Arg Val Arg Leu Ser Ile Cys Arg Asp Leu Tyr Asp Thr Leu
    130                 135                 140

Ser Ser Asp Asp Leu Tyr Tyr Glu Asn Lys Val Tyr Ser Leu Thr Leu
145                 150                 155                 160

Arg Arg Phe Leu Lys Ala Val Tyr Glu Asp Tyr Ala Leu Leu Ser Asp
                165                 170                 175

Cys Glu Arg Glu Arg Leu Ile Phe Ala Asp Asn Ile Ile Lys Ile Asn
            180                 185                 190

Glu Val Ile Lys Gln Asn Gly Ser Arg Tyr Tyr Ser Phe Ile Tyr Ala
        195                 200                 205

Tyr Ser Asn Met Tyr Ser Arg Glu Lys Arg Arg Ile Arg Leu Ile Pro
    210                 215                 220

Tyr Arg Ile Val Ser Asp Glu Tyr Lys Met Tyr Asn Tyr Leu Val Cys
225                 230                 235                 240

Leu Ser Asp Glu Lys Ser Ala Gly Lys Glu Phe Lys Ala Asp Ser Tyr
                245                 250                 255

Arg Ile Ser Arg Leu Ser Gly Leu Ser Ile Ala Glu Lys Leu Ser Gln
            260                 265                 270

Lys Glu Tyr Ser Ser Val Thr Glu Tyr Glu Arg Leu Lys Glu Gly His
        275                 280                 285

Val Lys Ser Val Lys His Leu Leu Ser Asp Pro Arg Phe Gly Ser Asp
    290                 295                 300

Glu Ser Asp Ile Ser Lys Val Tyr Leu Thr Glu Lys Gly Val Glu Met
305                 310                 315                 320

Phe Gly Lys Ile Leu Tyr Gln Arg Pro Ile Leu Lys Gly Asn Glu Lys
                325                 330                 335

Pro Lys Pro Asn Thr Val Asn Glu Phe Ile Ser Pro Pro Ile Gln Val
            340                 345                 350

Lys Tyr Tyr Phe Asn Lys Phe Gly Lys Asp Gly Val Ile Leu Ser Pro
        355                 360                 365

Ser Asp Ser Phe Glu Glu Met Arg Thr Leu Tyr Val Glu Gly Ala Glu
    370                 375                 380

Ala Tyr Asn Arg Glu Val Glu Met
385                 390
```

<210> SEQ ID NO 56
<211> LENGTH: 392
<212> TYPE: PRT
<213> ORGANISM: Ruminococcus sp.
<220> FEATURE:
<221> NAME/KEY: misc_feature
<222> LOCATION: (1)..(392)
<223> OTHER INFORMATION: WYL Ruminococcus sp. CAG:57

<400> SEQUENCE: 56

```
Met Leu Ile Pro Pro Ser Thr Phe Leu Pro Lys Arg Asp Lys Asn Val
```

```
1               5                   10                  15

Pro Tyr Ile Ala Glu Val Gln Ser Ile Pro Leu Ser Pro Ser Ala Tyr
            20                  25                  30

Ser Val Ile Ile Lys Asp Lys Ser Ile Phe Glu Thr Ser Leu Ser Pro
        35                  40                  45

Asn Gly Ser Val Ser Met Ser Ser Phe Leu Thr Ser Ile Phe Asp Ser
    50                  55                  60

Ala Tyr Ile Ala Ser Leu Lys Tyr Lys Ser Asp Asp Asn Tyr Lys Tyr
65                  70                  75                  80

Ile Gly Ile Pro Leu Leu Asn Ala Phe Val Glu Trp Gln Ile Glu Glu
                85                  90                  95

Ile Asp Asp Ser Leu Asp Asp Lys Ser Lys Glu Ile Ile Lys Ser Tyr
            100                 105                 110

Leu Ile Ser Lys Leu Ser Ala Lys Tyr Glu Lys Thr Lys Thr Glu Asn
        115                 120                 125

Ala Val Arg Val Arg Leu Ser Ile Cys Arg Asp Leu Tyr Asp Thr Leu
    130                 135                 140

Ser Ser Asp Asp Leu Tyr Tyr Glu Asn Lys Val Tyr Ser Leu Thr Leu
145                 150                 155                 160

Arg Arg Phe Leu Lys Ala Val Tyr Glu Asp Tyr Ala Leu Leu Ser Asp
                165                 170                 175

Cys Glu Arg Glu Arg Leu Ile Phe Ala Asp Asn Ile Ile Lys Ile Asn
            180                 185                 190

Glu Val Ile Lys Gln Asn Gly Ser Arg Tyr Tyr Ser Phe Ile Tyr Ala
        195                 200                 205

Tyr Ser Asn Met Tyr Ser Arg Glu Lys Arg Arg Ile Arg Leu Ile Pro
    210                 215                 220

Tyr Arg Ile Val Ser Asp Glu Tyr Lys Met Tyr Asn Tyr Leu Val Cys
225                 230                 235                 240

Leu Ser Asp Glu Lys Ser Ala Gly Lys Glu Phe Lys Ala Asp Ser Tyr
                245                 250                 255

Arg Ile Ser Arg Leu Ser Gly Leu Ser Ile Ala Glu Lys Leu Ser Gln
            260                 265                 270

Lys Glu Tyr Ser Ser Val Thr Glu Tyr Glu Arg Leu Lys Glu Gly His
        275                 280                 285

Val Lys Ser Val Lys His Leu Leu Ser Asp Pro Arg Phe Gly Ser Asp
    290                 295                 300

Glu Ser Asp Ile Ser Lys Val Tyr Leu Thr Glu Lys Gly Val Glu Met
305                 310                 315                 320

Phe Gly Lys Ile Leu Tyr Gln Arg Pro Ile Leu Lys Gly Asn Glu Lys
                325                 330                 335

Pro Lys Pro Asn Thr Val Asn Glu Phe Ile Ser Pro Pro Ile Gln Val
            340                 345                 350

Lys Tyr Tyr Phe Asn Lys Phe Gly Lys Asp Gly Val Ile Leu Ser Pro
        355                 360                 365

Ser Asp Ser Phe Glu Glu Met Arg Thr Leu Tyr Val Glu Gly Ala Glu
    370                 375                 380

Ala Tyr Asn Arg Glu Val Glu Met
385                 390
```

<210> SEQ ID NO 57
<211> LENGTH: 280
<212> TYPE: PRT
<213> ORGANISM: Ruminococcus flavefaciens
<220> FEATURE:
<221> NAME/KEY: misc_feature
<222> LOCATION: (1)..(280)
<223> OTHER INFORMATION: WYL Ruminococcus flavefaciens FD-1

<400> SEQUENCE: 57

```
Met Ile Ile Ala Ile Asn Gln Trp Lys Arg Arg Phe Ser Leu Val Ile
1               5                   10                  15

Tyr Gly Lys Ser Glu Gly Glu Thr Ile Val Lys Ile Lys Leu Leu Leu
            20                  25                  30

Ile Ser Leu Ala Tyr Leu Ile Ser Ile Tyr Leu Leu Cys Ser Pro Gly
        35                  40                  45

Cys Ile Gly Ile Phe Thr His Gly Met Leu Thr Thr Val Ile Gly Val
    50                  55                  60

Val Thr Met Leu Ala Ala Thr Gly Thr Tyr Gly Met Tyr Leu Tyr Ser
65                  70                  75                  80

Ser Ala Ile Gly Glu Arg Ser Leu Pro Glu Ile Pro Met Asn Lys Glu
                85                  90                  95

Thr Glu Tyr Ser Arg Tyr Lys Glu Leu Glu Asn Trp Phe Arg Ala Phe
            100                 105                 110

Arg Tyr Leu Asp Arg Asn Asn Asn Phe Ala Met Leu Ser Ser Asp Leu
        115                 120                 125

Ala Thr Ser Tyr His Asp Gly Leu Ile Arg Asp Asn Pro Phe Arg Asn
    130                 135                 140

Thr Glu Leu Gly Asp Arg Leu Gln Thr Thr Ser Ser Asp Ile Ser Ile
145                 150                 155                 160

Lys Tyr Asp Gln Thr Leu Lys Ile Leu Ser Glu Ser Phe Glu Lys Asn
                165                 170                 175

Asp Ile Thr Tyr Gln Asn Tyr Leu Ser Val Leu Asp Asn Val Leu Lys
            180                 185                 190

Leu Ser Ser Ser His Leu Lys Ala Ile Lys Lys Arg Val Cys Val Phe
        195                 200                 205

Asp Tyr Arg Thr Trp Ala Asp Asn Lys Asn Asp Glu Met Cys Arg Lys
    210                 215                 220

Tyr Ile Glu Glu Val Lys Ser Ser Val Ile Arg Leu Glu Glu Ile Glu
225                 230                 235                 240

Gly Lys Phe Asp Asn Leu Leu His Glu Leu Ile Cys Leu Ser Glu Ile
                245                 250                 255

Ser Glu Asp Pro Leu Leu Glu Met Gln Asp Leu Ile Glu Thr Thr Ser
            260                 265                 270

Asp Tyr Lys Ser Ile Glu Asp Gln
        275                 280
```

<210> SEQ ID NO 58
<211> LENGTH: 226
<212> TYPE: PRT
<213> ORGANISM: Ruminococcus albus
<220> FEATURE:
<221> NAME/KEY: misc_feature
<222> LOCATION: (1)..(226)
<223> OTHER INFORMATION: WYL Ruminococcus albus strain KH2T6

<400> SEQUENCE: 58

```
Met Cys Thr Trp Tyr Tyr Ala Glu Ala Lys Ser Leu Ser Phe Phe Ile
1               5                   10                  15

Asp Lys Ala Ser Gln Leu Pro Leu Ser Asp Ile Ile Met Asn Thr Met
            20                  25                  30
```

```
Ser Lys Ser Lys Ala Met Ser Gly Asn Ile Arg Pro Thr Asp Met Ala
        35                  40                  45

Ala Val Leu Ala Pro Asn Lys Gln Gly Asn Val Ala Val Phe Pro Met
    50                  55                  60

Ile Trp Gly Phe Thr His Glu Ser Thr Ser Lys Pro Val Ile Asn Cys
65                  70                  75                  80

Arg Ile Glu Ser Ala Asp Thr Lys Pro Leu Trp Lys Asp Ser Trp Tyr
                85                  90                  95

Arg Arg Arg Cys Val Ile Pro Ala Ser Trp Tyr Tyr Glu Trp Gly Val
            100                 105                 110

Pro Pro Ser Glu Gly Glu Leu Tyr His Lys Asn Glu Tyr Asn Lys Ile
        115                 120                 125

Gln Lys Glu Lys Tyr Ala Ile Gln Pro Glu Gly Ala Glu Ile Thr Tyr
    130                 135                 140

Leu Ala Gly Leu Tyr Arg Phe Glu Glu His Arg Gly Val Gln Val Pro
145                 150                 155                 160

Met Phe Ala Val Ile Thr Arg Glu Ser Val Glu Pro Val Ser Ser Ile
                165                 170                 175

His Asp Arg Met Pro Leu Ile Leu Gly Lys Asp Ser Leu Ser Glu Trp
            180                 185                 190

Ile His Pro Asn Gly Asp Pro Asn Lys Ile Ala Lys Thr Ala Leu Thr
        195                 200                 205

Lys Met Val Met Glu Lys Ala Ile Asp Tyr Pro Glu Pro Glu Pro Ser
    210                 215                 220

Phe Met
225


<210> SEQ ID NO 59
<211> LENGTH: 314
<212> TYPE: PRT
<213> ORGANISM: Ruminococcus flavefaciens
<220> FEATURE:
<221> NAME/KEY: misc_feature
<222> LOCATION: (1)..(314)
<223> OTHER INFORMATION: WYL Ruminococcus flavefaciens strain XPD3002

<400> SEQUENCE: 59

Met Glu Leu Phe Asn Glu Tyr Arg Asn Lys Ser Leu Arg Ala Phe Leu
1               5                   10                  15

Lys Leu Ala Glu Arg Ile Ser Tyr Gly Glu Glu Leu Ser Ile Asp Glu
            20                  25                  30

Phe Glu Ala Glu Tyr Tyr Arg Leu Ser Gly Asp Asn Lys Lys Ile Thr
        35                  40                  45

Ser Val Phe Tyr Lys Asn Thr Leu Tyr Asn Asp Lys Leu Pro Ile Phe
    50                  55                  60

Asp Thr Arg Glu Gly Lys Val Arg Leu Phe Gly Glu Pro Asp Lys Cys
65                  70                  75                  80

Ser Asn Lys His Ile Ser Asp Thr Leu Leu Lys Ser Glu Ile Thr Trp
                85                  90                  95

Leu His Asn Ala Leu Asn Asp Lys Leu Ser Lys Leu Phe Leu Ser Asp
            100                 105                 110

Glu Glu Arg Ile Ser Ile Asp Ala Lys Leu Ser Asp Tyr Thr Glu Tyr
        115                 120                 125

Tyr Lys Asn Ile Asp Asp Met Trp Arg Ser Asn Glu Asp Ile Ser Glu
    130                 135                 140

Glu Val Glu Lys Asn Phe Lys Ile Ile Leu Lys Ala Ile Asn Glu Lys
```

```
145                 150                 155                 160

Gln Ala Leu Ser Tyr Thr Phe Lys Asn Lys Asn Cys Glu Gly Phe Pro
                165                 170                 175

Val Arg Ile Glu Tyr Asp Glu Arg Thr Cys Arg Ile Tyr Met Ile Ile
            180                 185                 190

Tyr Asp Gly Asn Arg Phe Val Lys Ser Asp Ile Ser Lys Leu Ser Asp
        195                 200                 205

Ile Tyr Ile Thr Glu Asn Ser Ile Asp Thr Ile Pro Glu Ile Lys Asp
    210                 215                 220

Asp Met Leu Asn Lys Lys Ala Tyr Leu Pro Val Val Phe Thr Val Thr
225                 230                 235                 240

Asp Asp Lys Asn Arg Lys Ala Ile Asp Arg Ala Leu Leu Ala Phe Ser
                245                 250                 255

Val Tyr Asp His Val Val Glu Pro Ile Asp Glu Lys Thr Ala Arg Phe
            260                 265                 270

Thr Ile Gln Tyr Tyr Thr Met Asp Leu Asp Leu Leu Ile Lys Asp Ile
        275                 280                 285

Leu Ala Phe Gly Ser Asp Ile Lys Val Glu Ser Pro Arg Tyr Val Val
    290                 295                 300

Lys Arg Ile Thr Asp Ile Leu Arg Lys Val
305                 310


<210> SEQ ID NO 60
<211> LENGTH: 412
<212> TYPE: PRT
<213> ORGANISM: Eubacterium siraeum
<220> FEATURE:
<221> NAME/KEY: misc_feature
<222> LOCATION: (1)..(412)
<223> OTHER INFORMATION: RtcB Eubacterium siraeum

<400> SEQUENCE: 60

Met Ile Val Leu Glu Ile Ile Gly Glu Arg Asn Thr Ala Val Val Tyr
1               5                   10                  15

Gly Glu Ile Ile Asp Glu Cys Ala Val Ser Gln Ile Glu Glu Ile Cys
            20                  25                  30

Asn His Pro Ala Phe Glu Asn Ser Arg Ile Arg Ile Met Pro Asp Cys
        35                  40                  45

His Ala Gly Lys Gly Cys Val Ile Gly Phe Thr Cys Val Thr Ser Asn
    50                  55                  60

Arg Met Ile Val Pro Asn Ile Val Gly Val Asp Ile Gly Cys Gly Ile
65                  70                  75                  80

Leu Thr Thr Val Phe Thr Ala Asp Arg Glu Ile Asp Tyr Arg Ala Leu
                85                  90                  95

Asp Thr Phe Ile Arg Ser Asn Ile Pro Ser Gly Met Glu Ile His Asp
            100                 105                 110

Ser Val Ser Asp Thr Val Ala Glu Asn Thr Ala Leu Ile Ala Lys Val
        115                 120                 125

Asn Gly Ile Cys Asp Ala Ile Gly Glu Ser Ala Asp Val Asp Tyr His
    130                 135                 140

Leu Arg Ser Ile Gly Thr Leu Gly Gly Gly Asn His Phe Ile Glu Ile
145                 150                 155                 160

Asp Arg Leu Asn Asn Gly Asn Tyr Ala Leu Thr Val His Thr Gly Ser
                165                 170                 175

Arg Asn Leu Gly Lys Arg Ile Cys Gly Tyr Phe Gln Ser Asn Ala Ser
            180                 185                 190
```

```
Val Ile Asp Thr Glu Leu Arg Arg Ser Ile Leu Leu Arg His Arg Ser
        195                 200                 205

Ala Thr Thr Ser Glu Glu His Glu Glu Ile Asp Arg Arg Ala Ala Gln
    210                 215                 220

Ile Ala Pro Val Ser Lys Glu Leu Ala Phe Ile Thr Gly Glu Arg Tyr
225                 230                 235                 240

Asp Ser Tyr Ile Gly Cys Met Leu Asp Ala Lys Ala Leu Ala Ala Phe
                245                 250                 255

Asn Arg Thr Val Ile Ser Asp Arg Ile Met Ser Phe Leu Ala Asp Glu
            260                 265                 270

Tyr Gly Val Glu Ile Lys Asp Arg Phe Asp Thr Val His Asn Tyr Ile
        275                 280                 285

Asp Trp Tyr Asp Asp Thr His Thr Ser Val Val Ile Arg Lys Gly Ala
    290                 295                 300

Ile Ser Ala Arg Lys Gly Glu Arg Ile Val Ile Pro Leu Asn Met Arg
305                 310                 315                 320

Asp Gly Ile Ile Ile Ala His Gly Arg Gly Asn Glu Glu Trp Asn Cys
                325                 330                 335

Ser Ala Pro His Gly Ser Gly Arg Ala Tyr Ser Arg Ser Asp Ala Arg
            340                 345                 350

Arg Thr Phe Thr Leu Glu Glu Tyr Val Glu Glu Met Asp Gly Val Asn
        355                 360                 365

Thr Trp Ser Val Ser Glu Ser Thr Ile Asp Glu Cys Pro Met Ala Tyr
    370                 375                 380

Lys Pro Ser Glu Met Ile Ile Gly Ser Ile Gly Asp Thr Val Glu Ile
385                 390                 395                 400

Glu Ser Ile Ala His Thr Val Tyr Asn Phe Lys Ala
                405                 410
```

<210> SEQ ID NO 61
<211> LENGTH: 831
<212> TYPE: PRT
<213> ORGANISM: Artificial Sequence
<220> FEATURE:
<223> OTHER INFORMATION: Synthetic: WYL Eubacterium siraeum + C-term NLS

<400> SEQUENCE: 61

```
Met Lys Lys Thr Glu Lys Phe Asp Asp Val Gln Ser Gly Tyr Glu Tyr
1               5                   10                  15

Lys Tyr Phe Leu Glu Ser Ile Asp Lys Tyr Arg Ala Ala Val Gln Asn
            20                  25                  30

Ile Tyr Thr Tyr Gly Cys Phe Asn Gln Lys Gln Leu Ser Glu Gln Cys
        35                  40                  45

Asn Cys Ser Asp Gln Thr Ile Lys Lys Ala Phe Asn Phe Tyr Asn Leu
    50                  55                  60

Cys Leu Ala Asn Tyr Ile Lys Lys Lys Lys Gly Thr Leu Ser Lys Lys
65                  70                  75                  80

Ala Lys Gly Arg Pro Thr Glu Ala Lys Tyr Leu Glu Tyr Asp Arg Phe
                85                  90                  95

Thr Leu Asn Glu Asn Tyr Leu Tyr Asn Ile Tyr Leu Trp Ala Arg Ile
            100                 105                 110

Thr Lys Lys Gln Met Trp Ala Phe Ser Tyr Phe Arg Arg His Thr Ser
        115                 120                 125

Leu Leu Ile Asn Ala Ser Arg Thr Glu Ile Lys Asn Gln Leu Ser Asp
    130                 135                 140
```

```
Phe Phe Leu Tyr Phe Ser Glu Tyr Met Asp Arg Ser Lys Lys Ala Glu
145                 150                 155                 160

Asn Ser Gln Asp Leu Gly Tyr Ile Ile Asp Met Thr Ala Pro Thr Glu
                165                 170                 175

Lys Asn Met Leu Ile Ser Ser Met Cys Asp Ala Leu Ala Val Phe Gly
            180                 185                 190

Arg Lys Ala Pro Tyr Ser Val Pro Ala Tyr Ser Ile Ser His Lys Leu
        195                 200                 205

Lys Lys Leu Cys Gly Asn Asp Ser Lys Ser Leu Trp Ser Phe Met Tyr
    210                 215                 220

Asp Asn Tyr Asp Arg Ile Leu Tyr Asp Glu Ala Val Tyr Thr Ile Arg
225                 230                 235                 240

Gln Ala Ile Arg Asp Arg Lys Leu Ile Gly Tyr Gln Thr Val Gly Thr
                245                 250                 255

Glu Lys Gln Lys Ser Val Asn Tyr Val Val Pro Leu Lys Ile Met Tyr
            260                 265                 270

Glu Tyr Asn Leu Gly Arg Cys Tyr Leu Leu Tyr Ser Pro Leu Asn Ser
        275                 280                 285

Asp Ser Ile Ile Lys Ser Ile Arg Leu Asp Lys Leu Tyr Lys Val Ala
    290                 295                 300

Ala Tyr Glu Pro Asp Ser Ile Ile Asn Tyr Glu Lys Leu Tyr Asp Val
305                 310                 315                 320

Leu Ala Val Ala Glu Asn Glu Ile Trp Leu Ser Gly Asp Tyr Thr Lys
                325                 330                 335

Lys Asp Cys Leu Ser Arg Ile Val Leu Lys Asn Val Lys Pro Gln Ala
            340                 345                 350

Phe Ser Leu Ile Glu Lys Tyr Gly Val Cys Tyr Thr Glu Asp Arg Glu
        355                 360                 365

Ala Lys Thr Val Thr Phe Asn Ile Arg Lys Ala Asp Asp Ile Lys Pro
    370                 375                 380

Phe Ile Arg Thr Leu Gly Gly Asp Ala Val Ile Ser Glu Glu Asp Asn
385                 390                 395                 400

Pro Gly Leu Phe Arg Glu Phe Ala Tyr Asp Ala Arg Ile Gly Arg Gln
                405                 410                 415

Met Tyr Tyr Asp Asp Ser Phe Ala Asp Cys Pro Ala Glu Lys Asp Ser
            420                 425                 430

Gln Pro Ala Lys Asp Ser Lys Thr Ala Ser Gly Asn Asp Asn Ile Lys
        435                 440                 445

Lys Tyr Ala Ser Tyr Pro Thr Leu Arg Leu Phe Asn Lys Tyr Gly Ser
    450                 455                 460

Phe Met Asn Ile Leu Ala Glu Glu Leu Ala Glu His Ile Phe Ser Glu
465                 470                 475                 480

Ile Ile Arg Met Pro Val Glu Lys Arg Ala Gly Gln Ile Glu Tyr Ser
                485                 490                 495

Ser Asn Arg Leu Glu Arg Val Leu Asn Ser Tyr Phe Lys Ile Tyr Gly
            500                 505                 510

Phe Asp Glu Leu Arg Thr Glu Ala Ser Asn Ile Thr Glu Trp Phe Thr
        515                 520                 525

Lys Ala Thr Glu Glu Leu Ser Asp Ser Asp Tyr Ser Ser Trp Phe Ser
    530                 535                 540

Val Asn Gly Gly Lys Phe Glu Ala Val Ala Asp Leu Asn Glu Tyr Glu
545                 550                 555                 560
```

```
His Lys Gln Leu Leu Thr Asn Ile Glu Tyr Glu Tyr Leu Arg Leu Met
                565                 570                 575

Leu Gly Asp Pro Asp Ala Arg Ala Ile Ile Gly Asn Glu Tyr Cys Glu
            580                 585                 590

Lys Leu Ser Glu Tyr Val Gly Ser Ala Asp Thr Thr Leu Asp Glu Phe
        595                 600                 605

Phe Thr Val Arg Tyr Ala Asn Arg Asn Glu Lys Thr Ile Glu Asn Lys
    610                 615                 620

His Ser Val Leu Arg Thr Ile Met Arg Ala Met Asn Asn Glu Lys Lys
625                 630                 635                 640

Ala Asp Ile Glu Tyr Lys Gly Lys His Tyr Ile Cys Ser Ala Tyr Arg
                645                 650                 655

Phe Thr Tyr Ser Leu Arg Glu Arg Lys His Arg Leu Met Val Phe Asp
            660                 665                 670

Gly Asn Tyr Ile Met Gln Ile Asn Leu Cys Asp Ile Lys Asp Ala Gln
        675                 680                 685

Met Thr Lys Glu Pro Ser Leu Ser Asp Glu Glu Met Asn Lys Leu Leu
    690                 695                 700

Thr Glu Arg Lys Lys Tyr Ile Glu Ile Ala Ile Pro Gln Asn Ala Asp
705                 710                 715                 720

Ala Gln Gln Arg Asn Val Phe Glu Arg Ala Leu Arg Leu Phe Gly Gly
                725                 730                 735

Phe Glu Arg Tyr Ser Trp Asn Asp Ala Lys Asn Gly Glu Tyr Val Ile
            740                 745                 750

Ala Val Ala Tyr Tyr Glu Pro Asp Ile Ser Val Ser Ser Ser Ala Asp
        755                 760                 765

Arg Arg Ile Tyr Arg Arg Asp Thr Val Ala Ala Asp Ile Met Ser Leu
    770                 775                 780

Gly Arg Tyr Ala Arg Val Met Lys Gln Pro Gly Phe Glu Leu Asp Gly
785                 790                 795                 800

Val Arg Tyr Asp Ser Ser Leu Tyr Asp Tyr Ile Ser Lys Asn Tyr Ser
                805                 810                 815

Gly Thr Ala Ala Arg Tyr Glu Lys Pro Lys Lys Lys Arg Lys Val
            820                 825                 830


<210> SEQ ID NO 62
<211> LENGTH: 396
<212> TYPE: PRT
<213> ORGANISM: Artificial Sequence
<220> FEATURE:
<223> OTHER INFORMATION: Synthetic: WYL Ruminococcus sp.isolate
      2789STDY5834971 + C-term NLS

<400> SEQUENCE: 62

Met Leu Ile Leu Pro Ser Thr Phe Leu Pro Lys Arg Asp Lys Asn Val
1               5                   10                  15

Pro Tyr Ile Ala Glu Val Gln Ser Ile Pro Leu Ser Pro Ser Ala Tyr
            20                  25                  30

Ser Val Ile Ile Lys Asp Lys Ser Ile Phe Glu Thr Ser Leu Ser Pro
        35                  40                  45

Asn Gly Ser Val Ser Met Ser Ser Phe Leu Thr Ser Ile Phe Asp Ser
    50                  55                  60

Ala Tyr Ile Ala Ser Leu Lys Tyr Lys Ser Glu Lys Tyr Asn Gly Ile
65                  70                  75                  80

Pro Leu Leu Asn Ala Phe Val Lys Trp Gln Ile Glu Glu Ile Asn Asp
                85                  90                  95
```

```
Gly Leu Asp Asp Lys Ser Lys Glu Ile Ile Lys Ser Tyr Leu Ile Ser
            100                 105                 110

Lys Leu Ser Ala Lys Tyr Glu Lys Thr Lys Thr Glu Asn Ala Val Arg
        115                 120                 125

Val Arg Leu Ser Ile Cys Arg Asp Leu Tyr Asp Thr Leu Ser Ser Asp
    130                 135                 140

Asp Leu Tyr Tyr Glu Asn Lys Val Tyr Ser Ser Thr Leu Arg Arg Phe
145                 150                 155                 160

Leu Lys Ala Val Tyr Glu Asp Tyr Ala Leu Leu Ser Asp Cys Glu Arg
                165                 170                 175

Glu Arg Leu Ile Phe Ala Asp Asn Ile Ile Lys Ile Asn Glu Val Ile
            180                 185                 190

Lys Gln Asn Gly Ser Arg Tyr Tyr Ser Phe Ile Tyr Ala Tyr Ser Asn
        195                 200                 205

Met Tyr Ser Arg Glu Lys Arg Arg Ile Arg Leu Ile Pro Tyr Arg Ile
    210                 215                 220

Val Ser Asp Glu Tyr Lys Met Tyr Asn Tyr Leu Val Cys Leu Ser Asp
225                 230                 235                 240

Glu Lys Ser Ala Gly Lys Glu Phe Lys Ala Asp Ser Tyr Arg Ile Ser
                245                 250                 255

Arg Leu Ser Gly Leu Ser Ile Ala Glu Lys Leu Ser Gln Lys Glu Tyr
            260                 265                 270

Ser Ser Val Thr Glu Tyr Glu Arg Leu Lys Glu Gly His Val Lys Ser
        275                 280                 285

Val Lys His Leu Leu Ser Asp Pro Arg Phe Gly Ser Asp Glu Ser Asp
    290                 295                 300

Ile Ser Lys Val Tyr Leu Thr Glu Lys Gly Val Glu Met Phe Gly Lys
305                 310                 315                 320

Ile Leu Tyr Gln Arg Pro Ile Leu Lys Gly Asn Glu Lys Pro Lys Pro
                325                 330                 335

Asn Ala Val Asn Glu Phe Ile Ser Pro Pro Ile Gln Val Lys Tyr Tyr
            340                 345                 350

Phe Asn Lys Phe Gly Lys Asp Gly Val Ile Leu Ser Pro Ser Asp Ser
        355                 360                 365

Phe Glu Glu Met Arg Thr Leu Tyr Val Glu Gly Ala Glu Ala Tyr Asn
    370                 375                 380

Arg Glu Val Glu Met Pro Lys Lys Lys Arg Lys Val
385                 390                 395


<210> SEQ ID NO 63
<211> LENGTH: 399
<212> TYPE: PRT
<213> ORGANISM: Artificial Sequence
<220> FEATURE:
<223> OTHER INFORMATION: Synthetic: WYL Ruminococcus bicirculans +
      C-term NLS

<400> SEQUENCE: 63

Met Ser Met Thr Pro Ser Thr Phe Leu Pro Lys Arg Glu Asp Gly Val
1               5                   10                  15

Pro Tyr Ile Ala Glu Val Gln Ser Ile Pro Leu Ser Pro Ser Ala Tyr
            20                  25                  30

Ser Val Ile Ile Lys Asp Lys Ser Ile Phe Glu Thr Ser Leu Ser Pro
        35                  40                  45

Asn Gly Ser Val Ser Met Ser Ser Phe Leu Thr Ser Ile Phe Asp Ser
```

```
    50                  55                  60

Ala Tyr Ile Ala Ser Leu Lys Tyr Lys Ser Asp Asp Asn Tyr Lys Tyr
65                  70                  75                  80

Ile Gly Ile Pro Leu Leu Asn Ala Phe Val Lys Trp Gln Ile Glu Glu
                85                  90                  95

Ile Asp Asp Ser Leu Asp Asp Lys Ser Lys Glu Ile Ile Lys Ser Tyr
            100                 105                 110

Leu Ile Ser Lys Leu Ser Ala Lys Tyr Glu Lys Thr Lys Thr Glu Asn
        115                 120                 125

Ala Val Arg Val Arg Leu Ser Ile Cys Arg Asp Leu Tyr Asp Thr Leu
    130                 135                 140

Ser Ser Asp Asp Leu Tyr Tyr Glu Asn Lys Val Tyr Ser Ser Thr Leu
145                 150                 155                 160

Arg Arg Phe Leu Lys Ala Val Tyr Glu Asp Tyr Ala Leu Leu Ser Asp
                165                 170                 175

Cys Glu Arg Glu Arg Leu Ile Phe Ala Asp Asn Ile Ile Lys Ile Asn
            180                 185                 190

Glu Val Ile Lys Gln Asn Gly Ser Arg Tyr Tyr Ser Phe Ile Tyr Ala
        195                 200                 205

Tyr Ser Asn Met Tyr Ser Arg Glu Lys Arg Arg Ile Arg Leu Ile Pro
    210                 215                 220

Tyr Arg Ile Val Ser Asp Glu Tyr Lys Met Tyr Asn Tyr Leu Val Cys
225                 230                 235                 240

Leu Ser Asp Glu Lys Ser Ala Gly Lys Glu Phe Lys Ala Asp Ser Tyr
                245                 250                 255

Arg Ile Ser Arg Leu Ser Gly Leu Ser Ile Ala Glu Lys Leu Ser Gln
            260                 265                 270

Lys Glu Tyr Ser Ser Val Thr Glu Tyr Glu Arg Leu Lys Glu Gly His
        275                 280                 285

Val Lys Ser Val Lys His Leu Leu Ser Asp Pro Arg Phe Gly Ser Asp
    290                 295                 300

Glu Ser Asp Ile Ser Lys Val Tyr Leu Thr Glu Lys Gly Val Glu Met
305                 310                 315                 320

Phe Gly Lys Ile Leu Tyr Gln Arg Pro Ile Leu Lys Gly Asn Glu Lys
                325                 330                 335

Pro Lys Pro Asn Ala Val Asn Glu Phe Ile Ser Pro Pro Ile Gln Val
            340                 345                 350

Lys Tyr Tyr Phe Asn Lys Phe Gly Lys Asp Gly Val Ile Leu Ser Pro
        355                 360                 365

Ser Asp Ser Phe Glu Glu Met Arg Thr Leu Tyr Val Glu Gly Ala Glu
    370                 375                 380

Ala Tyr Asn Arg Glu Val Glu Met Pro Lys Lys Lys Arg Lys Val
385                 390                 395


<210> SEQ ID NO 64
<211> LENGTH: 399
<212> TYPE: PRT
<213> ORGANISM: Artificial Sequence
<220> FEATURE:
<223> OTHER INFORMATION: Synthetic: WYL Ruminococcus sp. isolate
      2789STDY5608892 + C-term NLS

<400> SEQUENCE: 64

Met Leu Ile Pro Pro Ser Thr Phe Leu Pro Lys Arg Asp Lys Asn Val
1               5                   10                  15
```

```
Pro Tyr Ile Ala Glu Val Gln Ser Ile Pro Leu Ser Pro Ser Ala Tyr
            20                  25                  30

Ser Val Ile Ile Lys Asp Lys Ser Ile Phe Glu Thr Ser Leu Ser Pro
        35                  40                  45

Asn Gly Ser Val Ser Met Ser Ser Phe Leu Thr Ser Ile Phe Asp Ser
    50                  55                  60

Ala Tyr Ile Ala Ser Leu Lys Tyr Lys Ser Asp Asp Asn Tyr Lys Tyr
65                  70                  75                  80

Ile Gly Ile Pro Leu Leu Asn Ala Phe Val Glu Trp Gln Ile Glu Glu
                85                  90                  95

Ile Asp Asp Ser Leu Asp Asp Lys Ser Lys Glu Ile Ile Lys Ser Tyr
            100                 105                 110

Leu Ile Ser Lys Leu Ser Ala Lys Tyr Glu Lys Thr Lys Thr Glu Asn
        115                 120                 125

Ala Val Arg Val Arg Leu Ser Ile Cys Arg Asp Leu Tyr Asp Thr Leu
    130                 135                 140

Ser Ser Asp Asp Leu Tyr Tyr Glu Asn Lys Val Tyr Ser Leu Thr Leu
145                 150                 155                 160

Arg Arg Phe Leu Lys Ala Val Tyr Glu Asp Tyr Ala Leu Leu Ser Asp
                165                 170                 175

Cys Glu Arg Glu Arg Leu Ile Phe Ala Asp Asn Ile Ile Lys Ile Asn
            180                 185                 190

Glu Val Ile Lys Gln Asn Gly Ser Arg Tyr Tyr Ser Phe Ile Tyr Ala
        195                 200                 205

Tyr Ser Asn Met Tyr Ser Arg Glu Lys Arg Arg Ile Arg Leu Ile Pro
    210                 215                 220

Tyr Arg Ile Val Ser Asp Glu Tyr Lys Met Tyr Asn Tyr Leu Val Cys
225                 230                 235                 240

Leu Ser Asp Glu Lys Ser Ala Gly Lys Glu Phe Lys Ala Asp Ser Tyr
                245                 250                 255

Arg Ile Ser Arg Leu Ser Gly Leu Ser Ile Ala Glu Lys Leu Ser Gln
            260                 265                 270

Lys Glu Tyr Ser Ser Val Thr Glu Tyr Glu Arg Leu Lys Glu Gly His
        275                 280                 285

Val Lys Ser Val Lys His Leu Leu Ser Asp Pro Arg Phe Gly Ser Asp
    290                 295                 300

Glu Ser Asp Ile Ser Lys Val Tyr Leu Thr Glu Lys Gly Val Glu Met
305                 310                 315                 320

Phe Gly Lys Ile Leu Tyr Gln Arg Pro Ile Leu Lys Gly Asn Glu Lys
                325                 330                 335

Pro Lys Pro Asn Thr Val Asn Glu Phe Ile Ser Pro Pro Ile Gln Val
            340                 345                 350

Lys Tyr Tyr Phe Asn Lys Phe Gly Lys Asp Gly Val Ile Leu Ser Pro
        355                 360                 365

Ser Asp Ser Phe Glu Glu Met Arg Thr Leu Tyr Val Glu Gly Ala Glu
    370                 375                 380

Ala Tyr Asn Arg Glu Val Glu Met Pro Lys Lys Lys Arg Lys Val
385                 390                 395


<210> SEQ ID NO 65
<211> LENGTH: 399
<212> TYPE: PRT
<213> ORGANISM: Artificial Sequence
<220> FEATURE:
<223> OTHER INFORMATION: Synthetic: WYL Ruminococcus sp. CAG:57 + C-term
```

NLS

<400> SEQUENCE: 65

```
Met Leu Ile Pro Pro Ser Thr Phe Leu Pro Lys Arg Asp Lys Asn Val
1               5                   10                  15

Pro Tyr Ile Ala Glu Val Gln Ser Ile Pro Leu Ser Pro Ser Ala Tyr
            20                  25                  30

Ser Val Ile Ile Lys Asp Lys Ser Ile Phe Glu Thr Ser Leu Ser Pro
        35                  40                  45

Asn Gly Ser Val Ser Met Ser Ser Phe Leu Thr Ser Ile Phe Asp Ser
    50                  55                  60

Ala Tyr Ile Ala Ser Leu Lys Tyr Lys Ser Asp Asp Asn Tyr Lys Tyr
65                  70                  75                  80

Ile Gly Ile Pro Leu Leu Asn Ala Phe Val Glu Trp Gln Ile Glu Glu
                85                  90                  95

Ile Asp Asp Ser Leu Asp Asp Lys Ser Lys Glu Ile Ile Lys Ser Tyr
            100                 105                 110

Leu Ile Ser Lys Leu Ser Ala Lys Tyr Glu Lys Thr Lys Thr Glu Asn
        115                 120                 125

Ala Val Arg Val Arg Leu Ser Ile Cys Arg Asp Leu Tyr Asp Thr Leu
    130                 135                 140

Ser Ser Asp Asp Leu Tyr Tyr Glu Asn Lys Val Tyr Ser Leu Thr Leu
145                 150                 155                 160

Arg Arg Phe Leu Lys Ala Val Tyr Glu Asp Tyr Ala Leu Leu Ser Asp
                165                 170                 175

Cys Glu Arg Glu Arg Leu Ile Phe Ala Asp Asn Ile Ile Lys Ile Asn
            180                 185                 190

Glu Val Ile Lys Gln Asn Gly Ser Arg Tyr Tyr Ser Phe Ile Tyr Ala
        195                 200                 205

Tyr Ser Asn Met Tyr Ser Arg Glu Lys Arg Arg Ile Arg Leu Ile Pro
    210                 215                 220

Tyr Arg Ile Val Ser Asp Glu Tyr Lys Met Tyr Asn Tyr Leu Val Cys
225                 230                 235                 240

Leu Ser Asp Glu Lys Ser Ala Gly Lys Glu Phe Lys Ala Asp Ser Tyr
                245                 250                 255

Arg Ile Ser Arg Leu Ser Gly Leu Ser Ile Ala Glu Lys Leu Ser Gln
            260                 265                 270

Lys Glu Tyr Ser Ser Val Thr Glu Tyr Glu Arg Leu Lys Glu Gly His
        275                 280                 285

Val Lys Ser Val Lys His Leu Leu Ser Asp Pro Arg Phe Gly Ser Asp
    290                 295                 300

Glu Ser Asp Ile Ser Lys Val Tyr Leu Thr Glu Lys Gly Val Glu Met
305                 310                 315                 320

Phe Gly Lys Ile Leu Tyr Gln Arg Pro Ile Leu Lys Gly Asn Glu Lys
                325                 330                 335

Pro Lys Pro Asn Thr Val Asn Glu Phe Ile Ser Pro Pro Ile Gln Val
            340                 345                 350

Lys Tyr Tyr Phe Asn Lys Phe Gly Lys Asp Gly Val Ile Leu Ser Pro
        355                 360                 365

Ser Asp Ser Phe Glu Glu Met Arg Thr Leu Tyr Val Glu Gly Ala Glu
    370                 375                 380

Ala Tyr Asn Arg Glu Val Glu Met Pro Lys Lys Lys Arg Lys Val
385                 390                 395
```

<210> SEQ ID NO 66
<211> LENGTH: 287
<212> TYPE: PRT
<213> ORGANISM: Artificial Sequence
<220> FEATURE:
<223> OTHER INFORMATION: Synthetic: WYL Ruminococcus flavefaciens FD-1 + C-term NLS

<400> SEQUENCE: 66

```
Met Ile Ile Ala Ile Asn Gln Trp Lys Arg Arg Phe Ser Leu Val Ile
1               5                   10                  15

Tyr Gly Lys Ser Glu Gly Glu Thr Ile Val Lys Ile Lys Leu Leu Leu
            20                  25                  30

Ile Ser Leu Ala Tyr Leu Ile Ser Ile Tyr Leu Leu Cys Ser Pro Gly
        35                  40                  45

Cys Ile Gly Ile Phe Thr His Gly Met Leu Thr Thr Val Ile Gly Val
    50                  55                  60

Val Thr Met Leu Ala Ala Thr Gly Thr Tyr Gly Met Tyr Leu Tyr Ser
65                  70                  75                  80

Ser Ala Ile Gly Glu Arg Ser Leu Pro Glu Ile Pro Met Asn Lys Glu
                85                  90                  95

Thr Glu Tyr Ser Arg Tyr Lys Glu Leu Glu Asn Trp Phe Arg Ala Phe
            100                 105                 110

Arg Tyr Leu Asp Arg Asn Asn Asn Phe Ala Met Leu Ser Ser Asp Leu
        115                 120                 125

Ala Thr Ser Tyr His Asp Gly Leu Ile Arg Asp Asn Pro Phe Arg Asn
    130                 135                 140

Thr Glu Leu Gly Asp Arg Leu Gln Thr Thr Ser Ser Asp Ile Ser Ile
145                 150                 155                 160

Lys Tyr Asp Gln Thr Leu Lys Ile Leu Ser Glu Ser Phe Glu Lys Asn
                165                 170                 175

Asp Ile Thr Tyr Gln Asn Tyr Leu Ser Val Leu Asp Asn Val Leu Lys
            180                 185                 190

Leu Ser Ser Ser His Leu Lys Ala Ile Lys Lys Arg Val Cys Val Phe
        195                 200                 205

Asp Tyr Arg Thr Trp Ala Asp Asn Lys Asn Asp Glu Met Cys Arg Lys
    210                 215                 220

Tyr Ile Glu Glu Val Lys Ser Ser Val Ile Arg Leu Glu Glu Ile Glu
225                 230                 235                 240

Gly Lys Phe Asp Asn Leu Leu His Glu Leu Ile Cys Leu Ser Glu Ile
                245                 250                 255

Ser Glu Asp Pro Leu Leu Glu Met Gln Asp Leu Ile Glu Thr Thr Ser
            260                 265                 270

Asp Tyr Lys Ser Ile Glu Asp Gln Pro Lys Lys Lys Arg Lys Val
        275                 280                 285
```

<210> SEQ ID NO 67
<211> LENGTH: 233
<212> TYPE: PRT
<213> ORGANISM: Artificial Sequence
<220> FEATURE:
<223> OTHER INFORMATION: Synthetic: WYL Ruminococcus albus strain KH2T6 + C-term NLS

<400> SEQUENCE: 67

```
Met Cys Thr Trp Tyr Tyr Ala Glu Ala Lys Ser Leu Ser Phe Phe Ile
1               5                   10                  15
```

```
Asp Lys Ala Ser Gln Leu Pro Leu Ser Asp Ile Ile Met Asn Thr Met
            20                  25                  30

Ser Lys Ser Lys Ala Met Ser Gly Asn Ile Arg Pro Thr Asp Met Ala
        35                  40                  45

Ala Val Leu Ala Pro Asn Lys Gln Gly Asn Val Ala Val Phe Pro Met
    50                  55                  60

Ile Trp Gly Phe Thr His Glu Ser Thr Ser Lys Pro Val Ile Asn Cys
65                  70                  75                  80

Arg Ile Glu Ser Ala Asp Thr Lys Pro Leu Trp Lys Asp Ser Trp Tyr
                85                  90                  95

Arg Arg Arg Cys Val Ile Pro Ala Ser Trp Tyr Tyr Glu Trp Gly Val
            100                 105                 110

Pro Pro Ser Glu Gly Glu Leu Tyr His Lys Asn Glu Tyr Asn Lys Ile
        115                 120                 125

Gln Lys Glu Lys Tyr Ala Ile Gln Pro Glu Gly Ala Glu Ile Thr Tyr
    130                 135                 140

Leu Ala Gly Leu Tyr Arg Phe Glu Glu His Arg Gly Val Gln Val Pro
145                 150                 155                 160

Met Phe Ala Val Ile Thr Arg Glu Ser Val Glu Pro Val Ser Ser Ile
                165                 170                 175

His Asp Arg Met Pro Leu Ile Leu Gly Lys Asp Ser Leu Ser Glu Trp
            180                 185                 190

Ile His Pro Asn Gly Asp Pro Asn Lys Ile Ala Lys Thr Ala Leu Thr
        195                 200                 205

Lys Met Val Met Glu Lys Ala Ile Asp Tyr Pro Glu Pro Glu Pro Ser
    210                 215                 220

Phe Met Pro Lys Lys Lys Arg Lys Val
225                 230
```

```
<210> SEQ ID NO 68
<211> LENGTH: 321
<212> TYPE: PRT
<213> ORGANISM: Artificial Sequence
<220> FEATURE:
<223> OTHER INFORMATION: Synthetic: WYL Ruminococcus flavefaciens strain
      XPD3002 + C-term NLS

<400> SEQUENCE: 68

Met Glu Leu Phe Asn Glu Tyr Arg Asn Lys Ser Leu Arg Ala Phe Leu
1               5                   10                  15

Lys Leu Ala Glu Arg Ile Ser Tyr Gly Glu Glu Leu Ser Ile Asp Glu
            20                  25                  30

Phe Glu Ala Glu Tyr Tyr Arg Leu Ser Gly Asp Asn Lys Lys Ile Thr
        35                  40                  45

Ser Val Phe Tyr Lys Asn Thr Leu Tyr Asn Asp Lys Leu Pro Ile Phe
    50                  55                  60

Asp Thr Arg Glu Gly Lys Val Arg Leu Phe Gly Glu Pro Asp Lys Cys
65                  70                  75                  80

Ser Asn Lys His Ile Ser Asp Thr Leu Leu Lys Ser Glu Ile Thr Trp
                85                  90                  95

Leu His Asn Ala Leu Asn Asp Lys Leu Ser Lys Leu Phe Leu Ser Asp
            100                 105                 110

Glu Glu Arg Ile Ser Ile Asp Ala Lys Leu Ser Asp Tyr Thr Glu Tyr
        115                 120                 125

Tyr Lys Asn Ile Asp Asp Met Trp Arg Ser Asn Glu Asp Ile Ser Glu
    130                 135                 140
```

```
Glu Val Glu Lys Asn Phe Lys Ile Ile Leu Lys Ala Ile Asn Glu Lys
145                 150                 155                 160

Gln Ala Leu Ser Tyr Thr Phe Lys Asn Lys Asn Cys Glu Gly Phe Pro
                165                 170                 175

Val Arg Ile Glu Tyr Asp Glu Arg Thr Cys Arg Ile Tyr Met Ile Ile
            180                 185                 190

Tyr Asp Gly Asn Arg Phe Val Lys Ser Asp Ile Ser Lys Leu Ser Asp
        195                 200                 205

Ile Tyr Ile Thr Glu Asn Ser Ile Asp Thr Ile Pro Glu Ile Lys Asp
    210                 215                 220

Asp Met Leu Asn Lys Lys Ala Tyr Leu Pro Val Val Phe Thr Val Thr
225                 230                 235                 240

Asp Asp Lys Asn Arg Lys Ala Ile Asp Arg Ala Leu Leu Ala Phe Ser
                245                 250                 255

Val Tyr Asp His Val Val Glu Pro Ile Asp Glu Lys Thr Ala Arg Phe
            260                 265                 270

Thr Ile Gln Tyr Tyr Thr Met Asp Leu Asp Leu Leu Ile Lys Asp Ile
        275                 280                 285

Leu Ala Phe Gly Ser Asp Ile Lys Val Glu Ser Pro Arg Tyr Val Val
    290                 295                 300

Lys Arg Ile Thr Asp Ile Leu Arg Lys Val Pro Lys Lys Lys Arg Lys
305                 310                 315                 320

Val
```

<210> SEQ ID NO 69
<211> LENGTH: 419
<212> TYPE: PRT
<213> ORGANISM: Artificial Sequence
<220> FEATURE:
<223> OTHER INFORMATION: Synthetic: RtcB Eubacterium siraeum + C-term NLS

<400> SEQUENCE: 69

```
Met Ile Val Leu Glu Ile Ile Gly Glu Arg Asn Thr Ala Val Val Tyr
1               5                   10                  15

Gly Glu Ile Ile Asp Glu Cys Ala Val Ser Gln Ile Glu Glu Ile Cys
            20                  25                  30

Asn His Pro Ala Phe Glu Asn Ser Arg Ile Arg Ile Met Pro Asp Cys
        35                  40                  45

His Ala Gly Lys Gly Cys Val Ile Gly Phe Thr Cys Val Thr Ser Asn
    50                  55                  60

Arg Met Ile Val Pro Asn Ile Val Gly Val Asp Ile Gly Cys Gly Ile
65                  70                  75                  80

Leu Thr Thr Val Phe Thr Ala Asp Arg Glu Ile Asp Tyr Arg Ala Leu
                85                  90                  95

Asp Thr Phe Ile Arg Ser Asn Ile Pro Ser Gly Met Glu Ile His Asp
            100                 105                 110

Ser Val Ser Asp Thr Val Ala Glu Asn Thr Ala Leu Ile Ala Lys Val
        115                 120                 125

Asn Gly Ile Cys Asp Ala Ile Gly Glu Ser Ala Asp Val Asp Tyr His
    130                 135                 140

Leu Arg Ser Ile Gly Thr Leu Gly Gly Gly Asn His Phe Ile Glu Ile
145                 150                 155                 160

Asp Arg Leu Asn Asn Gly Asn Tyr Ala Leu Thr Val His Thr Gly Ser
                165                 170                 175
```

```
Arg Asn Leu Gly Lys Arg Ile Cys Gly Tyr Phe Gln Ser Asn Ala Ser
            180                 185                 190

Val Ile Asp Thr Glu Leu Arg Arg Ser Ile Leu Leu Arg His Arg Ser
        195                 200                 205

Ala Thr Thr Ser Glu Glu His Glu Glu Ile Asp Arg Arg Ala Ala Gln
    210                 215                 220

Ile Ala Pro Val Ser Lys Glu Leu Ala Phe Ile Thr Gly Glu Arg Tyr
225                 230                 235                 240

Asp Ser Tyr Ile Gly Cys Met Leu Asp Ala Lys Ala Leu Ala Ala Phe
                245                 250                 255

Asn Arg Thr Val Ile Ser Asp Arg Ile Met Ser Phe Leu Ala Asp Glu
            260                 265                 270

Tyr Gly Val Glu Ile Lys Asp Arg Phe Asp Thr Val His Asn Tyr Ile
        275                 280                 285

Asp Trp Tyr Asp Asp Thr His Thr Ser Val Val Ile Arg Lys Gly Ala
    290                 295                 300

Ile Ser Ala Arg Lys Gly Glu Arg Ile Val Ile Pro Leu Asn Met Arg
305                 310                 315                 320

Asp Gly Ile Ile Ile Ala His Gly Arg Gly Asn Glu Glu Trp Asn Cys
                325                 330                 335

Ser Ala Pro His Gly Ser Gly Arg Ala Tyr Ser Arg Ser Asp Ala Arg
            340                 345                 350

Arg Thr Phe Thr Leu Glu Glu Tyr Val Glu Glu Met Asp Gly Val Asn
        355                 360                 365

Thr Trp Ser Val Ser Glu Ser Thr Ile Asp Glu Cys Pro Met Ala Tyr
    370                 375                 380

Lys Pro Ser Glu Met Ile Ile Gly Ser Ile Gly Asp Thr Val Glu Ile
385                 390                 395                 400

Glu Ser Ile Ala His Thr Val Tyr Asn Phe Lys Ala Pro Lys Lys Lys
                405                 410                 415

Arg Lys Val
```

<210> SEQ ID NO 70
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 1

<400> SEQUENCE: 70

```
cuacuauacu ggugcgaauu ugcacuaguc uaaaaucuua caucuuuccu ccucauccag     60

caaaau                                                                66
```

<210> SEQ ID NO 71
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 2

<400> SEQUENCE: 71

```
cuacuauacu ggugcgaauu ugcacuaguc uaaaaucaca auccugaagu aagugaagcu     60

acagac                                                                66
```

```
<210> SEQ ID NO 72
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
      target 3

<400> SEQUENCE: 72

cuacuauacu ggugcgaauu ugcacuaguc uaaaaucugu caaaaaucac aauccugaag     60

uaagug                                                                66


<210> SEQ ID NO 73
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
      target 4

<400> SEQUENCE: 73

cuacuauacu ggugcgaauu ugcacuaguc uaaaaucucu gucaaaaauc acaauccuga     60

aguaag                                                                66


<210> SEQ ID NO 74
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
      target 5

<400> SEQUENCE: 74

cuacuauacu ggugcgaauu ugcacuaguc uaaaauucuc uucacgagau ucacuaggac     60

cuucag                                                                66


<210> SEQ ID NO 75
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
      target 6

<400> SEQUENCE: 75

cuacuauacu ggugcgaauu ugcacuaguc uaaaaucucc ucucuucacg agauucacua     60

ggaccu                                                                66


<210> SEQ ID NO 76
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
      target 7

<400> SEQUENCE: 76

cuacuauacu ggugcgaauu ugcacuaguc uaaaaugucc ucuaggucca uguuacagcc     60

agaccc                                                                66


<210> SEQ ID NO 77
<211> LENGTH: 66
<212> TYPE: RNA
<213> ORGANISM: Artificial Sequence
```

<220> FEATURE:
<223> OTHER INFORMATION: Synthetic: CasM EGFR mRNA knockdown experiment
      target 8

<400> SEQUENCE: 77
cuacuauacu ggugcgaauu ugcacuaguc uaaaauaugu ccucuagguc cauguuacag     60
ccagac                                                                66

<210> SEQ ID NO 78
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
      target 9

<400> SEQUENCE: 78
cuacuauacu ggugcgaauu ugcacuaguc uaaaaucgcc aggagcgcug ccccggccgu     60
cccgga                                                                66

<210> SEQ ID NO 79
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
      target 10

<400> SEQUENCE: 79
cuacuauacu ggugcgaauu ugcacuaguc uaaaaugcgc caggagcgcu gccccggccg     60
ucccgg                                                                66

<210> SEQ ID NO 80
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
      target 11

<400> SEQUENCE: 80
cuacuauacu ggugcgaauu ugcacuaguc uaaaaugcag cgccaggagc gcugccccgg     60
ccgucc                                                                66

<210> SEQ ID NO 81
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
      target 12

<400> SEQUENCE: 81
cuacuauacu ggugcgaauu ugcacuaguc uaaaauagca gcgccaggag cgcugccccg     60
gccguc                                                                66

<210> SEQ ID NO 82
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
      target 13

<400> SEQUENCE: 82
cuacuauacu ggugcgaauu ugcacuaguc uaaaaucagc agcgccagga gcgcugcccc 60
ggccgu 66

<210> SEQ ID NO 83
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 14

<400> SEQUENCE: 83
cuacuauacu ggugcgaauu ugcacuaguc uaaaauccag cagcgccagg agcgcugccc 60
cggccg 66

<210> SEQ ID NO 84
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 15

<400> SEQUENCE: 84
cuacuauacu ggugcgaauu ugcacuaguc uaaaaugcca gcagcgccag gagcgcugcc 60
ccggcc 66

<210> SEQ ID NO 85
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 16

<400> SEQUENCE: 85
cuacuauacu ggugcgaauu ugcacuaguc uaaaaucagc cagcagcgcc aggagcgcug 60
ccccgg 66

<210> SEQ ID NO 86
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 17

<400> SEQUENCE: 86
cuacuauacu ggugcgaauu ugcacuaguc uaaaaugcag ccagcagcgc caggagcgcu 60
gccccg 66

<210> SEQ ID NO 87
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 18

<400> SEQUENCE: 87
cuacuauacu ggugcgaauu ugcacuaguc uaaaaucgca gccagcagcg ccaggagcgc 60
ugcccc 66

<210> SEQ ID NO 88
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 19

<400> SEQUENCE: 88
cuacuauacu ggugcgaauu ugcacuaguc uaaaaugcgc agccagcagc gccaggagcg 60
cugccc 66

<210> SEQ ID NO 89
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 20

<400> SEQUENCE: 89
cuacuauacu ggugcgaauu ugcacuaguc uaaaauagcg cagccagcag cgccaggagc 60
gcugcc 66

<210> SEQ ID NO 90
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 21

<400> SEQUENCE: 90
cuacuauacu ggugcgaauu ugcacuaguc uaaaaugagc gcagccagca gcgccaggag 60
cgcugc 66

<210> SEQ ID NO 91
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 22

<400> SEQUENCE: 91
cuacuauacu ggugcgaauu ugcacuaguc uaaaauagag cgcagccagc agcgccagga 60
gcgcug 66

<210> SEQ ID NO 92
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 23

<400> SEQUENCE: 92
cuacuauacu ggugcgaauu ugcacuaguc uaaaaucaga gcgcagccag cagcgccagg 60
agcgcu 66

<210> SEQ ID NO 93

<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 24

<400> SEQUENCE: 93
cuacuauacu ggugcgaauu ugcacuaguc uaaaaugcag agcgcagcca gcagcgccag 60
gagcgc 66

<210> SEQ ID NO 94
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 25

<400> SEQUENCE: 94
cuacuauacu ggugcgaauu ugcacuaguc uaaaaugggc agagcgcagc cagcagcgcc 60
aggagc 66

<210> SEQ ID NO 95
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 26

<400> SEQUENCE: 95
cuacuauacu ggugcgaauu ugcacuaguc uaaaaucggg cagagcgcag ccagcagcgc 60
caggag 66

<210> SEQ ID NO 96
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 27

<400> SEQUENCE: 96
cuacuauacu ggugcgaauu ugcacuaguc uaaaaugccg ggcagagcgc agccagcagc 60
gccagg 66

<210> SEQ ID NO 97
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 28

<400> SEQUENCE: 97
cuacuauacu ggugcgaauu ugcacuaguc uaaaaucgcc gggcagagcg cagccagcag 60
cgccag 66

<210> SEQ ID NO 98
<211> LENGTH: 66
<212> TYPE: RNA
<213> ORGANISM: Artificial Sequence
<220> FEATURE:

<223> OTHER INFORMATION: Synthetic: CasM EGFR mRNA knockdown experiment
      target 29

<400> SEQUENCE: 98
cuacuauacu ggugcgaauu ugcacuaguc uaaaauucgc cgggcagagc gcagccagca     60
gcgcca                                                                66

<210> SEQ ID NO 99
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
      target 30

<400> SEQUENCE: 99
cuacuauacu ggugcgaauu ugcacuaguc uaaaaucucg ccgggcagag cgcagccagc     60
agcgcc                                                                66

<210> SEQ ID NO 100
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
      target 31

<400> SEQUENCE: 100
cuacuauacu ggugcgaauu ugcacuaguc uaaaauacuc gccgggcaga gcgcagccag     60
cagcgc                                                                66

<210> SEQ ID NO 101
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
      target 32

<400> SEQUENCE: 101
cuacuauacu ggugcgaauu ugcacuaguc uaaaaugacu cgccgggcag agcgcagcca     60
gcagcg                                                                66

<210> SEQ ID NO 102
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
      target 33

<400> SEQUENCE: 102
cuacuauacu ggugcgaauu ugcacuaguc uaaaauaaaa gugcccaacu gcgugagcuu     60
guuacu                                                                66

<210> SEQ ID NO 103
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
      target 34

<400> SEQUENCE: 103
cuacuauacu ggugcgaauu ugcacuaguc uaaaauaucu ucaaaagugc ccaacugcgu 60
gagcuu 66

<210> SEQ ID NO 104
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 35

<400> SEQUENCE: 104
cuacuauacu ggugcgaauu ugcacuaguc uaaaauauga ucuucaaaag ugcccaacug 60
cgugag 66

<210> SEQ ID NO 105
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 36

<400> SEQUENCE: 105
cuacuauacu ggugcgaauu ugcacuaguc uaaaauccuc uggaggcuga gaaaaugauc 60
uucaaa 66

<210> SEQ ID NO 106
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 37

<400> SEQUENCE: 106
cuacuauacu ggugcgaauu ugcacuaguc uaaaauacau ccucuggagg cugagaaaau 60
gaucuu 66

<210> SEQ ID NO 107
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 38

<400> SEQUENCE: 107
cuacuauacu ggugcgaauu ugcacuaguc uaaaauaguu auugaacauc cucuggaggc 60
ugagaa 66

<210> SEQ ID NO 108
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 39

<400> SEQUENCE: 108
cuacuauacu ggugcgaauu ugcacuaguc uaaaauacag uuauugaaca uccucuggag 60
gcugag 66

<210> SEQ ID NO 109
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 40

<400> SEQUENCE: 109
cuacuauacu ggugcgaauu ugcacuaguc uaaaaucaca guuauugaac auccucugga 60
ggcuga 66

<210> SEQ ID NO 110
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 41

<400> SEQUENCE: 110
cuacuauacu ggugcgaauu ugcacuaguc uaaaauaccu cacaguuauu gaacauccuc 60
uggagg 66

<210> SEQ ID NO 111
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 42

<400> SEQUENCE: 111
cuacuauacu ggugcgaauu ugcacuaguc uaaaauagga ccaccucaca guuauugaac 60
auccuc 66

<210> SEQ ID NO 112
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 43

<400> SEQUENCE: 112
cuacuauacu ggugcgaauu ugcacuaguc uaaaaucaag gaccaccuca caguuauuga 60
acaucc 66

<210> SEQ ID NO 113
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 44

<400> SEQUENCE: 113
cuacuauacu ggugcgaauu ugcacuaguc uaaaauuucc caaggaccac cucacaguua 60
uugaac 66

<210> SEQ ID NO 114
<211> LENGTH: 66

<212> TYPE: RNA
<213> ORGANISM: Artificial Sequence
<220> FEATURE:
<223> OTHER INFORMATION: Synthetic: CasM EGFR mRNA knockdown experiment target 45

<400> SEQUENCE: 114
cuacuauacu ggugcgaauu ugcacuaguc uaaaauaaau ucccaaggac caccucacag 60
uuauug 66

<210> SEQ ID NO 115
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 46

<400> SEQUENCE: 115
cuacuauacu ggugcgaauu ugcacuaguc uaaaaucaaa uucccaagga ccaccucaca 60
guuauu 66

<210> SEQ ID NO 116
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 47

<400> SEQUENCE: 116
cuacuauacu ggugcgaauu ugcacuaguc uaaaauccaa auucccaagg accaccucac 60
aguuau 66

<210> SEQ ID NO 117
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 48

<400> SEQUENCE: 117
cuacuauacu ggugcgaauu ugcacuaguc uaaaauuuuc caaauuccca aggaccaccu 60
cacagu 66

<210> SEQ ID NO 118
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 49

<400> SEQUENCE: 118
cuacuauacu ggugcgaauu ugcacuaguc uaaaauuaau uuccaaauuc ccaaggacca 60
ccucac 66

<210> SEQ ID NO 119
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 50

<400> SEQUENCE: 119
cuacuauacu ggugcgaauu ugcacuaguc uaaaauguaa uuuccaaauu cccaaggacc 60
accuca 66

<210> SEQ ID NO 120
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 51

<400> SEQUENCE: 120
cuacuauacu ggugcgaauu ugcacuaguc uaaaauaggu aauuuccaaa uucccaagga 60
ccaccu 66

<210> SEQ ID NO 121
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 52

<400> SEQUENCE: 121
cuacuauacu ggugcgaauu ugcacuaguc uaaaaucaua gguaauuucc aaauucccaa 60
ggacca 66

<210> SEQ ID NO 122
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 53

<400> SEQUENCE: 122
cuacuauacu ggugcgaauu ugcacuaguc uaaaaucugc acauagguaa uuuccaaauu 60
cccaag 66

<210> SEQ ID NO 123
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 54

<400> SEQUENCE: 123
cuacuauacu ggugcgaauu ugcacuaguc uaaaaucucu gcacauaggu aauuuccaaa 60
uuccca 66

<210> SEQ ID NO 124
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 55

<400> SEQUENCE: 124
cuacuauacu ggugcgaauu ugcacuaguc uaaaauaauu ccucugcaca uagguaauuu 60
ccaaau 66

<210> SEQ ID NO 125
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 56

<400> SEQUENCE: 125
cuacuauacu ggugcgaauu ugcacuaguc uaaaauagau cauaauuccu cugcacauag 60
guaauu 66

<210> SEQ ID NO 126
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 57

<400> SEQUENCE: 126
cuacuauacu ggugcgaauu ugcacuaguc uaaaauauga ggacauaacc agccaccucc 60
uggaug 66

<210> SEQ ID NO 127
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 58

<400> SEQUENCE: 127
cuacuauacu ggugcgaauu ugcacuaguc uaaaaugcaa ugaggacaua accagccacc 60
uccugg 66

<210> SEQ ID NO 128
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 59

<400> SEQUENCE: 128
cuacuauacu ggugcgaauu ugcacuaguc uaaaauaauu cgcuccacug uguugagggc 60
aaugag 66

<210> SEQ ID NO 129
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 60

<400> SEQUENCE: 129
cuacuauacu ggugcgaauu ugcacuaguc uaaaauguuu uccaaaggaa uucgcuccac 60
uguguu 66

<210> SEQ ID NO 130
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 61

<400> SEQUENCE: 130
cuacuauacu ggugcgaauu ugcacuaguc uaaaauucug cagguuuucc aaaggaauuc 60
gcucca 66

<210> SEQ ID NO 131
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 62

<400> SEQUENCE: 131
cuacuauacu ggugcgaauu ugcacuaguc uaaaaugauc ugcagguuuu ccaaaggaau 60
ucgcuc 66

<210> SEQ ID NO 132
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 63

<400> SEQUENCE: 132
cuacuauacu ggugcgaauu ugcacuaguc uaaaaugaug aucugcaggu uuuccaaagg 60
aauucg 66

<210> SEQ ID NO 133
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 64

<400> SEQUENCE: 133
cuacuauacu ggugcgaauu ugcacuaguc uaaaauugau gaucugcagg uuuuccaaag 60
gaauuc 66

<210> SEQ ID NO 134
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 65

<400> SEQUENCE: 134
cuacuauacu ggugcgaauu ugcacuaguc uaaaauucug augaucugca gguuuuccaa 60
aggaau 66

<210> SEQ ID NO 135
<211> LENGTH: 66
<212> TYPE: RNA

<213> ORGANISM: Artificial Sequence
<220> FEATURE:
<223> OTHER INFORMATION: Synthetic: CasM EGFR mRNA knockdown experiment target 66

<400> SEQUENCE: 135
cuacuauacu ggugcgaauu ugcacuaguc uaaaauauuu ccucugauga ucugcagguu 60
uuccaa 66

<210> SEQ ID NO 136
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 67

<400> SEQUENCE: 136
cuacuauacu ggugcgaauu ugcacuaguc uaaaauauau uuccucugau gaucugcagg 60
uuuucc 66

<210> SEQ ID NO 137
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 68

<400> SEQUENCE: 137
cuacuauacu ggugcgaauu ugcacuaguc uaaaauuuuc guaguacaua uuuccucuga 60
ugaucu 66

<210> SEQ ID NO 138
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 69

<400> SEQUENCE: 138
cuacuauacu ggugcgaauu ugcacuaguc uaaaauuagg aauuuucgua guacauauuu 60
ccucug 66

<210> SEQ ID NO 139
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 70

<400> SEQUENCE: 139
cuacuauacu ggugcgaauu ugcacuaguc uaaaaucaua ggaauuuucg uaguacauau 60
uuccuc 66

<210> SEQ ID NO 140
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 71

<400> SEQUENCE: 140
cuacuauacu ggugcgaauu ugcacuaguc uaaaaucugc uaaggcauag gaauuuucgu 60
aguaca 66

<210> SEQ ID NO 141
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 72

<400> SEQUENCE: 141
cuacuauacu ggugcgaauu ugcacuaguc uaaaaugaua agacugcuaa ggcauaggaa 60
uuuucg 66

<210> SEQ ID NO 142
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 73

<400> SEQUENCE: 142
cuacuauacu ggugcgaauu ugcacuaguc uaaaauauag uuagauaaga cugcuaaggc 60
auagga 66

<210> SEQ ID NO 143
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 74

<400> SEQUENCE: 143
cuacuauacu ggugcgaauu ugcacuaguc uaaaauauca uaguuagaua agacugcuaa 60
ggcaua 66

<210> SEQ ID NO 144
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 75

<400> SEQUENCE: 144
cuacuauacu ggugcgaauu ugcacuaguc uaaaauuauu ugcaucauag uuagauaaga 60
cugcua 66

<210> SEQ ID NO 145
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 76

<400> SEQUENCE: 145
cuacuauacu ggugcgaauu ugcacuaguc uaaaauaguc cgguuuuauu ugcaucauag 60
uuagau 66

<210> SEQ ID NO 146
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
target 77

<400> SEQUENCE: 146
cuacuauacu ggugcgaauu ugcacuaguc uaaaaucuuc aguccgguuu uauuugcauc 60
auaguu 66

<210> SEQ ID NO 147
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
target 78

<400> SEQUENCE: 147
cuacuauacu ggugcgaauu ugcacuaguc uaaaauuggg cagcuccuuc aguccgguuu 60
uauuug 66

<210> SEQ ID NO 148
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
target 79

<400> SEQUENCE: 148
cuacuauacu ggugcgaauu ugcacuaguc uaaaaucaug ggcagcuccu ucaguccggu 60
uuuauu 66

<210> SEQ ID NO 149
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
target 80

<400> SEQUENCE: 149
cuacuauacu ggugcgaauu ugcacuaguc uaaaauuaaa uuucucaugg gcagcuccuu 60
cagucc 66

<210> SEQ ID NO 150
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment
target 81

<400> SEQUENCE: 150
cuacuauacu ggugcgaauu ugcacuaguc uaaaauuagc ccccagcgcc acgaccuccg 60
agcuac 66

<210> SEQ ID NO 151
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 82

<400> SEQUENCE: 151
cuacuauacu ggugcgaauu ugcacuaguc uaaaaugccu cccgacagag cgcuggugcu 60
agcccc 66

<210> SEQ ID NO 152
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 83

<400> SEQUENCE: 152
cuacuauacu ggugcgaauu ugcacuaguc uaaaauuucc agcaccgagc gcccuggccg 60
gugagu 66

<210> SEQ ID NO 153
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 84

<400> SEQUENCE: 153
cuacuauacu ggugcgaauu ugcacuaguc uaaaauagaa aaaagaagag ggauaaaacc 60
cggauc 66

<210> SEQ ID NO 154
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 85

<400> SEQUENCE: 154
cuacuauacu ggugcgaauu ugcacuaguc uaaaauggga aguagagcaa ucuccccaag 60
ccgucg 66

<210> SEQ ID NO 155
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 86

<400> SEQUENCE: 155
cuacuauacu ggugcgaauu ugcacuaguc uaaaaugggg aggaggugu agcuggggcu 60 gggggc 66

<210> SEQ ID NO 156
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 87

<400> SEQUENCE: 156
cuacuauacu ggugcgaauu ugcacuaguc uaaaaucacc ccgccuccgg gcgcgggcuc 60
cggccc 66

<210> SEQ ID NO 157
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 88

<400> SEQUENCE: 157
cuacuauacu ggugcgaauu ugcacuaguc uaaaaucacg gcuccuccga agcgagaaca 60
gcccag 66

<210> SEQ ID NO 158
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 89

<400> SEQUENCE: 158
cuacuauacu ggugcgaauu ugcacuaguc uaaaauuccg ggacggccgg ggcagcgcuc 60
cuggcg 66

<210> SEQ ID NO 159
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 90

<400> SEQUENCE: 159
cuacuauacu ggugcgaauu ugcacuaguc uaaaauccgg gacggccggg gcagcgcucc 60
uggcgc 66

<210> SEQ ID NO 160
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 91

<400> SEQUENCE: 160
cuacuauacu ggugcgaauu ugcacuaguc uaaaauggac ggccggggca gcgcuccugg 60
cgcugc 66

<210> SEQ ID NO 161
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 92

-continued

<400> SEQUENCE: 161
cuacuauacu ggugcgaauu ugcacuaguc uaaaaugacg gccggggcag cgcuccuggc 60
gcugcu 66

<210> SEQ ID NO 162
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 93

<400> SEQUENCE: 162
cuacuauacu ggugcgaauu ugcacuaguc uaaaauacgg ccggggcagc gcuccuggcg 60
cugcug 66

<210> SEQ ID NO 163
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 94

<400> SEQUENCE: 163
cuacuauacu ggugcgaauu ugcacuaguc uaaaaucggc cggggcagcg cuccuggcgc 60
ugcugg 66

<210> SEQ ID NO 164
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 95

<400> SEQUENCE: 164
cuacuauacu ggugcgaauu ugcacuaguc uaaaauggcc ggggcagcgc uccuggcgcu 60
gcuggc 66

<210> SEQ ID NO 165
<211> LENGTH: 66
<212> TYPE: RNA
<213> ORGANISM: Artificial Sequence
<220> FEATURE:
<223> OTHER INFORMATION: Synthetic: CasM EGFR mRNA knockdown experiment target 96

<400> SEQUENCE: 165
cuacuauacu ggugcgaauu ugcacuaguc uaaaauccgg ggcagcgcuc cuggcgcugc 60
uggcug 66

CRISPR-ASSOCIATED (CAS) PROTEIN

CROSS-REFERENCE TO RELATED APPLICATIONS

This application is a Division of U.S. application Ser. No. 17/097,880, filed 13 Nov. 2020 (now U.S. Pat. No. 11,293, 011), which is a Continuation of U.S. application Ser. No. 15/937,840, filed 27 Mar. 2018 (now U.S. Pat. No. 10,876, 101), which claims benefit of, and priority to, U.S. Provisional Application Nos. 62/477,494, filed 28 Mar. 2017, and 62/629,641, filed 12 Feb. 2018, the contents of each of which are incorporated herein by reference in their entireties.

TECHNICAL FIELD

The present invention relates to Clustered Regularly Interspaced Short Palindromic Repeats (CRISPR) systems. In particular, the invention relates to a new CRISPR-associated (Cas) protein, termed "CasM," and the uses of CasM for site-specific nucleic acid engineering.

BACKGROUND OF THE INVENTION

Clustered Regularly Interspaced Short Palindromic Repeats (CRISPR) and CRISPR-associated (Cas) proteins are found in prokaryotic immune systems. These systems provide resistance against exogenous genetic elements, such as viruses and plasmids, by targeting their nucleic acids for degradation, in a sequence-specific manner.

There are several different CRISPR-Cas systems and the nomenclature and classification of these have changed as the systems have been characterized. In particular, CRISPR-Cas systems have now been reclassified into two classes, containing several types and subtypes (Makarova et al., Nature Reviews Microbiology (2015) 13:1-15; Shmakov et al., Nature Reviews Microbiology (2017) 15; 169-182). This classification is based upon identifying all cas genes in a CRISPR-Cas locus and then determining the signature genes in each CRISPR-Cas locus, thereby determining whether the CRISPR-Cas systems should be placed in either Class 1 or Class 2 based upon the genes encoding the effector module, i.e., the proteins involved in the interference stage.

There remains a need to discover and characterize new CRISPR-associated (Cas) proteins, and their potential use for site-specific nucleic acid engineering.

SUMMARY

The present invention is based on the discovery of a new Cas protein, termed "CasM" herein. This protein shares no homology to any known Cas protein or to any known protein family.

Accordingly, in one aspect, the invention is directed to an isolated CasM protein capable of producing a single-strand break at an RNA target site when guided to the RNA target site by a cognate nucleic acid guide. In certain embodiments, the cognate nucleic acid guide comprises RNA, such, as crRNA, in additional embodiments, the CasM protein comprises an amino acid sequence selected from the group consisting of the amino acid sequence of SEQ ID NOS:37-44 or 45; an ortholog of the amino acid sequence of SEQ ID NOS:37-44 or 45, i.e., a CasM sequence from a species other than the species producing the reference sequence; and a variant of the amino acid sequence of SEQ ID NOS:37-44 or 45, e.g., an active homology of the reference amino acid sequence.

In further embodiments, the invention is directed to a complex comprising a CasM protein, and a cognate nucleic acid guide. In certain embodiments, the cognate nucleic acid guide in the complex comprises a repeat sequence and a spacer sequence, wherein the repeat sequence and the spacer sequence do not naturally occur together. In certain embodiments, the cognate nucleic acid guide comprises a modified base analog.

In additional embodiments, the cognate nucleic acid guide comprises RNA, such as, but not limited to, crRNA. In some embodiments, the cognate nucleic acid guide, such as crRNA, comprises a spacer sequence that is complementary to a DNA or RNA target sequence that occurs in a prokaryotic or eukaryotic cell.

In further embodiments, the crRNA/CasM protein complex is capable of binding to a first RNA target sequence complementary to the crRNA spacer sequence, wherein binding of the crRNA/CasM protein complex results in the cleavage of a first RNA target. In additional embodiments, after cleavage of the first RNA target sequence by the crRNA/CasM protein complex, the complex is capable of non-specific endonuclease activity toward any single-stranded RNA in a sequence independent manner.

In further embodiments, the complex modifies the transcription or translation of a target locus in cell.

In additional embodiments, the invention is directed to an isolated polynucleotide encoding a CasM protein, wherein the CasM protein is capable of producing a single-strand break at an RNA target site when guided to the RNA target site by a cognate nucleic acid guide. In certain embodiments, the cognate nucleic acid guide comprises RNA, such as crRNA. In additional embodiments, the CasM protein encoded by the polynucleotide comprises an amino acid sequence selected from the group consisting of the amino acid sequence of SEQ ID NOS:37-44 or 45; an ortholog of the amino acid sequence of SEQ ID NOS 37-44 or 45, i.e., a CasM sequence from a species other than the species producing the reference sequence; and a variant of the amino acid sequence of SEQ ID NOS:37-44 or 45, e.g., an active homolog of the reference amino acid sequence.

In further embodiments, the invention is directed to a modified polynucleotide encoding a CasM protein, wherein the CasM protein is capable of producing a single-strand break at an RNA target site when guided to the RNA target site by a cognate nucleic acid guide, wherein the polynucleotide is modified relative to its native sequence, such as modified for expression in a selected host cell. In additional embodiments, the CasM protein encoded by the polynucleotide comprises an amino acid sequence selected from the group consisting of the amino acid sequence of SEQ ID NOS:37-44 or 45; an ortholog of the amino acid sequence of SEQ ID NOS:37-44 or 45, i.e., a CasM sequence from a species other than the species producing the reference sequence; and a variant of the amino acid sequence of SEQ ID NOS:37-44 or 45, e.g., an active homolog of the reference amino acid sequence.

In certain embodiments, the polynucleotide is modified for expression in a bacterial cell, such as for expression in an *Escherichia coli* cell. In certain embodiments, the polynucleotide comprises the sequence of SEQ ID NOS:2-8 or 9.

In other embodiments, the polynucleotide is modified for expression in a eukaryotic cell, e.g., a mammalian cell, such as a human cell. In certain embodiments, the polynucleotide comprises the sequence of SEQ ID NOS:10-17 or 18.

In additional embodiments, the polynucleotide is modified for expression in a plant cell, such as for expression in a *Zea mays* (corn) cell. In certain embodiments the polynucleotide comprises the sequence of SEQ ID NOS:19-26 or 27.

In further embodiments, the invention is directed to a recombinant vector comprising a polynucleotide or modified polynucleotide as described herein, and at least one control element operably linked to the polynucleotide, whereby a CasM coding sequence in the polynucleotide is capable of being transcribed and translated in a host cell. In certain embodiments, at least one of the control elements is heterologous to the coding system.

In additional embodiments, the CasM protein encoded by the polynucleotide comprises an amino acid sequence selected from the group consisting of the amino acid sequence of SEQ ID NOS:37-44 or 45; an ortholog of the amino acid sequence of SEQ ID NOS:37-44 or 45; and a variant of the amino acid, sequence of SEQ ID NOS:37-44 or 45.

In further embodiments, the invention is directed to a host cell transformed with a recombinant vector described herein. In certain embodiments, the host cell is a prokaryotic or eukaryotic cell.

In additional embodiments, the invention is directed to a method of producing a CasM protein comprising providing a population of host cells transformed with a recombinant vector as described herein; and culturing the population of cells under conditions whereby the CasM protein encoded by the polynucleotide present in the recombinant vector is expressed.

In further embodiments, the invention is directed to a eukaryotic host cell comprising a CasM protein of a complex comprising the CasM protein, as described herein.

In additional embodiments, the invention is directed to a method of directing a CasM protein to a selected nucleic acid target sequence, comprising contacting the selected nucleic acid target sequence with a cognate nucleic acid guide/CasM complex that targets said selected nucleic acid target sequence, whereby the CasM protein is delivered to the nucleic acid target sequence. In certain embodiments, the nucleic acid target sequence comprises RNA, such as mRNA. In further embodiments, the method comprises producing one or more single- or double-strand breaks in the target sequence.

In additional embodiments, the method is performed in a cell, such as a prokaryotic or eukaryotic cell. In certain embodiments, the cell constitutively expresses the CasM protein. In other embodiments, e.g., when the cell does not constitutively express the CasM protein, the cognate nucleic acid guide is complexed to the CasM protein prior to delivery to the nucleic acid target sequence. In other embodiments, the cell constitutively expresses the CasM protein and the cognate nucleic acid guide. In additional embodiments, the complex modifies the transcription or translation of a selected nucleic acid sequence in a host cell, such as a sequence.

In further embodiments of the methods, the CasM protein comprises an amino acid sequence selected from the group consisting of the amino acid sequence of SEQ ID NOS:37-44 or 45; an ortholog of the amino acid sequence of SEQ ID NOS:37-44 or 45; and a variant of the amino acid sequence of SEQ ID NOS:37-44 or 45.

In other embodiments of the methods, a donor polynucleotide is delivered to the region of the selected nucleic acid target sequence.

In additional embodiments, the CasM protein is capable of processing the CRISPR repeat-spacer array into individual repeat-spacer elements. The CasM protein cleaves the array within the 5' region of each repeat sequence, giving rise to a processed crRNA comprising, in a 5' to 3' direction, a repeat sequence and a spacer element.

In some embodiments the repeat sequence comprises a secondary structure that is recognized by the CasM protein. The secondary structure of the repeat may comprise a stem, a stem-loop duplex, a pseudoknot, or a tripartite duplex. CasM protein homologs may only recognize the repeat sequence or secondary structure of their cognate repeat elements. Alternatively, CasM protein homologs may recognize the repeat sequence or secondary structure of non-cognate repeat elements.

In some embodiments the crRNA/CasM complex is capable of sequence-specific single-stranded RNA activity. Recognition and cleavage of an initial ssRNA complementary to the crRNA target sequence activates the CasM protein to carry out endonuclease activity toward any single-stranded RNA in a sequence-independent manner. The sequence-specific recognition of RNA of the crRNA/CasM complex facilitates the target knockdown of gene transcripts perturbing translation of a specific protein. The non-specific endonuclease activity of an activated crRNA/CasM complex in a cellular environment can result in cell death due to depletion of RNA encoding for essential gene transcripts. The specific RNA targeting and collateral endonuclease activity of an activated crRNA/CasM complex enables the sequence-specific selection of cells expressing a RNA transcript.

In a further aspect, the present invention relates to a method of screening and killing cells that have not been modified by a DNA targeting nuclease (e.g., a Type II Cas9 nuclease). This method comprises contacting a crRNA/Cas9 complex to a locus of interest in a population of cells. Contacting the NATNA/Cas9 complex results in DNA cleavage and subsequent repair of the break by the endogenous cellular repair machine and the introduction of insertion and deletions ("indels") at the break site. The targeting of the NATNA/Cas9 to a targeted locus that encodes an RNA transcript results in indels in an RNA transcript sequence. This modified RNA transcript sequence is different compared to a transcript from an unmodified cell (a wild-type cell). A cognate nucleic acid guide/CasM complex can then be targeted to the unmodified transcript, wherein recognition of the unmodified transcript by the complex results in activation of the sequence independent, single-stranded RNA targeting activity of the CasM protein and subsequent cell death. Alternatively, this method can be adapted to screen for the incorporation of a donor-polynucleotide into NATNA/Cas9 break site.

These aspects and other embodiments of the present invention will readily occur to those of ordinary skill in the art in view of the disclosure herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SEQUENCE LISTING

The sequences referred to herein are listed in the Sequence Listing submitted as an ASCII text file entitled "LOCN-006_C02US_SeqList.ST25.txt"-306 KB and was created on Nov. 13, 2020. The Sequence Listing entitled "LOCN-006_C02US_SeqList_ST25.txt" is incorporated herein by reference in its entirety.

DETAILED DESCRIPTION OF THE INVENTION

Figure 1:
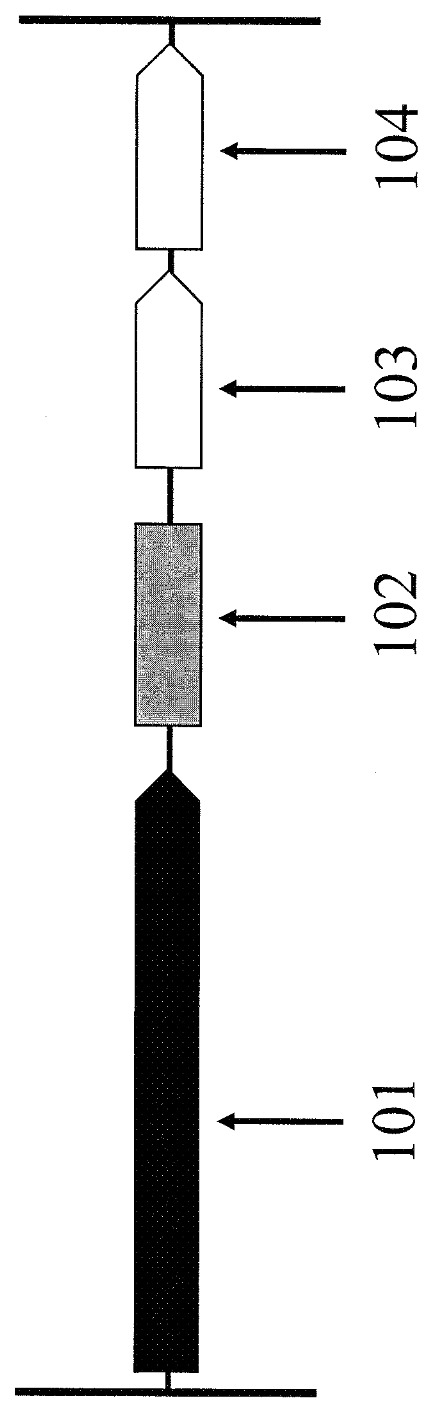
FIG. 1 depicts a representative CasM operon from *Eubacterium siraeum* (NCBI Accession No. NZ_DS4995.551.1).

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to a "guide/Cas complex" includes one or more such complexes, reference to "a polynucleotide" includes one or more polynucleotides, etc.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, preferred materials and methods are described herein.

In view of the teachings of the present specification, one of ordinary skill in the art can apply conventional techniques of immunology, biochemistry, chemistry, molecular biology, microbiology, cell biology, genomics, and recombinant polynucleotides, as taught, for example, by the following standard texts: Antibodies: A Laboratory Manual, Second edition, E. A. Greenfield, 2014, Cold Spring Harbor Laboratory Press, ISBN 978-1-936113-81-1; Culture of Animal Cells: A Manual of Basic Technique and Specialized Applications, 6th Edition, R. I. Freshney, 2010, Wiley-Blackwell, ISBN 978-0-470-52812-9; Transgenic Animal Technology, Third Edition: A Laboratory Handbook, 2014, C. A. Pinkert, Elsevier, ISBN 978-0124104907; The Laboratory Mouse, Second Edition, 2012, H. Hedrich, Academic Press, ISBN 978-0123820082 Manipulating the Mouse Embryo: A Laboratory Manual, 2013, R. Behringer, at al., Cold Spring Harbor Laboratory Press, ISBN 978-1936113019; PCR 2: A Practical Approach, 1995, M. J. McPherson, at al., IRL Press, ISBN 978-0199634248; Methods in Molecular Biology (Series), J. M. Walker, ISSN 1064-3745, Humana Press; RNA: A Laboratory Manual, 2010, D. C. Rio, et al., Cold Spring Harbor Laboratory Press, ISBN 978-0879698911; Methods in Enzymology (Series), Academic Press; Molecular Cloning: A Laboratory Manual (Fourth Edition), 2012, M. R. Green, et al., Cold Spring Harbor Laboratory Press, ISBN 978-1605500560; Bioconjugate Techniques, Third Edition, 2013, G. T. Hermanson, Academic Press, ISBN 978-0123822390; Methods in Plant Biochemistry and Molecular Biology, 1997, W. V. Dashek, CRC Press, ISBN 978-0849394805; Plant Cell Culture Protocols (Methods in Molecular Biology), 2012, V. M. Loyola-Vargas, et al., Humana Press, ISBN 978-1617798177; Plant Transformation Technologies, 2011, C. N. Stewart, et al., Wiley-Blackwell, ISBN 978-0813821955; Recombinant Proteins from Plants (Methods in Biotechnology), 2010, C. Cunningham, et al., Humana Press, ISBN 978-1617370212; Plant Genomics: Methods and Protocols (Methods in Molecular Biology), 2009, D. J. Somers, et al., Humana Press, ISBN 978-1588299970; Plant Biotechnology: Methods in Tissue Culture and Gene Transfer, 2008, R. Keshavachandran, et al., Orient Blackswan, ISBN 978-8173716164.

As used herein, "a CasM protein" refers to a CRISPR protein capable of targeting RNA and causing single-strand RNA breaks when guided to a target site by a crRNA, without the necessity of association with a tracrRNA. CasM proteins typically include two or more higher eukaryotic and prokaryotic nucleotide-binding (HEPN) domains found in protein family PF05168 in the C-terminal region of the CasM sequence. CasM proteins show synteny with one or more WYL domain-containing proteins and sometimes with RtcB (RNA 3'-terminal phosphate cyclase, group B) domain-containing proteins. Based on the foregoing characteristics, CasM may be classified as a Class 2 Type VI CRISPR-Cas system because it is a single effector protein containing two HEPN domains used for targeted ssRNA interference. However, CasM has a very low degree of sequence similarity to other Type VI subtypes. Exemplary CasM proteins, are shown in SEQ ID NOS:37-45, and are encoded by polynucleotides shown in SEQ ID NOS:28-36, respectively. These proteins display approximately 13.59% to 99.82% sequence identity to each other and show less than 8% sequence identity with other known CRISPR-Cas proteins. As used herein, the term "CasM protein" refers to a CasM protein derived from any species, subspecies, or strain of bacteria that encodes the CasM protein, as well as an ortholog of the CasM protein, i.e., a CasM protein from a species other than the species producing the reference CasM protein. For example, CasM orthologs of *Eubacterium siraeum* CasM, shown in Table 1, display approximately 13.59% to 99.82% sequence identity to each other. Thus, CasM orthologs are identified based on the CasM characteristics detailed herein. Reference to a CasM protein also encompasses a variant of the reference CasM protein, e.g., an active homolog of the reference amino acid sequence. Thus, CasM proteins include, but are not limited to, those proteins depicted in SEQ ID NOS:37-45, orthologs thereof, or variants thereof. Non-limiting examples of such proteins include CasM proteins from *Eubacterium siraeum; Ruminococcus* sp., such as from *Ruminococcus bicirculans; Ruminococcus flavefaciens*, such as, but not limited to, FD-1 and strain XPD3002; *Ruminococcus albus* such as, but not limited to, strain KH2T6*; Ruminococcus* sp. isolates, such as but not limited to, isolates 2789STDY5834971, 27895TDY5608892 and 2789STDY5834894.

By "dCasM protein" is meant a deactivated CasM protein lacking activity, such as catalytic and/or binding activity, also termed "dead CasM." Such molecules lack all or a portion of biological activity, such as nuclease and/or binding activity, and are therefore unable to bind and/or cleave a target nucleic acid of interest, respectively. In some embodiments, these deactivated CasM proteins can be used to regulate genes in a nucleic acid-guided manner. This is accomplished by introducing mutations that inactivate CasM nuclease function and typically involves mutating catalytic residues of the gene encoding CasM. dCasM can be used alone or in fusions to synthetically repress (CRISPR interference or CRISPRi) or activate (CRISPR activation or CRISPRa) gene expression. CRISPRi can work independently of host cellular machineries. In some embodiments a dCasM protein and a customized nucleic acid-targeting nucleic acid, i.e., a cognate nucleic acid guide designed with a complementary region to any gene of interest, are used to direct dCasM to a chosen genomic location. In other embodiments, dCasM can be fused to a transcription factor, such as a repressor, and the fused dCasM-transcription factor can then work in concert with cellular machineries. CRISPRa is carried out by dCasM-transcription factor (activator) fusions.

A "nucleic acid-targeting nucleic acid" (NATNA), as used herein, refers to one or more polynucleotides that guide a protein, such as a CasM protein, to preferentially target a nucleic acid target sequence present in a polynucleotide (relative to a polynucleotide that does not comprise the nucleic acid target sequence). Such NATNAs are also known herein as "cognate nucleic acid guides," or "cognate guides." NATNAs can comprise ribonucleotide bases (e.g., RNA); deoxyribonucleotide bases (e.g., DNA), combinations of ribonucleotide bases and deoxyribonucleotide bases (e.g., RNA/DNA), nucleotides, nucleotide analogs, modified nucleotides, and the like, as well as synthetic, naturally occurring, and non-naturally occurring modified backbone residues or linkages. Thus, a NATNA as used herein site-specifically guides a CasM, or a deactivated CasM, to a target nucleic acid. Many such NATNAs are known, such as but not limited to sgRNA (including miniature and truncated single-guide RNAs), crRNA, dual-guide RNA, including but not limited to, crRNA/tracrRNA molecules, as described herein, and the like, the use of which depends on the particular Cas protein. For a non-limiting description of exemplary NATNAs, see, e.g., PCT Publication No. WO 2014/150624 to May et al., published Sep. 29, 2014; PCT Publication No. WO 2015/200555 to May et al., published Mar. 10, 2016; PCT Publication No. WO 2016/201155 to Donohoue et al., published Dec. 15, 2016; PCT Publication No. WO 2017/027423 to Donohoue et al., published Feb. 16, 2017; and PCT Publication No. WO 2016/123230 to May et al., published Aug. 4, 2016; each of which is incorporated herein by reference in its entirety.

With reference to a NATNA or a cognate nucleic acid guide, a "spacer," "spacer sequence," or "spacer element," as used herein, refers to the polynucleotide sequence that can specifically hybridize to a target nucleic acid sequence. The spacer element interacts with the target nucleic acid sequence through hydrogen bonding between complementary base pairs (i.e., paired bases). A spacer element binds to a selected nucleic acid target sequence. Accordingly, the spacer element is the nucleic acid target-binding sequence. The spacer element determines the location of a Cas protein's site-specific binding and nucleolytic cleavage. Spacer elements range from approximately 17 to approximately 84 nucleotides in length and have an average length of 36 nucleotides (see, e.g., Marraffini, et al., "CRISPR interference: RNA-directed adaptive immunity in bacteria and archaea" Nature reviews Genetics (2010) 11:1814190). Variability of the functional length for a spacer element is known in the art (e.g., U.S. Patent Publication 2014/0315985 to May et al., published Oct. 23, 2014, incorporated herein by reference in its entirety). The terms "nucleic acid target binding sequence" and "spacer sequence" are used interchangeably herein.

The term "sgRNA" typically refers to a single-guide RNA (i.e., a single, contiguous polynucleotide sequence) that essentially comprises a or RNA connected at its 3' end to the 5' end of a tracrRNA through a "loop" sequence (see, e.g., U.S. Published Patent Application No. 2014/0068797 to Doudna et al., published 6 Mar. 2014, incorporated herein by reference in its entirety), sgRNA interacts with a cognate Cas protein essentially as described for tracrRNA/crRNA polynucleotides. Similar to crRNA, sgRNA, has a spacer, a region of complementarity to a potential DNA or RNA target sequence, adjacent a second region that forms base-pair hydrogen bonds that form a secondary structure, typically a stem structure. The term includes truncated single-guide RNAs (tru-sgRNAs) of approximately 17-18 nucleotides (nt) (see, e.g., et al., *Nat Biotechnol.* (2014) 32; 279-284). The term also encompasses functional miniature sgRNAs with expendable features removed, but that retain an essential and conserved module termed the "nexus" located in the portion of sgRNA that corresponds to tracrRNA (not crRNA). See, e.g., U.S. Patent Publication 2014/0315985 to May et al., published Oct. 23, 2014, incorporated herein by reference in its entirety; Briner et al., "Guide RNA Functional Modules Direct Cas9 Activity and Orthogonality," Molecular Cell (2014) 56:333-339.

As used herein, "dual-guide RNA" refers to a two-component RNA system for a polynucleotide component capable of associating with a cognate Cas protein. A representative CRISPR Class 2 Type II CRISPR-Cas-associated dual-guide RNA includes a Cas-crRNA and Cas-tracrRNA, paired by hydrogen bonds to form secondary structure (see, e.g., U.S. Published Patent Application No. 2014/0068797 to Doudna et al., published 6 Mar. 2014, incorporated herein by reference in its entirety; see also Jinek M., et al., Science 337:816-21 (2012)). A Cas-dual-guide RNA is capable of forming a nucleoprotein complex with a cognate Cas protein, wherein the complex is capable of targeting a nucleic acid target sequence complementary to the spacer sequence.

As used herein, the term "cognate" typically refers to a Cas protein (e.g., CasM protein) and one or more polynucleotides (e.g., a CRISPR-CasM-associated cognate nucleic acid guide) capable of forming a nucleoprotein complex for site-directed binding to a nucleic acid target sequence complementary to the nucleic acid target binding sequence present in one of the one or more polynucleotides.

The terms "wild-type," "naturally-occurring," "native," and "unmodified" are used herein to mean the typical (or most common) form, appearance, phenotype, or strain existing in nature; for example, the typical form of cells, organisms, characteristics, polynucleotides, proteins, macromolecular complexes, genes, RNAs, DNAs, or genomes as they occur in and can be isolated from a source in nature. The wild-type form, appearance, phenotype, or strain serve as the original parent before an intentional modification. Thus, mutant, variant, engineered, recombinant, and modified forms are not wild-type forms.

As used herein, the terms "engineered," "genetically engineered," "recombinant," "modified," and "non-naturally occurring" are interchangeable and indicate intentional human manipulation.

"Covalent bond," "covalently attached," "covalently bound," "covalently linked," "covalently connected," and "molecular bond" are used interchangeably herein, and refer to a chemical bond that involves the sharing of electron pairs between atoms. Examples of covalent bonds include, but are not limited to, phosphodiester bonds and phosphorothioate bonds.

"Non-covalent bond," "non-covalently attached," "non-covalently bound," "non-covalently linked," "non-covalent interaction," and "non-covalently connected" are used interchangeably herein, and refer to any relatively weak chemical bond that does not involve sharing of a pair of electrons. Multiple non-covalent bonds often stabilize die conformation of macromolecules and mediate specific interactions between molecules. Examples of non-covalent bonds include, but are not limited to hydrogen bonding, ionic interactions (e.g., $Na^{+}Cl^{-}$), van der Waals interactions, and hydrophobic bonds.

As used herein, "hydrogen bonding," "hydrogen base pairing," and "hydrogen bonded" are used interchangeably and refer to canonical hydrogen bonding and non-canonical hydrogen bonding including, but not limited to, "Watson-Crick-hydrogen-bonded base pairs" (W-C-hydrogen-bonded base pairs or W-C hydrogen bonding); "Hoogsteen-hydrogen-bonded base pairs" (Hoogsteen hydrogen bonding); and "wobble-hydrogen-bonded base pairs" (wobble hydrogen bonding). W-C hydrogen bonding, including reverse W-C hydrogen bonding, refers to purine-pyrimidine base pairing, that is, adenine:thymine, guanine:cytosine, and uracil: adenine. Hoogsteen hydrogen bonding, including reverse Hoogsteen hydrogen bonding, refers to a variation of base pairing in nucleic acids wherein two nucleobases, one on each strand, are held together by hydrogen bonds in the major groove. This non-W-C hydrogen bonding can allow a third strand to wind around a duplex and form triple-stranded helices. Wobble hydrogen bonding, including reverse wobble hydrogen bonding, refers to a pairing between two nucleotides in RNA molecules that does not follow Watson-Crick base pair rules. There are four major wobble base pairs; guanine:uracil, inosine (hypoxanthine): uracil, inosine-adenine, and inosine-cytosine. Rules for canonical hydrogen bonding and non-canonical hydrogen bonding are known to those of ordinary skill in the art (see, e.g. The RNA World, Third Edition (Cold Spring Harbor Monograph Series), R. F. Gesteland, Cold Spring Harbor Laboratory Press, ISBN 978-0879697396 (2005); The RNA World, Second Edition (Cold Spring Harbor Monograph Series), R. F. Gesteland, et al., Cold Spring Harbor Laboratory Press, ISBN 978-0879695613 (1999); The RNA World (Cold Spring Harbor Monograph Series), R. F. Gesteland, et al., Cold Spring Harbor Laboratory Press, ISBN 978-0879694562 (1993) (see, e.g., Appendix 1; Structures of Base Pairs Involving at Least Two Hydrogen Bonds, I. Tinoco); Principles of Nucleic Acid Structure, W. Saenger, Springer International Publishing AG, ISBN 978-0-387-90761-1 (1988); Principles of Nucleic Acid Structure, First Edition, S. Neidle, Academic Press, ISBN 978-01236950791 (2007)).

"Connect," "connected," and "connecting" are used interchangeably herein, and refer to covalent bond or a non-covalent bond between two macromolecules (e.g., polynucleotides, proteins, and the like). Thus, CasM and a cognate nucleic acid guide are "connected" in a cognate nucleic acid guide/CasM complex.

As used herein, the terms "nucleic acid," "nucleic acid sequence," "nucleotide sequence," "oligonucleotide," and "polynucleotide" are interchangeable and refer to a polymeric form of nucleotides. The nucleotides may be deoxyribonucleotides (DNA), ribonucleotides (RNA), analogs thereof, or combinations thereof, and may be of any length. Polynucleotides may perform any function and may have any secondary and tertiary structures. The terms encompass known analogs of natural nucleotides and nucleotides that are modified in the base, sugar and/or phosphate moieties. Analogs of a particular nucleotide have the same base-pairing specificity (e.g., an analog of A base pairs with T). A polynucleotide may comprise one modified nucleotide or multiple modified nucleotides. Examples of modified nucleotides include fluorinated nucleotides, methylated nucleotides, and nucleotide analogs. Nucleotide structure may be modified before or after a polymer is assembled. Following polymerization, polynucleotides may be additionally modified via, for example, conjugation with a labeling component or target binding component. A nucleotide sequence may incorporate non-nucleotide components. The terms also encompass nucleic acids comprising modified backbone residues or linkages, which are synthetic, naturally occurring, and non-naturally occurring, and have similar binding properties as a reference polynucleotide (e.g., DNA or RNA). Examples of such analogs include, but are not limited to, phosphorothioates, phosphoramidates, methyl phosphonates, chiral-methyl phosphonates, 2-O-methyl ribonucleotides, peptide-nucleic acids (PNAs), Locked Nucleic Acid (LNA™) (Exigon, Inc., Woburn, MA) nucleosides, glycol nucleic acid, bridged nucleic acids, and morpholino structures.

Peptide-nucleic acids (PNAs) are synthetic homologs of nucleic acids wherein the polynucleotide phosphate-sugar backbone is replaced by a flexible pseudo-peptide polymer, Nucleobases are linked to the polymer. PNAs have the capacity to hybridize with high affinity and specificity to complementary sequences of RNA and DNA.

In phosphorothioate nucleic acids, the phosphorothioate (PS) bond substitutes a sulfur atom for a non-bridging oxygen in the polynucleotide phosphate backbone. This modification makes the internucleotide linkage resistant to nuclease degradation, in some embodiments, phosphorothioate bonds are introduced between the last 3 to 5 nucleotides at the 5'-end or 3'-end sequences of a polynucleotide sequence to inhibit exonuclease degradation. Placement of phosphorothioate bonds throughout an entire oligonucleotide helps reduce degradation by nucleases as well.

Threose nucleic acid (TNA) is an artificial genetic polymer. The backbone structure of TNA comprises repeating threose sugars linked by phosphodiester bonds. TNA polymers are resistant to nuclease degradation. TNA can self-assemble by base-pair hydrogen bonding into duplex structures.

Linkage inversions can be introduced into polynucleotides through use of "reversed phosphoramidites" (see, e.g., ucalgary.ca/dnalab/synthesis/-modifications/linkages). A 3'-3' linkage at a terminus of a polynucleotide stabilizes the polynucleotide to exonuclease degradation by creating an oligonucleotide having two 5'-OH termini but lacking a 3'-OH terminus. Typically, such polynucleotides have phosphoramidite groups on the 5'-OH position and a dimethoxytrityl (DMT) protecting group on the 3'-OH position. Normally, the DMT protecting group is on the 5"-OH and the phosphoramidite is on the 3"-OH.

Polynucleotide sequences are displayed herein in the conventional 5' to 3' orientation unless otherwise indicated.

As used herein, the term "complementarity" refers to the ability of a nucleic acid sequence to form hydrogen bond(s) with another nucleic acid sequence (e.g., through traditional Watson-Crick base pairing). A percent complementarity indicates the percentage of residues in a nucleic acid molecule that can norm hydrogen bonds with a second nucleic acid sequence. When two polynucleotide sequences have 100% complementarity, the two sequences are perfectly complementary, i.e., all of a first polynucleotide's contiguous residues hydrogen bond with the same number of contiguous residues in a second polynucleotide.

As used herein, "binding" refers to a non-covalent interaction between macromolecules (e.g., between a protein and a polynucleotide, between a polynucleotide and a polynucleotide, between a protein and a protein, and the like). Such non-covalent interaction is also referred to as "associating" or "interacting" (e.g., if a first macromolecule interacts with a second macromolecule, the first macromolecule binds to second macromolecule in a noncovalent manner). Some portions of a binding interaction may be sequence-specific (the terms "sequence-specific binding," "sequence-specifically bind," "site-specific binding," and "site specifically binds" are used interchangeably herein). Sequence-specific binding, as used herein, typically refers to one or more cognate nucleic acid guides (i.e., NATNAs) capable of forming a complex with a protein (e.g., a CasM protein) to cause the protein to bind a nucleic acid sequence (e.g, RNA or DNA sequence) comprising a nucleic acid target sequence (e.g., a RNA or DNA target sequence) preferentially relative to a second nucleic acid sequence (e.g., a second RNA or DNA sequence) without the nucleic acid target binding sequence (e.g., the RNA or DNA target binding sequence). All components of a binding interaction do not need to be sequence-specific, such as contacts of a protein with phosphate residues in a DNA backbone. Binding interactions can be characterized by a dissociation constant (Kd). "Binding affinity" refers to the strength of the binding interaction. An increased binding affinity is correlated with a lower Kd.

As used herein, a Cas protein (e.g., a CasM protein) is said to "target" a polynucleotide if a cognate nucleic acid/Cas protein nucleoprotein complex associates with, binds and/or cleaves a polynucleotide at the nucleic acid target sequence within the polynucleotide.

As used herein, "single-strand break" (SSB) refers to cleavage of a single strand of RNA or DNA. A "double-strand break" (DSB) refers to both strands of a double-stranded segment of nucleic acid being severed. In some instances, if such a break occurs, one strand can be said to have a "sticky end" wherein nucleotides are exposed and not hydrogen bonded to nucleotides on the other strand. In other instances, a "blunt end" can occur wherein both strands remain fully base paired with each other.

As used herein, the term "recombination" refers to a process of exChange of genetic information between two polynucleotides.

As used herein, "nucleic acid repair," such as but not limited to DNA repair, encompasses any process whereby cellular machinery repairs damage to a nucleic acid molecule contained in the cell. The damage repaired can include single-strand breaks or double-strand breaks (DSBs). At least three mechanisms exist to repair DSBs: homology-directed repair (HDR), classical non-homologous end joining (c-NHEJ), and micro homology-mediated end joining (MMEJ), all defined below. "Nucleic acid repair" is also used herein to refer to nucleic acid repair resulting from human manipulation, wherein a target locus is modified, e.g., by inserting, deleting, or substituting nucleotides, all of which represent forms of genome editing.

As used herein, the term "homology-directed repair" or "HDR" refers to nucleic acid repair that takes place in cells, for example, during repair of double-strand and single-strand breaks in a nucleic acid molecule, such as DNA. HDR requires, nucleotide sequence homology and uses a "donor template" (donor template nucleic acid, such as DNA, polynucleotide donor, or oligonucleotide (used interchangeably herein) to repair the sequence where the double-strand break occurred (e.g., DNA target sequence). This results in the transfer of genetic information from, for example, the donor template DNA to the DNA target sequence. HDR may result in alteration of the nucleic acid target sequence (e.g., insertion, deletion, mutation) if the donor template sequence or oligonucleotide sequence differs from the target sequence and part or all of the donor template polynucleotide or oligonucleotide is incorporated into the target sequence. In some embodiments, an entire donor template polynucleotide, a portion of the donor template polynucleotide, or a copy of the donor polynucleotide is copied or integrated at the site of the target sequence.

By "donor polynucleotide" is meant a polynucleotide that can be directed to, and inserted into a target site of interest, such as an integration locus, to modify the target nucleic acid. All or a portion of the donor polynucleotide can be inserted into the target nucleic acid. The donor polynucleotide can be used for repair of the break in the target nucleic acid sequence resulting in the transfer of genetic information (i.e., polynucleotide sequences) from the donor at the site or in close proximity of the break. Accordingly, new genetic information (i.e., polynucleotide sequences) may be inserted or copied at a target site. The donor polynucleotide can be double- or single-strand RNA, DNA, a vector, plasmid, or the like. Thus, a donor polynucleotide can be an, insertion cassette, a recombinase expression vector, and the like. Non-symmetrical polynucleotide donors can also be used that are composed of two oligonucleotides. They are partially complementary, and each can include a flanking region of homology. The donor can be used to insert or replace polynucleotide sequences in a target sequence, for example, to introduce a polynucleotide that encodes a protein or functional RNA (e.g., siRNA), to introduce a protein tag, to modify a regulatory sequence of a gene, or to introduce a regulatory sequence to a gene (e.g. a promoter, an enhancer, an internal ribosome entry sequence, a start codon, a stop codon, a localization signal, or polyadenylation signal), to modify a nucleic acid sequence (e.g., introduce a mutation), and the like.

Targeted nucleic acid modifications using donor polynucleotides for large changes (e.g., more than 100 base pair (bp) insertions or deletions) traditionally use plasmid-based donor templates that contain homology arms flanking the site of alteration. Each arm can vary in length, but is typically longer than about 100 bp, such as 100-1500 bp, e.g., 100 . . . 200 . . . 300 . . . 400 . . . 500 . . . 600 . . . 700 . . . 800 . . . 900 . . . 1000 . . . 1500 by or any integer between these values. However, these numbers can vary, depending on the size of the donor polynucleotide and the target polynucleotide. This method can be used to generate large modifications, including insertion of reporter genes such as fluorescent proteins or antibiotic resistance markers. For transfection in cells, such as HEK cells, approximately 100-1000 nanograms (ng), 100 . . . 200 . . . 300 . . . 400 . . . 500 . . . 600 . . . 700 . . . 800 . . . 900 . . . 1000 ng or any integer between these values, of a typical size donor plasmid (e.g., approximately 5 kb) containing a NATNA/Cas vector, can be used for one well in 24-well plate. (See, e.g., Yang et al., "One Step Generation of Mice Carrying Reporter and Conditional Alleles by CRISPR/Cas-Mediated Genome Engineering" Cell (2013) 154:1370-1379).

Single-stranded and partially double-stranded oligonucleotides, such as DNA oligonucleotides, have been used in place of targeting plasmids for short modifications (e.g., less than 50 bp) within a defined locus without cloning. To achieve high HDR efficiencies, single-stranded oligonucleotides containing flanking sequences on each side that are homologous to the target region can be used, and can be oriented in either the sense or antisense direction relative to the target locus. The length of each arm can vary, but the length of at least one arm is typically longer than about 10 bases, such as from 10-150 bases, e.g., 10 . . . 20 . . . 30 . . . 40 . . . 50 . . . 60 . . . 70 . . . 80 . . . 90 . . . 100 . . . 110 . . . 120 . . . 130 . . . 140 . . . 150, or any integer within these ranges. However, these numbers can vary, depending on the size of the donor polynucleotide and the target polynucleotide. In some embodiments, the length of at least one arm is 10 bases or more. In other embodiments, the length of at least one arm is 20 bases or more. In yet other embodiments, the length of at least one arm is 30 bases or more. In some embodiments, the length of at least one arm is less than 100 bases. In further embodiments, the length of at least one arm is greater than 100 bases. In some embodiments, the length of at least one arm is zero bases. For single-stranded oligonucleotide design, typically an oligonucleotide with around 100-150 bp total homology is used. The mutation is introduced in the middle, giving 50-75 bp homology arms for a donor designed to be symmetrical about the target site. In other cases, no homology arms are required, and the donor polynucleotide is inserted using non-homologous repair mechanisms.

A "genomic region" is a segment of a chromosome in the genome of a host cell that is present on either side of the nucleic acid target sequence site or, alternatively, also includes a portion of the nucleic acid target sequence site. The homology arms of the donor polynucleotide have sufficient homology to undergo homologous recombination with the corresponding genomic regions. In some embodiments, the homology arms of the donor polynucleotide share significant sequence homology to the generic region immediately flanking the nucleic acid target sequence site; it is recognized that the homology arms can be designed to have sufficient homology to genomic regions farther from the nucleic acid target sequence site.

As used herein the terms "classical non-homologous end joining" or "c-NREJ" refer to the repair of double-strand breaks in DNA by direct ligation of one end of the break to the other end of the break without a requirement for a donor template DNA. NHEJ in the absence of a donor template DNA often results in small insertions or deletions of nucleotides at the site of the double-strand break, also referred to as "indels." This DNA repair pathway is genetically defined and requires the activity of Ligase IV, DNA-PKes, Polμ, Polλ, and the Ku70/80 heterodimer, among other proteins (see, e.g., Sfeir and Symington, *Trends Biochem Sci* (2015) 40:701-714).

"Microhomology-mediated end joining (MMEJ)," a form of alternative nonhomologous end-joining (alt-NHEJ), is another pathway for repairing double-strand breaks in DNA. MMEJ is associated with deletions flanking a DSB and involves alignment of microhomologous sequences internal to the broken ends before joining. The proposed mechanism entails 5'-3' resection of the DNA ends at a DSB, annealing of the microhomologies (1-16 nucleotides of homology), removal of heterologous flaps, gap filling DNA synthesis, and ligation. MMEJ is genetically defined and requires the activity of CtlP, PARP1, Polθ, Lig1 and Lig3, among other proteins (see, e.g., Sfeir and Symington, "Microhomology-Mediated End Joining: A Back-up Survival Mechanism or Dedicated Pathway?" Trends Biochem Sci (2015) 40:701-714).

Alternative mechanisms of nucleic acid insertion that do not require sequence homology between the donor and the target sequence can also be used for nucleic acid insertion. These mechanisms involve various components of the cellular repair machinery and it is to be understood that the scope of the invention is not bound by the use of any particular mechanism for insertion of nucleic acid after target nucleic acid is cut or nicked by a site-specific polynucleotide.

"Gene," as used herein, refers to a polynucleotide sequence comprising exon(s) and related regulatory sequences. A gene may further comprise intron(s) and/or untranslated region(s) (UTR(s)).

As used herein, "expression" refers to transcription of a polynucleotide from a DNA template, resulting in, for example, a messenger RNA (mRNA) or other RNA transcript (e.g., non-coding, such as structural or scaffolding RNAs). The term further refers to the process through which transcribed mRNA is translated into peptides, polypeptides, or proteins. Transcripts and encoded polypeptides may be referred to collectively as "gene product(s)." Expression may include splicing the mRNA in a eukaryotic cell, if the polynucleotide is derived from genomic DNA.

As used herein, the term "modulate" refers to a change in the quantity, degree or amount of a function. For example, a cognate nucleic acid guide/CasM protein complex, as disclosed herein, may modulate the activity of a promoter sequence by binding to a nucleic acid target sequence at or near the promoter. Depending on the action occurring after binding, the cognate nucleic acid guide/CasM protein complex can induce, enhance, suppress, or inhibit transcription of a gene operatively linked to the promoter sequence. Thus, "modulation" of gene expression includes both gene activation and gene repression.

Modulation can be assayed by determining any characteristic directly or indirectly affected by the expression of the target gene. Such characteristics include, e.g., changes in RNA or protein levels, protein activity, product levels, expression of the gene, or activity level of reporter genes. Accordingly, the terms "modulating expression," "inhibiting expression," and "activating expression" of a gene can refer to the ability of a cognate guide/CasM protein complex to change, activate, or inhibit transcription of a gene.

The terms "vector" and "plasmid" are used interchangeably and as used herein refer to a polynucleotide vehicle to introduce genetic material into a cell. Vectors can be linear or circular. Vectors can integrate into a target genome of a host cell or replicate independently in a host cell. Vectors can comprise, for example, an origin of replication, a multicloning site, and/or a selectable marker. An expression vector typically comprises an expression cassette. Vectors and plasmids include, but are not limited to, integrating vectors, prokaryotic plasmids, eukaryotic plasmids, plant synthetic chromosomes, episomes, viral vectors, cosmids, and artificial chromosomes. An expression vector typically comprises an expression cassette.

As used herein the term "expression cassette" is a polynucleotide construct, generated recombinantly or synthetically, comprising regulatory sequences operably linked to a selected polynucleotide to facilitate expression of the selected polynucleotide in a host cell. For example, the regulatory sequences can facilitate transcription of the selected polynucleotide in a host cell, or transcription and translation of the selected polynucleotide in a host cell. An expression cassette can, for example, be integrated in, the gnome of a host cell or be present in a vector to form an expression vector.

As used herein, a "targeting vector" is a recombinant DNA or RNA construct typically comprising tailored DNA or RNA arms, homologous to genomic DNA or RNA derived therefrom, that flank elements of a target gene or nucleic acid target sequence (e.g., a SSB or DSB). A targeting vector comprises a donor polynucleotide. Elements of the target sequence can be modified in a number of ways including deletions and/or insertions. A defective target gene can be replaced by a functional target gene, or in the alternative a functional gene can be knocked out. Optionally, the donor polynucleotide of a targeting vector comprises a selection cassette comprising a selectable marker that is introduced into the target gene. Targeting regions (i.e., nucleic acid target sequences) adjacent or within a target gene or region can be used to affect regulation of gene expression.

As used herein, the terms "regulatory sequences," "regulatory elements," and "control elements" are interchangeable and refer to polynucleotide sequences that are upstream (5' non-coding sequences), within, or downstream (3 non-translated sequences) of a polynucleotide target to be expressed. Regulatory sequences influence, for example, the timing of transcription, amount or level of transcription, RNA processing or stability, and/or translation of the related structural nucleotide sequence. Regulatory sequences may include activator binding sequences, enhancers, introns, polyadenylation recognition sequences, promoters, transcription start sites, repressor binding sequences, stem-loop structures, translational initiation sequences, internal ribosome entry sites (IRES), translation leader sequences, transcription termination sequences (e.g., polyadenylation signals and poly-U sequences), translation termination sequences, primer binding sites, and the like.

Regulatory elements include those that direct constitutive, inducible, and repressible expression of a nucleotide sequence in many types of host cells and those that direct expression of the nucleotide sequence only in certain host cells (e.g., tissue-specific regulatory sequences). In some embodiments, a vector comprises one or more pol III promoters, one or more pol II promoters, one or more pol I promoters, or combinations thereof. Examples of pol II promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer; see, e.g., Boshart, M., et al., Cell 41:521-530 (1985)), the SV40 promoter, the dihydrofolate reductase promoter, the β-actin promoter, the phosphoglycerol kinase (PGK) promoter, and the EF1α promoter. It will be appreciated by those skilled in the art that the design of an expression vector may depend on such factors as the choice of the host cell to be transformed, the level of expression desired, and the like. A vector can be introduced into host cells to thereby produce transcripts, proteins, or peptides, including fusion proteins or peptides, encoded by nucleic acids as described herein.

As used herein the term "operably linked" refers to polynucleotide sequences or amino acid sequences placed into a functional relationship with one another. For instance, a promoter or enhancer is operably linked to a coding sequence if it regulates, or contributes to the modulation of, the transcription of the coding sequence. Operably linked DNA sequences encoding regulatory sequences arc typically contiguous to the coding sequence. However, enhancers can function when separated from a promoter by up to several kilobases or more. Accordingly, some polynucleotide elements may be operably linked but not contiguous.

As used herein, the term "expression" refers to transcription of a polynucleotide from a DNA template, resulting in, for example, an mRNA or other RNA transcript (e.g., non-coding, such as structural or scaffolding RNAs). The term further refers to the process through which transcribed mRNA is translated into peptides, polypeptides, or proteins. Transcripts and encoded polypeptides may be referred to collectively as "gene product." Expression may include splicing the mRNA in a eukaryotic cell, if the polynucleotide is derived from genomic DNA.

As used herein, the term "sequence identity" generally refers to the percent identity of bases or amino acids determined by comparing a first polynucleotide or polypeptide to a second polynucleotide polypeptide using algorithms having various weighting parameters. Sequence identity between two polypeptides or two polynucleotides can be determined using sequence alignment by various methods and computer programs (e.g., BLAST, CS-BLAST, FASTA, HMMER, L-ALIGN, etc.), available through the worldwide web at sites including GENBANK (ncbi.nlm.nih.gov/genbank/) and EMBL-EBI (ebi.ac.uk.). Sequence identity between two polynucleotides or two polypeptide sequences is generally calculated using the standard default parameters of the various methods or computer programs. Generally, Cas proteins, such as CasM homologs, for use herein will have at least about 75% or more sequence identity to the wild-type or naturally occurring sequence of the Cas protein of interest, such as about 80%, such as about 85%, 90%, 91%, 92%, 93%, 94%, 95%, 96%, 97%, 98%, 99%, or complete identity. CasM orthologs can vary widely from the reference sequence. For example, CasM orthologs shown in Table 1 display approximately 13.59% to 99.82% sequence identity to each other. Thus, CasM orthologs are identified based on the CasM characteristics detailed herein.

As used herein, "hybridization," "hybridize," or "hybridizing" is the process of combining two complementary single-stranded DNA or RNA molecules so as to form a single double-stranded molecule (DNA/DNA, DNA/RNA, RNA/RNA) through hydrogen base pairing. Hybridization stringency is typically determined by the hybridization temperature and the salt concentration of the hybridization buffer; e.g., high temperature and low salt provide high stringency hybridization conditions. Examples of salt concentration ranges and temperature ranges for different hybridization conditions are as follows: high stringency, approximately 0.01M to approximately 0.05M salt, hybridization temperature 5° C. to 10° C. below $T_m$; moderate stringency, approximately 0.16M to approximately 0.33M salt, hybridization temperature 20° C. to 29° C. below $T_m$; and low stringency, approximately 0.33M to approximately 0.82M salt, hybridization temperature 40° C. to 48° C. below $T_m$. $T_m$ of duplex nucleic acids is calculated by standard methods well-known in the art (see, e.g., Maniatis, T., et al., Molecular Cloning; A Laboratory Manual, Cold Spring Harbor Laboratory Press: New York (1982); Casey, J., et al., Nucleic Acids Research 4:1539-1552 (1977); Bodkin, D. K., et al., Journal of Virological Methods 10(1): 45-52 (1985); Wallace, R. B., et al., Nucleic Acids Research 9(4):879-894 (1981)). Algorithm prediction tools to estimate $T_m$ are also widely available. High stringency conditions for hybridization typically refer to conditions under which a polynucleotide complementary to a target sequence predominantly hybridizes with the target sequence, and substantially does not hybridize to non-target sequences. Typically, hybridization conditions are of moderate stringency, preferably high stringency.

As used herein, the term "amino acid" refers to natural and synthetic (unnatural) amino acids, including amino acid analogs, modified amino acids, peptidomimetics, glycine, and D or L optical isomers.

As used herein, the terms "peptide," "polypeptide," and "protein" are interchangeable and refer to polymers of amino acids. A polypeptide may be of any length. It may be branched or linear, it may be interrupted by non-amino acids, and it may comprise modified amino acids. The terms may be used to refer to an amino acid polymer that has been modified through, for example, acetylation, disulfide bond formation, glycosylation, lipidation, phosphorylation, cross-linking, and/or conjugation (e.g., with a labeling component or ligand). Polypeptide sequences are displayed herein in the conventional N-terminal to C-terminal orientation.

Polypeptides and polynucleotides can be made using routine techniques in the field of molecular biology (see, e.g., standard texts set forth above). Further, essentially any polypeptide or polynucleotide can be custom ordered from commercial sources.

The terms "fusion protein" and "chimeric protein," as used herein, refer to a single protein created by joining two or more proteins, protein domains, or protein fragments that do not naturally occur together in a single protein. For example, a fusion protein can contain a first domain from a CasM protein and a second domain from a different Cas protein. The modification to include such domains in fusion proteins may confer additional activity on the modified site-directed polypeptides. Such activities can include nuclease activity, methyltransferase activity, demethylase activity, DNA or RNA repair activity, DNA or RNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity) that modifies a polypeptide associated with nucleic acid target sequence (e.g., a histone) A fusion protein can also comprise epitope tags (e.g., histidine tags, FLAG® (Sigma Aldrich, St. Louis, MO) tags, Myc tags), reporter protein sequences (e.g., glutathione-S-transferase, beta-galactosidase, luciferase, green fluorescent protein, cyan fluorescent protein, yellow fluorescent protein), and/or nucleic acid binding domains (e.g., a DNA binding domain, an RNA binding domain). A fusion protein can also comprise activator domains (e.g., heat shock transcription factors, NFKB activators) or repressor domains (e.g., a KRAB domain). As described by Lupo, A. et al., Current Genomics 14(4): 268-278 (2013), the KRAB domain is a potent transcriptional repression module and is located in the amino-terminal sequence of most C2H2 zinc finger proteins (see, e.g., Margolin, J., et al., Proceedings of the National Academy of Sciences of the United States of America 91:4509-4513 (1994); Witzgall, R., et al., Proceedings of the National Academy of Sciences of the United States of America 91:4514-4518 (1994)). The KRAB domain typically binds to co-repressor proteins and/or transcription factors via protein-protein interactions, causing transcriptional repression of genes to which KRAB zinc finger proteins (KRAB-ZFPs) bind (see, e.g., Friedman J. R., et al., Genes & Development 10:2067-2678 (1996)). In some embodiments, linker nucleic acid sequences are used to join the two or more proteins, protein domains, or protein fragments.

A "moiety," as used herein, refers to a portion of a molecule. A moiety can be a functional group or describe a portion of a molecule with multiple functional groups (e.g., that share common structural aspects). The terms "moiety" and "functional group" are typically used interchangeably; however, a "functional group" can more specifically refer to a portion of a molecule that comprises some common chemical behavior. "Moiety" is often used as a structural description. In some embodiments, a 5' terminus, a 3' terminus, or a 5' terminus and a 3' terminus (e.g., a non-native 5' terminus and/or a non-native 3' terminus in a first stem element) can comprise one or more moieties.

As used herein, the term "isolated" can refer to a nucleic acid or polypeptide that, by the hand of a human, exists apart from its native environment and is therefore not a product of nature. Isolated means substantially pure. An isolated nucleic acid or polypeptide can exist in a purified form and/or can exist in a non-native environment such as, for example, in a recombinant cell.

As used herein, a "host cell" generally refers to a biological cell. A cell is the basic structural, functional and/or biological unit of an organism. A cell can originate from any organism having one or more cells. Examples of host cells include, but are not limited to: a prokaryotic cell, eukaryotic cell, a bacterial cell, an archaeal cell, a cell of a single-cell eukaryotic organism, a protozoal cell, a cell from a plant (e.g., cells from plant crops (such as soy, tomatoes, sugar beets, pumpkin, bay, cannabis, tobacco, plantains, yams, sweet potatoes, cassava, potatoes, wheat, sorghum, soybean, rice, corn, maize, oil-producing Brassica (e.g., oil-producing rapeseed and canola), cotton, sugar cane, sunflower, millet, and alfalfa), fruits, vegetables, grains, seeds, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens C. agardh*, and the like), seaweeds (e.g., kelp), a fungal cell (e.g., a yeast cell or a cell from a mushroom), an animal cell, a cell from an invertebrate animal (e.g., fruit fly, cnidarian, echinoderm, nematode, and the like), a cell from a vertebrate animal (e.g., fish, amphibian, reptile, bird, or mammal), a cell from a mammal (e.g., a pig, a cow, a goat, a sheep, a rodent, a rat, a mouse, a non-human primate, a human, and the like). Furthermore, a cell can be a stem cell or a progenitor cell.

As used herein, "stem cell" refers to a cell that has the capacity for self-renewal, i.e., the ability to go through numerous cycles of cell division while maintaining the undifferentiated state. Stem cells can be totipotent, pluripotent, multipotent, oligopotent, or unipotent. Stem cells can be embryonic, fetal, amniotic, adult, or induced pluripotent stem cells.

As used herein, "induced pluripotent stem cells" refers to a type of pluripotent stem cell that is artificially derived from a non-pluripotent cell, typically an adult somatic cell, by inducing expression of specific genes.

"Plant," as used herein, refers to whole plants, plant organs, plant tissues, germplasm, seeds, plant cells, and progeny of the same. Plant cells include, without limitation, cells from seeds, suspension cultures, embryos, meristematic regions, callus tissue, leaves, roots, shoots, gametophytes, sporophytes, pollen, and microspores. Plant parts include differentiated and undifferentiated tissues including, but not limited to roots, stems, shoots, leaves, pollens, seeds, tumor tissue, and various forms of cells and culture (e.g., single cells, protoplasts, embryos, and callus tissue). The plant tissue may be in plant or in a plant organ, tissue or cell culture, "Plant organ" refers to plant tissue or a group of tissues that constitute a morphologically and functionally distinct part of a plant.

"Subject," as used herein, refers to any member of the phylum Chordata, including, without limitation, humans and other primates; including non-human primates such as rhesus macaques, chimpanzees and other monkey and ape species; farm animals, such as cattle, sheep, pigs, goats, and horses; domestic mammals, such as dogs and cats; laboratory animals, including rabbits, mice, rats, and guinea pigs; birds, including domestic, wild, and game birds, such as chickens, turkeys, and other gallinaceous birds, ducks, and geese; and the like. The term does not denote a particular age or gender. Thus, the term includes adult, young, and newborn individuals as well as male and female. In some embodiments, a host cell is derived, from a subject (e.g., stem cells, progenitor cells, or tissue-specific cells). In some embodiments, the subject is a non-human subject.

As used herein, "transgenic organism" refers to an organism whose genome is genetically modified. The term includes, the progeny (any generation) of a transgenic organism, provided that the progeny has the genetic modification.

CRISPR Systems

The CRISPR (Clustered Regularly Interspaced Short Palindromic Repeats) genomic locus is found in the genomes of many prokaryotes (e.g., bacteria and archaea). CRISPR loci provide resistance to foreign invaders (e.g., virus, phage) in prokaryotes. In this way, the CRISPR system functions as a type of immune system to help defend prokaryotes against foreign invaders. There are three main stages in CRISPR-Cas immune systems; (1) acquisition, (2) expression, and (3) interference. Acquisition involves cleaving the genome of invading viruses and plasmids and integrating segments (termed protospacers) of the genomic DNA into the CRISPR locus of the host organism. The segments that are integrated into the host genome are known as spacers, which mediate protection from subsequent attack by the same (or sufficiently related) virus or plasmid. Expression involves transcription of the CRISPR locus and subsequent enzymatic processing to produce short mature CRISPR RNAs, each containing a single spacer sequence. Interference is induced after the CRISPR RNAs associate with Cas proteins to form of complexes, which are then targeted to complementary protospacers in foreign genetic elements to induce nucleic acid degradation.

Currently, two classes of CRISPR systems have been described, Class 1 and Class 2, based upon the genes encoding the effector module, i.e., the proteins involved in the interference stage. Class 1 systems have a multi-subunit crRNA-effector complex, whereas Class 2 systems have a single protein, such as Cas9, Cpf1, C2c1, C2c2, C2c3, or a crRNA-effector complex. Class 1 systems comprise Type I, Type III and Type IV systems, Class 2 systems comprise Type II, Type V and Type VI systems.

To date, there are six types (Types I-VI) and 19 subtypes of CRISPR systems categorized within these classes (Makarova et al, *Nature Reviews Microbiology* (2015) 13:1-15; Shmakov et al., *Nature Reviews Microbiology* (201) 15:169-182).

CRISPR loci are currently characterized as including a number of short repeating sequences referred to as "repeats." Repeats can form hairpin structures and/or repeats can be unstructured single-stranded sequences. The repeats occur clusters. Repeats frequently diverge between species. Repeats are regularly interspaced with unique intervening sequences, referred to as "spacers," resulting in a repeat-spacer-repeat locus architecture. Spacers are identical to or are homologous with known foreign invader sequences. In some instances, a spacer-repeat unit encodes a crisprRNA (crRNA). A crRNA refers to the mature form of the spacer-repeat unit. A crRNA contains a spacer sequence that is involved in targeting a target nucleic acid (e.g., possibly as a surveillance mechanism against foreign nucleic acid). Thus, crRNA has a region of complementarity to a potential DNA or RNA target sequence and in some cases, e.g., in currently characterized Type II systems, a second region that forms base-pair hydrogen bonds with a transactivating CRISPR RNA (tracrRNA) to form a secondary structure, typically to form at least a stem structure. In this context, the tracrRNA and a crRNA interact through a number of base-pair hydrogen bonds to form secondary RNA structures. Complex formation between tracrRNA/crRNA and a Cas protein results in conformational change of the Cas protein that facilitates binding to DNA, nuclease activities of the Cas protein, and crRNA-guided site-specific DNA cleavage by the nuclease. For a Cas protein/tracrRNA/crRNA complex to cleave a DNA target sequence, the DNA target sequence is adjacent to a cognate protospacer adjacent motif (PAM).

A CRISPR locus comprises polynucleotide sequences encoding for CRISPR Associated Genes (cas) genes. Cas genes are involved in the biogenesis and/or the interference stages of crRNA function. Cas genes display extreme sequence (e.g., primary sequence) divergence between species and homologs. Some Cas genes comprise homologous secondary and/or tertiary structures. Cas genes are typically named according to the organism from which they are derived. For example, Cas genes in *Staphylococcus epidermidis* can be referred to as Csm-type, Cas genes in *Streptococcus thermophilus* can be referred to as Csn-type, and Cas genes in *Pyrococcus furiosus* can be referred to as Cmr-type.

The integration stage of a CRISPR system refers to the ability of the CRISPR locus to integrate new spacers into the crRNA array upon being infected by a foreign invader. Acquisition of the foreign invader spacers can help confer immunity to subsequent attacks by the same foreign invader. Integration typically occurs at the leader end of the CRISPR locus. Cas proteins are involved in integration of new spacer sequences. Integration proceeds similarly for some types of CRISPR systems (e.g., Types I-III).

Mature crRNAs are processed from a longer polycistronic CRISPR, locus transcript pre-crRNA array). A pre-crRNA array comprises a plurality of crRNAs. The repeats in the pre-crRNA array are recognized by cas genes. Cas genes bind to the repeats and cleave the repeats. This action can liberate the plurality of crRNAs, crRNAs can be subjected to further events to produce the mature crRNA form such as trimming (e.g., with an exonuclease). A crRNA may comprise all, some, or none of the CRISPR repeat sequence.

Interference refers to the stage in the CRISPR system that is functionally responsible for combating, infection by a foreign invader. CRISPR interference follows a similar mechanism to RNA interference (RNAi: e.g., wherein a target RNA is targeted (e.g., hybridized) by a short interfering RNA (siRNA)), which results in target RNA degradation and/or destabilization. Currently characterized CRISPR systems perform interference of a target nucleic acid by coupling crRNAs and Cas genes, thereby forming CRISPR ribonucleoproteins (RNPs). crRNA of the RNP guides the RNP to foreign invader nucleic acid, (e.g., by recognizing the foreign invader nucleic acid through hybridization). Hybridized target foreign invader nucleic acid-crRNA units are subjected to cleavage by Cas proteins. Target nucleic acid interference typically requires a protospacer adjacent motif (PAM) in a target nucleic acid.

By a "CRISPR-Cas system" as used herein, is meant any of the various CRISPR-Cas classes, types, and subtypes. Class I systems comprise Type I, Type III, and Type IV systems. Type I systems are currently characterized as having a Cas3 protein that has helicase activity and cleavage activity. Type I systems are further divided into several subtypes that have a defined combination of signature genes and distinct features of operon organization.

To date, it appears that all Type III systems possess a cas10 gene, which encodes a multidomain protein containing a Palm domain (a variant of the RNA recognition motif (RRM)) that is homologous to the core domain of numerous nucleic acid polymerases and cyclases and that is the largest subunit of Type III crRNA-effector complexes. All Type III loci also encode the small subunit protein, one Cas5 protein and typically several Cas7 proteins. Type III is also further divided into several subtypes.

Type IV systems encode a minimal multisubunit crRNA-effector complex comprising a partially degraded large subunit, Csf1, Cas5, Cas7, and in some cases, a putative small subunit Type IV systems lack cas1 and cas2 genes. Type IV systems do not have subtypes, but there are two distinct variants. One Type IV variant has a DinG family helicase, whereas a second Type IV variant lacks a Dine; family her ease, but has a gene encoding a small α-helical protein. An example of an organism with a Type IV system is *Acidithiobacillus ferrooxidans.*

Class 2 systems comprise Type II, Type V, and Type VI systems. Type II systems include cas1, cas2 and cas9 genes. There are two strands of RNA in Type II systems, a crRNA and a tracrRNA, that hybridizes to a complementary region of pre-crRNA causing maturation of the pre-crRNA to crRNA. The duplex formed by the tract-RNA and crRNA is recognized by, and associates with a multidomain protein, Cas9, encoded by the cas9 gene, which combines the functions of the crRNA-effector complex with target DNA cleavage. Cas9 is directed to a target nucleic acid by a sequence of the crRNA, that is complementary to, and hybridizes with, a sequence in the target nucleic acid.

In Type V systems, nucleic acid target sequence binding involves a Cas12a protein and the crRNA, as does the nucleic acid target sequence cleavage. In Type V systems, the RuvC-like nuclease domain of Cas12a protein cleaves both strands of the nucleic acid target sequence in a sequential fashion (Swarts, et al., *Mol. Cell* (2017) 66:221-233.e4), producing 5' overhangs, which contrasts with the blunt ends generated by Cas9 protein cleavage.

The Cas12a protein cleavage activity of Type V systems does not require hybridization of crRNA to tracrRNA to form a duplex; rather Type V systems use a single crRNA that has a stem-loop structure forming an internal duplex. Cas12a protein binds the crRNA in a sequence- and structure-specific manner by recognizing the stem loop and sequences adjacent to the stem loop, most notably the nucleotides 5' of the spacer sequence, which hybridizes to the nucleic acid target sequence. This stem-loop structure is typically in the range of 15 to 19 nucleotides in length. Substitutions that disrupt this stem-loop duplex abolish cleavage activity, whereas other substitutions that do not disrupt the stem-loop duplex do not abolish cleavage activity.

Type VI systems include the Cas13a protein (also known as Class 2 candidate 2 protein, or C2c2) which does not share sequence similarity with other CRISPR effector proteins (see Abudayyeh, et al *Science* (2016) 353:aaf5573). Cas 13a proteins have two HEPN domains and possess single-stranded RNA cleavage activity. Cas13a proteins are similar to Cas12a proteins in requiring a crRNA for nucleic acid target sequence binding and cleavage, but not requiring tracrRNA. Also, similar to Cas12a protein, the crRNA for Cas13a proteins forms a stable hairpin, or stem-loop structure, that aids in association with the Cas 13a protein. Type VI systems have a single polypeptide RNA endonuclease that utilizes a single crRNA to direct RNA cleavage in a target-dependent fashion. Additionally, after hybridizing to the target RNA complementary to the spacer, Cas13a protein becomes a promiscuous RNA endonuclease exhibiting non-specific endonuclease activity toward any single-stranded RNA in a sequence independent manner (see East-Seletsky, et al., *Nature* (2016) 538:270-273).

As is readily apparent, the discovery and characterization of CRISPR systems is currently evolving.

Production of CRISPR Components

In all of the embodiments described herein, the various components can be produced by synthesis, or for example, using expression cassettes encoding CasM, a cognate guide, etc. The various components can be provided to a cell or used in vitro. These components can be present on a single cassette or multiple cassettes, in the same or different constructs. Expression cassettes typically comprise regulatory sequences functional in host cells into which they are introduced. Regulatory sequences are involved in one or more of the following: regulation of transcription, post-transcriptional regulation, and regulation of translation. Expression cassettes can be present in expression vectors and introduced into a wide variety of host cells including bacterial cells, yeast cells, plant cells, and mammalian cells.

In one aspect, all or a portion of the various components for use herein are produced in vectors, including expression vectors, comprising polynucleotides encoding therefor. Vectors useful for producing components for use in the present methods include plasmids, viruses (including phage), and integratable nucleic acid fragments (i.e., fragments integratable into the host genome by homologous recombination). A vector replicates and functions independently of the host genome, or may, in some instances, integrate into the genome itself. Suitable replicating vectors will contain a replicon and control sequences derived from species compatible with the intended expression host cell. In some embodiments, polynucleotides encoding one or more of the various components are operably linked to an inducible promoter, a repressible promoter, or a constitutive promoter. Expression vectors can also include polynucleotides encoding protein tags (e.g., poly-His tags, hemagglutinin tags, fluorescent protein tags, bioluminescent tags, nuclear localization tags). The coding sequences for such protein tags can be fused to the coding sequences or can be included in an expression cassette, for example, in a targeting vector.

General methods for construction of expression vectors are known in the art. Expression vectors for most host cells are commercially available. There are several commercial software products designed to facilitate selection of appropriate vectors and construction thereof, such as insect cell vectors for insect cell transformation and gene expression in insect cells, bacterial plasmids for bacterial transformation and gene expression in bacterial cells, yeast plasmids for cell transformation and gene expression in yeast and other fungi, mammalian vectors for mammalian cell transformation and gene expression in mammalian cells or mammals, viral vectors (including retroviral, lentiviral, and adenoviral vectors) for cell transformation and gene expression and methods to easily enable cloning of such polynucleotides. SnapGene™ (GSL Biotech LLC, Chicago, Ill.; snapgene.com/resources/plasmid_files/your_time_is_valuable/), for example, provides an extensive list of vectors, individual vector sequences, and vector maps, as well as commercial sources for many of the vectors.

Several expression vectors have been designed for expressing guide polynucleotides. See, e.g., Shen et al. *Nat. Methods* (2014) 11:399-402. Additionally, vectors and expression systems are commercially available, such as from New England Biolabs (Ipswich, MA) and Clontech Laboratories (Mountain View, CA). Vectors can be designed to simultaneously express a target-specific NATNA using a U2 or U6 promoter, a CasM and/or dCasM, and if desired, a marker protein, for monitoring transfection efficiency and/or for further enriching/isolating transfected cells by flow cytometry.

For example, the various components can be incorporated into mammalian vectors for use in mammalian cells. A large number of mammalian vectors suitable for use with the systems of the present invention are commercially available (e.g., from Life Technologies, Grand Island, NY; NeoBiolab, Cambridge, MA; Promega, Madison, Wisc.; DNA20, Menlo Park, CA; Addgene, Cambridge, MA).

Vectors derived from mammalian viruses can also be used for expressing the various components of the present methods in mammalian cells. These include vectors derived from viruses such as adenovirus papovirus, herpesvirus, polyomavirus, cytomegalovirus, lentivirus, retrovirus, vaccinia and Simian Virus 40 (SV40) (see, e.g., Kaufman, R. J., *Molec. Biotech*. (2000) 16:151-160; Cooray et al., *Methods Enzymol*. (2012) 507:29-57). Regulatory sequences operably linked to the components can include activator binding sequences, enhancers, introns, polyadenylation recognition sequences, promoters, repressor binding sequences, stem-loop structures, translational initiation sequences, translation leader sequences, transcription termination sequences, translation termination sequences, primer binding sites, and the like. Commonly used promoters are constitutive mammalian promoters CMV, EF1a, SV40, PGK1 (mouse or human), Ubc, CAG, CaMKIIa, and beta-Act, and others known in the art (Khan, K. H. *Advanced Pharmaceutical Bulletin* (2013) 3:257-263). Furthermore, mammalian RNA polymerase III promoters, including H1 and U6, can be used.

Numerous mammalian cell lines have been utilized for expression of gene products including HEK 293 (Human embryonic kidney) and CHO (Chinese hamster ovary). These cell lines can be transfected by standard methods (e.g., using calcium phosphate or polyethyleneimine (PEI), or electroporation). Other typical mammalian cell lines include, but are not limited to: HeLa, U2OS, 549, HT1080, CAD, P19, NIH 3T3, L929, N2a, Human embryonic kidney 293 cells, MCF-7, Y79, SO-Rb50, Hep G2, DUKX-X11, J558L; and Baby hamster kidney (BHK) cells.

Vectors can be introduced into and propagated in a prokaryote, prokaryotic vectors are well known in the art. Typically a prokaryotic vector comprises an origin of replication suitable for the target host cell (e.g., oriC derived from *E. coli*, pUC derived from pBR322, pSC101 derived from *Salmonella*), 15A origin (derived from p15A) and bacterial artificial chromosomes). Vectors can include a selectable marker (e.g., genes encoding resistance for ampicillin, chlora.mphenicol, gentamicin, and kanamycin). Zeocin™ (Life Technologies, Grand Island, NY) can be used as a selection in bacteria, fungi (including yeast), plants and mammalian cell lines. Accordingly, vectors can be designed that carry only one drug resistance gene for Zeocin for selection work in a number of organisms. Useful promoters are known for expression of proteins in prokaryotes, for example, T5, T7, Rhamnose (inducible), Arabinose (inducible), and PhoA (inducible). Furthermore, T7 promoters are widely used in vectors that also encode the T7 RNA polymerase. Prokaryotic vectors can also include ribosome binding sites of varying strength, and secretion signals (e.g., mal, sec, tat, ompC, and pelB). In addition, vectors can comprise RNA polymerase promoters for the expression of NATNAs. Prokaryotic RNA polymerase transcription termination sequences are also well known (e.g., transcription termination sequences from *Streptococcus pyogenes*).

Expression of proteins in prokaryotes is typically carried out in *E. coli* with vectors containing constitutive or inducible promoters directing the expression of either fusion or non-fusion proteins.

In some embodiments, a vector is a yeast expression vector comprising one or more components of the above-described methods. Examples of vectors for expression in *Saccharomyces cerivisae* include, but are not limited to, the following: pYepSec1, pMFa, pJRY88, pYES2, and picZ. Methods for gene expression in yeast cells are known in the art (see, e.g., Methods in Enzymology, Volume 194, "Guide to Yeast Genetics and Molecular and Cell Biology, Part A," (2004) Christine Guthrie and Gerald R. Fink (eds.), Elsevier Academic Press, San Diego, CA). Typically, expression of protein-encoding genes in yeast requires a promoter operably linked to a coding region of interest plus a transcriptional terminator. Various yeast promoters can be used to construct expression cassettes for expression of genes in yeast.

CasM Proteins

CasM, a new CRISPR-Cas protein, is described herein. CasM displays nucleic acid binding activity and produces breaks, such as singe-strand breaks (SSBs) or DSBs, when brought into proximity with a nucleic acid target sequence, e.g., by association with a cognate nucleic acid guide, such as a cognate crRNA. As shown in the Examples herein, CasM targets RNA and is capable of cleaving ssRNA, such as when delivered to a genomic target when complexed with a crRNA, without the necessity of association with a tracrRNA. CasM proteins typically include two or more higher eukaryotic and prokaryotic nucleotide-binding (EPN)) domains found in protein family PF05168, in the C-terminal region of the CasM sequence. CasM proteins show synteny with one or more WYL domain-containing proteins and sometimes with RtcB (RNA 3'-terminal phosphate cyclase, group B) domain-containing proteins. Based on the foregoing characteristics, CasM may be classified as a Class 2 Type VI CRISPR-Cas system. However, CasM has a very low degree of sequence similarity to other Type VI subtypes.

Exemplary CasM proteins are shown in SEQ ID NOS: 37-45, and are encoded by polynucleotides shown in SEQ ID NOS:28-36, respectively. These proteins display approximately 13.59% to 99.82% sequence identity to each other and show less than 8% sequence identity with other known CRISPR-Cas proteins. CasM has been found in several species and isolates including, without limitation, *Eubacterium siraeum; Ruminococcus* sp., such as from *Ruminococcus bicirculans; Ruminococcus flavefaciens*, such as, but not limited to, FD-1 and strain XPD3002; *Ruminococcus albus* such as, but not limited to, strain KH2T6*; Ruminococcus* sp. *isolates*, such as but not limited to, isolates 2789STDY5834971, 2789STDY5608892 and 2789STDY5834894. However, is it to be understood that the term "CasM" refers to a protein derived from any species, subspecies or strain of bacteria that encodes a CasM protein, as well as orthologs thereof, or variants thereof. Representative CasM proteins include, but are not limited to, those proteins depicted as SEQ ID NOS:37-45 (see Table 1), orthologs thereof, or variants thereof. CasM proteins are approximately 800 to approximately 1000 amino acids in length.

TABLE 1

Representative CasM Proteins

| Species/Isolate | SEQ ID NO |
|---|---|
| *Eubacterium siraeum* | SEQ ID NO: 37 |
| *Ruminococcus* sp., isolate 2789STDY5834971 | SEQ ID NO: 38 |
| *Ruminococcus bicirculans* | SEQ ID NO: 39 |
| *Ruminococcus* sp., isolate 2789STDY5608892 | SEQ ID NO: 40 |
| *Ruminococcus* sp. CAG:57 | SEQ ID NO: 41 |
| *Ruminococcus flavefaciens* FD-1 | SEQ ID NO: 42 |
| *Ruminococcus albus* strain KH2T6 | SEQ ID NO: 43 |
| *Ruminococcus flavefaciens* strain XPD3002 | SEQ ID NO: 44 |
| *Ruminococcus* sp., isolate 2789STDY5834894 | SEQ ID NO: 45 |

Analysis of these CasM protein sequences indicates the presence of two HEPN domains in the C-terminal region of the sequences. The HEPN domain is often involved in nucleic acid binding and can function as a metal-independent RNase in certain instances.

CasM systems display strong synteny with an open reading frame in WYL domain-(protein family PF13280) containing proteins. The sequences for WYL domains in various species that encode CasM proteins are shown as SEQ ID NOS:52-59 (see Table 2). WYL domains share similarities with CRISPR-associated Rossman fold (CARF) domains and are thought to bind ligands derived from host-virus conflict and regulate CRISPR-Cas systems. A WYL domain protein (s117009) has been shown to be a negative regulator of the I-D CRISPR-Cas system in *Synechocystis* sp. (Hein et al., *RNA Biol.* (2013) 10: 852-864. In some instances, the WYL-containing protein contains at least two WYL domains. These duplications are consistent with the hypothesized multimeric assembly of these ligand-binding domains (Schumacher et al., *EMBO J.* (2002) 21:1210-4218). The N-termini of these WYL domains contain homology to transcriptional repressor CopG and the ParD anti-toxin domain. For use in eukaryotes, the WYL domain-containing proteins can be modified with a N- or C-terminal nuclear localization signal sequence (NLS). SEQ ID NOS:61-68 present exemplary WYL domain-containing proteins modified with a seven amino acid C-terminal NLS tag derived from the SV40 Large T-antigen.

TABLE 2

WYL domain sequences in various CasM-containing species

| Species/Isolate | SEQ ID NO |
|---|---|
| *Eubacterium siraeum* | SEQ ID NO: 52 |
| *Ruminococcus* sp., isolate 2789STDY5834971 | SEQ ID NO: 53 |
| *Ruminococcus bicirculans* | SEQ ID NO: 54 |
| *Ruminococcus* sp., isolate 2789STDY5608892 | SEQ ID NO: 55 |
| *Ruminococcus* sp. CAG:57 | SEQ ID NO: 56 |
| *Ruminococcus flavefaciens* FD-1 | SEQ ID NO: 57 |
| *Ruminococcus albus* strain KH2T6 | SEQ ID NO: 58 |
| *Ruminococcus flavefaciens* strain XPD3002 | SEQ ID NO: 59 |

RtcB (RNA 3'-terminal phosphate cyclase, group B) is a protein domain superfamily and a RtcB homolog (SEQ ID NO. 60) proximal to the CasM loci has been identified. It has previously been reported that the CARF domain has sequence similarity with the N-terminal domain of the RtcR protein, which acts as the regulator of the Rtc RNA repair system. The Rtc system is comprised of the 3'-terminal phosphate cyclase RtcA and the RNA ligase RtcB. The RtcB domain-containing proteins can be modified with a N- or C-terminal NLS for use in eukaryotes. A RtcB domain with an associated NLS derived from the SV40 Large T-antigen is shown in SEQ ID NO:69.

A modified CasM protein can have a low degree of sequence identity, a moderate degree of sequence identity, or a high degree of sequence identity over its length to a reference CasM protein, depending on the intended function of the CasM in question. By a "high degree of sequence identity" is meant approximately 90% sequence identity to 100% sequence identity, for example, about 90% . . . 95% . . . 98% sequence identity or higher. A "moderate degree of sequence identity" is typically between about 80% sequence identity to about 85% sequence identity, for example, about 80% identity or higher, such as about 85% sequence identity. A "low degree of sequence identity" is typically between about 50% identity and 75% identity, for example, about 50% identity, preferably about 60% identity to about 75% identity.

In some embodiments, the amino acid sequence of the reference CasM protein may be modified by deletion, insertion, or substitution of one or more amino acid residues (either conservative or non-conservative in nature), such that the activity of the CasM protein is either largely retained, enhanced, or reduced. These modifications may be deliberate, as through site-directed mutagenesis, or may be accidental, such as through mutations of hosts that produce the proteins or errors due to PCR amplification.

Conservative substitutions are generally those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine axe sometimes classified as aromatic amino acids. It is reasonably predictable that an isolated replacement of Leucine with isoleucine or valine, an aspartate with a glutamate, a threonine with a serine, or a similar conservative replacement of an amino acid with a structurally related amino acid, will not have a major effect on the desired biological activity. For example, the CasM protein may include up to about 5-10 conservative or non-conservative amino acid substitutions, or even up to about 15-100 or more, e.g., 50 or more, conservative or non-conservative amino acid substitutions, or any number between 5-100, so long as the desired function of the molecule remains intact.

In other embodiments, it may be desirable to modify one or more catalytic domains in order to render a nuclease-deactivated CasM protein, also termed "catalytically inactive," "catalytically dead CasM," "dead CasM," or "dCasM," such that the protein either fails to produce nucleic acid breaks, and/or binds a target sequence but does not cleave it. Such molecules lack all or a portion of nuclease activity and are unable to cleave a nucleic acid of interest and can therefore be used to regulate genes in a nucleic acid-guided manner. These dCasM proteins can be used alone or in fusions to synthetically repress (CRISPRi) or activate (CRISPRa) gene expression.

The CasN1 proteins can either be directly isolated and purified from bacteria, or synthetically or recombinantly produced using polynucleotides encoding the same.

CasM Polynucleotides

Nucleic aid sequences encoding representative CasM proteins are shown in SEQ NOS:28-36 (see. Table 3) and these polynucleotides can be used to produce CasM proteins as described herein.

TABLE 3

Representative CasM DNA Sequences

| Species/Isolate | SEQ ID NO |
|---|---|
| *Eubacterium siraeum* | SEQ ID NO: 28 |
| *Ruminococcus* sp., isolate 2789STDY5834971 | SEQ ID NO: 29 |
| *Ruminococcus bicirculans* | SEQ ID NO: 30 |
| *Ruminococcus* sp., isolate 2789STDY5608892 | SEQ ID NO: 31 |
| *Ruminococcus* sp. CAG:57 | SEQ ID NO: 32 |
| *Ruminococcus flavefaciens* FD-1 | SEQ ID NO: 33 |
| *Ruminococcus albus* strain KH2T6 | SEQ ID NO: 34 |
| *Ruminococcus flavefaciens* strain XPD3002 | SEQ ID NO: 35 |
| *Ruminococcus* sp., isolate 2789STDY5834894 | SEQ ID NO: 36 |

These polynucleotides can be designed to encode native CasM proteins, such as the proteins depicted in SEQ ID NOS:37-45 (see Table 1); homologs thereof, including orthologs found in other species; or other variants thereof. Moreover, a casM polynucleotide sequence can be modified to have a low degree of sequence identity, a moderate degree of sequence identity, or a high degree of sequence identity, over its length to a reference casM polynucleotide, depending on the intended function of the encoded CasM in question. By "a high degree of sequence identity" is meant approximately 90% sequence identity to 100% sequence identity, for example, about 90% . . . 95% . . . 98% sequence identity or higher. A "moderate degree of sequence identity" is typically between about 80% sequence identity to about 85% sequence identity, for example, about 80% identity or higher, such as about 85% sequence identity. A "low degree of sequence identity" is typically between about 50% identity and 75% identity, for example, about 50% identity, preferably about 60% identity to about 75% identity.

In some embodiments, the polynucleotide sequences are modified to enhance expression in a selected host cell. Codon usage bias refers to differences in the frequency of occurrence of synonymous codons in coding DNA. For example, for the 20 standard amino acids in the genetic code, there are 64 different codons (61 codons encoding for amino acids, and 3 stop codons). The overabundance in the number of codons allows several amino acids to be encoded by more than one codon. The genetic codes of different organisms are often biased towards the usage of one of the several codons that encode a particular amino acid. Thus, a greater frequency of one codon will be found than expected by chance in particular organisms. Accordingly, in order to enhance expression in a particular host cell, it is often desirable to manipulate polynucleotides to include codons that are biased for expression in the selected host cell. Several software packages are available online for this, purpose. For example, a database from Integrated DNA Technologies, Coralville, IA (idtdna.com/CodonOpt), is a tool for producing modified sequences for expression in dozens of organisms. GeneScript, Piscataway, NJ, also provides modification tools through the OptimumGene™ algorithm (genscript.com/codon opt.html?src=google&gclid=CIX3uoqexdICFRSUfgodu3sA1Q). See also, U.S. Pat. No. 8,326,547, incorporated herein by reference in its entirety.

Typically, polynucleotide sequences modified for expression in particular host cells will display from about 50%-99% sequence identity to the native sequences, such as 60%-95%, e.g. 65% . . . 70% . . . 75% . . . 80% . . . 85% . . . 90% . . . 95% or more sequence identity, or any integer between these ranges, to the native sequences.

Using these tools, polynucleotide sequences can be modified for expression in any commonly used host cell, such as but not limited to, bacterial cells and eukaryotic cells, including without limitation, bacterial cells such as *E. coli, Lactococcus Pseudomonas* systems, *Streptomyces* systems, *Bacillus subtilis* systems, *Brevibacillus* systems, coryneform bacteria, and halophilic bacteria; algal cells; yeast and other fungal cells; plant cells; mammalian cells such as human cells; insect cells, and the like.

SEQ ID NOS:1-9 show representative CasM-encoding polynucleotide sequences modified for expression in *E. coli* cells (see Table 4). SEQ ID NOS:10-18 show representative CasM-encoding polynucleotide sequences modified for expression in human cells (see Table 5). SEQ ID NOS:19-27 show CasM-encoding polynucleotide sequences modified for expression in *Zea mays* cells (see Table 6).

TABLE 4

Representative casM DNA Sequences Modified for Expression in *E. coli*

| Species/Isolate | SEQ ID NO |
|---|---|
| *Eubacterium siraeum* | SEQ ID NO: 1 |
| *Ruminococcus* sp., isolate 2789STDY5834971 | SEQ ID NO: 2 |
| *Ruminococcus bicirculans* | SEQ ID NO: 3 |
| *Ruminococcus* sp., isolate 2789STDY5608892 | SEQ ID NO: 4 |
| *Ruminococcus* sp. CAG:57 | SEQ ID NO: 5 |
| *Ruminococcus flavefaciens* FD-1 | SEQ ID NO: 6 |
| *Ruminococcus albus* strain KH2T6 | SEQ ID NO: 7 |
| *Ruminococcus flavefaciens* strain XPD3002 | SEQ ID NO: 8 |
| *Ruminococcus* sp., isolate 2789STDY5834894 | SEQ ID NO: 9 |

TABLE 5

Representative casM DNA Sequences Modified for Expression in Human Cells

| Species/Isolate | SEQ ID NO |
|---|---|
| *Eubacterium siraeum* | SEQ ID NO: 10 |
| *Ruminococcus* sp., isolate 2789STDY5834971 | SEQ ID NO: 11 |
| *Ruminococcus bicirculans* | SEQ ID NO: 12 |
| *Ruminococcus* sp., isolate 2789STDY5608892 | SEQ ID NO: 13 |
| *Ruminococcus* sp. CAG:57 | SEQ ID NO: 14 |
| *Ruminococcus flavefaciens* FD-1 | SEQ ID NO: 15 |
| *Ruminucuccus albus* strain KH2T6 | SEQ ID NO: 16 |
| *Ruminococcus flavefaciens* strain XPD3002 | SEQ ID NO: 17 |
| *Ruminococcus* sp., isolate 2789STDY5834894 | SEQ ID NO: 18 |

TABLE 6

Representative casM DNA Sequences Modified for Expression in *Zea mays*

| Species/Isolate | SEQ ID NO |
|---|---|
| *Eubacterium siraeum* | SEQ ID NO: 19 |
| *Ruminococcus* sp., isolate 2789STDY5834971 | SEQ ID NO: 20 |
| *Ruminococcus bicirculans* | SEQ ID NO: 21 |
| *Ruminococcus* sp., isolate 2789STDY5608892 | SEQ ID NO: 22 |

TABLE 6-continued

| Representative casM DNA Sequences Modified for Expression in *Zea mays* | |
|---|---|
| Species/Isolate | SEQ ID NO |
| *Ruminococcus* sp. CAG:57 | SEQ ID NO: 23 |
| *Ruminococcus flavefaciens* FD-1 | SEQ ID NO: 24 |
| *Ruminococcus albus* strain KH2T6 | SEQ ID NO: 25 |
| *Ruminococcus flavefaciens* strain XPD3002 | SEQ ID NO: 26 |
| *Ruminococcus* sp., isolate 2789STDY5834894 | SEQ ID NO: 27 |

The casM polynucleotides can also be modified to include sequences encoding N- or C-terminal nuclear to localization signal sequences (NLS), such as for expression in eukaryotic cells. Such sequences are known, and include, without limitation, an NLS tag derived from the SV40 Large T-antigen. Such as tag is present at the C-terminus of the proteins shown in SEQ ID NOS:61-69 (i.e., the last seven amino acids in these sequences).

The casM polynucleotides can be used to recombinantly produce CasM proteins using methods well known in the art.

CasM Complexes

CasM proteins can be complexed to a cognate nucleic acid guide (cognate guide/CasM complex) in order to deliver CasM in proximity with a target nucleic acid sequence. A cognate guide, such as a crRNA, is a polynucleotide that site-specifically guides a CasM nuclease, or a deactivated CasM nuclease, to a target nucleic acid region. The binding specificity is determined jointly by the complementary region on the cognate guide and a short DNA motif (protospacer adjacent motif or PAM) juxtaposed to the complementary region. The spacer present in the guide specifically hybridizes to a target nucleic acid sequence and determines the location of a Cas protein's site-specific binding and nucleolytic cleavage.

Cognate guide/CasM complexes can be produced using methods well known in the art. For example, the guide components of the complexes can be produced in vitro and CasM components can be recombinantly produced and then the guides and CasM proteins can be complexed together using methods known in the art. Additionally, cell lines constitutively expressing CasM proteins can be developed and can be transfected with the guide components, and complexes can be purified from the cells using standard purification techniques, such as but not limited to affinity, ion exchange and size exclusion chromatography. See, e.g., Jinek M., et al., "A programmable dual-RNA-guided DNA endonuclease in adaptive bacterial immunity," Science (2012) 337:816-821.

Alternatively, the components, is the cognate guides and casM polynucleotides may be provided separately to a cell, e.g., using separate constructs, or together, in a single construct, or in any combination, and complexes can be purified as above.

Methods of designing particular guides, such as for use in the complexes, are known. See, e.g., Briner et al., "Guide RNA Functional Modules Direct Cas9 Activity and Orthogonality," Molecular Cell (2014) 56:333-339. To do so, the genomic sequence for the gene to be targeted is first identified. The exact region of the selected gene to target will depend on the specific application. For example, in order to activate or repress a target gene using, for example, Cas activators or repressors, cognate guide/CasM complexes can be targeted to the promoter driving expression of the gene of interest. For genetic knockouts, guides are commonly designed to target 5' constitutively expressed exons which reduces the chances or removal of the targeted region from mRNA due to alternative splicing. Exons near the N-terminus can be targeted because frameshift mutations here will increase the likelihood of the production of a nonfunctional protein product. Alternatively, cognate guides can be designed to target exons that code for known essential protein domains. In this regard, non-frameshift mutations such as insertions or deletions are more likely to alter protein function when they occur in protein domains that are essential for protein function. For gene editing using HDR, the target sequence should be close to the location of the desired edit. In this case, the location where the edit is desired is identified and a target sequence is selected nearby.

The guides can be delivered to a cell. If the cell constitutively expresses a CasM nuclease, the CasM nuclease will then be recruited to the target site to cleave the target nucleic acid. If the cell does not express a CasM nuclease, complexes of cognate guide/CasM can be delivered to the cells to make breaks in the genome, thereby triggering the repair pathways in the cells.

Treated cells are then screened using methods well known in the art, such as using high-throughput screening techniques including, but not limited to, fluorescence-activated cell sorting (FACS)-based screening platforms, microfluidics-based screening platforms, and the like. These techniques are well known in the art. See, e.g., Wojcik, et al., *Int. J. Molec. Sci.* (2015) 16:24918-24945. The cells can then be expanded and re-transfected with additional cognate guide/CasM complexes to introduce further diversity and this process can be repeated iteratively until a population with the desired properties is obtained. Single cell clones are sorted from the population, expanded and sequenced to recover the mutations that resulted in the desired function.

Applications of CasM

Due to its RNA-targeting abilities, CasM can be used to edit RNA and in some embodiments, to treat diseases caused by toxic RNA or improperly spliced RNA.

In some embodiments cognate guide/CasM complexes, such as, but not limited to crRNA/Cash complexes, are capable of sequence-specific ssRNA activity. Recognition and cleavage of an initial ssRNA complementary to the crRNA target sequence activates the CasM protein to carry out endonuclease activity toward any single-stranded RNA in a sequence-independent manner. The sequence-specific recognition of RNA of the crRNA/CasM complex facilitates the target knockdown of gene transcripts perturbing translation of a specific protein. The non-specific endonuclease activity of an activated crRNA/CasM complex in a cellular environment can result in cell death due to depletion of RNA encoding for essential gene transcripts. Thus, the specific RNA targeting and collateral endonuclease activity of an activated crRNA/CasM complex enables the sequence-specific selection of cells expressing a RNA transcript.

Thus, in further aspects, CasM complexes, such as, but not limited to crRNA/CasM complexes, can be used in methods of screening and killing cells, such as bacterial cells, that have not been modified by a DNA targeting nuclease (i.e., a Type II Cas9 nuclease). This method comprises contacting a NATNA/Cas9 complex to a locus of interest in a population of cells. Contacting the NATNA/Cas9 complex with the locus results in DNA cleavage and subsequent repair of the break by the endogenous cellular repair machine and the introduction of indels at the break site. The targeting of the NATNA/Cas9 complex to a targeted locus that encodes an RNA transcript results in indels in an RNA transcript sequence. This modified RNA transcript sequence is different compared to a transcript from an unmodified cell (a wild-type cell). A crRNA/CasM complex can then be targeted to the unmodified transcript, wherein crRNA/CasM recognition of the unmodified transcript results in activation of the sequence independent, single-stranded RNA targeting activity of the CasM protein and subsequent cell death. Alternatively, this method can be adapted to screen for the incorporation of a donor-polynucleotide into NATNA/Cas9 break site.

In another aspect, CasM complexes can by targeted to a eukaryotic exon coding region to cause exon skipping. This method comprises contacting a crRNA/deactivated CasM complex, such as, but not limited to a crRNA/dCasM complex, with either a donor site (5' end of an intron), a branch site (proximal to the 3' end of an intron), or an acceptor site (5' of an exon) of a pre-mRNA. Contacting the crRNA/dCasM complex to the various regions involved in exon splice events prevents the proper splicing of one of more exons together and causes the target exon to be "skipped", and thus is not included in the mature mRNA and therefore omitted from the translated polypeptide sequence.

In yet another aspect, CasM complexes are used for the detection of one or more target molecules in vitro. This method comprises contacting a cognate guide/CasN4 complex, such as a crRNA complex, with a ssRNA target of interest within a pool of nucleic acids. The crRNA/CasM complex can be added to a sample potential containing the ssRNA target of interest, in combination with a quenched fluorescent RNA reporters for example a RNA hexamer with a 6-Carboxyfluorescein at the 5' end and a Iowa Black® FQ quencher (Integrated DNA Technologies, Coralville, IA) at the 3' end. Contacting of the crRNA/CasM complex with the ssRNA target, activates the CasM protein to carry out collateral cleavage of the quenched fluorescent RNA reporter where cleavage of the reporter and resulting in an increase fluorescence that can by read out using a spectrophotometer. The gain in fluorescence is used as a measure of the presents of a ssRNA target of interest.

In another aspect, CasM can be used for the targeted cleavage of an endogenous mRNA transcript while simultaneously delivering an exogenous mRNA transcript in cells. This method comprises contacting a cognate guide/CasM complex, with a disease-associated endogenous mRNA transcript, while simultaneously delivering of a mRNA coding for the non-disease exogenous polypeptide into a cell. Thus, the disease-associated phenotype is repressed while the non-disease phenotype is restored.

The CasM proteins described herein can also be used with associated cognate guides in order to activate or repress a target gene, to knockout a gene, to produce a nonfunctional protein product, or to alter protein function. The present invention includes methods of modulating in vitro or in vivo transcription using the various components and complexes described herein. In one embodiment, a cognate guide/CasM protein complex can repress gene expression by interfering with transcription when the cognate guide directs nucleic acid target binding of the complex to the promoter region of the gene. Use of the complexes to reduce transcription also includes complexes wherein the CasM protein is fused to a known down-regulator of a target gene (e.g., a repressor polypeptide). For example, expression of a gene is under the control of regulatory sequences to which a repressor polypeptide can bind. A cognate guide can direct nucleic acid target-binding of a repressor protein complex to the sequences encoding the regulatory sequences or adjacent the regulatory sequences such that binding of the repressor protein complex brings the repressor protein into operable contact with the regulatory sequences. Similarly, CasM can be fused to an activator polypeptide to activate or increase expression of a gene under the control of regulatory sequences to which an activator polypeptide can bind.

In one embodiment, CasM can be fused with a nuclease, or a mutant or an active portion thereof, as well as a cognate guide, in order to bring the nuclease into proximity with a target nucleic acid sequence, wherein the nuclease can produce a single-strand or double-strand break. In this way, a locus-specific cut in a target nucleic acid can be achieved using a cognate guide in combination with CasM, and the nuclease of interest. For example, it may be desirable to associate CasM with a restriction endonuclease in order to cleave at a particular restriction site in a target nucleic acid sequence. The restriction endonuclease can be selected from any of the various types of restriction endonucleases, such as, but not limited to, type I, II, III or IV. See, e.g., PCT Publication No. WO 2013/098244 to Brouns et al., published 4 Jul. 2013, incorporated herein by reference in its entirety, for methods of producing complexes between a Cas protein and a restriction endonuclease.

Using the methods described herein, any desired nucleic acid sequence, and in particular RNA sequences, for modification can be targeted, including without limitation, protein coding mRNA sequences, in order to reduce or restore the function of the gene product; regions that have a propensity to incorporate nucleotide sequences from a donor template, termed "HDR hotspots" herein; safe harbor regions, i.e., regions where nucleotide sequences can be inserted without disrupting neighboring gene function; non-coding regulatory regions in nucleic acid sequences; and the like.

Protein coding sequences, including RNA such as mRNA, for targeting by the methods described herein include, but are not limited to, mammalian antibodies (ABs) (IgG, IgA, IgM, IgE), antibody fragments such as Fc regions, antibody Fab regions, antibody heavy chains, antibody light chains, antibody CDRs, nanobodies, chimeric antibodies and other IgG domains; T cell receptors (TCR); endonucleases and exonucleases, such as TALENS, CRISPR nucleases such as Cas9, Cas3, Cpfl, ZnFN, mega nucleases, nuclease domains such as HNH domain, RuvC domain; recombinases such as Cre, Tre, Brec1, Flp, γ-integrase, IntI4 integrase, XerD recombinase, HP1 integrase; DNA topoisomerases; transposons such as the Tc1/mariner family, Tol2, piggyBac, Sleeping beauty; RAG proteins; retrotransposons such as LTR-retrotransposons and non-LTR retrotransposons (Alu, SINE, LINE); enzymes including but, not limited to arginases, glycosydases, proteases, kinases, and glycosylation enzymes such as glycosyltransferase; anticoagulants such as protein C, Protein S and antithrombin; coagulants such as thrombin; nucleases such as DNAses, RNAses, helicases, GTPases; DNA or RNA binding proteins; reporter molecules, such as Green Fluorescent Protein (GFP); cell penetrating peptides and their fusions with cargo proteins; membrane proteins such as GPCRs, pain receptors such as TRP channels and ion channels; cell surface receptors including but not limited to EGFR, FGFR, VEGFR, IGFR and ephrin receptor; cell adhesion molecules like integrins and cadherins; ion channels; rhodopsins; immunoreceptors such as CD28, CD80, PD-1, PD-L1, CTLA-4, CXCR4, CXCR5, B2M, TRACA, TRBC; proteins known to be involved with genetic defects; secreted proteins including but not limited to hormones, cytokines, growth factors; vaccine antigens such as viral proteins from human immunodeficiency virus (HIV), Dengue, cytomegalovirus (CMV), Ebola, Zika and oncolytic viruses; snake toxin proteins and peptides including but not limited to phospholipases and metalloproteases; ribosomal cyclic peptides.

The present invention also encompasses genome engineering methods for preventing or treating diseases, disorders, and conditions using the various methods described herein. In one embodiment, a genome engineering method uses the introduction of nucleic acid sequences into an organism or cells of an organism (e.g., patient) to achieve expression of components of the present invention to provide modification of a target function. For example, cells from an organism may be engineered, ex vivo, by (i) introduction of vectors comprising expression cassettes expressing the various components, (ii) direct introduction of a NATNA and/or donor polynucleotides and CasM proteins, or (iii) introduction of combinations of these components. The engineered cells are provided to an organism (e.g., patient) to be treated.

Examples of genome engineering and techniques for therapy are known in the art (see, e.g., Kay, M. A., *Nature Reviews Genetics* (2011) 12:316-328; Wang et al., *Discov. Med*. (2014) 18:67-77; Wang et al., *Discov. Med*. (2014) 18:151-61; "The Clinibook: Clinical Gene Transfer State of the Art," Odile Cohen-Haguenauer (Editor), EDP Sciences (Oct. 31, 2012), ISBN-10: 2842541715).

In some aspects, components of the present invention are delivered using nanoscale delivery systems, such as nanoparticles. Additionally, liposomes and other particulate delivery systems can be used. For example, vectors including the components of the present methods can be packaged in liposomes prior to delivery to the subject or to cells derived therefrom, such as described in U.S. Pat. Nos. 5,580,859; 5,264,618; 5,703,055, each of which is incorporated herein by reference in its entirety. Lipid encapsulation is generally accomplished using liposomes that are able to stably bind or entrap and retain nucleic acid.

The methods described herein can also be used to generate non-human genetically modified organisms, such as mice, plants, and the like.

While preferred embodiments of the present invention have been shown and described herein, it will be obvious to those skilled in the art that such embodiments are provided by way of example only. From the above description and the following Examples, one skilled in the art can ascertain essential characteristics of this invention, and without departing from the spirit and scope thereof, can make changes, substitutions, variations, and modifications of the invention to adapt it to various usages and conditions. Such changes, substitutions, variations, and modifications are also intended to fall within the scope of the present disclosure.

EXPERIMENTAL

Aspects of the present invention are further illustrated in the following Examples. Efforts have been made to ensure accuracy with respect to numbers used (e.g., amounts, concentrations, percent changes, etc.) but some experimental errors and deviations should be accounted for. Unless indicated otherwise, temperature is in degrees Centigrade and pressure is at or near atmospheric. It should be understood that these Examples, while indicating some embodiments of the invention, are given by way of illustration only.

The following Examples are not intended to limit the scope of what the inventors regard as various aspects of the present invention.

Example 1

Discovery of a New CRISPR-Associated (Cas) Protein In Silico

This Example describes the in silico discovery of a new Cas protein, termed "CasM," from genomic sequencing data. The overall approach used was similar to methods described in Shmakov et al., "Discovery and functional characterization of diverse Class 2 CRISPR-Cas systems" *Molecular Cell* (2015) 60:385-397. In particular a computational pipeline was used to search sequencing claw for CRISPR arrays in whole genomes and metagenic contigs.

Every contig or genome in the data set was inspected to determine if it contained a CRISPR array using Minced (github.com/ctSkennertor/minced) and PILERCR (drive5.com/pilercr/).

Any time a CRISPR array was found in a contig or genome, the surrounding DNA sequence (up to 10 kilobases on either side of the CRISPR array) was further inspected for open reading frames (ORFs) using the tool getorf (emboss-.sourceforge.net/apps/cvs/emboss/apps/getorf.html).

The primary amino acid sequence of each predicted ORF was analyzed for potential functional domain annotations using the tool HHPred (homology detection & structure prediction by HMM-HMM comparison; toolkit.tuebingen.mpg.de/hhpred). HHPred allows the user to specify which databases to compare the amino acid sequence against to find similar protein domains. The databases searched included PFAM (which includes a large collection of protein families; http://pfam.xfam.org/), PDB (protein databank; wwpdb.org), CDD (conserved domain database; ncbi.nlm.nih.gov/Structure/cdd/cdd.shtml), and KEGG (Kyoto Encyclopedia of Genes and Genomes; genome.jp/kegg/).

Using these tools, ORFs encoding a new putative CRISPR-associated protein, termed "CasM," was found in several species in the Clostridia family. The ORFs are proximal to a predicted HTH DNA binding protein with homology to, a CRISPR-associated WYL domain. See FIG. 1 for a representative map of a CRISPR operon found in *Eubacterium siraeum* (Genome Accession No. NZ_DS499551.1, coordinates 211.800-220.497). The various CRISPR locus features are described in Table 7.

TABLE 7

| CasM CRISPR locus for *Eubacterium siraeum* (FIG. 1) |
|---|
| 101 corresponds to the CasM open reading frame (ORF) (Protein accession: WP_005358205.1) |
| 102 corresponds to a CRISPR Array |
| 103 corresponds to an ORF containing a RctB RNA ligase domain (Protein accession: WP_005358214.1) |
| 104 corresponds to an ORF containing a WYL DNA binding domain (Protein accession: WP_005358216.1) |

The results of HHPred analysis were analyzed to determine if the CasM-encoding ORFs had predicted domains commonly found in CRISPR-associated proteins. No annotations were found for CasM, thus indicating that the protein was novel.

The sequences for the various native CasM proteins are shown in SEQ ID NOS:37-45 (see Table 1) and the native polynucleotides encoding therefor are shown in SEQ ID NOS:28-36 (see Table 3). This protein has no significant homology to any known protein families or to any Class 2 Cas effectors.

Example 2

Codon Modification of Native casM Sequences

This Example describes the process of codon optimizing CasM coding sequences to improve expression in selected host cells.

Native casM nucleotide sequences were retrieved from the reference genomes or metagenomic contigs of the host microbes as described in Example 1. The amino acid sequences of the coding regions were generated with the ExPASy DNA translation tool (web.expasy.org/translate/). Next, these amino acid sequences were entered into the Integrated DNA Technologies (Coralville, IA) Codon Optimisation tool (idtdna.com/CodonOpt). "Amino acid" was chosen for the "Sequence Type" option and "Gene" was chosen for the "Product Type" option. For each native casM sequence, codon modifications were performed to increase expression in *E. coli*, human, and *Zea mays* cells.

SEQ ID NOS:1-9 show the modified sequences for use in *E. coli* (see Table 4). SEQ ID NOS:10-19 show the modified sequences for use in human cells (see Table 5). SEQ ID NOS:20-27 show the modified sequences for use in *Z. mays* cells (see Table 6). Table 8 shows the percent identity of the modified sequences to the native sequences.

TABLE 8

| Percent Sequence Identity to Native casM Sequences | | | |
|---|---|---|---|
| casM bacterial strain | modified for *E. coli* cells | modified for human cells | modified for *Z. mays* cells |
| *Eubacterium siraeum* | 75% | 77% | 77% |
| *Ruminococcus* sp., isolate 2789STDY5834971 | 77% | 76% | 76% |
| *Ruminococcus bicirculans* | 76% | 76% | 77% |
| *Ruminococcus* sp., isolate 2789STDY5608892 | 76% | 75% | 77% |
| *Ruminococcus* sp. CAG:57 | 76% | 77% | 76% |
| *Ruminococcus flavefaciens* FD-1 | 76% | 77% | 76% |
| *Ruminococcus albus* strain KH2T6 | 76% | 77% | 77% |
| *Ruminococcus flavefaciens* strain XPD3002 | 76% | 77% | 77% |
| *Ruminococcus* sp., isolate 2789STDY5834894 | 75% | 76% | 78% |

Example 3

Production of CasM Expression Plasmids for DNA Interference Assays

This Example describes the production of plasmids that express the CasM protein.

The modified casM nucleotide sequences set forth in Example 2 were synthesized in vitro. The DNA sequences were cloned into an appropriate plasmid for expression in *E. coli*.

For *E. coli* expression, the *E. coli*-modified sequences were cloned into a p14A plasmid backbone using appropriate restriction nucleases. The plasmid backbone contained a T7 promoter upstream of the CasM coding sequence to facilitate transcription in cells.

The p14A plasmid backbone also contained a cloning site enabling the insertion of a minimal CRISPR array. The minimal CRISPR array contained one repeat sequence, followed by one spacer sequence, followed by one repeat sequence. The plasmid backbone also contained a T7 promoter upstream of the CRISPR array site, a kanamycin resistance gene, and a ColE1 origin of replication.

Similar techniques are used for preparing plasmids for expression in human and *Zea mays* cells. Once the plasmids are produced, they are transfected into the selected cell, e.g., *E. coli*, human, or plant cells (e.g., *Zea mays* cells).

Example 4

Plasmid Interference Assay

This Example describes the use of CasM in an assay to evaluate its ability to cleave double-stranded DNA in the form of a target plasmid. The overall approach is similar to methods used in Burnstein et al., *Nature* (2016) 542:237-241.

The CasM expression plasmid in Example 3 is transformed into *E. coli* cells. The cells are grown in a medium containing kanamycin to select only for cells that contain the CasM expression plasmid.

A target plasmid is constructed that contains the spacer sequence contained in the CRISPR array of the CasM expression plasmid. Adjacent to the spacer sequence is a randomized PAM sequence of 7 nucleotides. Plasmid libraries containing randomized PAM sequences are assembled by annealing a DNA oligonucleotide containing a target with a 7 nt randomized PAM region with a primer and extended with Klenow Fragment (New England Biolabs, Ipswitch, MA). The double-stranded DNA is digested with EcoRI and NcoI and ligated into a pUC19 backbone. The ligated library is transformed into *E. coli* DH5α and cells are harvested, the plasmids extracted and purified. 200 ng of the pooled library is transformed into electro-competent *E. coli* harboring a CRISPR locus or a control plasmid with no locus. The transformed cells are plated on selective media containing carbenicillin (100 mg $L^{-1}$) and chloramphenicol (30 mg $L^{-1}$) for 30 hours at 25° C. Plasmid DNA is extracted and the PAM sequence is amplified with adapters for Illumina sequencing. The 7 nt PAM region is extracted and PAM frequencies calculated for each 7 nt sequence. PAM sequences depleted above the specified threshold are used to generate a sequence logo with WebLogo (weblogo.berkeley.edu). If depleted PAMs are present, this shows that the nuclease is a double-stranded DNA nuclease.

Example 5

Targeted Modification of HEK293 Cells Using CasM

This Example illustrates the use of CasM to modify human embryonic kidney (HEK293) cells at specific target locations.

casM polynucleotides are transfected into HEK293 cells constitutively expressing a CasM-GFP fusion (HEK293-CasM-GFP), using the Nucleofector™ 96-well Shuttle System (Lonza, Allendale, NJ) and the following protocol. The casM polynucleotides are designed to target the FUT8 gene. Equal molar amounts of casM polynucleotide components are prepared in an annealing buffer (1.25 in HEPES, 0.625 mM $MgCl_2$, 9.375 mM KCl at pH 7.5), incubated for 2 minutes at 95° C., removed from the thermocycler, allowed to equilibrate to room temperature, and dispensed in a 10 μL final volume in a 96-well plate. Culture medium is aspirated from HEK293-CasM-GFP cells, and the cells are washed once with calcium and magnesium-free PBS and then trypsinized by the addition of TrypLE (Life Technologies, Grand Island, NY) followed by incubation at 37° C. for 3-5 minutes. Trypsinized cells are gently pipetted up and down to form a single cell suspension and added to DMEM complete culture medium composed of DMEM culture medium (Life Technologies, Grand Island, NY) containing 10% FBS (Fisher Scientific, Pittsburgh, PA) and supplemented with penicillin and streptomycin (Life Technologies, Grand Island, NY).

The cells are then pelleted by centrifugation for 3 minutes at 200×g, the culture medium aspirated and cells resuspended in PBS. The cells are counted using the Countess™ II Automated Cell Counter (Life Technologies, Grand Island, NY). $2.2\times10^7$ cells are transferred to a 50 ml tube and pelleted. The PBS is aspirated and the cells resuspended in Nucleofector™ SF (Lonza, Allendale, NJ) solution to a density of $1\times10^7$ cells/mL. 20 μL of the cell suspension are then added to individual wells containing 10 μL of casM polynucleotide components and the entire volume is transferred to the wells of a 96-well Nucleocuvette™ Plate (Lonza, Allendale, NJ). The plate is loaded onto the Nucleofector™ 96-well Shuttle™ (Lonza, Allendale, NJ) and cells are nucleofected using the 96-CM-130 Nucleofector™ program (Lonza, Allendale, NJ). Post-nucleofection, 70 μL DMEM complete culture medium is added to each well and 50 μL of the cell suspension are transferred to a collagen coated 96-well cell culture plate containing 150 μL pre-warmed DMEM complete culture medium. The plate is then transferred to a tissue culture incubator and maintained at 37° C. in 5% $CO_2$ for 48 hours.

Genomic DNA (gDNA) is prepped using the QuickExtract DNA extraction solution (Illumina, San Diego, CA) pursuant to the manufacturer instructions. Sequencing amplicons of between 150 bp to 200 bp are designed to span the CasM RNP FUT8 target site. Using previously isolated gDNA, a first PCR is performed using Herculase II Fusion DNA Polyinerase™ (Agnew, Santa Clara, CA) with primers comprising an adapter sequences and a sequence specific to the region flanking the PUT8 target site. A second PCR is performed using the amplicons of the first round of PCR as template at $1/20^{th}$ the volume of the PCR reaction volume. The second PCR uses a second set of primers comprising a sequence complementary to the adapter sequence of the first primer pair, a barcode index sequence unique to each sample, and a flow cell adapter sequence. Amplicons are pooled and analyzed on a 2% TBE gel and bands of expected amplicon sizes are gel purified using the QIAES II Gel extraction Kit™ (Qiagen, Venlo, Luxembourg). The concentrations of purified amplicons are evaluated using the double-stranded DNA BR. Assay Kit and Qubit System™ (Life Technologies, South San Francisco, CA) and library quality determined using the Agilent DNA100Chip and Agilent Bioanalyzer 2100 System™ (Agilent, Santa Clara, CA). After validation of library quality, the library is sequenced on a MiSeq Benchtop Sequencer™ (Illumina, San Diego, CA) with the MiSeq Reagent Kit v2™ (300 cycles, Illumina, San Diego, CA) per manufacturer instructions for 151 bp paired end reads.

The identity of products in the sequencing data is analyzed based upon the index barcode sequence adapted onto the amplicon in the second round of PCR. A computational script is used to process the MiSeq data by executing the following tasks:

1. Joining paired end reads with the aid of fastq-join (Amnesty 2011: code.google.com/p/ea-utils);
2. Validating the sequence reads for appropriate primer sequences being present at both 5' and 3' ends of the read sequence using fastx_barcode_splitter (hannonlab.cshl.edu/fastx_toolkit/index.html); reads lacking correct primer sequences at both ends are discarded.
3. Comparing Read sequences to expected wild type FUT8 sequence; identical read sequences are classified as having the same indel modification.

Other chromosomal loci within HEK293 cells are similarly modified by selection of an appropriate spacer sequence for the CasM RNP. Selection is specific to a specific gene target and the procedure outlined in this Example is readily modifiable by one of ordinary skill in the art for other gene targets.

This procedure can provide data to verify the CasM RNP and to detect nucleic acid guided nuclease activity at targeted loci in HEK293 cells.

Example 6

CasM CRISPR Array Processing Assay

Example describes the CRISPR array processing activity of a CasM protein. The following method may be practiced with other CasM protein homologs to characterize their CRISPR array processing capabilities.

A. Identification of the CRISPR Array Repeat Sequence

Figure 2:
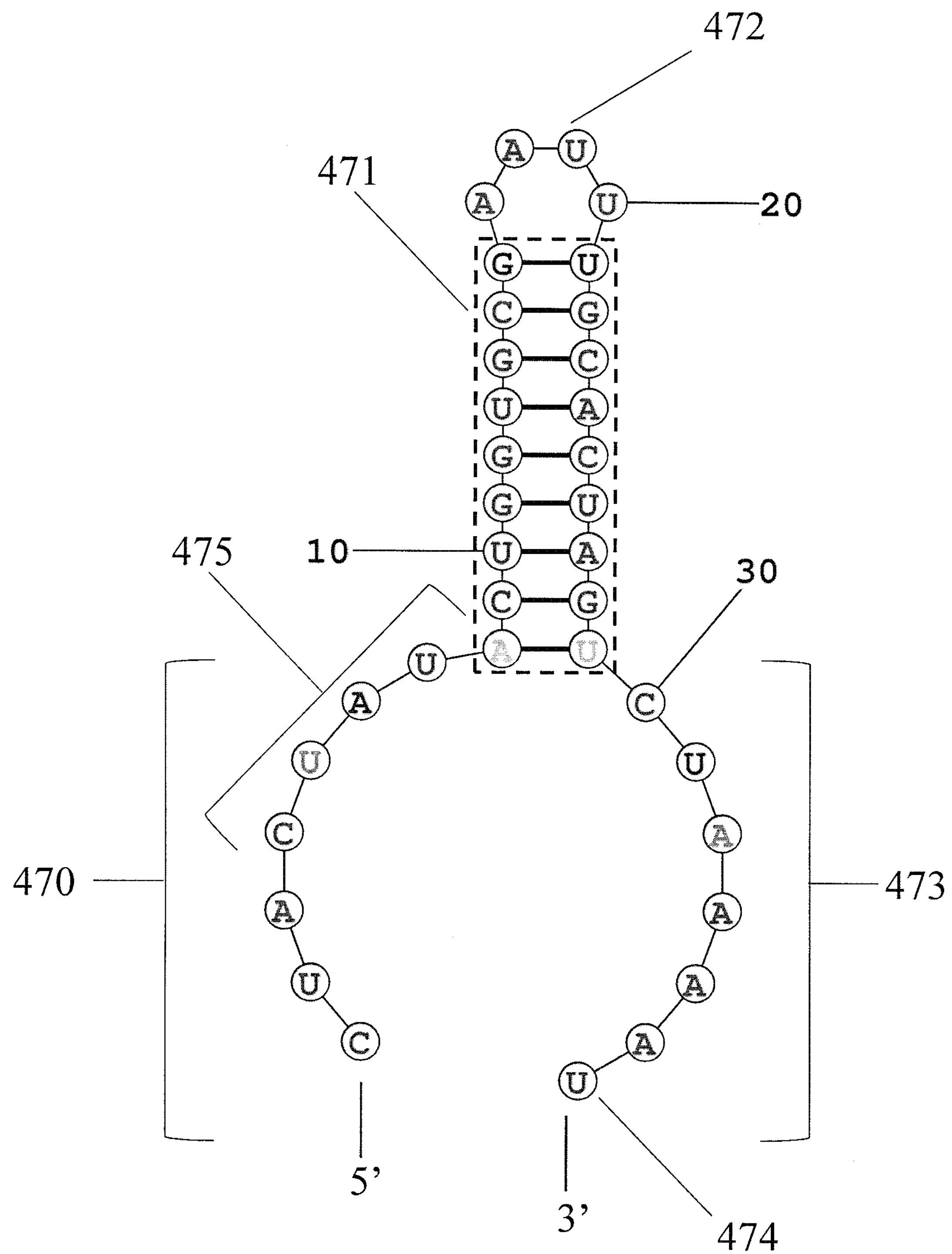
FIG. 2 shows a structure of a CasM repeat sequence (SEQ ID NO:51).

The CRISPR array of the CasM protein homolog (SEQ ID NO:39) was analyzed in silico and the repeat sequence identified. The in silico structure of a CRISPR repeat sequence (SEQ ID NO:51) associated with the CasM protein (SEQ ID NO:39) as predicted using an RNA folding algorithm (rna.urmc.rochester.edu/RNA structureWeb/Servers/Predict1.html) is shown in FIG. 2 (SEQ ID NO:51). The various CRISPR repeat sequence structural components represented in FIG. 2 are described in Table 9.

TABLE 9

| Numerical Indicators Used to Illustrate CasM CRISPR Repeat Sequence Structural Components (FIG. 2) |
|---|
| 470 corresponds to a 5' repeat handle sequence |
| 471 corresponds to a stem-duplex formed by a first stem duplex stand hybridized to a second stem duplex strand |
| 472 corresponds to a loop sequences |
| 473 corresponds to a 5' repeat handle sequence |
| 474 corresponds to the 3' attachment point of a spacer sequence |
| 475 corresponds to the CRISPR repeat processing positions performed by CasM upon guide binding |
| 10 indicates the tenth nucleotide position |
| 20 indicates the twentieth nucleotide position |
| 30 indicates the thirtieth nucleotide position |

Figure 4:
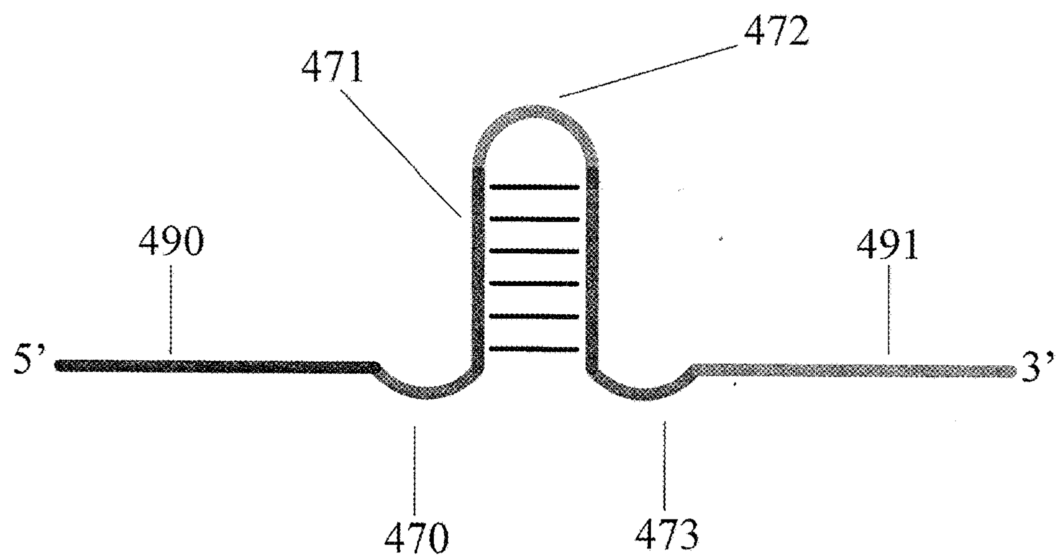
FIG. 4 shows a depiction of a synthetic CasM CRISPR array.

The repeat sequence was used to design a CRISPR array by incorporating spacer sequences 5', 3', or both 5' and 3' of the repeat sequence. The sequences were used for synthesis as RNA. The synthetic CasM CRISPR array is represented in FIG. 4 and structural components 470-473 are detailed in Table 9. Additional components 490 and 491 correspond to a first 5' and a first 3' spacer sequence, respectively. The CRISPR array components are shown in Table 10.

TABLE 10

CRISPR Array Components

| SEQ ID NO: | CRISPR Array Configuration | Sequence | Size (nt) |
|---|---|---|---|
| SEQ ID NO: 46 | spacer-repeat-spacer | UGAUACUGCUUUGAUGUCAGCAUUGC AUAUCUACUAUACUGGUGCGAAUUUG CACUAGUCUAAAAUCUAUAACCAUAA GUUCUUCUGCGUUCAUAU | 96 |

TABLE 10-continued

CRISPR Array Components

| SEQ ID NO: | CRISPR Array Configuration | Sequence | Size (nt) |
|---|---|---|---|
| SEQ ID NO: 47 | spacer-repeat | UGAUACUGCUUUGAUGUCAGCAUUGCAUAUCUACUAUACUGGUGCGAAUUUGCACUAGUCUAAAAU | 66 |
| SEQ ID NO: 48 | repeat-spacer | CUACUAUACUGGUGCGAAUUUGCACUAGUCUAAAAUUGAUACUGCUUUGAUGUCAGCAUUGCAUAU | 66 |

*CRISPR repeat sequence is underlined

SEQ ID NO:46 comprises, in a 5' to 3' orientation, CRISPR array structural components 490, 470-473, and 491. SEQ ID NO:47 comprises, in a 5' to 3' orientation, CRISPR array structural components 490 and 470-473. SEQ ID NO:48 comprises, in a 5' to 3' orientation, CRISPR array structural components 470-473 and 491.

Alternative to synthesis, CRISPR arrays may be made via PCR using 3' overlapping primers containing DNA sequences corresponding to CRISPR array components and incorporation of a T7 promoter sequence 5' of the CRISPR arrays, followed by in vitro transcription.

B. CasM Purification

The CasM protein coding sequence was codon-optimized for expression in *E. coli* and incorporated into a modified pET plasmid backbone downstream of a maltose binding protein (MBP) using appropriate restriction nucleases. The plasmid backbone contained a T7-Lac promoter upstream of the MBP-CasM coding sequence to facilitate transcription in cells. Additionally, the plasmid backbone contained an kanamycin resistance gene and a ColE1 origin of replication.

The CasM expression plasmid was transformed into Rosetta2 (DE3) cells, and cells were grown in two 1 L shake flasks at 37° C. until cells reached an optical density of 0.6, after which protein expression was induced by addition of 0.5 mM IPTG. Cells were then incubated at 16° C. overnight.

Cells were collected via centrifugation and lysed via sonication. Cell debris was pelleted, and the clarified lysate was purified using a combination of HisTrap column chromatography, followed by cleavage of the MBP tag, and finally cation exchange column chromatography. Final purified protein was quantified using a NanoDrop™ 2000 spectrophotometer (ThermoFisher, Waltham, MA), and stored at −80° C., C. In Vitro CRISPR Array Processing Synthetic CRISPR array reagents were resuspended in water to a final concentration of 250 μM and diluted to a working concentration of 250 nM. CRISPR arrays were incubated at 95° C. for two minutes and cooled by 0.5° C./sec in a thermocycler to a final temperature of 25° C.

Figure 3:
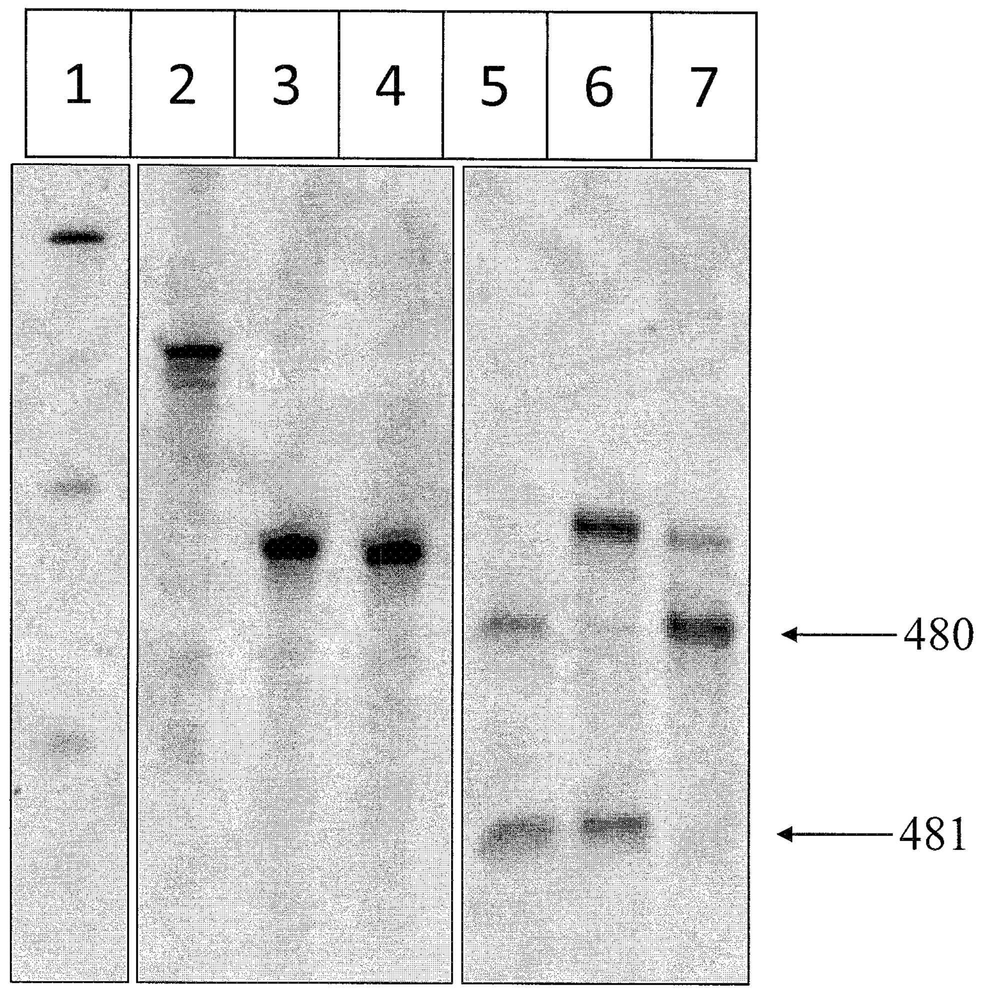
FIG. 3 shows the results of the in vitro CRISPR array cleavage assay described in the Examples.

CasM was diluted to a final concentration of 500 nM in 1× cleavage buffer (20 mM HEPES, 100 mM KCl, 5 mM $MgCl_2$, and 5% glycerol at pH 7.4). The reaction was initiated by addition of CasM protein to denatured CRISPR arrays in a final reaction volume of 12 μL, followed by incubation at 37° C. for 15 minutes. The reaction was terminated by heat inactivation at 95° C. for 2 minutes, and 6 of the reaction was mixed with 6 μL of 2×RNA loading buffer (New England Biolabs, Ipswich, MA). Low Range ssRNA Ladder™ (New England Biolabs, Ipswich, MA) was diluted 125-fold in water and 7 μL were mixed with 7 μL of 2×RNA Loading Dye™ (New England Biolabs, Ipswich, MA) and incubated at 90° C. for 4 minutes and then incubated on ice for 5 minutes. CRISPR array processing reactions and ssRNA ladder were analyzed on a Mini-PROTEAN 15% TEE-Urea™ (Bio-RAD, Hercules, CA) run at 200 V for 1 hour in 1×TBE running buffer. The gel was stained using 2×SYBR Gold™ (MilliporeSigma, St. Louis, MI) for 15 minutes and visualized using a Gel Doc™ EZ System™ (Bio-RAD, Hercules, CA). The results of the CRISPR array processing reactions are shown in FIG. 3 and lane order is presented in Table 11.

TABLE 11

CRISPR Array Cleavage Gel Lane Order

| Lane | CRISPR Array Configuration | SEQ ID NO: | CasM |
|---|---|---|---|
| 1 | Low Range ssRNA Ladder | | |
| 2 | spacer-repeat-spacer | SEQ ID NO: 46 | − |
| 3 | spacer-repeat | SEQ ID NO: 47 | − |
| 4 | repeat-spacer | SEQ ID NO: 48 | − |
| 5 | spacer-repeat-spacer | SEQ ID NO: 46 | + |
| 6 | spacer-repeat | SEQ ID NO: 47 | + |
| 7 | repeat-spacer | SEQ ID NO: 48 | + |

The results of the CRISPR array cleavage assays (FIG. 3) demonstrated that the CasM protein is capable of processing a cognate CRISPR array. The three bands shown in Lane 1 correspond to 150, 80 and 50 nucleotide standards of the Low Range ssRNA Ladder™ (New England Biolabs, Ipswich, MA), respectively). Indicator 480 in FIG. 3 corresponds to a processed CasM crRNA comprising a portion of the CRISPR repeat sequence and a spacer sequence. Indicator 481 corresponds to RNA species cleaved from the 5' end of the CRISPR array following addition of CasM.

The CasM cleaved nucleotides in the 5' region of the repeat element (FIG. 3, comparing Lane 2 to 5; comparing Lane 3 to Lane 6), and exhibited no cleavage 3' of the repeat element (FIG. 3, comparing Lane 4 to Lane 7). crRNA proceeded from the CasM CRISPR array and therefore had a 5' repeat element and a spacer element 3' of the repeat. In the absence of CasM, no cleavage of the crRNA was observed (FIG. 3, Lanes 2, 3, and 4).

Figure 5:
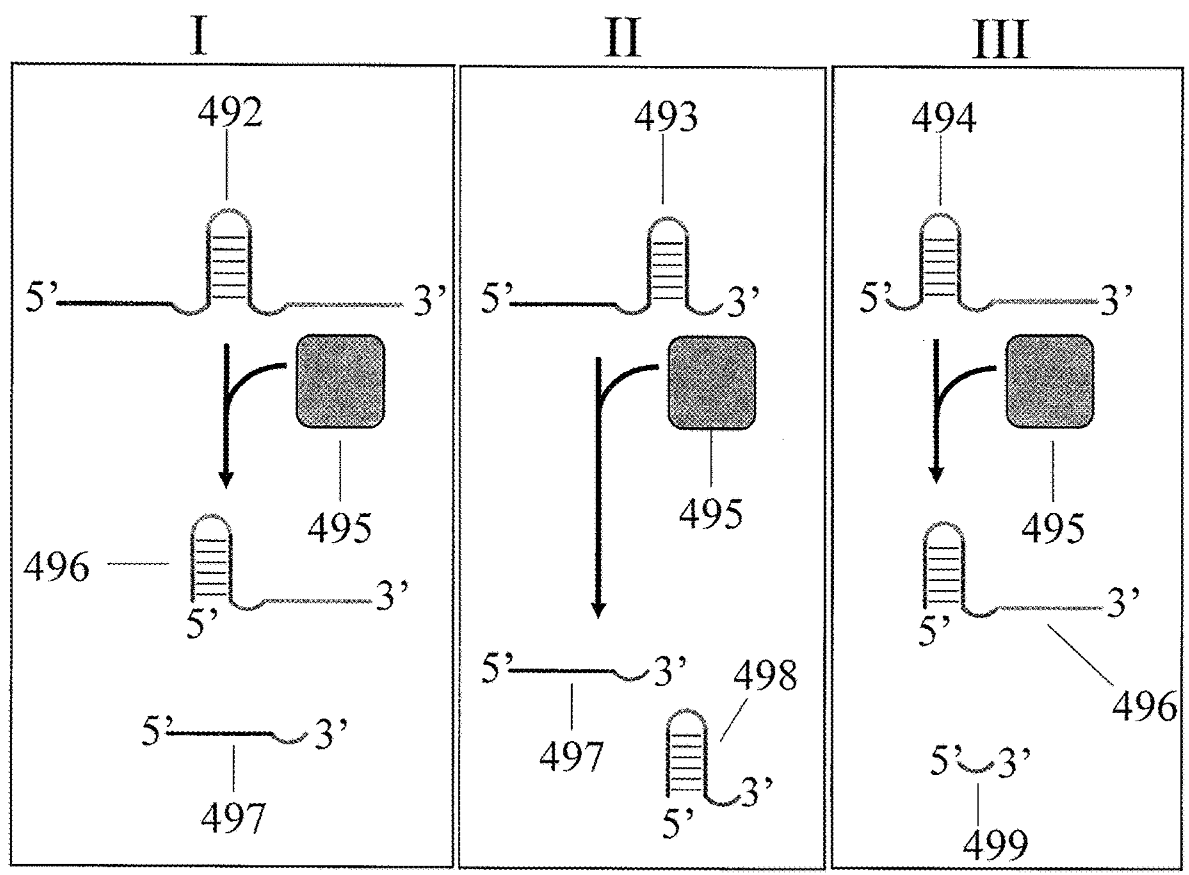
FIG. 5 shows a representation of the results of the in vitro CRISPR array cleavage assay results shown in FIG. 3 and described in the Examples.

Schematics of the crRNA processing regimes are depicted in FIG. 5. In FIG. 5, panel I corresponds to the reaction in FIG. 3, Lane 5; FIG. 5 panel II corresponds to the reaction in FIG. 3, Lane 6; and FIG. 5 panel III corresponds to the reaction in FIG. 3, Lane 7. The various components represented in FIG. 5 are described in Table 12.

TABLE 12

| Numerical Indicators Used to Illustrate the Results of the in vitro CRISPR Array Cleavage Assay (FIG. 5) |
|---|
| 492 corresponds to a spacer-repeat-spacer CRISPR array (SEQ ID. NO: 46) |
| 493 corresponds to a spacer-repeat CRISPR array (SEQ ID. NO: 47) |
| 494 corresponds to a repeat-spacer CRISPR array (SEQ ID. NO: 48) |
| 495 corresponds to a CasM protein |
| 496 corresponds to a processed crRNA |
| 497 corresponds to a RNA species cleaved from the 5' end of the CRISPR array |
| 498 corresponds to a processed CRISPR repeat sequence |
| 499 corresponds to a RNA species cleaved from the 5' end of the CRISPR repeat sequence |

Example 7

CasM ssRNA Cleavage Assay

This Example illustrates the use of a crRNA/CasM protein complex to carry out ssRNA cleavage. The following method may be practiced with other CasM protein and crRNA to cleave ssRNA targets.

A. Generation of ssRNA Target

A ssRNA target was generated via PCR amplification of a 224 nucleotide target sequence from a plasmid. A T7 promoter sequence was incorporated into the 5' end of the reverse PCR primer (SEQ ID NO:50) for transcription. The primers used for ssRNA target DNA template are presented in Table 13.

TABLE 13 ssRNA Target DNA Template Primers

| SEQ ID NO: | Name | Sequence |
|---|---|---|
| SEQ ID NO: 49 | Forward primer | CGAAATTAATACGACTCACTATAGG TTTCGATTATGCGGCCGTGT |
| SEQ ID NO: 50 | Reverse primer | AGGAGATATACCATGGGCAGCA |

* T7 Promoter sequence underlined.

The primers were present at a concentration of 400 nM each. PCR reactions were performed using Q5 Hot Start High-Fidelity 2× Master Mix™ (New England Biolabs, Ipswich, MA) following the manufacturer's instructions with 10 ng of plasmid template. PCR assembly reactions were carried out using the following thermal cycling conditions: 98° C. for 2 minutes; 20 cycles of 10 seconds at 98° C.; 15 seconds at 60° C.; 30 seconds at 72° C.; and a final extension at 72° C. for 2 minutes. DNA product quality was evaluated after the PCR reaction by agarose gel electrophoresis (1.5%, SYBR® Safe; Life Technologies, Grand Island, NY).

Between 0.1-0.5 μg of the amplified ssRNA target DNA template was used as a template for transcription using T7 High Yield RNA Synthesis Kit™ (New England Biolabs, Ipswich, MA) for approximately 16 hours at 37° C. Transcription reactions were treated with DNase 1 (New England Biolabs, Ipswich, MA) and purified using GeneJet RNA Cleanup and Concentration Kit™ (Life Technologies, Grand Island, NY). The quality of the transcribed RNA was checked by agarose gel electrophoresis (2%, SYBR® Safe; Life Technologies, Grand Island, NY) and quantified using the Quant-iT™ RNA Assay Kit™ (ThermoFisher, Waltham, MA).

B. Designing CasM crRNA

The 224 nucleotide ssRNA target sequence was probed in silico for a 30 nucleotide target sequence. The target sequence was appended in silico to the 3' end of the CasM crRNA repeat sequence and the crRNA sequence was provided to a commercial manufacturer for synthesis.

C. ssRNA Cleavage Assay

Synthetic crRNA reagents were resuspended in water to a final concentration of 250 μM and diluted to a suitable working concentration of 250 nM. In vitro transcribed ssRNA target was diluted to 43 ng/μL in water. Both the crRNA and the ssRNA target reagents were separately incubated, at 95° C. for two minutes and cooled by 0.5° C./sec in a thermocycler to a final temperature of 25° C. The CasM protein was diluted to various concentrations in water and 1× cleavage buffer. Denatured crRNA was added at various concentrations to the CasM protein and incubated in a thermocycler for 10 minutes at 37° C. The cleavage reactions were initiated by the addition of the ssRNA target to a final concentration of 56.4 nM in a final, reaction volume of 12 μL. The concentration of each component in the various reactions is shown in Table 14.

TABLE 14 ssRNA Targeting Reaction Component Concentrations

| Reaction | nM CasM | nM crRNA | nM ssRNA target | Molar ratio CasM:crRNA:ssRNA target |
|---|---|---|---|---|
| 1 | 11.3 | 33.8 | 56.4 | 0.2:0.6:1 |
| 2 | 22.5 | 67.6 | 56.4 | 0.4:1.2:1 |
| 3 | 33.8 | 101.5 | 56.4 | 0.6:1.8:1 |
| 4 | 45.1 | 135.3 | 56.4 | 0.8:2.4:1 |
| 5 | 56.4 | 169.1 | 56.4 | 1:3:1 |
| 6 | 112.7 | 338.2 | 56.4 | 2:6:1 |
| 7 | 225.5 | 676.4 | 56.4 | 4:12:1 |
| 8 | 338.2 | 1014.6 | 56.4 | 6:18:1 |
| 9 | 450.9 | 1352.8 | 56.4 | 8:24:1 |
| 10 | 563.7 | 1691.0 | 56.4 | 10:30:1 |
| 11 | 0.0 | 0.0 | 56.4 | 0:3:1 |
| 12 | 56.4 | 0.0 | 56.4 | 1:0:1 |
| 13 | 0.0 | 169.1 | 56.4 | 0:3:1 |
| 14 | 0.0 | 169.1 | 0.0 | 1:3:0 |

Figure 6:
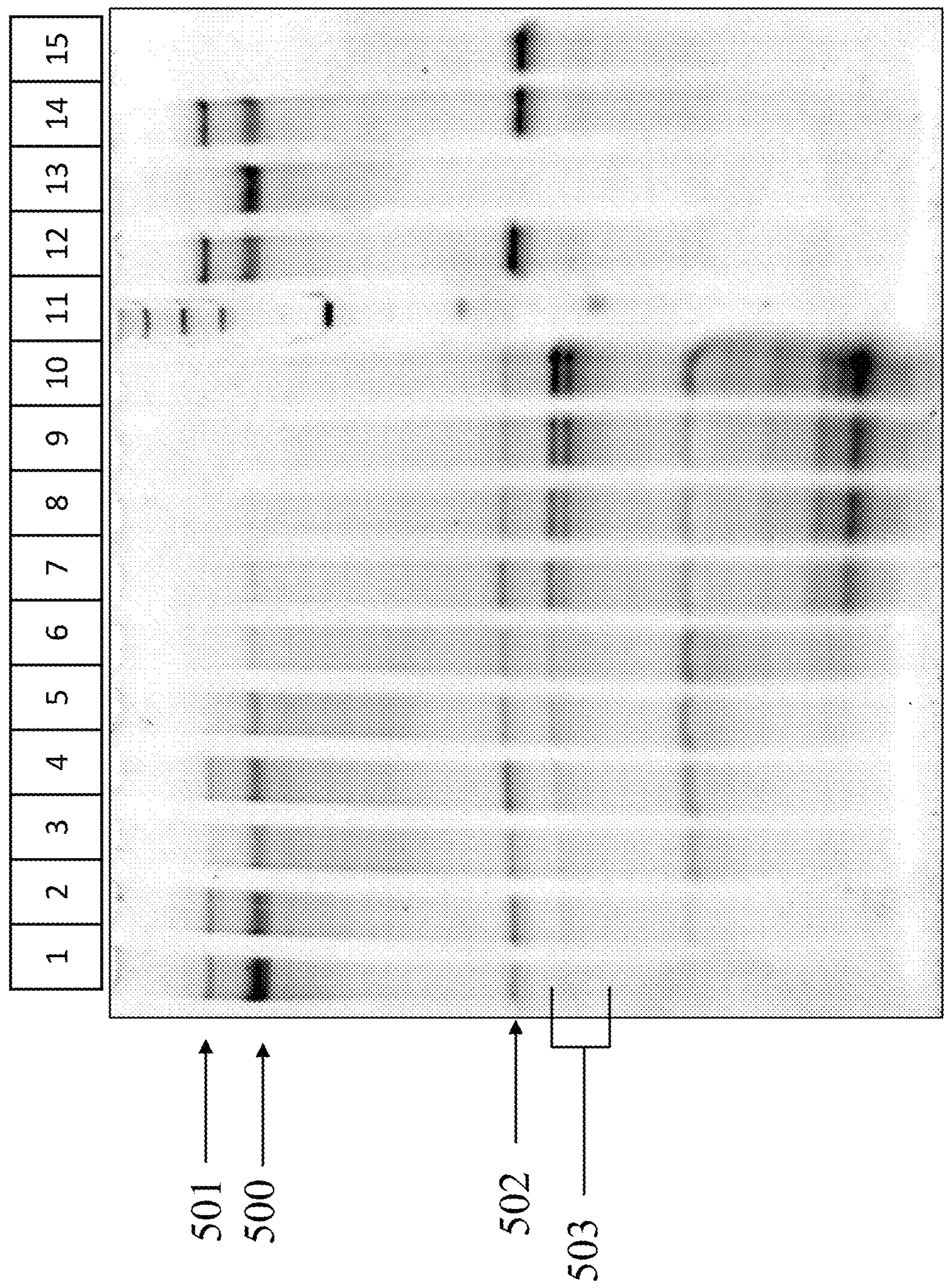
FIG. 6 shows the results of the CasM ssRNA cleavage assay described in the Examples.

Samples were mixed and centrifuged briefly before being incubated for 1 hour at 37° C. Reactions were terminated by incubating the reaction at 95° C. for 2 minutes followed by the addition of 100 U/μL of Proteinase K (New England Biolabs, Ipswich, MA), 4 M urea, 5 μM DTT, 50 μM EDTA and incubation at 37° C. for 15 minutes. 7 μL of each reaction was mixed with 6 μL of 2×RNA Loading Dye (New England Biolabs, Ipswich, MA) and incubated at 90° C. for two minutes. Low Range ssRNA Ladder™ (New England Biolabs, Ipswich, MA) was diluted 125-fold in water and 7 μL were mixed with 7 μL of 2×RNA Loading Dye™ (New England Biolabs, Ipswich, MA) and incubated at 90° C. for 4 minutes and then incubated on ice for 5 minutes. Cleavage reactions and ssRNA ladder were analyzed on a Mini-PROTEAN 15% TBE-Urea™ (BioRAD, Hercules, CA), run at 200 V for 1 hour in 1×TBE running buffer. Gel was stained using 2×SYBR Gold™ (Life Technologies, Grand Island, NY) for 15 minutes and visualized with using a Gel Doc EZ System™ (BioRAD, Hercules, CA). The results of the crRNA cleavage assay are shown in FIG. 6 and the components of each lane shown in Table 15. Numerical indicator 500 corresponds to the ssRNA target. Numerical indicator 501 corresponds to a ssRNA target hybridized to the spacer sequences of the CasM crRNA. Numerical indicator 502 corresponds to an unprocessed CasM crRNA. Numerical indicator 503 corresponds to the processed CasM crRNA species.

TABLE 15 ssRNA Cleavage Gel Lane Order

| Lane | Molar ratio CasM:crRNA:ssRNA target |
|---|---|
| 1 | 0.2:0.6:1 |
| 2 | 0.4:1.2:1 |
| 3 | 0.6:1.8:1 |
| 4 | 0.8:2.4:1 |
| 5 | 1:3:1 |

TABLE 15-continued

| ssRNA Cleavage Gel Lane Order | |
|---|---|
| Lane | Molar ratio CasM:crRNA:ssRNA target |
| 6 | 2:6:1 |
| 7 | 4:12:1 |
| 8 | 6:18:1 |
| 9 | 8:24:1 |
| 10 | 10:30:1 |
| 11 | ssRNA Ladder |
| 12 | 0:3:1 |
| 13 | 1:0:1 |
| 14 | 0:3:1 |
| 15 | 1:3:0 |

The results of the ssRNA cleavage assay shown in FIG. 6 demonstrated that a CasM:crRNA protein complex was capable of ssRNA target cleavage. The results of this procedure demonstrate that increasing the amount of CasM: crRNA complexes resulted in decreased amounts of ssRNA target (FIG. 6, indicator 500) visualized on the gel (FIG. 6, Lanes 1-10).

Example 8

Production of CasM and RtcB Expression Plasmids for MS2 Phage Drop Plaque Assays This Example describes the production of plasmids for the expression of CasM, RtcB (RNA 3'-terminal phosphate cyclase, group B), and a corresponding CRISPR array in *E. coli* for use in a MS2 phage drop plaque assay. The following method can be practiced with other CasM, RtcB, and CRISPR array homologs.

The casM and rtcB nucleotide sequence from *Eubacterium siraeum* (SEQ ID NO:37 and SEQ ID NO:60, respectively) are selected and codon optimized for expression in *E. coli*. The *E. coli*-modified sequences are cloned into a p14A plasmid backbone using appropriate restriction nucleases. The plasmid backbone contains a T7 promoter upstream of each protein coding sequence to facilitate transcription in cells. Two control plasmids, one containing only the casM gene sequence under the control of a T7 promoter and the other plasmid only containing the rtcB gene sequence under the control of a T7 promoter, can also constructed.

A spacer sequence that has homology with the MS2 phase genome is engineered in silico flanked 5' and 3' by the *Eubacterium siraeum* CasM CRISPR repeat sequence. A non-targeting spacer with no homology to the MS2 phage or *E. coli* genome, is similarly engineered as a control. Both sequences are subcloned into separate plasmids between an upstream T7 promoter sequence and a downstream transcription terminator sequence.

Example 9

MS2 Phage Drop Plaque Assay

This Example describes the use of CasM and RtcB in an assay to evaluate the ability of the RtcB protein to modulate CasM's sequence-specific and collateral nuclease activity in *E. coli*. The method set forth herein is adapted from Smargon et al., *Molec. Cell* (2017) 65:618-630. Not all of the following steps are required for screening, nor must the order of the steps be as presented.

The expression plasmids constructed in Example 8 are in and in combination transformed into BL21(AI) *E. coli* cells from a commercial provider, such as Invitrogen (Carlsbad, CA). Transformed cells are grown overnight at 37° C., with shaking, in lysogeny broth (LB) supplemented with 100 μg/mL carbenicillin, to select for cells that contain the CasM expression plasmid.

The following day, cells are diluted 1:100 and then grown at 37° C., with shaking, to an OD600 of 2.0. The cells are then mixed with 4 mL of carbenicillin-containing top Agar (10 g/L tryptone, 5 g/L yeast extract, 10 g/L sodium chloride, 5 g/L agar) and poured onto LB-antibiotic base plates. The top agar also contains 0.2% arabinose to induce expression of the casM, ricB and CRISPR array coding sequences. 10-fold serial dilutions of MS2 phage (ATCC 15597-B1, Manassas VA) are made in LB and then spotted onto hardened top agar with a multi-channel pipette. Plaque formation is assessed after overnight incubation of the spotted plates at 37° C.

To assess whether the RtcB protein modulates CasM cleavage activity, the relative plaque formation is determined by comparing cells expressing CasM, RtcB, and the CRISPR array targeting MS2 phage; cells expressing CasM and the CRISPR array targeting MS2 phage, and cells expressing CasM and the CRISPR array not targeting MS2 phage; cells expressing CasM and RtcB only.

Example 10

Introduction of CasM RNP Complexes into Target Cells

This Example illustrates the design and delivery of CasM and crRNA ribonucleoprotein (RNP) complexes into human cells to enable mRNA cleavage of the human epidermal growth factor receptor (EGFR) gene and subsequent knockdown of EGFR gene expression.

A. Production of CasM Complexes and Transformation into Cells

Mature crRNAs (SEQ ID NOS:70-165) were designed to target the EGFR locus in the human genome. Each crRNA contained a 5' 36 nt repeat (SEQ ID NO:51) followed by a 30 at spacer. crRNAs were designed to target 72 unique sequences complementary to the egfr mRNA within exons 1-3. Sequences were designed such that flanking sequences within 1 bp were not biased by any nucleotide. As negative controls, not predicted to induce cleavage, crRNAs were also designed to target (1) eight genomic sequences upstream of the predicted egfr mRNA; (2) eight sequences complementary to the vegfa mRNA exon 1; and (3) eight sequences identical to the egfr mRNA.

Double-stranded DNA (dsDNA) guide templates containing upstream T7 promoter sequences were created by annealing complementary oligonucleotides (Integrated DNA Technologies, Coralville, IA) at a final concentration of 10 μM in annealing buffer (30 mM HEPES, 300 mM KCL), then incubating at 95° C. for, two minutes, and then slowly cooled to approximately 25° C., and incubated for an additional 20 minutes. Following annealing, guides were transcribed with T7 RNA polymerase HiScribe™ T7 High Yield RNA Synthesis Kit™ (New England Biolabs, Ipswich, MA) according to manufacturer's instructions. Next, samples were digested with RNase-free DNase-I (New England Biolabs, Ipswich, MA) according to manufacturer's instructions, then purified using RNAClean XP™ beads (Beckman Coulter, Indianapolis, IN).

For RNAClean XP™ bead purification, 30 μL of sample was combined with 155 μL of 100% isopropanol and 10 μL of 3 M sodium acetate and then mixed thoroughly. Next, 50 μL of RNAClean XP™ beads were incubated on a magnet for three minutes to allow separation of the liquid and beads, and the supernatant was removed. Subsequently, the samples containing crRNA were added to the beads, mixed, incubated at approximately 25° C. for five minutes, then incubated on a magnet for three minutes. Finally, the supernatant was removed, the beads were washed once with 83% ethanol, dried, and then the crRNA was eluted in 20 μL of molecular biology grade water. crRNAs were quantified using ribogreen and then normalized to 1 μg/μL.

To assemble CasM RNPs, 120 pmols of each unique crRNA were added to a well then incubated at 95° C. for two minutes followed by 5° C. for approximately 10 minutes. Next, the denatured crRNA guides were combined with 20 pmol of CasM (SEQ ID NO:39) in RNP assembly buffer (20 mM HEPES; pH 7.4, 10 mM $MgCl_2$, 150 mM KCl, 5% glycerol) and then incubated at 37° C. for 10 minutes.

B. Transfection of CasM RNP Complexes into Eukaryotic Cells

HeLa cells (ATCC, Manassas, VA) were cultured in suspension in DMEM medium supplemented with 10% FBS and 1× Antibiotic-Antimycotic Solution (Mediatech, Inc., Manassas, VA) at 37° C., 5% CO2 and 100% humidity. HeLa cells were transfected using the Nucleofector® 96-well Shuffle System (Lonza, Allendale, NJ). Prior to nucleofection, 5 μl of the CasM:crRNA RNPs were assembled in individual wells of a 96-well plate. HeLa cells were transferred to a 50 ml conical centrifuge tube and centrifuged at 200×G for live minutes. The media was aspirated and the cell pellet was washed in calcium and magnesium-free PBS. The cells were centrifuged once more and resuspended in Nucleofector SF™ buffer (Lonza, Allendale, NJ) at a concentration of $5\times10^6$ cells/ml. 20 μl of this cell suspension was added to the CasM:crRNA RNPs in the 96 well plate, mixed, and then the entire volume was transferred to a 96-well Nucleocuvette™ Plate. The plate was then loaded into the Nucleofector 96-well Shuttle™ and cells were nucleofected using the 96-CN-114 Nucleofector™ program (Lonza, Allendale, NJ). Immediately following nucleofection, 75 μl of complete DMEM medium was added to each well of the 96-well Nucleocuvette™ Plate. Half of the contents of each well were then transferred to a 96-well tissue culture plate containing 150 μl of complete DMEM medium. This procedure was then repeated in order to plate a duplicate for each well, one which would be used for lysis and genomic DNA analysis, and one for FACS analysis. The cells were cultured at 37° C., 5% CO2 and 100% humidity for approximately 5 days.

C. FACS Analysis of CasM Mediated EGFR Knockdown

Fluorescence activated cell sorting (FACS) analysis was performed 5 days after nucleofection of HeLa cells with EGFR-targeting CasM2 RNPs. In brief: $2\times10^5$-$4\times10^5$ cells/well were detached with TrypLE Express (Gibco), stained with 2 μL APC anti-human EGFR (Clone AY13, Sony Biotechnology) in 100 μL, total volume and then analyzed using Intellicyte Flow Cytometer (Intellicyt, Albuquerque, N.M.). Results from these experiments are shown in Table 16.

TABLE 16

CasM Mediated EGFR knockdown

| Name | % EGFR negative cells | transcription | crRNA SEQ ID NO. |
|---|---|---|---|
| Untransfected reference cell | 2% | n/a | — |
| Intergenic target-1 | 5% | Intergenic | SEQ ID NO: 70 |
| Intergenic target-2 | 6% | Intergenic | SEQ ID NO: 71 |
| Intergenic target-3 | 9% | Intergenic | SEQ ID NO: 72 |
| Intergenic target-4 | 8% | Intergenic | SEQ ID NO: 73 |
| Intergenic target-5 | 5% | Intergenic | SEQ ID NO: 74 |
| Intergenic target-6 | 6% | Intergenic | SEQ ID NO: 75 |
| Intergenic target-7 | 6% | Intergenic | SEQ ID NO: 76 |
| Intergenic target-8 | 4% | Intergenic | SEQ ID NO: 77 |
| Exon 1 target-1 | 6% | Exon 1/28 | SEQ ID NO: 78 |
| Exon 1 target-2 | 5% | Exon 1/28 | SEQ ID NO: 79 |
| Exon 1 target-3 | 5% | Exon 1/28 | SEQ ID NO: 80 |
| Exon 1 target-4 | 4% | Exon 1/28 | SEQ ID NO: 81 |
| Exon 1 target-5 | 6% | Exon 1/28 | SEQ ID NO: 82 |
| Exon 1 target-6 | 5% | Exon 1/28 | SEQ ID NO: 83 |
| Exon 1 target-7 | 6% | Exon 1/28 | SEQ ID NO: 84 |
| Exon 1 target-8 | 6% | Exon 1/28 | SEQ ID NO: 85 |
| Exon 1 target-9 | 4% | Exon 1/28 | SEQ ID NO: 86 |
| Exon 1 target-10 | 3% | Exon 1/28 | SEQ ID NO: 87 |
| Exon 1 target-11 | 3% | Exon 1/28 | SEQ ID NO: 88 |
| Exon 1 target-12 | 2% | Exon 1/28 | SEQ ID NO: 89 |
| Exon 1 target-13 | 4% | Exon 1/28 | SEQ ID NO: 90 |
| Exon 1 target-14 | 4% | Exon 1/28 | SEQ ID NO: 91 |
| Exon 1 target-15 | 5% | Exon 1/28 | SEQ ID NO: 92 |
| Exon 1 target-16 | 4% | Exon 1/28 | SEQ ID NO: 93 |
| Exon 1 target-17 | 6% | Exon 1/28 | SEQ ID NO: 94 |
| Exon 1 target-18 | 6% | Exon 1/28 | SEQ ID NO: 95 |
| Exon 1 target-19 | 6% | Exon 1/28 | SEQ ID NO: 96 |
| Exon 1 target-20 | 5% | Exon 1/28 | SEQ ID NO: 97 |
| Exon 1 target-21 | 5% | Exon 1/28 | SEQ ID NO: 98 |
| Exon 1 target-22 | 5% | Exon 1/28 | SEQ ID NO: 99 |
| Exon 1 target-23 | 6% | Exon 1/28 | SEQ ID NO: 100 |
| Exon 1 target-24 | 5% | Exon 1/28 | SEQ ID NO: 101 |
| Exon 2 target-1 | 6% | Exon 2/28 | SEQ ID NO: 102 |
| Exon 2 target-2 | 7% | Exon 2/28 | SEQ ID NO: 103 |
| Exon 2 target-3 | 11% | Exon 2/28 | SEQ ID NO: 104 |
| Exon 2 target-4 | 5% | Exon 2/28 | SEQ ID NO: 105 |
| Exon 2 target-5 | 6% | Exon 2/28 | SEQ ID NO: 106 |
| Exon 2 target-6 | 8% | Exon 2/28 | SEQ ID NO: 107 |
| Exon 2 target-7 | 11% | Exon 2/28 | SEQ ID NO: 108 |
| Exon 2 target-8 | 10% | Exon 2/28 | SEQ ID NO: 109 |
| Exon 2 target-9 | 13% | Exon 2/28 | SEQ ID NO: 110 |
| Exon 2 target-10 | 8% | Exon 2/28 | SEQ ID NO: 111 |
| Exon 2 target-11 | 10% | Exon 2/28 | SEQ ID NO: 112 |
| Exon 2 target-12 | 8% | Exon 2/28 | SEQ ID NO: 113 |
| Exon 2 target-13 | 13% | Exon 2/28 | SEQ ID NO: 114 |
| Exon 2 target-14 | 16% | Exon 2/28 | SEQ ID NO: 115 |
| Exon 2 target-15 | 19% | Exon 2/28 | SEQ ID NO: 116 |
| Exon2 target-16 | 11% | Exon 2/28 | SEQ ID NO: 117 |
| Exon 2 target-17 | 10% | Exon 2/28 | SEQ ID NO: 118 |
| Exon 2 target-18 | 19% | Exon 2/28 | SEQ ID NO: 119 |
| Exon 2 target-19 | 20% | Exon 2/28 | SEQ ID NO: 120 |
| Exon 2 target-20 | 25% | Exon 2/28 | SEQ ID NO: 121 |
| Exon 2 target-21 | 15% | Exon 2/28 | SEQ ID NO: 122 |
| Exon 2 target-22 | 17% | Exon 2/28 | SEQ ID NO: 123 |
| Exon 2 target-23 | 14% | Exon 2/28 | SEQ ID NO: 124 |
| Exon 2 target-24 | 12% | Exon 2/28 | SEQ ID NO: 125 |
| Exon 3 target-1 | 7% | Exon 3/28 | SEQ ID NO: 126 |
| Exon 3 target-2 | 7% | Exon 3/28 | SEQ ID NO: 127 |
| Exon 3 target-3 | 9% | Exon 3/28 | SEQ ID NO: 128 |
| Exon 3 target-4 | 9% | Exon 3/28 | SEQ ID NO: 129 |
| Exon 3 target-5 | 8% | Exon 3/28 | SEQ ID NO: 130 |
| Exon 3 target-6 | 11% | Exon 3/28 | SEQ ID NO: 131 |
| Exon 3 target-7 | 12% | Exon 3/28 | SEQ ID NO: 132 |
| Exon 3 target-8 | 12% | Exon 3/28 | SEQ ID NO: 133 |
| Exon 3 target-9 | 10% | Exon 3/28 | SEQ ID NO: 134 |
| Exon 3 target-10 | 9% | Exon 3/28 | SEQ ID NO: 135 |
| Exon 3 target-11 | 11% | Exon 3/28 | SEQ ID NO: 136 |
| Exon 3 target-12 | 40% | Exon 3/28 | SEQ ID NO: 137 |
| Exon 3 target-13 | 17% | Exon 3/28 | SEQ ID NO: 138 |
| Exon 3 target-14 | 15% | Exon 3/28 | SEQ ID NO: 139 |
| Exon 3 target-15 | 12% | Exon 3/28 | SEQ ID NO: 140 |
| Exon 3 target-16 | 21% | Exon 3/28 | SEQ ID NO: 141 |
| Exon 3 target-17 | 48% | Exon 3/28 | SEQ ID NO: 142 |

TABLE 16-continued

| CasM Mediated EGFR knockdown | | | |
|---|---|---|---|
| Name | % EGFR negative cells | transcription | crRNA SEQ ID NO. |
| Exon 3 target-18 | 41% | Exon 3/28 | SEQ ID NO: 143 |
| Exon 3 target-19 | 19% | Exon 3/28 | SEQ ID NO: 144 |
| Exon 3 target-20 | 9% | Exon 3/28 | SEQ ID NO: 145 |
| Exon 3 target-21 | 19% | Exon 3/28 | SEQ ID NO: 146 |
| Exon 3 target-22 | 8% | Exon 3/28 | SEQ ID NO: 147 |
| Exon 3 target-23 | 8% | Exon 3/28 | SEQ ID NO: 148 |
| Exon 3 target-24 | 6% | Exon 3/28 | SEQ ID NO: 149 |
| VEGFA target-1 | 6% | Exon 1/8 | SEQ ID NO: 150 |
| VEGFA target-2 | 8% | Exon 1/8 | SEQ ID NO: 151 |
| VEGFA target-3 | 8% | Exon 1/8 | SEQ ID NO: 152 |
| VEGFA target-4 | 7% | Exon 1/8 | SEQ ID NO: 153 |
| VEGFA target-5 | 8% | Exon 1/8 | SEQ ID NO: 154 |
| VEGFA target-6 | 7% | Exon 1/8 | SEQ ID NO: 155 |
| VEGFA target-7 | 6% | Exon 1/8 | SEQ ID NO: 156 |
| VEGFA target-8 | 8% | Exon 1/8 | SEQ ID NO: 157 |
| Nontargeting target-1 | 5% | Exon 1/28 | SEQ ID NO: 158 |
| Nontargeting target-2 | 7% | Exon 1/28 | SEQ ID NO: 159 |
| Nontargeting target-3 | 6% | Exon 1/28 | SEQ ID NO: 160 |
| Nontargeting target-4 | 6% | Exon 1/28 | SEQ ID NO: 161 |
| Nontargeting target-5 | 6% | Exon 1/28 | SEQ ID NO: 162 |
| Nontargeting target-6 | 6% | Exon 1/28 | SEQ ID NO: 163 |
| Nontargeting target-7 | 7% | Exon 1/28 | SEQ ID NO: 164 |
| Nontargeting target-8 | 4% | Exon 1/28 | SEQ ID NO: 165 |

The data presented in Table 16 shows that CasM did not produce egfr knockdown when targeted to (1) sequences upstream of the predicted exon 1 start site using SEQ ID NOS:70-77; (2) an unrelated vascular endothelial growth factor A (vegfa) gene using SEQ ID NOS:150-157); or (3) the reverse complement of sequences contained in egfr exon 1 mRNA using SEQ ID NOS:158-165. Conversely, CasM enabled approximately 40% egfr knockdown when targeted to mRNA sequences contained in exon 2 using SEQ ID NO:102-125, and exon 3 of egfr using SEQ ID NO:126-149.

Although preferred embodiments of the subject methods have been described in some detail, it is understood that obvious variations can be made without departing from the spirit and the scope of the invention as defined by the appended claims.

The invention claimed is:

1. A Clustered Regularly Interspaced Short Palindromic Repeats (CRISPR)-associated (Cas) nucleoprotein complex, wherein the nucleoprotein complex comprises a Cas protein having at least 95 percent sequence identity to the amino acid sequence of SEQ ID NO: 40; and a cognate nucleic acid guide comprising a repeat sequence and a spacer sequence, wherein the repeat sequence and the spacer sequence do not naturally occur together, wherein the Cas protein and the cognate nucleic acid guide form the nucleoprotein complex, and wherein the nucleoprotein complex is capable of site-directed binding to a target nucleic acid sequence.

2. The Cas nucleoprotein complex of claim 1, wherein the cognate nucleic acid guide comprises a crRNA.

3. The Cas nucleoprotein complex of claim 1, wherein the Cas protein comprises an N- or C-terminal nuclear localization signal sequence (NLS).

4. The Cas nucleoprotein complex of claim 1, wherein the cognate nucleic acid guide comprises a modified base analog.

5. A eukaryotic cell comprising the Cas nucleoprotein complex of claim 1.

6. The eukaryotic cell of claim 5, further comprising one or more additional Cas nucleoprotein complexes.

7. The eukaryotic cell of claim 6, wherein the eukaryotic cell is a human cell.

8. The Cas nucleoprotein complex of claim 1, wherein the Cas protein is catalytically active.

9. The Cas nucleoprotein complex of claim 1, wherein the Cas protein is catalytically inactive.

10. The Cas nucleoprotein complex of claim 1, wherein the Cas protein comprises a fusion protein.

11. A method of directing a Clustered Regularly Interspaced Short Palindromic Repeats (CRISPR)-associated (Cas) nucleoprotein complex to a selected nucleic acid target sequence, the method comprising:

contacting the selected nucleic acid target sequence with one or more nucleoprotein complexes comprising:

a Clustered Regularly Interspaced Short Palindromic Repeats (CRISPR)-associated (Cas) protein, wherein the Cas protein has at least 95 percent sequence identity to the amino acid sequence of SEQ ID NO: 40; and a cognate nucleic acid guide comprising a repeat sequence and a spacer sequence, wherein the repeat sequence and the spacer sequence do not naturally occur together, wherein the Cas protein and the cognate nucleic acid guide form the nucleoprotein complex, and wherein the nucleoprotein complex binds to the selected nucleic acid target sequence.

12. The method of claim 11, wherein the nucleic acid target sequence comprises RNA.

13. The method of claim 11, wherein the method is performed in a cell.

* * * * *